(12) United States Patent
Frankel et al.

(10) Patent No.: US 8,148,129 B2
(45) Date of Patent: Apr. 3, 2012

(54) GENERATION OF POTENT DOMINANT NEGATIVE TRANSCRIPTIONAL INHIBITORS

(75) Inventors: Alan Frankel, Mill Valley, CA (US); Robert Nakamura, San Francisco, CA (US); Chandreyee Das, Brookline, MA (US); Ivan D'Orso, San Francisco, CA (US); Jocelyn Grunwell, San Mateo, CA (US)

(73) Assignee: The Regents of the University of California, Oakland, CA (US)

( * ) Notice: Subject to any disclaimer, the term of this patent is extended or adjusted under 35 U.S.C. 154(b) by 806 days.

(21) Appl. No.: 11/765,592

(22) Filed: Jun. 20, 2007

(65) Prior Publication Data

US 2008/0096813 A1    Apr. 24, 2008

Related U.S. Application Data

(60) Provisional application No. 60/817,927, filed on Jun. 30, 2006.

(51) Int. Cl.
*C12N 7/00* (2006.01)
(52) U.S. Cl. .................................. 435/235.1
(58) Field of Classification Search ........... None
See application file for complete search history.

(56) References Cited

U.S. PATENT DOCUMENTS

| | | | |
|---|---|---|---|
| 6,599,692 B1 | 7/2003 | Case et al. | |
| 6,607,882 B1 | 8/2003 | Cox, III et al. | |
| 6,777,185 B2 | 8/2004 | Case et al. | |
| 6,824,978 B1 | 11/2004 | Cox, III et al. | |
| 6,933,113 B2 | 8/2005 | Case et al. | |
| 6,979,539 B2 | 12/2005 | Cox, III et al. | |
| 7,013,219 B2 | 3/2006 | Case et al. | |
| 7,070,934 B2 | 7/2006 | Cox, III et al. | |
| 7,163,824 B2 | 1/2007 | Cox, III et al. | |
| 7,220,719 B2 | 5/2007 | Case et al. | |
| 7,235,354 B2 | 6/2007 | Case et al. | |
| 7,262,054 B2 | 8/2007 | Jamieson et al. | |
| 7,273,923 B2 | 9/2007 | Jamieson et al. | |
| 2003/0082552 A1* | 5/2003 | Wolffe et al. ............... | 435/6 |

OTHER PUBLICATIONS

Cramer et al., Coupling of Transcription with Alternative Splicing: RNA Pol II Promoters Modulate SF2/ASF and 9G8 Effects on an Exonic Splicing Enhancer, Molecular Cell, 1999, 4:251-258.*
Cama-Carvalho et al., Nucleocytoplasmic shuttling of heterodimeric splicing factor U2AF, JBC, Published on Dec. 15, 2000 as Manuscript M008759200.*
Rosonina et al., Gene Expression: The Close Coupling of Transcription and Splicing, Current Biology, vol. 12, R319-R321, Apr. 30, 2002.*
Peled-Zehavi et al., 2001, Molecular and Cellular Biology, 21(15):5232-5241.*
Zou et al., Journal of Biological Chemistry, 2000, 275(9):6051-6054.*

* cited by examiner

*Primary Examiner* — Zachariah Lucas
*Assistant Examiner* — Nicole Kinsey White
(74) *Attorney, Agent, or Firm* — Morgan, Lewis & Bockius LLP; Annette S. Parent

(57) ABSTRACT

The present invention provides methods and compositions for regulating gene expression using transcription factors linked to proteins that localize to the transcriptional machinery.

21 Claims, 22 Drawing Sheets

SEQUENCE LISTING

<160> NUMBER OF SEQ ID NOS: 15

<210> SEQ ID NO 1
<211> LENGTH: 8
<212> TYPE: PRT
<213> ORGANISM: Homo sapiens

<400> SEQUENCE: 1

Pro Pro Lys Lys Lys Arg Lys Val
1               5

<210> SEQ ID NO 2
<211> LENGTH: 24
<212> TYPE: DNA
<213> ORGANISM: Homo sapiens

<400> SEQUENCE: 2
ctgcatccgg agtacttcaa gaac                                      24

<210> SEQ ID NO 3
<211> LENGTH: 24
<212> TYPE: DNA
<213> ORGANISM: Homo sapiens

<400> SEQUENCE: 3
aaccagagaa gacccagtac aggc                                      24

<210> SEQ ID NO 4
<211> LENGTH: 29
<212> TYPE: DNA
<213> ORGANISM: Homo sapiens

<400> SEQUENCE: 4
atgtatagat tgaagaaga gctgtttct                                  29

<210> SEQ ID NO 5
<211> LENGTH: 29
<212> TYPE: DNA
<213> ORGANISM: Homo sapiens

<400> SEQUENCE: 5
gataaatcgt atttgtcaat cagagtgct                                 29

<210> SEQ ID NO 6
<211> LENGTH: 20
<212> TYPE: DNA
<213> ORGANISM: Homo sapiens

```
<400> SEQUENCE: 6
tactagcggt tttacgggcg                                               20

<210> SEQ ID NO 7
<211> LENGTH: 24
<212> TYPE: DNA
<213> ORGANISM: Homo sapiens

<400> SEQUENCE: 7
tcgaacagga ggagcagaga gcga                                          24

<210> SEQ ID NO 8
<211> LENGTH: 20
<212> TYPE: DNA
<213> ORGANISM: Homo sapiens

<400> SEQUENCE: 8
gaagagtctg gagagttctg                                               20

<210> SEQ ID NO 9
<211> LENGTH: 20
<212> TYPE: DNA
<213> ORGANISM: Homo sapiens

<400> SEQUENCE: 9 cctttccct tctgagccaa                                                20

<210> SEQ ID NO 10
<211> LENGTH: 18
<212> TYPE: DNA
<213> ORGANISM: Homo sapiens

<400> SEQUENCE: 10
tatatcaggg ccgcgctg                                                 18

<210> SEQ ID NO 11
<211> LENGTH: 22
<212> TYPE: DNA
<213> ORGANISM: Homo sapiens

<400> SEQUENCE: 11
ggctccacaa ggaactgact tc                                            22

<210> SEQ ID NO 12
<211> LENGTH: 19
<212> TYPE: DNA
<213> ORGANISM: Homo sapiens

<400> SEQUENCE: 12
atcccgtggc tccgcggac                                                19

<210> SEQ ID NO 13
<211> LENGTH: 20
<212> TYPE: DNA
<213> ORGANISM: Homo sapiens

<400> SEQUENCE: 13
gcaaactcca ctggaaccac                                               20

<210> SEQ ID NO 14
<211> LENGTH: 22
<212> TYPE: DNA
<213> ORGANISM: Homo sapiens
```

```
<400> SEQUENCE: 14
aacccttccc ctagcaacag at                                          22

<210> SEQ ID NO 15
<211> LENGTH: 23
<212> TYPE: DNA
<213> ORGANISM: Homo sapiens

<400> SEQUENCE: 15
ctagcacagg gactccactt atg                                         23
```

GENERATION OF POTENT DOMINANT NEGATIVE TRANSCRIPTIONAL INHIBITORS

CROSS-REFERENCES TO RELATED APPLICATIONS

The present application claims the benefit of U.S. Ser. No. 60/817,927, filed Jun. 30, 2006, herein incorporated by reference in its entirety.

STATEMENT AS TO RIGHTS TO INVENTIONS MADE UNDER FEDERALLY SPONSORED RESEARCH OR DEVELOPMENT

This invention was made with government support under Grant Nos. R01 AI29135 and R41CA 103407, awarded by the National Institutes of Health. The government has certain rights in this invention.

BACKGROUND OF THE INVENTION

The regulation of gene expression by transcription factors is a fundamental aspect of the physiology of all cells, whether prokaryotic or eukaryotic. In eukaryotic organisms, for instance, a variety of transcription factors govern cell growth, differentiation, and death. The appropriate spatial and temporal expression of specific transcription factors governs development. As examples, transcription factors such as Myc and E2F control progression through the cell cycle; homeodomain, paired box, and forkhead transcription factors, among others, are involved in embryonic development; p53 is involved with tumor suppression and cell death; steroid hormone receptors, such as sex hormone, glucocorticoid, mineralocorticoid, and thyroid hormone receptors have pleiotrophic effects on various aspects of physiology.

The aberrant expression of transcription factors can lead to abnormal development and various disease states. The inappropriate expression of proto-oncogenes such as c-Myc through chromosomal translocation can lead to cancers such as Burkitt's lymphoma. The formation of a PML-RARa fusion protein has been shown to be responsible for acute promyelocytic leukemia. Loss of p53 expression results in increased susceptibility to various cancers. The inappropriate expression or loss of expression of heart specific transcription factors such as Tbx1, Tbx5, NRx2.5, Gata4, Sal4, and Eya4 have been shown to result in congenital heart defects.

Improved methods for regulating gene expression by modulating transcription factor function would result in more optimal treatment of many diseases.

One disease which might be approached by modulating transcription factor function is acquired immune deficiency syndrome (AIDS). Human immunodeficiency virus (HIV) has been identified as the etiological agent responsible for AIDS, a fatal disease characterized by destruction of the immune system and the inability to fight off life threatening opportunistic infections. Recent statistics indicate that as many as 33 million people worldwide are infected with the virus. In addition to the large number of individuals already infected, the virus continues to spread. Estimates from 1998 point to close to 6 million new infections in that year alone. In the same year there were approximately 2.5 million deaths associated with HIV and AIDS.

HIV is a member of the class of viruses known as retroviruses. The retroviral genome is composed of RNA, which is converted to DNA by reverse transcription. This retroviral DNA is then stably integrated into a host cell's chromosome and, employing the replication machinery of the host cells, produces new retroviral particles and advances the infection to other cells. HIV appears to have a particular affinity for the human T-4 lymphocyte cell, which plays a vital role in the body's immune system. HIV infection of these white blood cells depletes this white cell population. Eventually, the immune system is rendered inoperative and ineffective against various opportunistic diseases such as, among others, pneumocystic carini pneumonia, Kaposi's sarcoma, and cancer of the lymph system.

There are currently a number of antiviral drugs available to combat the infection. These drugs can be divided into four classes based on the viral protein they target and their mode of action. In particular, one class of such antiviral drugs are competitive inhibitors of the aspartyl protease expressed by HIV. Other agents are nucleoside reverse transcriptase inhibitors that behave as substrate mimics to halt viral cDNA synthesis. A class of non-nucleoside reverse transcriptase inhibitors inhibit the synthesis of viral cDNA via a non-competitive (or uncompetitive) mechanism. Another class are drugs that block viral fusion. Used alone, these drugs show effectiveness in reducing viral replication. However, the effects are only temporary as the virus readily develops resistance to all known agents.

As indicated above, a number of critical points in the HIV life cycle have been identified as possible targets for antiviral drugs including (1) the initial attachment of the virion to the T-4 lymphocyte or macrophage site; (2) the transcription of viral RNA to viral DNA (reverse transcriptase, RT); and (3) the processing of gag-pol protein by HIV protease. An additional, potentially attractive therapeutic target is transcription of the HIV genome. Transcription of the HIV genome is essential for replication of the virus after integration of viral DNA into a host cell chromosome. However, attempts to target HIV transcription have been hampered, in part, by the fact that transcription of the integrated HIV genome utilizes the host cell transcriptional machinery as well as viral transcription factors. Thus, therapies that attempt to target the transcription of the HIV genome may also interfere with transcription of normal host cell genes. Attempts have been made to target specifically HIV transcription by the generation of dominant negative forms of Tat, a virally encoded transcription factor. However, these dominant forms have been shown to have poor activity at inhibiting HIV transcription and viral replication.

Effective new methods to target underexploited aspects of the HIV lifecycle, such as transcription of the HIV genome would be desirable.

BRIEF SUMMARY OF THE INVENTION

The present application demonstrates that potent dominant negative regulators of transcription can be generated by linking a transcription factor to a protein that localizes to the transcriptional machinery.

In one embodiment, a method of regulating transcription of a gene is provided in which a nucleic acid construct is expressed in a cell in an amount sufficient for modulation of transcription, where the construct contains a first nucleic acid sequence encoding a transcription factor protein or a fragment thereof linked to a second nucleic acid sequence encoding a protein or a fragment thereof that localizes to the transcriptional machinery. In various aspects, the transcription factor protein can be viral transcription factors, nuclear proto-oncogene or oncogene proteins, nuclear tumor suppressor proteins, heart specific transcription factors, and immune system transcription factors. In some further aspects, the viral transcription factors can be HIV-Tat, HPV-E2, HPV-E7, BPV-E2, Adenovirus IVa2, HSV-1 ICP4, EBNA-LP, EBNA-2, EBNA-3A, EBNA-3B, EBNA-3C, BZLF-1, CMV-IE-1, CMV-IE2, HHSV-8 K bZIP, HBV Hbx, Poxvirus Vaccinia, VETF, HCV NS5A, T-Ag, Adenovirus E1A, Herpesvirus VP16, HTLV Tax, Hepadnavirus X protein, or Baculovirus AcNPV IE-1. In some further aspects, the nuclear proto-oncogene or oncogene proteins can be Abl, Myc, Myb, Rel, Jun, Fos, Spl, Apl, NF-κB, STAT 3 or 5, β-catenin, Notch, GLI, or PML-RARα. In some further aspects, heart specific transcription factors can be Nkx 2, 3, 4, or 5, TBX5, GATA 4, 5, or 6, or MEF2. In some further aspects, the immune cell specific transcription factor can be Ikaros, PU.1, PAX-5, Oct-2, or BOB.1/OBF.1.

In various embodiments, the transcription factor can be a dominant negative transcription factor, or fragment thereof. In further embodiments, the transcription factor can be either a transcriptional activator or repressor. In yet further embodiments, the transcription factor can be an activation domain (AD) fragment of the transcription factor. In yet further embodiments, the transcription factor can be Tat or an activation domain fragment or other fragment of Tat.

In some embodiments, the protein or a fragment thereof that localizes to the transcriptional machinery is a protein with nuclear localization, a component of the transcriptional machinery, or a protein that functions in co-transcriptional processing of RNA. In some aspects, the protein that functions in co-transcriptional processing of RNA is a capping factor, a splicing factor, a polyadenylation factor, an RNA export factor, or a translation factor. In some aspects, the splicing factor is an RS domain containing protein. In yet other aspects, the splicing factor is SF1, U2AF65, or 9G8, and the polyadenylation factor is CstF1.

In some embodiments, the modulation of transcription is inhibition of transcription by at least 25%, or at least 50%, or at least 75%, or at least 95%. In some aspects, the modulation of transcription is by inhibition of transcriptional initiation, or elongation, or termination. In some embodiments, the modulation of transcription is activation of transcription.

In some embodiments, the cell is a T-cell infected with an immunodeficiency virus that can be HIV, FIV, SIV, or BIV. In yet further embodiments, the cell is a cancer cell, heart cell, or immune system cell. In some aspects, the cancer cell is a carcinoma, sarcoma, adenocarcinoma, lymphoma, leukemia, or solid tumors of the kidney, breast, lung, bladder, colon, ovarian, prostate, pancreas, stomach, brain, head and neck, skin, uterine, testicular, glioma, esophagus, or liver. In some aspects, the immune system cell can be a B-cell, T-cell, macrophage, or dendritic cell.

Also included as embodiments are vectors and cells containing the nucleic acids of the embodiments above, as well as, the proteins encoded by these nucleic acids. In further aspects, a composition comprising the nucleic acid construct or protein of the above embodiments and a physiologically acceptable carrier is provided.

In yet further embodiments, a method of regulating transcription of a gene is provided by expressing a nucleic acid construct in a cell in an amount sufficient for modulation of transcription, in which the construct contains a first nucleic acid sequence encoding a transcription factor protein or a fragment thereof linked to a second nucleic acid sequence encoding a splicing factor or a fragment thereof.

In still further embodiments, a method of inhibiting replication of an immunodeficiency virus by expressing a nucleic acid construct in a cell in an amount sufficient for modulation of viral transcription, in which the construct contains a first nucleic acid sequence encoding a transcription factor protein or a fragment thereof linked to a second nucleic acid sequence encoding a protein or a fragment thereof that localizes to the transcriptional machinery.

In another embodiment, provided is a method of inhibiting replication of an immunodeficiency virus by expressing in a cell a nucleic acid construct in an amount sufficient for modulation of viral transcription, in which the construct contains a first nucleic acid sequence encoding a Tat protein or a fragment thereof linked to a second nucleic acid sequence encoding a protein or a fragment thereof that localizes to the transcriptional machinery.

In another embodiment, provided is a method of inhibiting replication of an immunodeficiency virus by expressing in a cell a nucleic acid construct in an amount sufficient for modulation of viral transcription, in which the construct contains a first nucleic acid sequence encoding a transcription factor protein or a fragment thereof linked to a second nucleic acid sequence encoding a splicing factor or a fragment thereof.

In another embodiment, provided is a method of treating a subject infected with an immunodeficiency virus by administering a nucleic acid construct in an amount sufficient for inhibition of viral transcription, in which the construct contains a first nucleic acid sequence encoding a transcription factor or a fragment thereof linked to a second nucleic acid sequence encoding a protein or a fragment thereof that localizes to the transcriptional machinery. In some aspects, the treating is with a protein of the embodiments above.

In another embodiment, provided is a method of inhibiting transcription of a HIV genome in a cell by expressing in the cell a nucleic acid construct in an amount sufficient for inhibition of the transcription of the HIV genome, in which the construct contains a first nucleic acid sequence encoding a Tat protein or a fragment thereof linked to a second nucleic acid sequence encoding a U2AF65 protein or a fragment thereof.

In another embodiment, provided is a method of treating a subject with cancer by expressing in the subject a nucleic acid construct in an amount sufficient for modulation of transcription, in which the construct contains a first nucleic acid sequence encoding a transcription factor protein or a fragment thereof linked to a second nucleic acid sequence encoding a protein or a fragment thereof that localizes to the transcriptional machinery. In some aspects, the treating is with a protein of the embodiments above.

In another embodiment, provided is a method of treating or preventing a disease in a subject by expressing in the subject a nucleic acid construct in an amount sufficient for modulation of transcription, in which the construct contains a first nucleic acid sequence encoding a transcription factor protein or a fragment thereof linked to a second nucleic acid sequence encoding a protein or a fragment thereof that localizes to the transcriptional machinery, where the disease is viral infection, cancer, heart disease, and inflammation.

In another embodiment, provided is a method of validating a target by expressing a nucleic acid construct in a cell in an amount sufficient for modulation of transcription of the gene for the target, in which the construct contains a first nucleic acid sequence encoding a transcription factor protein or a fragment thereof linked to a second nucleic acid sequence encoding a protein or a fragment thereof that localizes to the transcriptional machinery, where altered expression of the gene for the target provides target confirmation.

(hnRNPA1), TATA box binding protein (TBP), hypoxanthine phosphoribosyltransferase 1 (HPRT1), HLA-DQA 1 major histocompatibility complex, class II, (MHCII), Interleukin 8 (IL-8), and androgen receptor (AR). Like HIV, the IL-8, androgen receptor, and HLA-DQA1 promoters require PTEF-b.

Figure 10A:
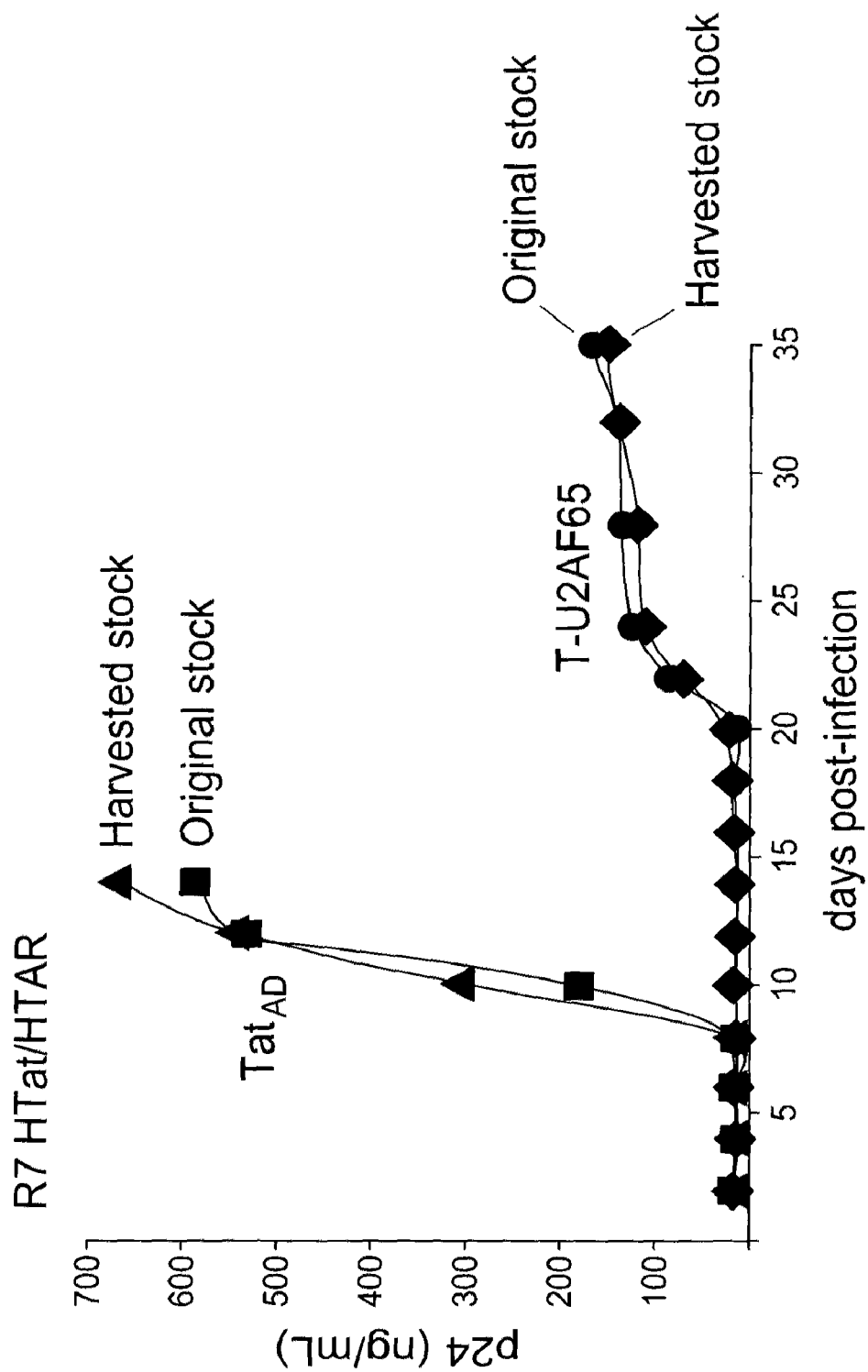
Figure 10B:
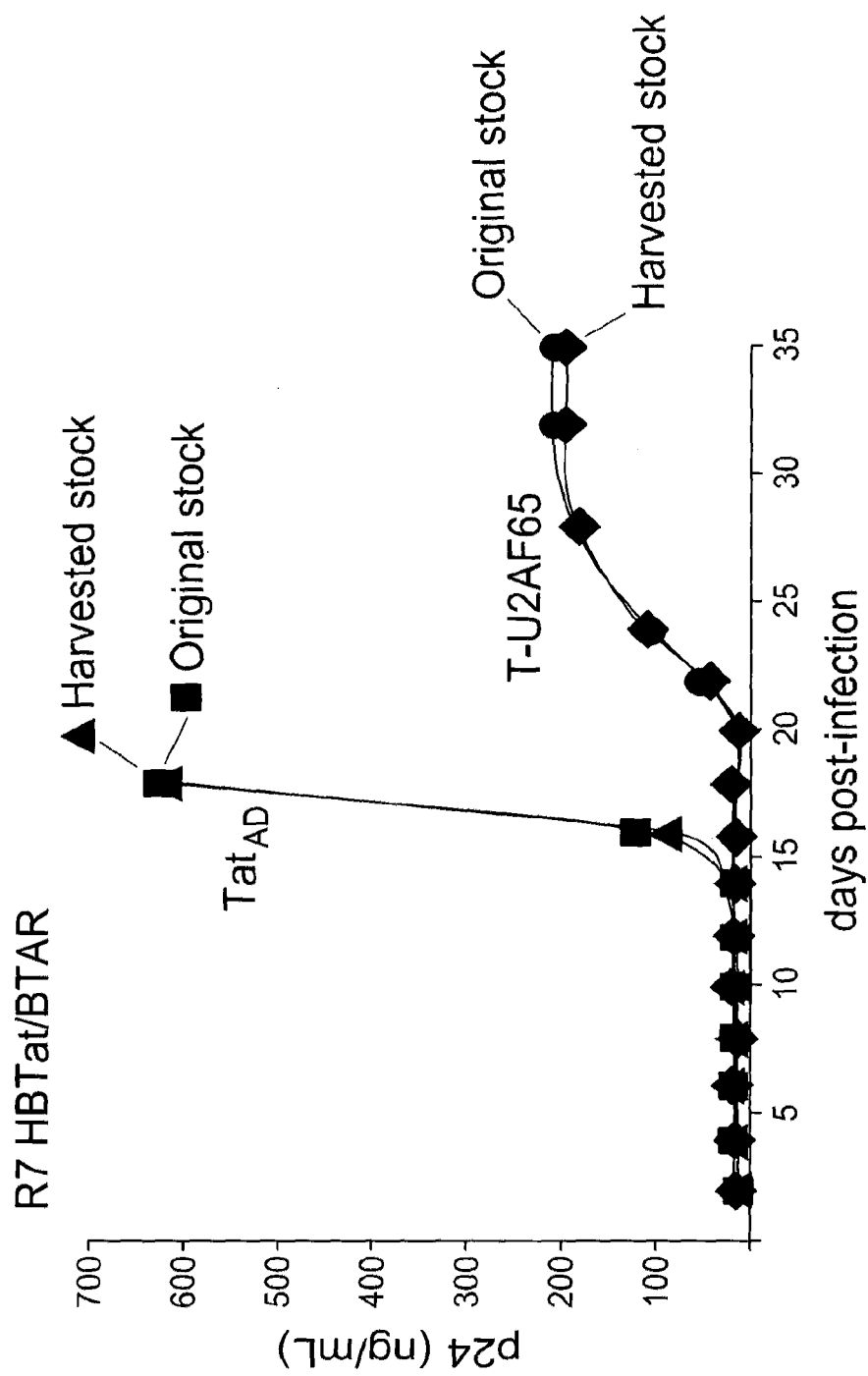

FIG. 10 shows re-infection of dominant negative-expressing cells with slowly-replicating viruses shows the same growth kinetics as the initial infection. SupT1 cells expressing $Tat_{AD}$ and T-U2AF65 were re-infected with viral stocks harvested from day 30 of the first set of infections (see arrows in FIGS. 4a and 4b). a, Re-infection using the HIV Tat-TAR-dependent virus. b, Re-infection using the BIV Tat-TAR-dependent virus.

DETAILED DESCRIPTION OF THE INVENTION

Introduction

The gene product of a dominant negative mutation interferes with the function of a normal, wild-type gene product within the same cell. This usually occurs if the gene product of the dominant negative mutation can still interact with the same elements as the wild-type product, but blocks some aspect of the wild-type protein's function. As an example, in the case of multi-subunit protein complexes, an inactive dominant negative protein can bind to wild-type components of the complex rendering the resulting complex less active or inactive. Genetic engineering has allowed the construction of dominant negative forms of many different types of proteins. In the case of transcription factors, one approach has been to generate transcription factors that lack a gene activation domain but which retain a DNA binding domain. When expressed in cells, such dominant negative proteins are able to bind to their cognate DNA recognition sites thus preventing the binding of a wild type transcription factor and leading to reduced expression of a target gene. However, typically, for dominant negative inhibition to occur, a great excess of dominant negative protein must be expressed in order to effectively out compete the wild-type protein.

A dominant negative approach has previously been used in an attempt to inhibit transcription of the HIV genome and thus viral replication. When a truncated form of Tat, lacking the basic domain, was tested in transient co-transfection experiments, it was found that an 8-30 fold molar excess of the dominant negative Tat over wild-type Tat was required to inhibit the expression of a reporter gene under the control of the HIV-LTR.

The inventors have devised a new method of generating potent dominant negative transcriptional inhibitors for pharmaceutical treatment of diseases, gene therapy, target validation, disease diagnosis, and mechanistic studies of transcription, among other applications. As discussed above, previously described dominant negative transcription factors typically act by competing with other interacting factors or by creating defective oligomers, thus requiring a large excess of inhibitor while providing only a modest amount of inhibition. The inventors have discovered that linking a protein which localizes to the transcriptional machinery to a transcription factor can effectively target and generate high local concentrations of a dominant negative protein, thereby efficiently out-competing wild-type protein when expressed at stoichiometric amounts. In particular, the inventors have made the unexpected finding that fusion of the Tat protein or a fragment thereof, such as the Tat activation domain (Tat AD), to a protein that localizes to the transcriptional machinery, results in a potent inhibitor of transcription of the HIV genome. In particular, when Tat or Tat AD is fused to the splicing factors, SF1 or U2AF65, a potent dominant negative effect is observed. While one embodiment of this invention as described below in the Examples relates to the inhibition of HIV transcription and viral replication, it will be clear to the skilled artisan that the methods of the present invention can be used to generate dominant negative forms of other transcription factors and other classes of proteins.

Dominant Negative Tat

Immediately after HIV infects a cell, the viral RNA is copied into DNA, and the proviral genome is transported to the nucleus where it is integrated into the host genome. Once integrated into the host chromosome, the HIV proviral genome is subject to regulation by a variety of cellular transcription factors, as well as, by virally encoded factors. Among these virally encoded factors, the trans-activator protein (Tat) provides the primary control of HIV transcription.

Transcription of the HIV genome begins at the viral LTR when the host cell RNA polymerase complex binds to the HIV promoter. The HIV LTR, however, is a poor promoter in the absence of Tat. In the absence of Tat, only non-processive (basal) transcription of the HIV genome is observed. However, upon recruitment of Tat to the transcriptional complex at the promoter, transcription of the HIV genome is greatly stimulated. Recruitment of Tat to the HIV promoter is mediated at least in part by the binding of Tat to a short RNA sequence that forms a stem-loop, termed the transactivation-responsive region (TAR), which lies just downstream of the initiation site for transcription. Transcription of TAR by the basal transcriptional machinery to form the TAR RNA stem loop allows Tat to join the complex and stimulate transcription. Upon binding of Tat, it is believed that other cellular factors are recruited to the transcriptional complex that convert the complex into a form that is competent for processive transcript elongation.

In one embodiment of this invention, the inventors have made a fusion of the Tat protein or a fragment thereof, such as the Tat activation domain (Tat AD), to proteins that localize to the transcriptional machinery. When Tat or Tat AD is fused to splicing factors, such as, SF1 or U2AF65, a potent dominant negative effect is observed. Without limiting themselves to any particular mechanism of action, and as explained below in greater detail, the inventors have found that the fused splicing factor proteins act as tethering domains, directing the Tat fusion protein to RNA polymerase at the HIV-1 promoter thus blocking the activity of incoming wild-type Tat proteins. This results in a high local concentration of the inhibiting fusion protein at the site of action.

DEFINITIONS

As used herein, the following terms have the meanings ascribed to them unless specified otherwise.

A "dominant negative" gene product or protein is one that interferes with the function of another gene product or protein. The other gene product affected can be the same or different from the dominant negative protein. Dominant negative gene products can be of many forms, including truncations, full length proteins with point mutations or fragments thereof, or fusions of full length wild type or mutant proteins or fragments thereof with other proteins. The level of inhibition observed can be very low. For example, it may require a large excess of the dominant negative protein compared to the functional protein or proteins involved in a process in order to see an effect. It may be difficult to see effects under normal biological assay conditions.

A "transcription factor" is a protein that regulates transcription. Transcription factors may bind directly to DNA or RNA or may interact with the transcriptional machinery via protein-protein interactions with no direct nucleic acid contact to modulate transcription. Transcription factors in general are reviewed in Barnes and Adcock, Clin. Exp. Allergy 25 Suppl. 2: 46-9 (1995), Roeder, Methods Enzymol. 273: 165-71 (1996), and Brivanlou and Darnell, Science 1 Feb. 2002: 813-818 (2002), among other sources.

A "promoter" is defined as an array of nucleic acid control sequences that direct transcription. As used herein, a promoter typically includes necessary nucleic acid sequences near the start site of transcription, such as, in the case of certain RNA polymerase II type promoters, a TATA element, enhancer, CCAAT box, SP-1 site, etc. As used herein, a promoter also optionally includes distal enhancer or repressor elements, which can be located as much as several thousand base pairs from the start site of transcription. The promoters often have an element that is responsive to transactivation by a DNA-binding moiety such as a polypeptide, e.g., a nuclear receptor, Gal4, the lac repressor and the like.

A "target site" is the nucleic acid sequence recognized by a transcription factor protein. A single target site typically has about four to about ten or more base pairs. The target site is in any position that allows regulation of gene expression, e.g., adjacent to, up- or downstream of the transcription initiation site; proximal to an enhancer or other transcriptional regulation element such as a repressor (e.g., SP-1 binding sites, hypoxia response elements, nuclear receptor recognition elements, p53 binding sites, etc.), RNA polymerase pause sites; and intron/exon boundaries.

"Linking" or "fusing" as used in this application refers to entities that are directly linked, or linked via an amino acid linker, the size and composition of which can vary, or linked via a chemical linker.

The term "transcriptional machinery" generally refers to the complex of cellular components responsible for making RNA from a DNA template and related co-transcriptional RNA processing. The complex responsible for transcription in a cell is referred to as RNA polymerase. During transcription, a variety of factors join the RNA polymerase complex to effect various aspects of transcription and co-transcriptional RNA processing as described below. In eukaryotic cells, three forms of RNA polymerase exist, termed RNA polymerases I, II, and III. RNA polymerase I synthesizes a pre-rRNA 45S, which matures into 28 S, 18S and 5, 8 S rRNAs which form the major RNA portions of the ribosome. RNA polymerase II synthesizes precursors of mRNAs and most snRNA. Because of the large variety of cellular genes are transcribed by thus polymerase, RNAP II is subject to the highest level of control, requiring a wide range of transcription factors depending on the promoter. RNA polymerase III is responsible for the synthesis of tRNAs, rRNA 5S and other small RNAs found in the nucleus and cytosol. Additionally, other RNA polymerase types are found in mitochondria and chloroplasts.

A 550 kDa complex of 12 subunits, RNAP II is the most intensively studied type of RNA polymerase. A wide range of transcription factors are required for it to bind to its promoters and to begin transcription. In the process of transcription, there are three main stages: (1) initiation, which requires construction of the RNA polymerase complex on the gene's promoter; (2) elongation, during which the RNA transcript is made from the DNA template; (3) and termination, the step at which the formation of the RNA transcript is completed and disassembly of the RNA polymerase complex occurs.

The components of the transcriptional machinery that may be targeted by this invention comprise any factor that is brought into the RNA polymerase complex and can be exemplified by the order in which the TAFs (TBP Associated Factors) attach to form a polymerase complex on a promoter. TBP (TATA Binding Protein) and an attached complex of TAFs, collectively known as TFIID (Transcription Factor for polymerase II D), bind at the TATA box, although not all promoters have the TATA box. TFIIA (three subunits) binds TFIID and DNA, stabilizing the first interactions. TFIIB binds between TFIID and the location of Pol II binding in the near future. TFIIB binds partially sequence specifically, with some preference for BRE. TFIIF and Pol II (two subunits, RAP30 and RAP74, showing some similarity to bacterial sigma factors) enter the complex together. TFIIF helps to speed up the polymerization process. TFIIE enters the complex, and helps to open and close the PolII's 'Jaw' like structure, which enables movement down the DNA strand. TFIIE and TFIIH enter concomitantly. Finally TFIIH binds. TFIIH is a large protein complex that contains among others the CDK7/cyclin H kinase complex and a DNA helicase. TFIIH has three functions: it binds specifically to the template strand to ensure that the correct strand of DNA is transcribed and melts or unwinds the DNA (ATP dependently) to separate the two strands using its Helicase activity. It has a kinase activity that phosphorylates the C-terminal domain (CTD) of Pol II at the amino acid serine. This switches the RNA polymerase to start producing RNA, which marks the end of initiation and the start of elongation. Finally it is essential for Nucleotide Excision Repair (NER) of damaged DNA. TFIIH and TFIIE strongly interact with one another. TFIIE affects TFIIH's catalytic activity. Without TFIIE, TFIIH will not unwind the promoter. Mediator then encases all the transcription factors and the Pol II. Mediator interacts with enhancers, areas very far away (upstream or downstream) that help regulate transcription.

A "protein that localizes to the transcriptional machinery" is one that is capable of associating or interacting with the transcriptional machinery as described above or a component thereof. The association or interaction may be non-covalent or covalent and may be reversible or non-reversible. Examples of proteins that localize to the transcriptional machinery include nuclear localized proteins, RNA processing proteins, components of the transcriptional machinery, and proteins involved in co-transcriptional processes. Among the co-transcriptional processes that are subjects of the invention are capping, splicing, polyadenylation, RNA export, translation.

An RS domain containing protein (also referred to in the literature as an SR protein) is a protein with a domain that contains multiple arginine and serine di-peptides (single-letter code RS) and/or serine and arginine di-peptides (single-letter code SR). RS domains are found in a number of cellular proteins, particularly those involved with pre-mRNA splicing and RNA processing events.

A "transcriptional activator" and a "transcriptional repressor" refer to proteins or effector domains of proteins that have the ability to modulate transcription, by binding directly to DNA or RNA or by interacting with the transcriptional machinery via protein-protein interactions with no direct nucleic acid contact. Such proteins include, e.g., transcription factors and co-factors (e.g., KRAB, MAD, ERD, SID, nuclear factor kappa B subunit p65, early growth response factor 1, and nuclear hormone receptors, VP16, VP64), endonucleases, integrases, recombinases, methyltransferases, histone acetyltransferases, histone deacetylases etc. Activators and repressors include co-activators and co-repressors (see, e.g., Utley et al., *Nature* 394:498-502 (1998)).

The terms "modulating transcription" "inhibiting transcription" and "activating transcription" of a gene refer to the ability of a dominant negative to activate or inhibit transcription of a gene. Activation includes prevention of transcriptional inhibition (i.e., prevention of repression of gene expression) and inhibition includes prevention of transcriptional activation (i.e., prevention of gene activation).

Modulation can be assayed by determining any parameter that is indirectly or directly affected by the expression of the target gene. Such parameters include, e.g., changes in RNA or protein levels, changes in protein activity, changes in product levels, changes in downstream gene expression, changes in reporter gene transcription (luciferase, CAT, β-galactosidase, β-glucuronidase, GFP (see, e.g., Mistili & Spector, *Nature Biotechnology* 15:961-964 (1997)); changes in signal transduction, phosphorylation and dephosphorylation, receptor-ligand interactions, second messenger concentrations (e.g., cGMP, cAMP, IP3, and $Ca^{2+}$), cell growth, and neovascularization. These assays can be in vitro, in vivo, and ex vivo. Such functional effects can be measured by any means known to those skilled in the art, e.g., measurement of RNA or protein levels, measurement of RNA stability, identification of downstream or reporter gene expression, e.g., via chemiluminescence, fluorescence, colorimetric reactions, antibody binding, inducible markers, ligand binding assays; changes in intracellular second messengers such as cGMP and inositol triphosphate (IP3); changes in intracellular calcium levels; cytokine release, and the like.

To determine the level of gene expression modulation by a dominant negative construct, cells contacted with nucleic acids encoding dominant negative or dominant negative proteins are compared to control cells which have not received this treatment. Control samples are assigned a relative gene expression activity value of 100%. Modulation/inhibition of gene expression is achieved when the gene expression activity value relative to the control is about 80%, preferably 50% (i.e., 0.5× the activity of the control), more preferably 25%, more preferably 5-0%. Modulation/activation of gene expression is achieved when the gene expression activity value relative to the control is 110%, more preferably 150% (i.e., 1.5× the activity of the control), more preferably 200-500%, more preferably 1000-2000% or more.

The term "heterologous" is a relative term, which when used with reference to portions of a nucleic acid indicates that the nucleic acid comprises two or more subsequences that are not found in the same relationship to each other in nature. For instance, a nucleic acid that is recombinantly produced typically has two or more sequences from unrelated genes synthetically arranged to make a new functional nucleic acid, e.g., a promoter from one source and a coding region from another source. The two nucleic acids are thus heterologous to each other in this context. When added to a cell, the recombinant nucleic acids would also be heterologous to the endogenous genes of the cell. Thus, in a chromosome, a heterologous nucleic acid would include an non-native (non-naturally occurring) nucleic acid that has integrated into the chromosome, or a non-native (non-naturally occurring) extrachromosomal nucleic acid. In contrast, a naturally translocated piece of chromosome would not be considered heterologous in the context of this patent application, as it comprises an endogenous nucleic acid sequence that is native to the mutated cell.

Similarly, a heterologous protein indicates that the protein comprises two or more subsequences that are not found in the same relationship to each other in nature (e.g., a "fusion protein," where the two subsequences are encoded by a single nucleic acid sequence). See, e.g., Ausubel, supra, for an introduction to recombinant techniques.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (naturally occurring) form of the cell or express a second copy of a native gene that is otherwise normally or abnormally expressed, under expressed or not expressed at all.

An "expression vector" is a nucleic acid construct, generated recombinantly or synthetically, with a series of specified nucleic acid elements that permit transcription of a particular nucleic acid in a host cell, and optionally integration or replication of the expression vector in a host cell. The expression vector can be part of a plasmid, virus, or nucleic acid fragment, of viral or non-viral origin. Typically, the expression vector includes an "expression cassette," which comprises a nucleic acid to be transcribed operably linked to a promoter. The term expression vector also encompasses naked DNA operably linked to a promoter.

By "host cell" is meant a cell that contains an expression vector or nucleic acid encoding a dominant negative protein of the invention. The host cell typically supports the replication or expression of the expression vector. Host cells may be prokaryotic cells such as *E. coli*, or eukaryotic cells such as yeast, fungal, protozoal, higher plant, insect, or amphibian cells, or mammalian cells such as CHO, HeLa, 293, COS-1, and the like, e.g., cultured cells (in vitro), explants and primary cultures (in vitro and ex vivo), and cells in vivo.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms also apply to amino acid polymers in which one or more amino acid residues is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

The term "substantially identical" indicates that two or more nucleotide sequences share a majority of their sequence. Generally, this will be at least about 90% of their sequence and preferably about 95% of their sequence. Another indication that sequences are substantially identical is if they hybridize to the same nucleotide sequence under stringent conditions (see, e.g., Sambrook and Russell, eds, *Molecular Cloning: A Laboratory Manual*, 3rd Ed, vols. 1-3, Cold Spring Harbor Laboratory Press, 2001; and *Current Protocols in Molecular Biology*, Ausubel, ed. John Wiley & Sons, Inc. New York, 1997). Stringent conditions are sequence-dependent and will be different in different circumstances. Generally, stringent conditions are selected to be about 5° C. (or less) lower than the thermal melting point (Tm) for the specific sequence at a defined ionic strength and pH. The $T_m$ of a DNA duplex is defined as the temperature at which 50% of the nucleotides are paired and corresponds to the midpoint of the spectroscopic hyperchromic absorbance shift during DNA melting. The $T_m$ indicates the transition from double helical to random coil.

Typically, stringent conditions will be those in which the salt concentration is about 0.2×SSC at pH 7 and the temperature is at least about 60° C. For example, a nucleic acid of the invention or fragment thereof can be identified in standard filter hybridizations using the nucleic acids disclosed here under stringent conditions, which for purposes of this disclosure, include at least one wash (usually 2) in 0.2×SSC at a temperature of at least about 60° C., usually about 65° C., sometimes 70° C. for 20 minutes, or equivalent conditions. For PCR, an annealing temperature of about 5° C. below Tm, is typical for low stringency amplification, although annealing temperatures may vary between about 32° C. and 72° C., e.g., 40° C., 42° C., 45° C., 52° C., 55° C., 57° C., or 62° C., depending on primer length and nucleotide composition or high stringency PCR amplification, a temperature at, or slightly (up to 5° C.) above, primer Tm is typical, although high stringency annealing temperatures can range from about 50° C. to about 72° C., and are often 72° C., depending on the primer and buffer conditions (Ahsen et al., *Clin Chem.* 47:1956-61, 2001). Typical cycle conditions for both high and low stringency amplifications include a denaturation phase of 90° C.-95° C. for 30 sec-2 min., an annealing phase lasting 30 sec.-10 min., and an extension phase of about 72° C. for 1-15 min.

The terms "identical" or percent "identity," in the context of two or more nucleic acids, refer to two or more sequences or subsequences that are the same or have a specified percentage of nucleotides that are the same (i.e., at least 70% identity, preferably at least 75%, 80%, 85%, 90%, 95%, 96%, 97%, 98%, or 99% identity, over a specified region, when compared and aligned for maximum correspondence over a comparison window, or designated region as measured using a BLAST or BLAST 2.0 sequence comparison algorithms with default parameters described below, or by manual alignment and visual inspection. Such sequences are then said to be "substantially identical." This definition also refers to the complement of a test sequence. Preferably, the identity exists over a region that is at least about 15, 20 or 25 nucleotides in length, or more preferably over a region that is 50-100 nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 15 to 600, usually about 20 to about 200, more usually about 50 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the default parameters described herein, to determine percent sequence identity for the nucleic acids described herein. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=-4 and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Administering" an expression vector, nucleic acid, protein, or a delivery vehicle to a cell comprises transducing, transfecting, electroporating, translocating, fusing, phagocytosing, shooting or ballistic methods, etc., i.e., any means by which a protein or nucleic acid can be transported across a cell membrane and preferably into the nucleus of a cell.

A "delivery vehicle" refers to a compound, e.g., a liposome, toxin, or a membrane translocation polypeptide, which is used to administer dominant negative proteins. Delivery vehicles can also be used to administer nucleic acids encoding dominant negative proteins of the invention, e.g., a lipid: nucleic acid complex, an expression vector, a virus, and the like.

Design of Dominant Negative Proteins

The dominant negative proteins of the invention comprise any of a number of possible fusions of a transcription factor or other protein, or fragment thereof, with a protein that is capable of localization to the transcriptional machinery, such as nuclear localized proteins, RNA processing proteins, components of the transcriptional machinery, and proteins involved in co-transcriptional processes. Among the co-transcriptional processes that are subjects of the invention are capping, splicing, polyadenylation, RNA export, translation. The transcription factor can be derived from any of a number of species including, and not limited to, viruses, HIV, bacteria, yeast, *Drosophila, C. elegans, Xenopus*, mouse, monkey, and human. For human applications, a human TF is generally preferred. One of skill in the art will recognize that a wide variety of transcription factor proteins known in the art may be used in this invention. See Goodrich et al., *Cell* 84:825-30 (1996), Barnes & Adcock, *Clin. Exp. Allergy* 25 Suppl. 2:46-9 (1995), and Roeder, *Methods Enzymol.* 273:165-71 (1996) for general reviews of transcription factors. Databases dedicated to transcription factors are known (see, e.g., *Science* 269:630 (1995)). Nuclear hormone receptor transcription factors are described in, for example, Rosen et al., *J. Med. Chem.* 38:4855-74 (1995). The C/EBP family of transcription factors are reviewed in Wedel et al., *Immunobiology* 193:171-85 (1995). Coactivators and co-repressors that mediate transcription regulation by nuclear hormone receptors are reviewed in, for example, Meier, *Eur. J. Endocrinol.* 134(2): 158-9 (1996); Kaiser et al., *Trends Biochem. Sci.* 21:342-5 (1996); and Utley et al., *Nature* 394:498-502 (1998)). GATA transcription factors, which are involved in regulation of hematopoiesis, are described in, for example, Simon, *Nat. Genet.* 11:9-11 (1995); Weiss et al., *Exp. Hematol.* 23:99-107. TATA box binding protein (TBP) and its associated TAF polypeptides (which include TAF30, TAF55, TAF80, TAF 110, TAF 150, and TAF250) are described in Goodrich & Tjian, *Curr. Opin. Cell Biol.* 6:403-9 (1994) and Hurley, *Curr. Opin. Struct. Biol.* 6:69-75 (1996). The STAT family of transcription factors are reviewed in, for example, Barahmand-Pour et al., *Curr. Top. Microbiol. Immunol.* 211:121-8 (1996). Transcription factors involved in disease are reviewed in Aso et al., *J. Clin. Invest.* 97:1561-9 (1996).

As further examples, the transcription factor may be chosen from any of a number of different classes of known transcription factors such as those that contain homeodomains, POU domains, Helix-Loop-Helix (HLH), Zinc Fingers, Leucine Zippers, or Winged Helix, to name but a few of the structural motifs found in transcription factors. Currently, there are about 2000 known transcription factors. See, e.g., Brivanlou and Darnell, Science, 295: 813-818 (2002). Among some of the better known transcription factors include: c-Myc and Max, c-Fos and c-Jun, CREB, c-ErbA, c-Ets, GATA c-Myb, MyoD KF-kB, RAR, and SRF, to name a few.

Among the classes of transcription factors that find use in this invention are viral transcription factors, nuclear proto-oncogene or oncogene proteins, nuclear tumor suppressor proteins, heart specific transcription factors, and immune cell transcription factors. The viral transcription factors useful in the practice of this invention include: HIV-Tat, HPV-E2, HPV-E7, BPV-E2, Adenovirus IVa2, HSV-1 ICP4, EBNA-LP, EBNA-2, EBNA-3A, EBNA-3B, EBNA-3C, BZLF-1, CMV-IE-1, CMV-IE2, HHSV-8 K bZIP, HBV Hbx, Poxvirus Vaccinia, VETF, HCV NS5A, T-Ag, Adenovirus EIA, Herpesvirus VP16, HTLV Tax, Hepadnavirus X protein, and Baculovirus AcNPV IE-1, among others. The nuclear proto-oncogene or oncogene proteins and nuclear tumor suppressor proteins transcription factors useful in the practice of this invention include: Abl, Myc, Myb, Rel, Jun, Fos, Sp I, Apl, NF-κB, STAT 3 or 5, β-catenin, Notch, GLI, PML-RARα and p53, among others. The heart specific transcription factors useful in the practice of this invention include: Nkx 2, 3, 4, or 5, TBX5, GATA 4, 5, or 6, and MEF2, among others. The immune cell specific transcription factors useful in the practice of this invention include: Ikaros, PU.1, PAX-5, Oct-2, and BOB.1/OBF.1, among others. A non limiting list of transcription factors that may be used in the practice of this invention is provided in Table 3. The transcription factors useful in the practice of this invention can be human as well as derived from yeast or higher eukaryotes such as viruses, HIV, *Drosophila, C. elegans, Xenopus*, or mouse, among other species.

In the practice of this invention, the transcription factor can be either a transcriptional activator or repressor, examples of which are well known in the art. Non-limiting examples of transcriptional activators and repressors are provided in Table 3.

Proteins that localize to the transcriptional machinery include: components of the transcriptional machinery, nuclear localized proteins, RNA processing proteins, components of the transcriptional machinery, and proteins involved in co-transcriptional processes and RNA processing.

Among the components of the transcriptional machinery that may be used in the practice of this invention are TAFs, CDK7, cyclin H, DNA helicase, unwinding enzymes, transcription factors, among others.

A wide range of proteins have been shown to localize to the nucleus and may be used in the practice of this invention. A non-limiting list of such proteins is provided in Table 1.

Among the co-transcriptional processes and RNA processing activities that are subjects of the invention are capping, splicing, polyadenylation, RNA export, and translation. Accordingly, proteins involved in capping, splicing, polyadenylation, RNA export, and translation may be used in the practice of this invention. Splicing factors represent one particular class of proteins involved in co-transcriptional processing of RNA and are suitable for the practice of this invention. As many as 300 factors are known to comprise the spliceosome. The protein components of spliceosomes are disclosed in Rappsilber, J., Ryder, U., Lamond, A. I., and Mann, M. (2002) Genome Res 12(8), 1231-1245 and Zhou, Z., Licklider, L. J., Gygi, S. P., and Reed, R. (2002) Nature 419(6903), 182-185, among other sources. Many splicing factors useful for the practice of this invention are compiled in Table 2. Particular examples of splicing factors useful in the practice of this invention include SF1, U2AF65, and 9G8.

The RS domain is a structural and functional feature characteristic of many nuclear proteins, particularly splicing factors. A large number of RS domain proteins are known in the art, and many have been identified through a genome-wide survey of RS domain proteins from various species. See Boucher et al., RNA 7:1693-1701 (2001). Among the classes of known RS domain containing proteins that may be used in the practice of the invention are those listed in the table below.

In one embodiment of the invention, HIV Tat protein, or a fragment thereof, can used as the transcription factor in a dominant negative fusion protein as described herein. The human Tat protein is an 86 amino acid protein that is required efficient viral gene expression. The Tat sequence has been subdivided into several distinct regions based on structure and function: a N-terminal activation region (amino acids 1-19), a cysteine-rich domain (amino acids 20-31), a core region (amino acids 32-47), a basic region (amino acids 48-57), and a glutamine-rich region (amino acids 60-76). See Karn, J. (ref). In one particular embodiment, a full length Tat is linked to the splicing factors SF1 or U2AF65. In another embodiment, the Tat activation domain (Tat AD) is linked to the splicing factors SF1 or U2AF65.

Generation of Nucleic Acids Encoding Dominant Negative Proteins.

Dominant negative polypeptides and nucleic acids of the invention can be made using routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)). In addition, essentially any nucleic acid can be custom ordered from any of a variety of commercial sources. Similarly, peptides and antibodies can be custom ordered from any of a variety of commercial sources.

Expression Vectors for Nucleic Acids Encoding Dominant Negative Proteins

A nucleic acid encoding a dominant negative protein is typically cloned into intermediate vectors for transformation into prokaryotic or eukaryotic cells for replication and/or expression. Intermediate vectors are typically prokaryote vectors, e.g., plasmids, or shuttle vectors, or insect vectors, for storage or manipulation of the nucleic acid encoding dominant negative proteins or production of protein. The nucleic acid encoding a dominant negative protein is also typically cloned into an expression vector, for administration to a plant cell, animal cell, preferably a mammalian cell or a human cell, fungal cell, bacterial cell, or protozoal cell.

To obtain expression of a cloned gene or nucleic acid, a nucleic acid encoding a dominant negative protein is typically subcloned into an expression vector that contains a promoter to direct transcription. Suitable bacterial and eukaryotic promoters are well known in the art and described, e.g., in Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994). Bacterial expression systems for expressing a dominant negative protein are available in, e.g., *E. coli, Bacillus* sp., and *Salmonella* (Palva et al., Gene 22:229-235 (1983)). Kits for such expression systems are commercially available. Eukaryotic expression systems for mammalian cells, yeast, and insect cells are well known in the art and are also commercially available.

The promoter used to direct expression of a nucleic acid encoding a dominant negative protein depends on the particular application. For example, a strong constitutive promoter is typically used for expression and purification of a dominant negative protein. In contrast, when a dominant negative protein is administered in vivo for gene regulation, either a constitutive or an inducible promoter is used, depending on the particular use of the dominant negative protein. In addition, a preferred promoter for administration of a dominant negative protein can be a weak promoter, such as HSV TK or a promoter having similar activity. The promoter typically can also include elements that are responsive to transactivation, e.g., hypoxia response elements, Gal4 response elements, lac repressor response element, and small molecule control systems such as tet-regulated systems and the RU-486 system (see, e.g., Gossen & Bujard, *PNAS* 89:5547 (1992); Oligino et al., *Gene Ther.* 5:491-496 (1998); Wang et al., *Gene Ther.* 4:432-441 (1997); Neering et al., *Blood* 88:1147-1155 (1996); and Rendahl et al., *Nat. Biotechnol.* 16:757-761 (1998)).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to the nucleic acid sequence encoding the dominant negative protein, and signals required, e.g., for efficient polyadenylation of the transcript, transcriptional termination, ribosome binding sites, or translation termination. Additional elements of the cassette may include, e.g., enhancers, and heterologous spliced intronic signals.

The particular expression vector used to transport the genetic information into the cell is selected with regard to the intended use of the dominant negative protein, e.g., expression in plants, animals, bacteria, fungus, protozoa etc. (see expression vectors described below). Standard bacterial expression vectors include plasmids such as pBR322 based plasmids, pSKF, pET23D, and commercially available fusion expression systems such as GST and LacZ. A preferred fusion protein is the maltose binding protein, "MBP." Such fusion proteins are used for purification of the dominant negative protein. Epitope tags can also be added to recombinant proteins to provide convenient methods of isolation, for monitoring expression, and for monitoring cellular and subcellular localization, e.g., c-myc or FLAG.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

Some expression systems have markers for selection of stably transfected cell lines such as thymidine kinase, hygromycin B phosphotransferase, and dihydrofolate reductase. High yield expression systems are also suitable, such as using a baculovirus vector in insect cells, with a dominant negative protein encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of recombinant sequences.

Standard transfection methods are used to produce bacterial, mammalian, yeast or insect cell lines that express large quantities of protein, which are then purified using standard techniques (see, e.g., Colley et al., *J. Biol. Chem.* 264:17619-17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, naked DNA, plasmid vectors, viral vectors, both episomal and integrative, and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

Assays for Determining Regulation of Gene Expression by Dominant Negative Proteins A variety of assays can be used to determine the level of gene expression regulation by dominant negative proteins. The activity of a particular dominant negative protein can be assessed using a variety of in vitro and in vivo assays, by measuring, e.g., protein or mRNA levels, product levels, enzyme activity, tumor growth; transcriptional activation or repression of a reporter gene such as a fluorescent protein (e.g., GFP); second messenger levels (e.g., cGMP, cAMP, IP3, DAG, $Ca^{2+}$); cytokine and hormone production levels; and neovascularization, using, e.g., immunoassays (e.g., ELISA and immunohistochemical assays with antibodies), hybridization assays (e.g., RNase protection, northerns, in situ hybridization, oligonucleotide array studies), colorimetric assays, amplification assays, enzyme activity assays, tumor growth assays, phenotypic assays, and the like.

Dominant negative proteins are typically first tested for activity in vitro using cultured cells, e.g., 293 cells, CHO cells, VERO cells, BHK cells, HeLa cells, COS cells, and the like. Preferably, human cells are used. The dominant negative protein is often first tested using a transient expression system with a reporter gene, and then regulation of the target endogenous gene is tested in cells and in animals, both in vivo and ex vivo. The dominant negative protein can be recombinantly expressed in a cell, recombinantly expressed in cells transplanted into an animal, or recombinantly expressed in a transgenic animal, as well as administered as a protein to an animal or cell using delivery vehicles described below. The cells can be immobilized, be in solution, be injected into an animal, or be naturally occurring in a transgenic or non-transgenic animal.

Modulation of gene expression is tested using one of the in vitro or in vivo assays described herein. Samples or assays are treated with a dominant negative protein and compared to control samples without the test compound, to examine the extent of modulation.

The effects of the dominant negative proteins can be measured by examining any of the parameters described above. Any suitable gene expression, phenotypic, or physiological change can be used to assess the influence of a dominant negative protein. When the functional consequences are determined using intact cells or animals, one can also measure a variety of effects such as tumor growth, neovascularization, hormone release, transcriptional changes to both known and uncharacterized genetic markers (e.g., northern blots or oligonucleotide array studies), changes in cell metabolism such as cell growth or pH changes, and changes in intracellular second messengers such as cGMP.

Assays for dominant negative protein regulation of endogenous gene expression can be performed in vitro. In one preferred in vitro assay format, dominant negative protein regulation of endogenous gene expression in cultured cells is measured by examining protein production using an ELISA assay (see Examples VI and VII). The test sample is compared to control cells treated with an empty vector or an unrelated dominant negative protein that is targeted to another gene.

In another embodiment, dominant negative protein regulation of endogenous gene expression is determined in vitro by measuring the level of target gene mRNA expression. The level of gene expression is measured using amplification, e.g., using PCR, LCR, or hybridization assays, e.g., northern hybridization, RNase protection, dot blotting. RNase protection is used in one embodiment (see Example VIII and FIG. 10). The level of protein or mRNA is detected using directly or indirectly labeled detection agents, e.g., fluorescently or radioactively labeled nucleic acids, radioactively or enzymatically labeled antibodies, and the like, as described herein.

Alternatively, a reporter gene system can be devised using the target gene promoter operably linked to a reporter gene such as luciferase, green fluorescent protein, CAT, or β-gal. The reporter construct is typically co-transfected into a cultured cell. After treatment with the dominant negative protein of choice, the amount of reporter gene transcription, translation, or activity is measured according to standard techniques known to those of skill in the art.

Another example of an assay format useful for monitoring dominant negative protein regulation of endogenous gene expression is performed in vivo. This assay is particularly useful for examining dominant negative proteins that inhibit expression of tumor promoting genes, genes involved in tumor support, such as neovascularization (e.g., VEGF), or that activate tumor suppressor genes such as p53. In this assay, cultured tumor cells expressing the dominant negative protein of choice are injected subcutaneously into an immune compromised mouse such as an athymic mouse, an irradiated mouse, or a SCID mouse. After a suitable length of time, preferably 4-8 weeks, tumor growth is measured, e.g., by volume or by its two largest dimensions, and compared to the control. Tumors that have statistically significant reduction (using, e.g., Student's T test) are said to have inhibited growth. Alternatively, the extent of tumor neovascularization can also be measured. Immunoassays using endothelial cell specific antibodies are used to stain for vascularization of the tumor and the number of vessels in the tumor. Tumors that have a statistically significant reduction in the number of vessels (using, e.g., Student's T test) are said to have inhibited neovascularization.

Transgenic and non-transgenic animals are also used as a preferred embodiment for examining regulation of endogenous gene expression in vivo. Transgenic animals typically express the dominant negative protein of choice. Alternatively, animals that transiently express the dominant negative protein of choice, onto which the dominant negative protein has been administered in a delivery vehicle, can be used. Regulation of endogenous gene expression is tested using any one of the assays described herein.

Nucleic Acids Encoding Dominant Negative Proteins and Gene Therapy

Conventional viral and non-viral based gene transfer methods can be used to introduce nucleic acids encoding engineered dominant negative proteins in mammalian cells or target tissues. Such methods can be used to administer nucleic acids encoding dominant negative proteins to cells in vitro. Preferably, the nucleic acids encoding dominant negative proteins are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene therapy procedures, see Anderson, *Science* 256:808-813 (1992); Nabel & Feigner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds) (1995); and Yu et al., *Gene Therapy* 1:13-26 (1994).

Methods of non-viral delivery of nucleic acids encoding engineered dominant negative proteins include lipofection, microinjection, ballistics, virosomes, liposomes, immunoliposomes, polycation or lipid:nucleic acid conjugates, naked DNA, artificial virions, and agent-enhanced uptake of DNA. Lipofection is described in e.g., U.S. Pat. No. 5,049,386, U.S. Pat. No. 4,946,787; and U.S. Pat. No. 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids encoding engineered dominant negative protein take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of dominant negative proteins could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vector that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications where transient expression of the dominant negative protein is preferred, adenoviral based systems are typically used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, PNAS 81:6466-6470 (1984); and Samulski et al., *J. Virol.* 63:03822-3828 (1989).

In particular, at least six viral vector approaches are currently available for gene transfer in clinical trials, with retroviral vectors by far the most frequently used system. All of these viral vectors utilize approaches that involve complementation of defective vectors by genes inserted into helper cell lines to generate the transducing agent.

pLASN and MFG-S are examples are retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 by inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)).

Replication-deficient recombinant adenoviral vectors (Ad) are predominantly used for colon cancer gene therapy, because they can be produced at high titer and they readily infect a number of different cell types: Most adenovirus vectors are engineered such that a transgene replaces the Ad E1a, E1b, and E3 genes; subsequently the replication defector vector is propagated in human 293 cells that supply deleted gene function in trans. Ad vectors can transduce multiply types of tissues in vivo, including nondividing, differentiated cells such as those found in the liver, kidney and muscle system tissues. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell: Such cells include 293 cells, which package adenovirus, and ψ2 cells or PA317 cells, which package retrovirus. Viral vectors used in gene therapy are usually generated by producer cell line that packages a nucleic acid vector into a viral particle. The vectors typically contain the minimal viral sequences required for packaging and subsequent integration into a host, other viral sequences being replaced by an expression cassette for the protein to be expressed. The missing viral functions are supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., *PNAS* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a dominant negative protein nucleic acid (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba et al., *J. Exp. Med.* 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+(panB cells), GR-1 (granulocytes), and Tad (differentiated antigen presenting cells) (see Inaba et al., *J. Exp. Med.* 176:1693-1702 (1992)).

Vectors (e.g., retroviruses, adenoviruses, liposomes, etc.) containing therapeutic dominant negative protein nucleic acids can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention, as described below (see, e.g., *Remington's Pharmaceutical Sciences,* 17th ed., 1989).

Delivery Vehicles for Dominant Negative Proteins

An important factor in the administration of polypeptide compounds, such as the dominant negative proteins of the present invention, is ensuring that the polypeptide has the ability to traverse the plasma membrane of a cell, or the membrane of an intra-cellular compartment such as the nucleus. Cellular membranes are composed of lipid-protein bilayers that are freely permeable to small, nonionic lipophilic compounds and are inherently impermeable to polar compounds, macromolecules, and therapeutic or diagnostic agents. However, proteins and other compounds such as liposomes have been described, which have the ability to translocate polypeptides such as dominant negative proteins across a cell membrane.

For example, "membrane translocation polypeptides" have amphiphilic or hydrophobic amino acid subsequences that have the ability to act as membrane-translocating carriers. In one embodiment, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, *Current Opinion in Neurobiology* 6:629-634 (1996)). Another subsequence, the h (hydrophobic) domain of signal peptides, was found to have similar cell membrane translocation characteristics (see, e.g., Lin et al., *J. Biol. Chem.* 270:1 4255-14258 (1995)).

Examples of peptide sequences which can be linked to a dominant negative protein of the invention, for facilitating uptake of dominant negative protein into cells, include, but are not limited to: an 11 amino acid peptide of the tat protein of HIV; a 20 residue peptide sequence which corresponds to amino acids 84-103 of the p16 protein (see Fahraeus et al., *Current Biology* 6:84 (1996)); the third helix of the 60-amino acid long homeodomain of Antennapedia (Derossi et al., *J. Biol. Chem.* 269:10444 (1994)); the h region of a signal peptide such as the Kaposi fibroblast growth factor (K-FGF) h region (Lin et al., supra); or the VP22 translocation domain from HSV (Elliot & O'Hare, *Cell* 88:223-233 (1997)). Other suitable chemical moieties that provide enhanced cellular uptake may also be chemically linked to dominant negative proteins. For example, nuclear localization signals may be appended to enhance uptake into the nuclear compartment of cells.

Toxin molecules also have the ability to transport polypeptides across cell membranes. Often, such molecules are composed of at least two parts (called "binary toxins"): a translocation or binding domain or polypeptide and a separate toxin domain or polypeptide. Typically, the translocation domain or polypeptide binds to a cellular receptor, and then the toxin is transported into the cell. Several bacterial toxins, including *Clostridium perfringens* iota toxin, diphtheria toxin (DT), *Pseudomonas* exotoxin A (PE), pertussis toxin (PT), *Bacillus anthracis* toxin, and pertussis adenylate cyclase (CYA), have been used in attempts to deliver peptides to the cell cytosol as internal or amino-terminal fusions (Arora et al., *J. Biol. Chem.,* 268:3334-3341 (1993); Perelle et al., *Infect. Immun.,* 61:5147-5156 (1993); Stenmark et al., *J. Cell Biol.* 113:1025-1032 (1991); Donnelly et al., *PNAS* 90:3530-3534 (1993); Carbonetti et al., *Abstr. Annu. Meet. Am. Soc. Microbiol.* 95:295 (1995); Sebo et al., *Infect. Immun.* 63:3851-3857 (1995); Klimpel et al., *PNAS U.S.A.* 89:10277-10281 (1992); and Novak et al., *J. Biol. Chem.* 267:17186-17193 1992)).

Such subsequences can be used to translocate dominant negative proteins across a cell membrane. Dominant negative proteins can be conveniently fused to or derivatized with such sequences. Typically, the translocation sequence is provided as part of a fusion protein. Optionally, a linker can be used to link the dominant negative protein and the translocation sequence. Any suitable linker can be used, e.g., a peptide linker.

The dominant negative protein can also be introduced into an animal cell, preferably a mammalian cell, via a liposomes and liposome derivatives such as immunoliposomes. The term "liposome" refers to vesicles comprised of one or more concentrically ordered lipid bilayers, which encapsulate an aqueous phase. The aqueous phase typically contains the compound to be delivered to the cell, i.e., a dominant negative protein.

The liposome fuses with the plasma membrane, thereby releasing the drug into the cytosol. Alternatively, the liposome is phagocytosed or taken up by the cell in a transport vesicle. Once in the endosome or phagosome, the liposome either degrades or fuses with the membrane of the transport vesicle and releases its contents.

In current methods of drug delivery via liposomes, the liposome ultimately becomes permeable and releases the encapsulated compound (in this case, a dominant negative protein) at the target tissue or cell. For systemic or tissue specific delivery, this can be accomplished, for example, in a passive manner wherein the liposome bilayer degrades over time through the action of various agents in the body. Alternatively, active drug release involves using an agent to induce a permeability change in the liposome vesicle. Liposome membranes can be constructed so that they become destabilized when the environment becomes acidic near the liposome membrane (see, e.g., PNAS 84:7851 (1987); Biochemistry 28:908 (1989)). When liposomes are endocytosed by a target cell, for example, they become destabilized and release their contents. This destabilization is termed fusogenesis. Dioleoylphosphatidylethanolamine (DOPE) is the basis of many "fusogenic" systems.

Such liposomes typically comprise a dominant negative protein and a lipid component, e.g., a neutral and/or cationic lipid, optionally including a receptor-recognition molecule such as an antibody that binds to a predetermined cell surface receptor or ligand (e.g., an antigen). A variety of methods are available for preparing liposomes as described in, e.g., Szoka et al., Ann. Rev. Biophys. Bioeng. 9:467 (1980), U.S. Pat. Nos. 4,186,183, 4,217,344, 4,235,871, 4,261,975, 4,485,054, 4,501,728, 4,774,085, 4,837,028, 4,235,871, 4,261,975, 4,485,054, 4,501,728, 4,774,085, 4,837,028, 4,946,787, PCT Publication No. WO 91\17424, Deamer & Bangham, Biochim. Biophys. Acta 443:629-634 (1976); Fraley, et al., PNAS 76:3348-3352 (1979); Hope et al., Biochim. Biophys. Acta 812:55-65 (1985); Mayer et al., Biochim. Biophys. Acta 858: 161-168 (1986); Williams et al., PNAS 85:242-246 (1988); Liposomes (Ostro (ed.), 1983, Chapter 1); Hope et al., Chem. Phys. Lip. 40:89 (1986); Gregoriadis, Liposome Technology (1984) and Lasic, Liposomes: from Physics to Applications (1993)). Suitable methods include, for example, sonication, extrusion, high pressure/homogenization, microfluidization, detergent dialysis, calcium-induced fusion of small liposome vesicles and ether-fusion methods, all of which are well known in the art.

In certain embodiments of the present invention, it is desirable to target the liposomes of the invention using targeting moieties that are specific to a particular cell type, tissue, and the like. Targeting of liposomes using a variety of targeting moieties (e.g., ligands, receptors, and monoclonal antibodies) has been previously described (see, e.g., U.S. Pat. Nos. 4,957, 773 and 4,603,044).

Examples of targeting moieties include monoclonal antibodies specific to antigens associated with neoplasms, such as prostate cancer specific antigen and MAGE. Tumors can also be diagnosed by detecting gene products resulting from the activation or over-expression of oncogenes, such as ras or c-erbB2. In addition, many tumors express antigens normally expressed by fetal tissue, such as the alphafetoprotein (AFP) and carcinoembryonic antigen (CEA). Sites of viral infection can be diagnosed using various viral antigens such as hepatitis B core and surface antigens (HBVc, HBVs) hepatitis C antigens, Epstein-Barr virus antigens, human immunodeficiency type-1 virus (HIV1) and papilloma virus antigens. Inflammation can be detected using molecules specifically recognized by surface molecules which are expressed at sites of inflammation such as integrins (e.g., VCAM-1), selectin receptors (e.g., ELAM-1) and the like.

Standard methods for coupling targeting agents to liposomes can be used. These methods generally involve incorporation into liposomes lipid components, e.g., phosphatidylethanolamine, which can be activated for attachment of targeting agents, or derivatized lipophilic compounds, such as lipid derivatized bleomycin. Antibody targeted liposomes can be constructed using, for instance, liposomes which incorporate protein A (see Renneisen et al., J. Biol. Chem., 265: 16337-16342 (1990) and Leonetti et al., PNAS 87:2448-2451 (1990).

Doses of Dominant Negative Proteins

For therapeutic applications of dominant negative proteins, the dose administered to a patient, in the context of the present invention should be sufficient to effect a beneficial therapeutic response in the patient over time. In addition, particular dosage regimens can be useful for determining phenotypic changes in an experimental setting, e.g., in functional genomics studies, and in cell or animal models. The dose will be determined by the condition of the patient, as well as the body weight or surface area of the patient to be treated. The size of the dose also will be determined by the existence, nature, and extent of any adverse side-effects that accompany the administration of a particular compound or vector in a particular patient.

The appropriate dose of an expression vector encoding a dominant negative protein can also be calculated by taking into account the average rate of dominant negative protein expression from the promoter and the average rate of dominant negative protein degradation in the cell. Preferably, a weak promoter such as a wild-type or mutant HSV TK is used.

In determining the effective amount of a dominant negative protein to be administered in the treatment or prophylaxis of disease, the physician evaluates circulating plasma levels of the dominant negative protein or nucleic acid encoding the dominant negative protein, potential dominant negative protein toxicities, progression of the disease, and the production of anti-dominant negative protein antibodies. Administration can be accomplished via single or divided doses.

Pharmaceutical Compositions and Administration

Dominant negative proteins and expression vectors encoding dominant negative proteins can be administered directly to the patient for modulation of gene expression and for therapeutic or prophylactic applications, for example, cancer, ischemia, diabetic retinopathy, macular degeneration, rheumatoid arthritis, psoriasis, HIV infection, sickle cell anemia, Alzheimer's disease, muscular dystrophy, neurodegenerative diseases, vascular disease, cystic fibrosis, stroke, and the like. Examples of microorganisms that can be inhibited by dominant negative protein gene therapy include pathogenic bacteria, e.g., chlamydia, rickettsial bacteria, mycobacteria, staphylococci, streptococci, pneumococci, meningococci and conococci, klebsiella, proteus, serratia, pseudomonas, legionella, diphtheria, salmonella, bacilli, cholera, tetanus, botulism, anthrax, plague, leptospirosis, and Lyme disease bacteria; infectious fungus, e.g., Aspergillus, Candida species; protozoa such as sporozoa (e.g., Plasmodia), rhizopods (e.g., Entamoeba) and flagellates (Trypanosoma, Leishmania, Trichomonas, Giardia, etc.); viral diseases, e.g., hepatitis (A, B, or C), herpes virus (e.g., VZV, HSV-1, HSV-6, HSV-II, CMV, and EBV), HIV, Ebola, adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, poliovirus, rabies virus, and arboviral encephalitis virus, etc.

Administration of therapeutically effective amounts is by any of the routes normally used for introducing dominant negative protein into ultimate contact with the tissue to be treated. The dominant negative proteins are administered in any suitable manner, preferably with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., Remington's Pharmaceutical Sciences, 17th ed. 1985)).

The dominant negative proteins, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

Functional Genomics Assays

Dominant negative proteins also have use for assays to determine the phenotypic consequences and function of gene expression. The recent advances in analytical techniques, coupled with focussed mass sequencing efforts have created the opportunity to identify and characterize many more molecular targets than were previously available. This new information about genes and their functions will speed along basic biological understanding and present many new targets for therapeutic intervention. In some cases analytical tools have not kept pace with the generation of new data. An example is provided by recent advances in the measurement of global differential gene expression. These methods, typified by gene expression microarrays, differential cDNA cloning frequencies, subtractive hybridization and differential display methods, can very rapidly identify genes that are up or down-regulated in different tissues or in response to specific stimuli. Increasingly, such methods are being used to explore biological processes such as, transformation, tumor progression, the inflammatory response, neurological disorders etc. One can now very easily generate long lists of differentially expressed genes that correlate with a given physiological phenomenon, but demonstrating a causative relationship between an individual differentially expressed gene and the phenomenon is difficult. Until now, simple methods for assigning function to differentially expressed genes have not kept pace with the ability to monitor differential gene expression.

Using conventional molecular approaches, over expression of a candidate gene can be accomplished by cloning a full-length cDNA, subcloning it into a mammalian expression vector and transfecting the recombinant vector into an appropriate host cell. This approach is straightforward but labor intensive, particularly when the initial candidate gene is represented by a simple expressed sequence tag (EST). Under expression of a candidate gene by "conventional" methods is yet more problematic. Antisense methods and methods that rely on targeted ribozymes are unreliable, succeeding for only a small fraction of the targets selected. Gene knockout by homologous recombination works fairly well in recombinogenic stem cells but very inefficiently in somatically derived cell lines. In either case large clones of syngeneic genomic DNA (on the order of 10 kb) should be isolated for recombination to work efficiently.

The dominant negative protein technology can be used to rapidly analyze differential gene expression studies. Engineered dominant negative proteins can be readily used to up or down-regulate any endogenous target gene. This makes the dominant negative protein technology ideal for analysis of long lists of poorly characterized differentially expressed genes.

This specific example of using engineered dominant negative proteins to add functional information to genomic data is merely illustrative. Any experimental situation that could benefit from the specific up or down-regulation of a gene or genes could benefit from the reliability and ease of use of engineered dominant negative proteins.

Additionally, greater experimental control can be imparted by dominant negative proteins than can be achieved by more conventional methods. This is because the production and/or function of an engineered dominant negative protein can be placed under small molecule control. Examples of this approach are provided by the Tet-On system, the ecdysone-regulated system and a system incorporating a chimeric factor including a mutant progesterone receptor. These systems are all capable of indirectly imparting small molecule control on any endogenous gene of interest or any transgene by placing the function and/or expression of a dominant negative protein under small molecule control.

Transgenic Mice

A further application of the dominant negative protein technology is manipulating gene expression in transgenic animals. Conventional down-regulation of gene expression in transgenic animals is plagued by technical difficulties. Gene knockout by homologous recombination is the method most commonly applied currently. This method requires a relatively long genomic clone of the gene to be knocked out (ca. 10 kb). Typically, a selectable marker is inserted into an exon of the gene of interest to effect the gene disruption, and a second counter-selectable marker provided outside of the region of homology to select homologous versus non-homologous recombinants. This construct is transfected into embryonic stem cells and recombinants selected in culture. Recombinant stem cells are combined with very early stage embryos generating chimeric animals. If the chimerism extends to the germline homozygous knockout animals can be isolated by back-crossing. When the technology is successfully applied, knockout animals can be generated in approximately one year. Unfortunately two common issues often prevent the successful application of the knockout technology; embryonic lethality and developmental compensation. Embryonic lethality results when the gene to be knocked out plays an essential role in development. This can manifest itself as a lack of chimerism, lack of germline transmission or the inability to generate homozygous back crosses. Genes can play significantly different physiological roles during development versus in adult animals. Therefore, embryonic lethality is not considered a rationale for dismissing a gene target as a useful target for therapeutic intervention in adults. Embryonic lethality most often simply means that the gene of interest can not be easily studied in mouse models, using conventional methods.

Developmental compensation is the substitution of a related gene product for the gene product being knocked out. Genes often exist in extensive families. Selection or induction during the course of development can in some cases trigger the substitution of one family member for another mutant member. This type of functional substitution may not be possible in the adult animal. A typical result of developmental compensation would be the lack of a phenotype in a knockout mouse when the ablation of that gene's function in an adult would otherwise cause a physiological change. This is a kind of false negative result that often confounds the interpretation of conventional knockout mouse models.

A few new methods have been developed to avoid embryonic lethality. These methods are typified by an approach using the cre recombinase and lox DNA recognition elements. The recognition elements are inserted into a gene of interest using homologous recombination (as described above) and the expression of the recombinase induced in adult mice post-development. This causes the deletion of a portion of the target gene and avoids developmental complications. The method is labor intensive and suffers form chimerism due to non-uniform induction of the recombinase.

The use of engineered dominant negative proteins to manipulate gene expression can be restricted to adult animals using the small molecule regulated systems described in the previous section. Expression and/or function of a dominant negative protein can be switched off during development and switched on at will in the adult animals. This approach relies on the expression of the dominant negative protein only; homologous recombination is not required. Because the dominant negative proteins are trans dominant, there is no concern about germline transmission or homozygosity. These issues dramatically affect the time and labor required to go from a poorly characterized gene candidate (a cDNA or EST clone) to a mouse model. This ability can be used to rapidly identify and/or validate gene targets for therapeutic intervention, generate novel model systems and permit the analysis of complex physiological phenomena (development, hematopoiesis, transformation, neural function etc.). Chimeric targeted mice can be derived according to Hogan et al., *Manipulating the Mouse Embryo: A Laboratory Manual*, (1988); *Teratocarcinomas and Embryonic Stem Cells: A Practical Approach*, Robertson, ed., (1987); and Capecchi et al., *Science* 244:1288 (1989).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

Example 1

Dominant Negative Inhibition of Transcription by Linking Tat to a Protein that Localizes to the Transcriptional Machinery The Tat-hybrid assay, in which Tat fused to a heterologous RNA-binding domain (RBD) elicits activation of an HIV-1 LTR reporter plasmid containing a cognate RNA-binding site, has been useful for studying RNA-protein interactions in living cells[6]. However, as with other types of fusion protein assays, dominant negative proteins can be generated unintentionally that score as false negatives. We discovered a novel class of highly potent dominant negatives, exemplified by Tat fusions to splicing factors, whose potency appears to be dictated by cotranscriptional recruitment to the HIV promoter.

Figure 1A:
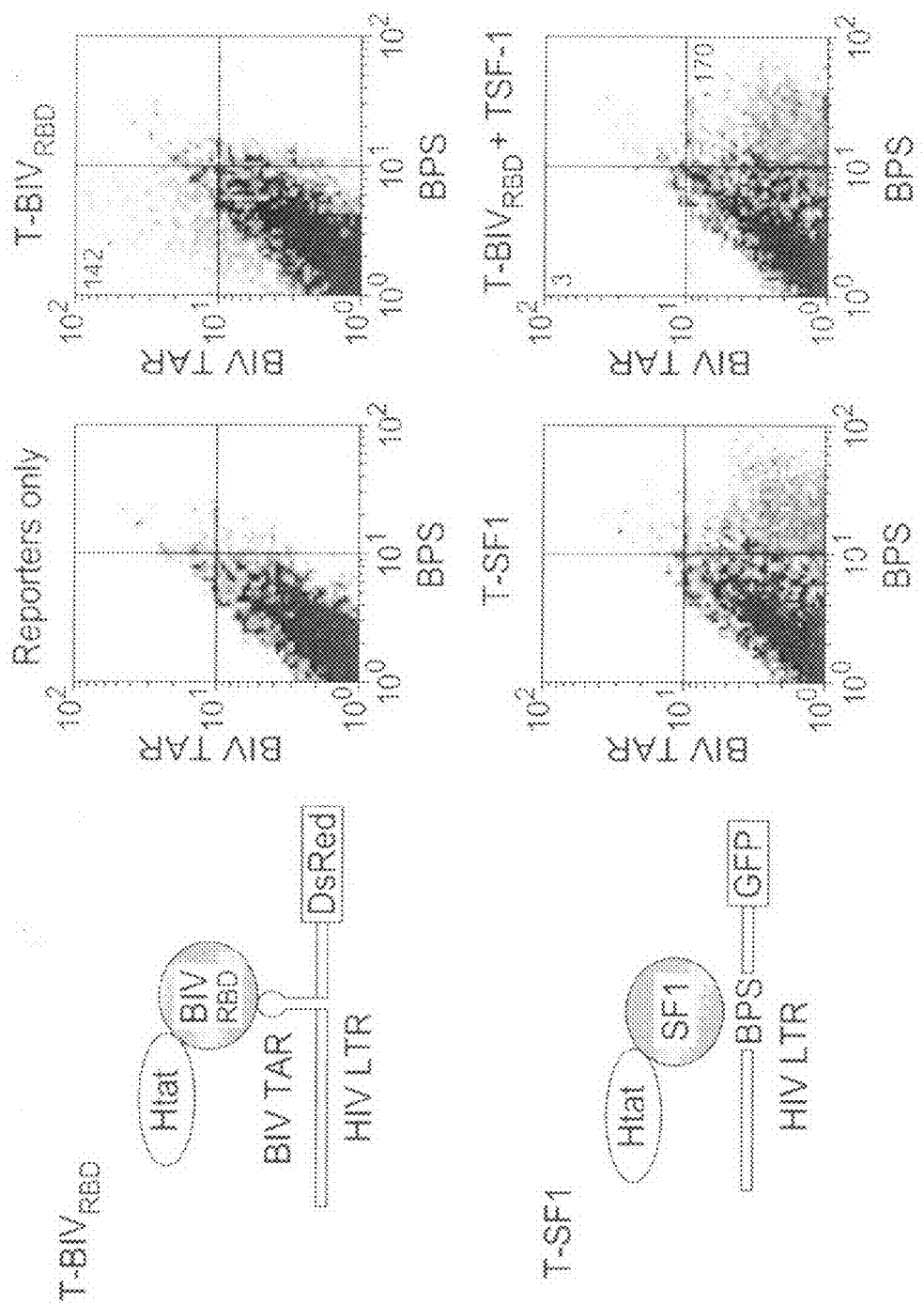
FIG. 1 shows a potent dominant negative Tat inhibitor identified in a reporter assay. a, Left, Schematic of a dual reporter fluorescence assay in which T-BIV$_{RBD}$ (HIV Tat$_{AD}$ with the BIV TatRBD) is used to activate an HIV LTR-DsRed reporter engineered with BIV TAR RNA in place of HIV TAR. The T-SF1 fusion protein is used to activate an HIV LTR-GFP reporter engineered with a BPS RNA site. Right, HeLa cells were co-transfected with both reporters and T-SF1 or T-BIV$_{RBD}$ expressors as indicated and sorted by flow cytometry. Expression of GFP is shown in green and DsRed in red. Numbers in each quadrant represent fold activation, calculated as the number of cells in the quadrant multiplied by their average fluorescence, relative to the same values calculated for the reporters alone. b, Dose response curves of T-SF1 activation on an LTR-HTAR-FFL reporter and T-SF1-mediated inhibition of T-BIV$_{RBD}$ activity on a LTR-BTAR-RL reporter. c, Potent inhibition by T-U2AF65 is independent of the RNA-protein interaction. Left, dose response curves showing inhibition of T-BIV$_{RBD}$-mediated activation of a BIV TAR reporter by Tat$_{AD}$ and T-U2AF65. Right, dose response curves showing inhibition of T-Rev-mediated activation of a RREIIB reporter by Tat$_{AD}$ and T-U2AF65. The arrows indicate stoichiometric DNA concentrations of inhibitor and activator (5 ng). d, Promoter specificity of T-U2AF65. HeLa cells were transiently transfected with reporter, activator, and several concentrations of T-U2AF65 plasmids at the ratios indicated. For the heat shock response, endogenous HSF1 was activated 24 hr post-transfection cells with 50 µM AsNO2 for 12 hr. p53 activity was measured on SAOS2 cells. Activities of all activators were normalized to a cotransfected CMV-RL reporter control.

We devised a dual-fluorescence Tat-hybrid assay to monitor RNA-binding specificity using two pairs of orthogonal reporters and Tat fusions, herein referred to as T-fusions. To calibrate the assay, T-BIV$_{RBD}$, a fusion between the HIV Tat activation domain (AD) and the RBD of bovine immunodeficiency virus (BIV) Tat, was used to activate a BIV TAR (BTAR)-DsRed reporter, while T-SF1, a Tat fusion to human splicing factor SF1, was used to activate a branch point sequence (BPS)-GFP reporter (FIG. 1a). When transfected on their own, both T-BIV$_{RBD}$ and T-SF1 strongly activated only their cognate RNA reporters. Strikingly, however, activation via the T-BIV$_{RBD}$-BTAR interaction was strongly inhibited when both T-fusions were co-transfected (3-fold activation) whereas activation via the T-SF1-BPS interaction was unafected (170-fold).

Figure 1B:
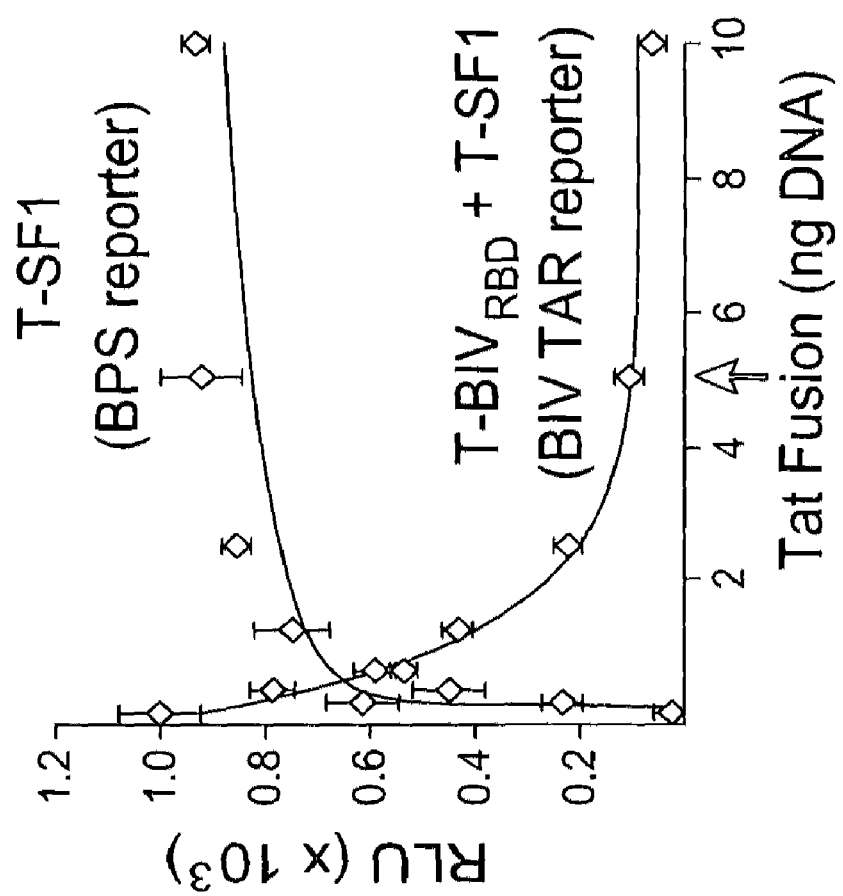
Figure 6:
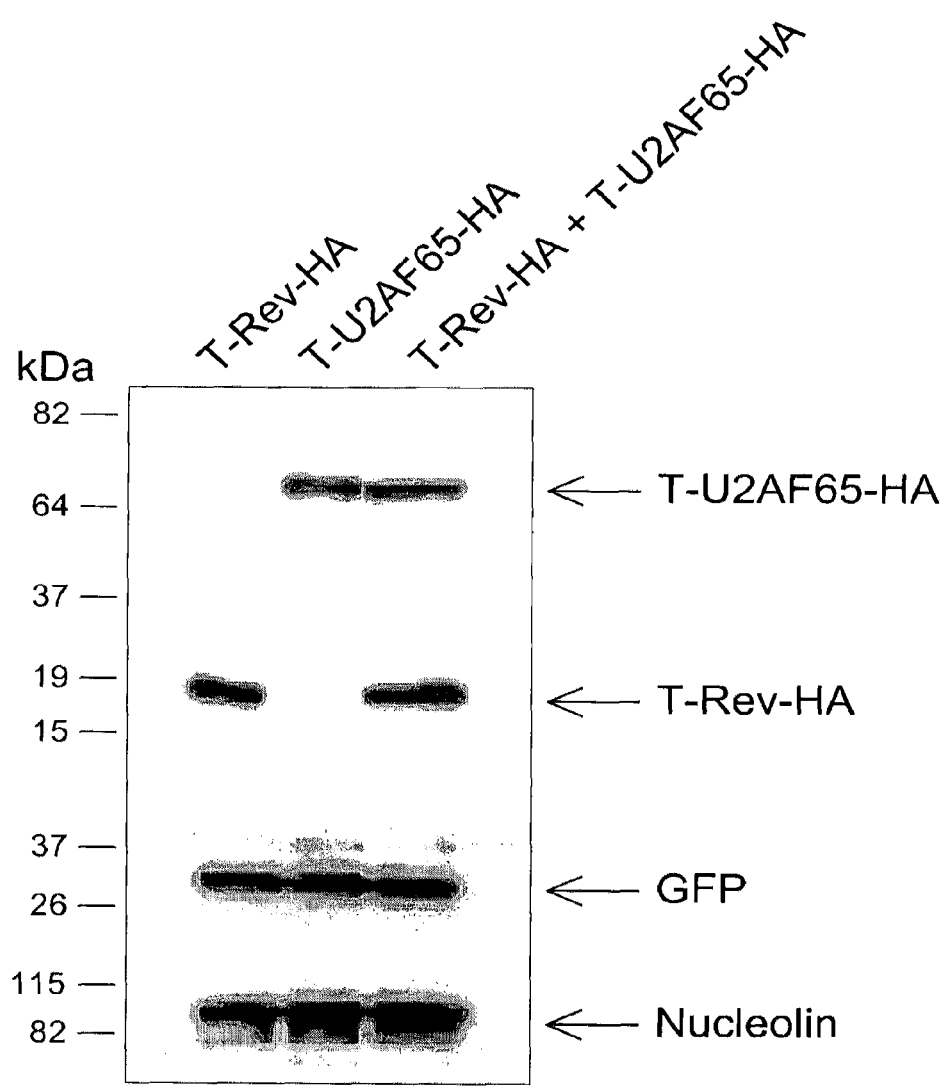
FIG. 6 shows relative expression levels of Tat activator and dominant negative. HeLa cells were co-transfected with HA-tagged versions of the T-Rev activator and/or the T-U2AF65 inhibitor along with a GFP-expresor to normalize for transfection efficiency. Nuclear extracts were probed for expression levels with an anti-HA antibody, an anti-GFP antibody, and an anti-C23 nucleolin antibody to provide a protein loading control.

Using a more quantitative luciferase reporter, we found that inhibition was remarkably potent, with a stoichiometric amount of T-SF1 plasmid DNA (5 ng) sufficient to almost completely block activation mediated by the BIV Tat-BTAR interaction (FIG. 1b). The dose response of inhibition by T-SF1 mirrors activation of a BPS reporter (FIG. 1b), demonstrating that T-SF1 functions as an activator through its cognate RNA-binding site. We confirmed that the high potency observed in the transfection experiments accurately reflected relative protein stoichiometries by Western blot analysis of HA-tagged Tat activator and dominant negative proteins (FIG. 6). It is clear that the high potency results from the fusion, as SF1 alone does not inhibit Tat activation (data not shown) and it is known that the Tat AD without an RBD is a very weak dominant negative[4,5]. Given that several splicing factors, including SF1 and U2AF65, interact with CTD-associated factors or directly with RNAP II[7], we hypothesized that the SF1 moiety targets the T-fusion to RNAP II. We propose a model in which this recruitment step increases the local concentration of the non-activating T-fusion at the HIV promoter thereby out-competing the wild-type Tat activator (see below).

Figure 1C:
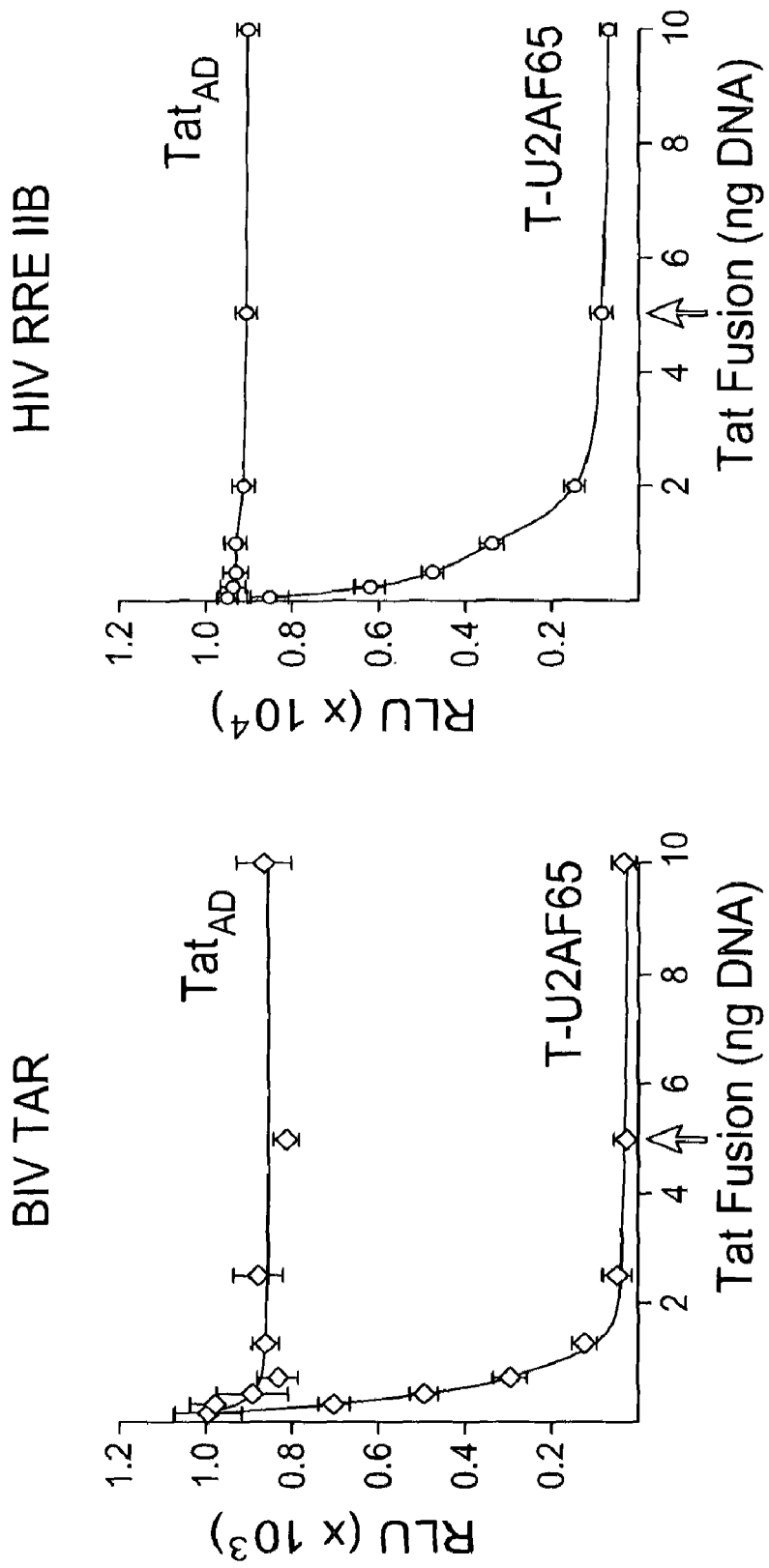

If the targeting hypothesis is correct, then T-fusions to other RNAP II-localized splicing factors might show a similar phenotype. Indeed, T-U2AF65 is an even more potent inhibitor (FIG. 1c, left panel). U2AF65 fusions to either full-length Tat or the Tat AD are equally potent (FIG. 5), showing that the Tat RBD is dispensable for the dominant negative function. T-U2AF65 also is a potent inhibitor of Tat activation when mediated by the Rev-RRE IIB RNA interaction (FIG. 1c, right panel), further demonstrating that the inhibitor functions independently of the RNA-protein interaction. The Tat AD alone is a poor inhibitor (FIG. 1c), again showing the requirement of the targeting moiety. Besides splicing factors, other proteins interact with RNAP II before, during, or after pre-initiation complex (PIC) formation, including other RNA-processing proteins that are co-transcriptionally recruited to the CTD[2]. T-fusions to some, but not all, of these factors inhibited Tat-mediated activation to different extents, but none was as potent as T-U2AF65 (FIG. 7).

Figure 1D:
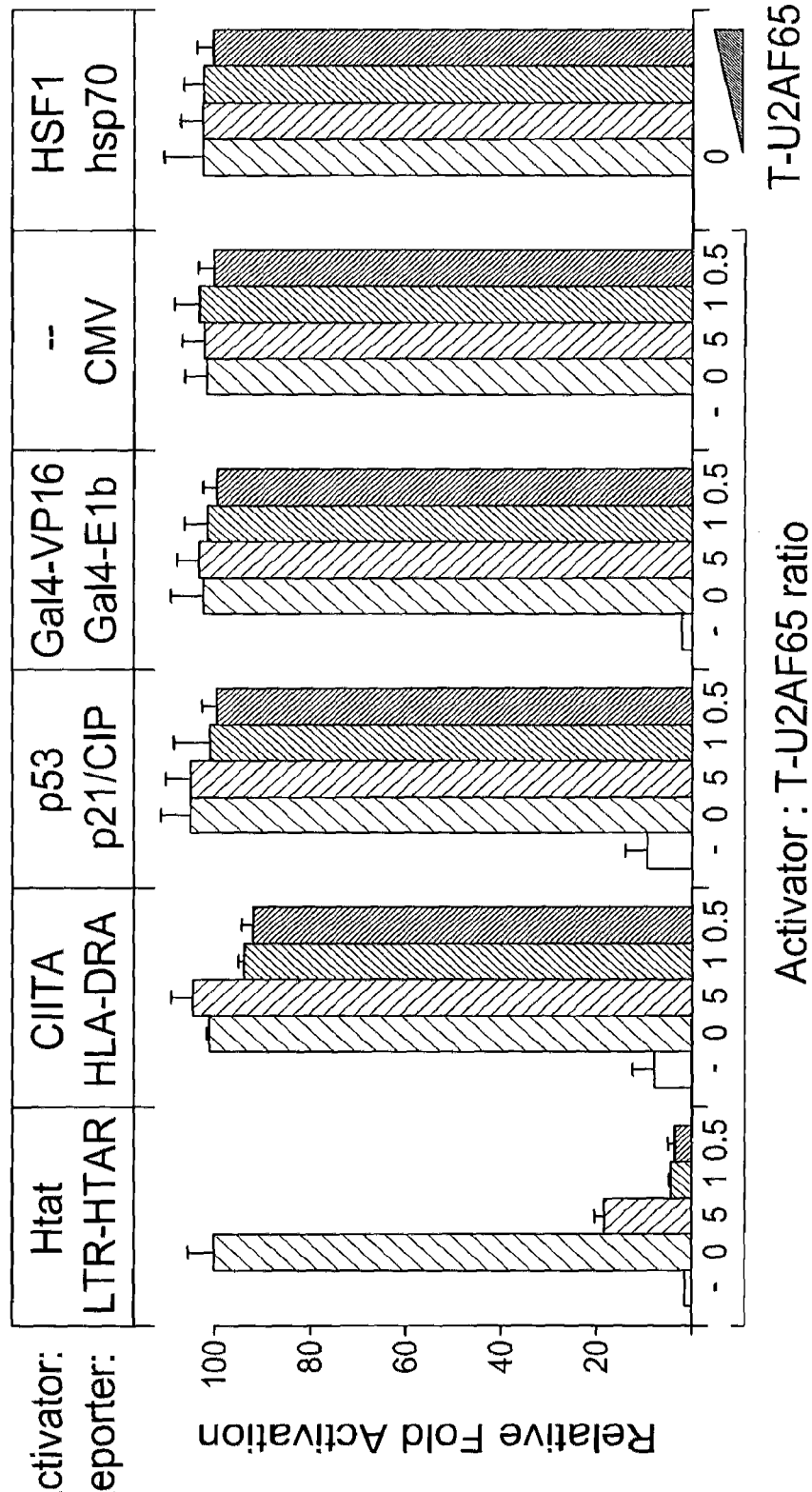

The specificity of inhibition for the HIV promoter was assessed by measuring effects of T-U2AF65 on other reporter-activator combinations. No inhibition was observed in any case, including activation by the P-TEFb-dependent MHC class II transactivator (CIITA) and heat-shock factor 1 (HSF1), as well as p53 and GAL4-VP16, and constitutive expression from the cytomegalovirus (CMV) promoter (FIG. 1d). Furthermore, no inhibition of cellular promoters was observed in stable cell lines expressing T-U2AF65 (FIG. 9).

Example 2

Figure 2A:
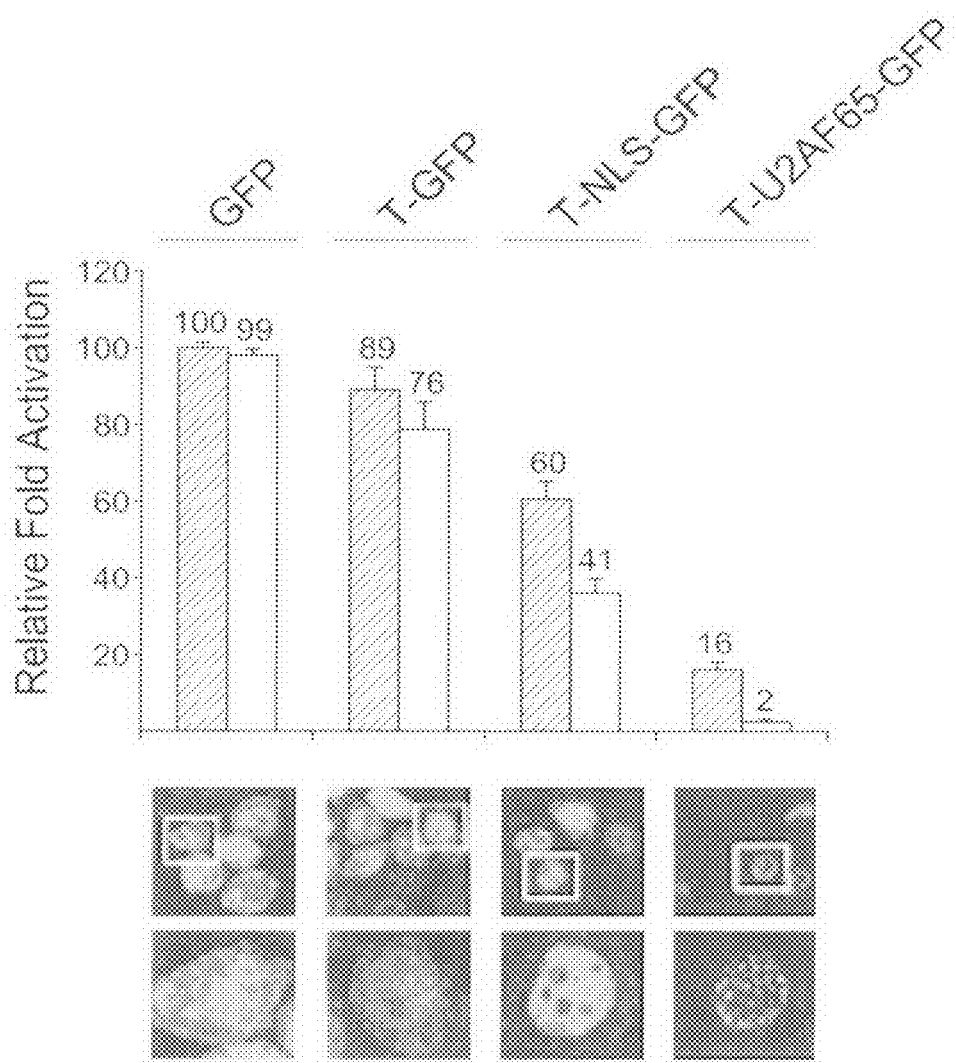
FIG. 2 shows contributions of subcellular localization and protein domains to dominant negative activity. a, HeLa cells were transiently co-transfected with an LTR-RREIIB-FFL reporter plasmid, T-Rev activator, and various inhibitors at 1:0.25 (grey bar) or 1:1 (black bar) ratios of activator to inhibitor. Activation levels are plotted relative to T-Rev without inhibitor, and confocal images of each GFP-tagged inhibitor are shown below the plot, including 3× magnification images (of boxed cells above) to highlight the subcellular compartments. T-NLS contains the 8 amino acid NLS of SV40 T-Ag (PPKKKRKV) (SEQ ID NO 1). b, Relative activities of T-U2AF65 RS domain and Tat AD variants, as determined in panel a, with corresponding confocal images. T-U2AF65ΔRS tagged with HA contains a deletion of the first 90 amino acids of U2AF65 and T-RS contains only residues 2-73 of U2AF65. K41A denotes a Tat AD mutation that abolishes interactions with cyclin T1$_{12}$. Confocal images of each HA-tagged inhibitor are shown below the plot, including 3× magnification images (of boxed cells above) to highlight the subcellular compartments.
Figure 7:
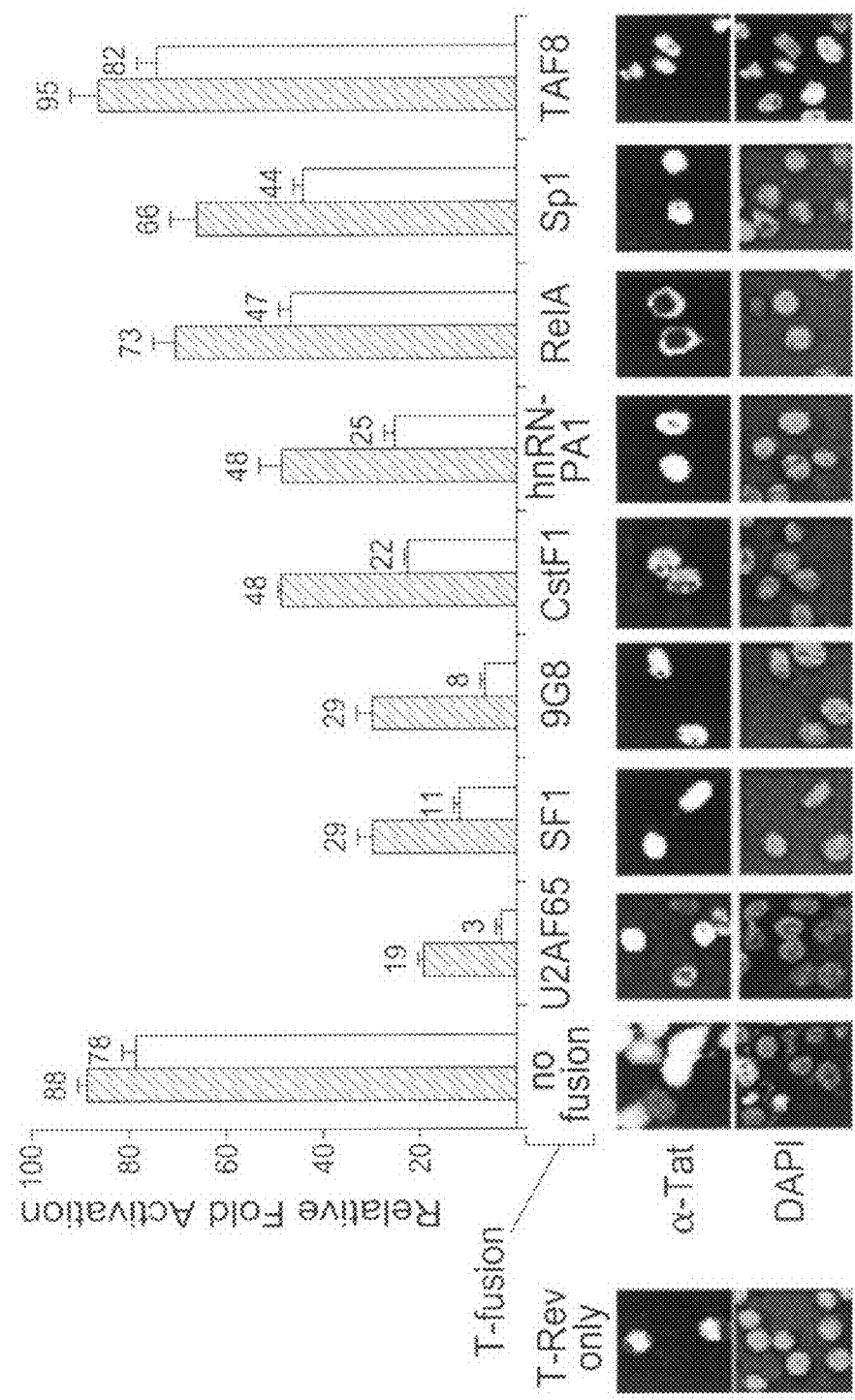
FIG. 7 shows inhibition activities of other T-fusions. HeLa cells were co-transfected with an HIV LTR-RREIIB-FFL reporter plasmid along with the T-Rev activator in the absence or presence of the N-terminal T-fusions at sub-stoichiometric 1:0.25 (black bars) or stoichiometric 1:1 (gray bars) activator: inhibitor ratios. The data shown is normalized to activation by T-Rev alone. Nuclear DAPI staining and indirect immunofluorescence confocal images of the activator and each Tat-fusion protein are shown above, using an anti-Tat antibody and Alexa-488 or Alexa-546 coupled anti-mouse antibodies.

Effect of Localization of the Dominant Negative Protein on Inhibition of Transcription To begin examining the effect of localization on inhibitor activity, we first asked whether nuclear localization alone might account for some of its potency, particularly because a variety of T-fusions showed activity, albeit not as strong as T-U2AF65 (FIG. 7). We generated T-fusions to GFP with or without a nuclear localization signal (NLS) and observed very weak dominant negative activity for the AD fusion alone (T-GFP) and only slightly enhanced inhibition for T-NLS-GFP (FIG. 2a). This result is consistent with the mild dominant negative phenotype observed for a Tat 1-53 truncation mutant that deletes part of the RNA-binding domain but still retains an NLS[5]. In contrast, T-U2AF65-GFP is a highly potent inhibitor (FIG. 2a), indicating that nuclear localization is not the major factor contributing to potency. T-GFP is distributed in the cytoplasm and nucleus, like unfused GFP, whereas T-NLS-GFP is greater than 95% nuclear and absent from the nucleolus, as expected (FIG. 2a). T-U2AF65-GFP shows a striking subnuclear pattern of "speckle-associated patches" (FIG. 2a). Related patterns are seen with RS-domain containing proteins[8,9], which include U2AF65, prompting us to examine the domains of T-U2AF65 important for inhibition.

Figure 2B:
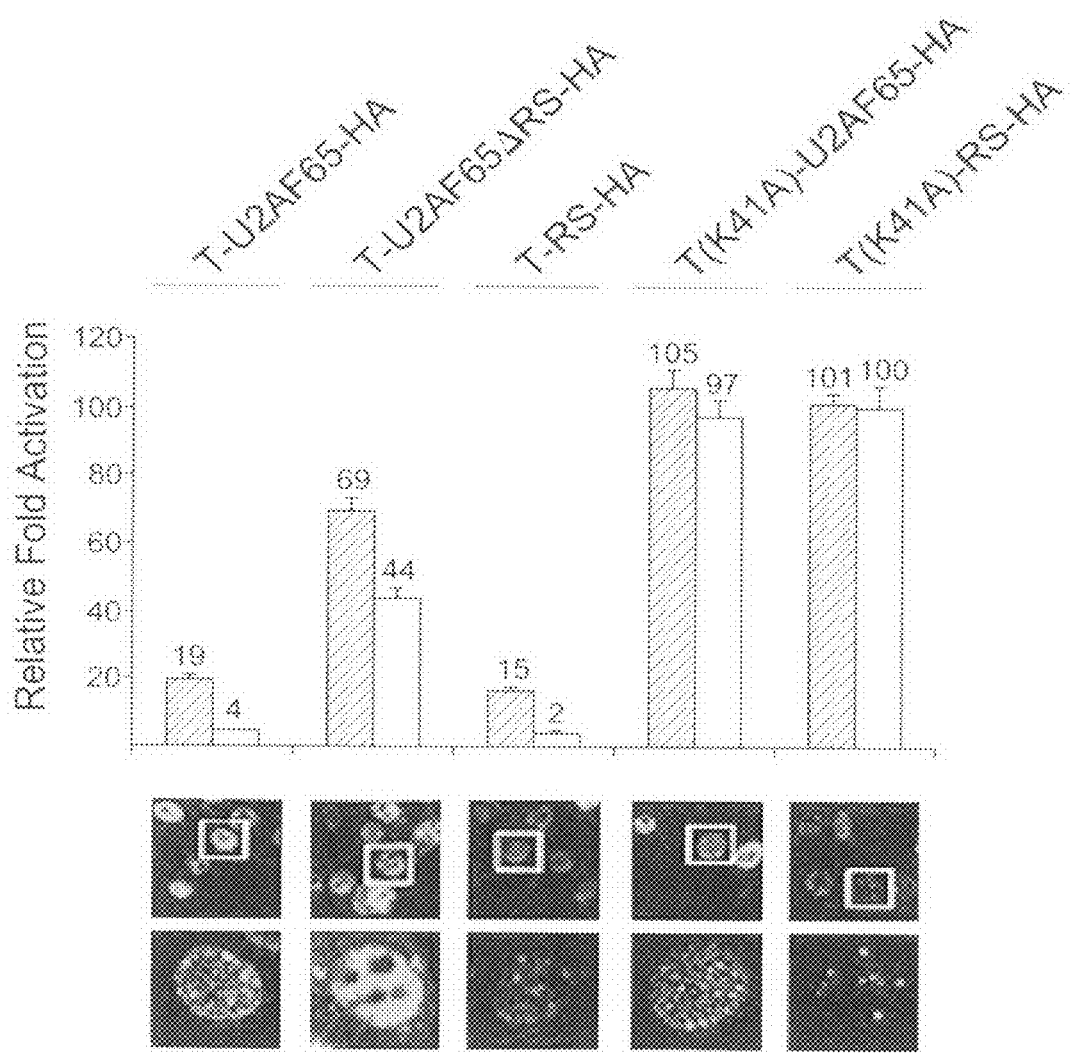
Figure 8:
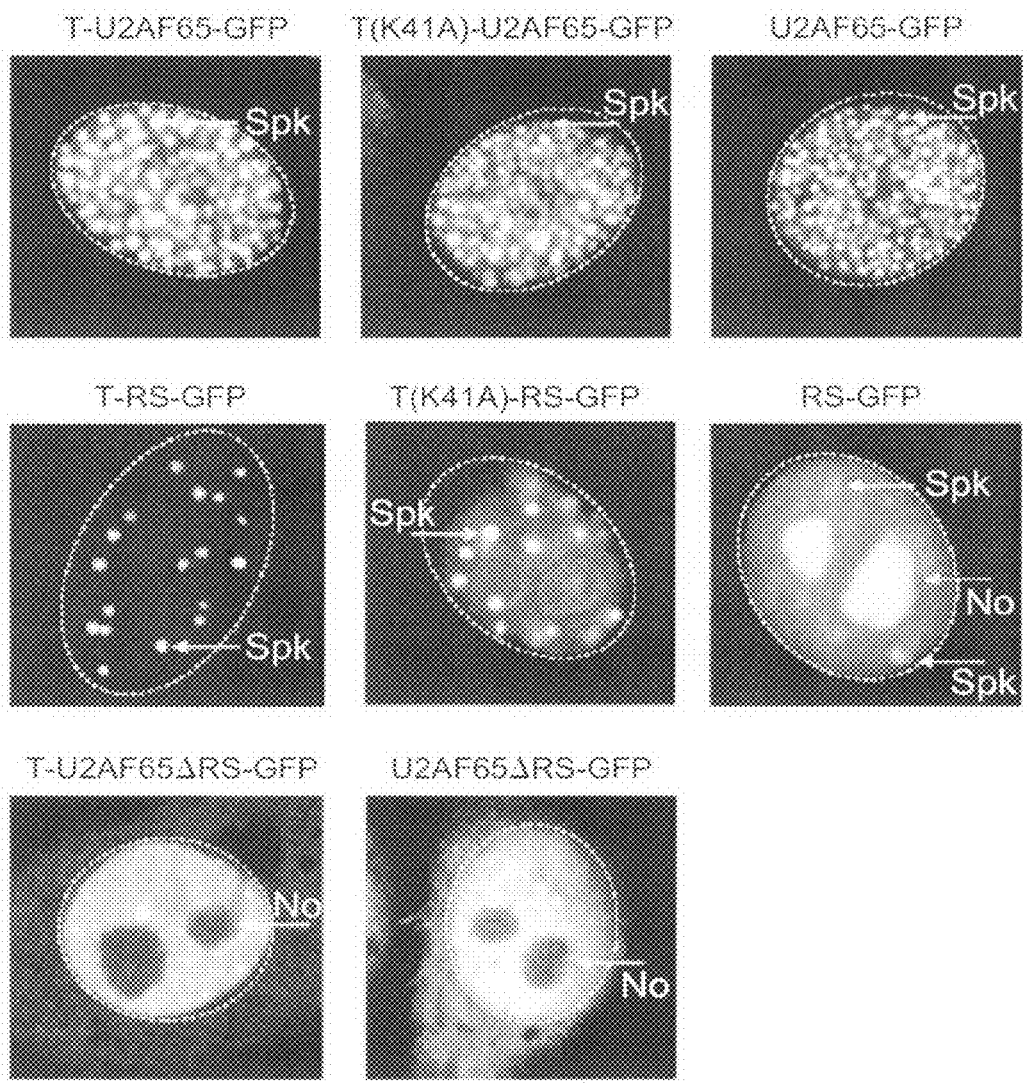
FIG. 8 shows subnuclear localization of U2AF65, T-U2AF65, and variants. HeLa cells were transfected with pEGFP-N3 plasmids expressing GFP fused to: U2AF65, T-U2AF65 (active dominant negative), T(K41A)-U2AF65 (inactive dominant negative), RS (U2AF65 RS domain only), T-RS (active dominant negative), T(K41A)-RS (inactive dominant negative), U2AF65ΔRS, and T-U2AF65ΔRS.

The RS domains of U2AF65 and other splicing factors help recruit these proteins to regions of active splicing within the nucleus[8,9] and also are believed to interact with RNAP II during transcription complex asembly[9]. The presence of RNAP II and splicing and mRNA-export factors suggests an active role for the "speckle-associated patches" in mRNA processing, although they are otherwise considered mainly as storage sites for factors involved in mRNA metabolism[10,11]. To test the possible involvement of RS domains in dominant negative inhibition, we generated a T-fusion lacking the RS domain (T-U2AF65ΔRS, which contains U2AF65 residues 91-475) and a second with the RS domain alone (T-RS, which contains U2AF65 residues 2-73). Of these, only T-RS remained a potent inhibitor (FIG. 2b). T-RS shows a speckle pattern even more striking than full-length T-U2AF65, with T-RS concentrated in only about 10-30 speckles. To confirm that the Tat AD also is important for inhibition, we generated T-U2AF65 and T-RS mutants with a Lys41-to-Ala substitution in the AD that disrupts interactions with transcriptional co-activators, particularly P-TEFb[12]. Both are inactive as inhibitors despite having the same localization patterns as the non-mutant versions (FIGS. 2b and 8). U2AF65 RS-domain fusions to other transcriptional ADs, including VP16 and E1A, do not inhibit Tat-mediated activation (D'Orso and Frankel, unpublished observations), further demonstrating the specificity of inhibition and the requirement for the Tat AD. Thus, both an RS domain and a functional Tat AD are necessary and sufficient to generate the potent dominant negative phenotype. We envisage a model in which the U2AF65 RS-domain targets the T-fusion to subnuclear compartments (speckles) where transcription complexes are assembling, thereby facilitating the interaction of the Tat AD with one or more factors of the transcriptional machinery assembling at the HIV promoter.

Example 3

Recruitment of the Dominant Negative Protein to the Transcriptional Machinery

Figure 3A:
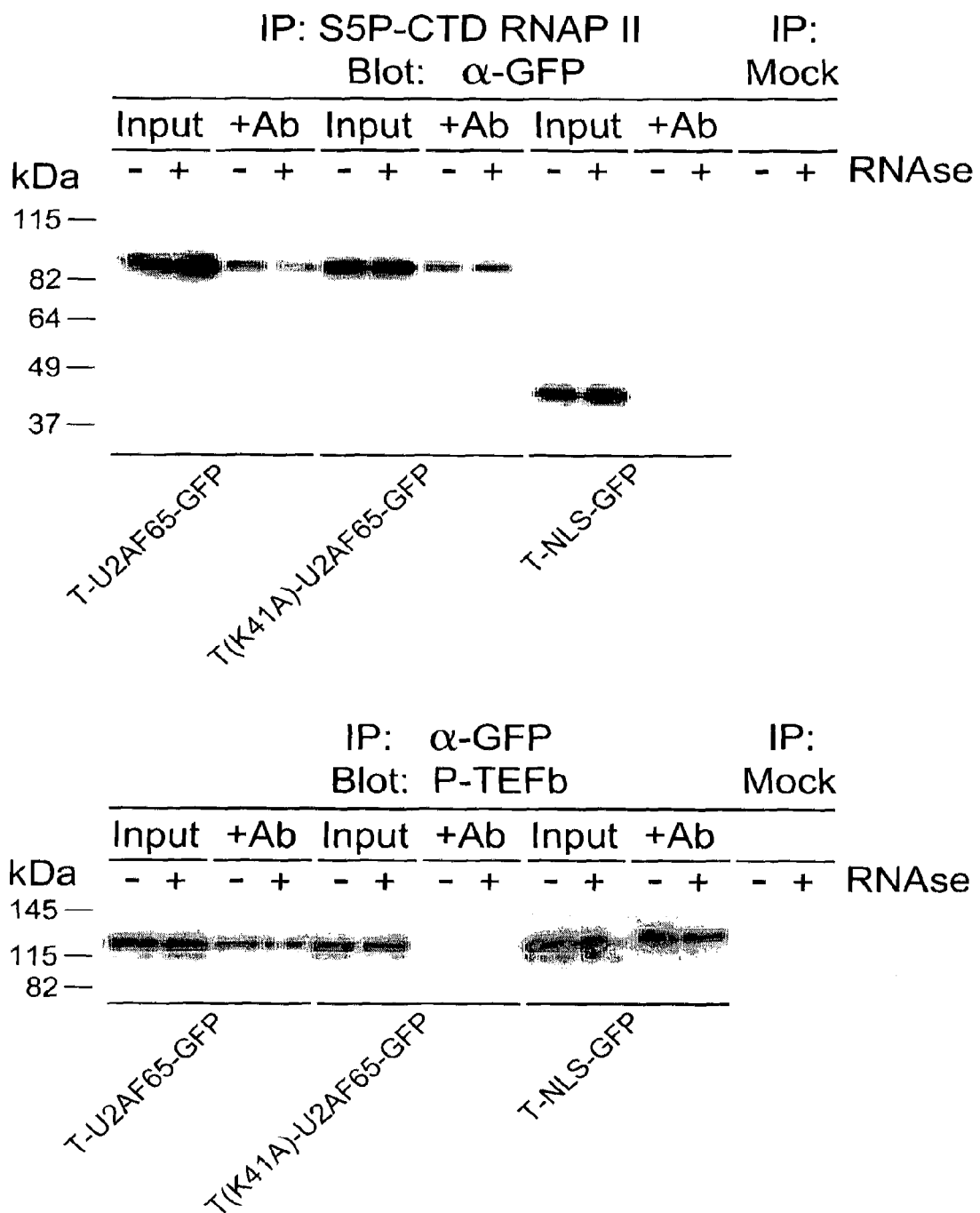
FIG. 3 shows recruitment of the dominant negative to the HIV promoter via RNAP II blocks transcription elongation. a, T-U2AF65 interacts with RNAP II and P-TEFb. GFP-tagged T-U2AF65, T(K41A)-U2AF65 and T-NLS proteins were immunoprecipitated from cell extracts and analyzed by Western blot using the indicated antibodies. b, T-U2AF65 colocalizes with RNAP II and SC35$_{15}$. Following HeLa cell transfection, GFP-tagged T-U2AF65 was visualized by confocal microscopy along with immunostained RNAP II and SC35. c, T-U2AF65 blocks transcription elongation. Cells were transfected with Tat or T-U2AF65 as indicated, and RNase protection was performed with a promoter proximal (Pp) probe directed to the LTR and a promoter distal (Pd) probe directed to the FFL ORF to quantify transcription rates in these regions of the LTR-HTAR-FFL reporter. d, Recruitment of RNAP II and T-U2AF65 to the HIV promoter. Left, activation and inhibition levels of a HeLa LTR-RREIIB-FFL reporter cell line used for ChIP assays, with the ratio of inhibitor to activation indicated. Right, ChIP assays from cells transfected with the HA- or GFP-tagged proteins indicated (panels 2-5) or untransfected cells (panel 1), using antibodies directed against HA, GFP, or RNAP II and monitoring the Pd and Pd regions. Mock lanes used normal rabbit IgG for the IP as a specificity control, and input refers to PCR reactions from isolated chromatin samples prior to the IP. e, Promoter-specific recruitment of T-U2AF65. ChIP assays were carried out in HeLa LTR-RRE-IIB-FFL cells transfected with T-U2AF65 or a T-NLS control using primers for HIV, gapdh, hsp70, p21/CIP, HLA-DRA and cad promoters. Known transcription factors that activate each promoter are indicated in parentheses. The percent of input DNA is shown for each individual ChIP experiment, and the amount of DNA used in the GFP lane is twice that for RNAP II.
Figure 3B:
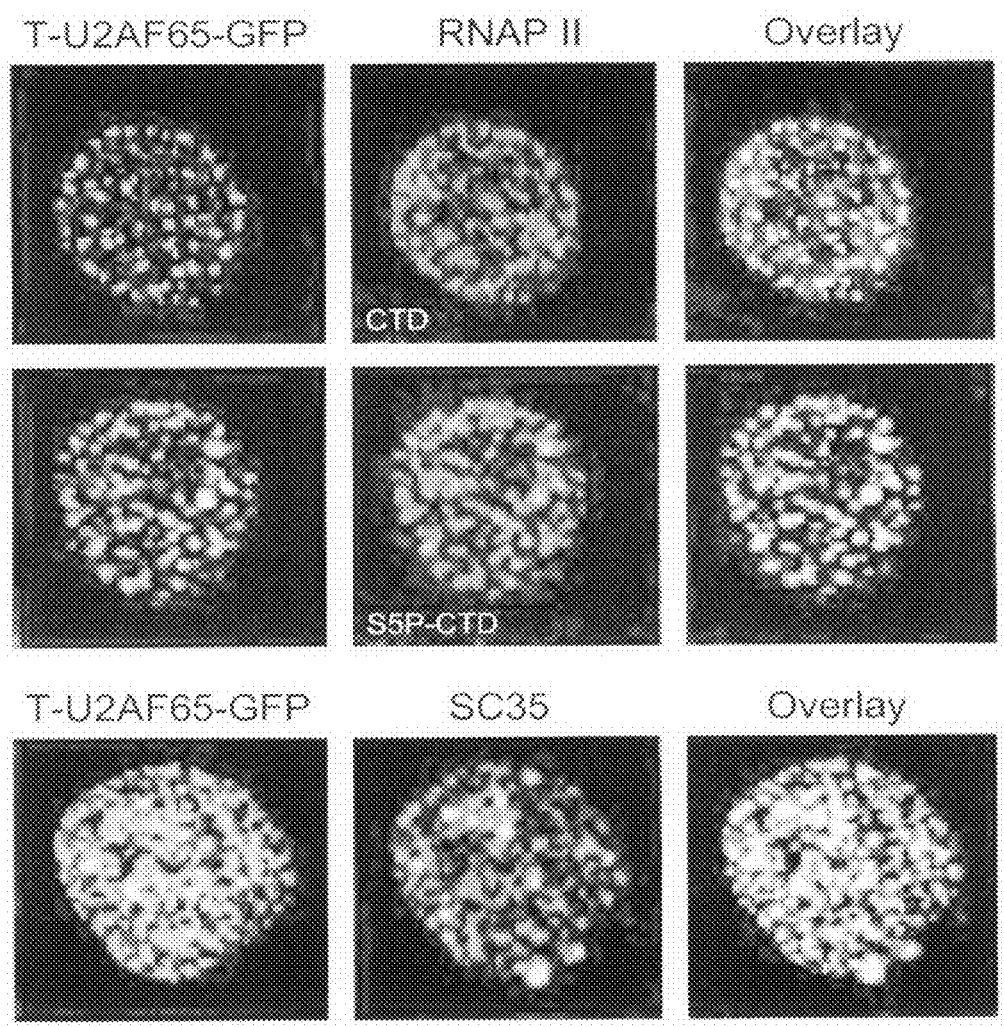

To examine the recruitment of T-U2AF65 to the transcriptional machinery, we first analyzed possible interactions with RNAP II by co-immunoprecipitation using antibodies against the Ser5-phosphorylated CTD (Ser5P-CTD), known as RNAP IIa. T-U2AF65-GFP, as well as the K41A Tat AD mutant, are complexed with RNAP IIa in a RNA-independent manner (FIG. 3a). Strikingly, no interaction is seen with T-NLS-GFP lacking the U2AF65 moiety despite the reported interaction of Tat with RNAP II in vitro[13]. Identical results were obtained using antibodies that recognize RNAPII with unphosphorylated CTD (data not shown). Thus, it appears that the U2AF65 RS moiety localizes the inhibitor to transcription complexes more efficiently than the Tat AD, consistent with the observations that U2AF65 interacts with RNAP II[7] and that fusing an RS domain to a cytoplasmic reporter protein results in nuclear localization and interaction with RNAP II[9,14]. The interaction with RNAP II was confirmed by immunofluorescence, in which T-U2AF65-GFP was seen to co-localize with both unphosphorylated and Ser5P-CTD forms of polymerase (FIG. 3b). Partial co-localization (~18%) was observed with SC35, a marker of speckle-associated patches[15]. Consistent with the hypothesis that the RS domain drives the interaction with RNAP II, T-RS-GFP showed the same co-localization as the full-length U2AF65 T-fusion (data not shown). In addition to interacting with RNAP II, T-U2AF65-GFP also is complexed to P-TEFb (FIG. 3a), as is the Tat AD fusion without the U2AF65 moiety. The Tat AD K41A mutation, known to abrogate the Tat-cyclin T1 interaction[12], eliminates the interaction of T-U2AF65-GFP with P-TEFb, supporting the hypothesis that inhibitor potency results from bivalent interactions involving both the Tat AD and RS domain.

Example 4

Targeting of the Dominant Negative Protein to the HIV Promoter

Figure 3C:
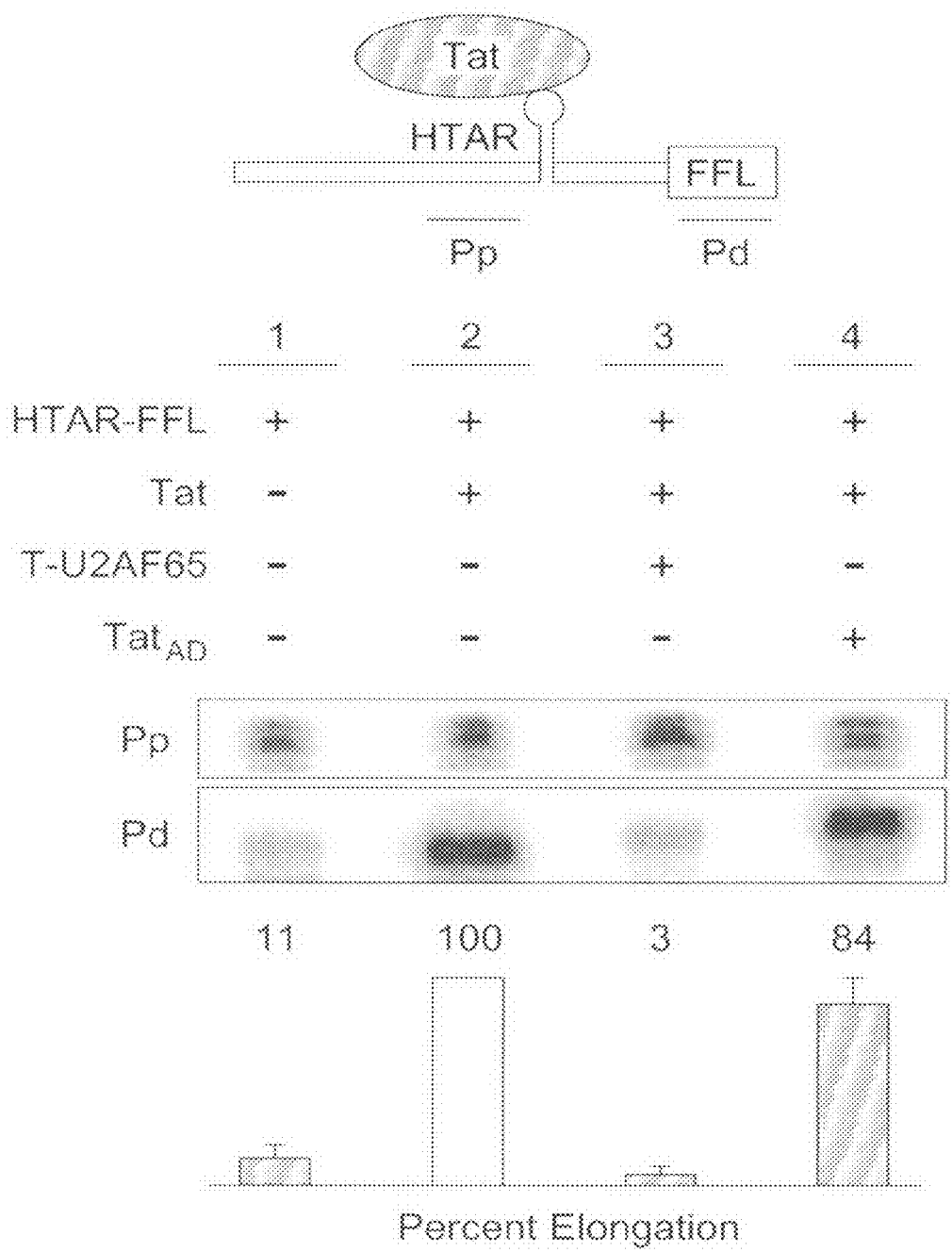
Figure 3D:
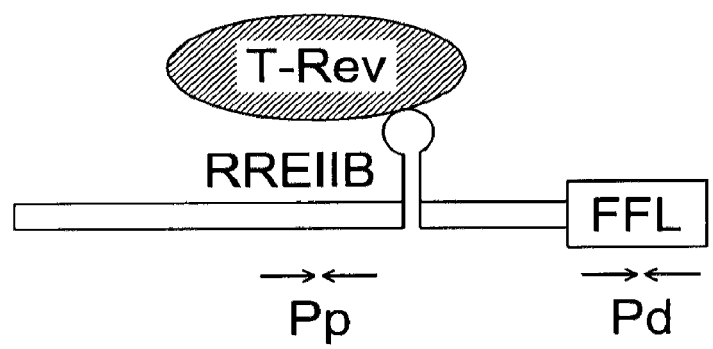
Figure 3D:
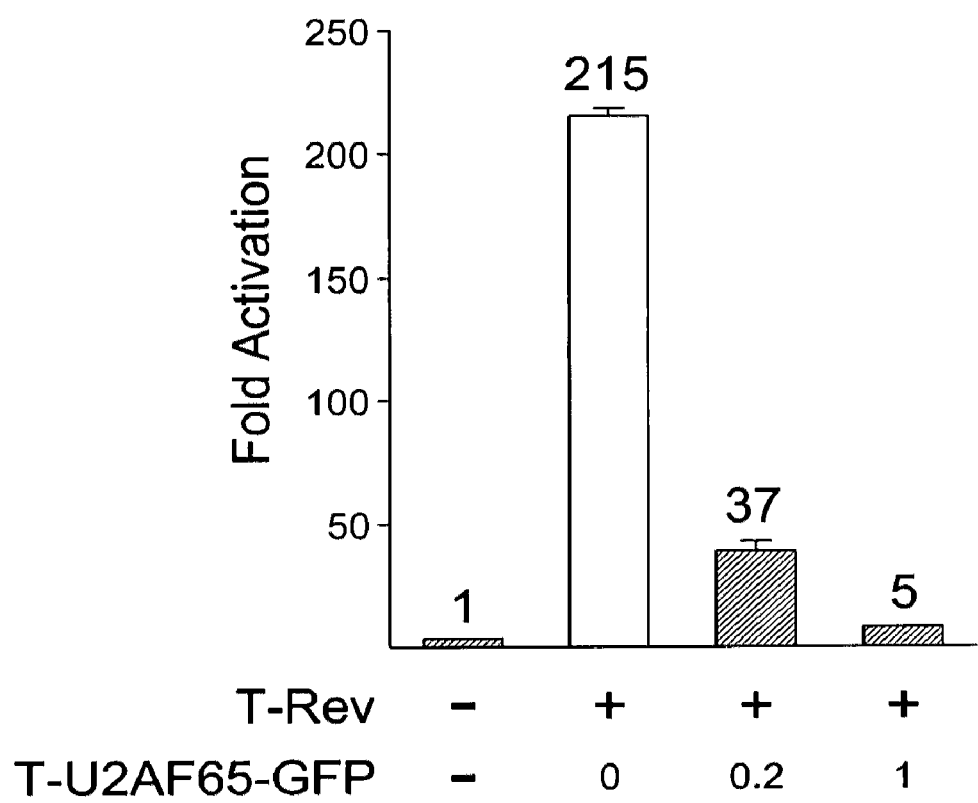

A primary function of Tat is to enhance transcription elongation[3] but it also participates in pre-initiation complex assembly[3,16]. RNase protection experiments using promoter proximal (Pp) and distal (Pd) probes indicate that the T-U2AF65 dominant negative primarily inhibits elongation (FIG. 3c). Tat transfected into HeLa cells substantially enhances transcription in the Pd but not Pp region of a luciferase reporter (compare lanes 1 and 2), as previously reported 3, whereas a stoichiometric amount of co-transfected T-U2AF65 reduces transcription in the Pd region to basal levels but does not effect Pp transcription (lane 3). Inhibition is dose responsive (data not shown) and requires the U2AF65 moiety as the Tat AD alone shows little inhibition (lane 4). We next used chromatin immunoprecipitation (ChIP) assays to examine recruitment of RNAP II, Tat, and T-U2AF65 to the HIV promoter and to test the hypothesis that the inhibitor is efficiently localized to the promoter. To assess complex assembly in an integrated chromatin context, we generated a stable HeLa cell line carrying an LTR-RREIIB-FFL reporter, which was strongly activated by T-Rev (215-fold) and inhibited by T-U2AF65 in a dose-responsive manner (FIG. 3d). In the absence of T-Rev, RNAP II is detected in the Pp but not Pd region (panel 1), implying a block to elongation, while RNAP II is seen in both regions following T-Rev transfection (panel 2), as previously reported[16,17]. The level of RNAP II detected in the Pp region increases ~5-fold in the presence of Tat, consistent with the proposed role of Tat in transcription complex assembly[16]. The T-Rev-HA activator was also detected in the Pp region (panel 2) but, notably, the T-U2AF65-GFP inhibitor showed even higher occupancy (panel 3); consistent with the observation that U2AF65 can be detected in the Pp region in the absence of Tat[17]. To more directly evaluate competition between the activator and inhibitor, we co-transfected both plasmids and observed strong occupancy of T-U2AF65-GFP in the Pp region whereas no T-Rev-HA could be detected (panel 4). Furthermore, the Tat AD alone, without the U2AF65 moiety, was not detectable at the promoter (panel 5, T-NLS-GFP). Thus, the ChIP experiments support the hypothesis that the T-U2AF65 inhibitor is recruited to the HIV promoter through an interaction with RNAP II, efficiently pre-loading the inhibitor into transcription complexes and blocking entry of the Tat activator.

Figure 3E:
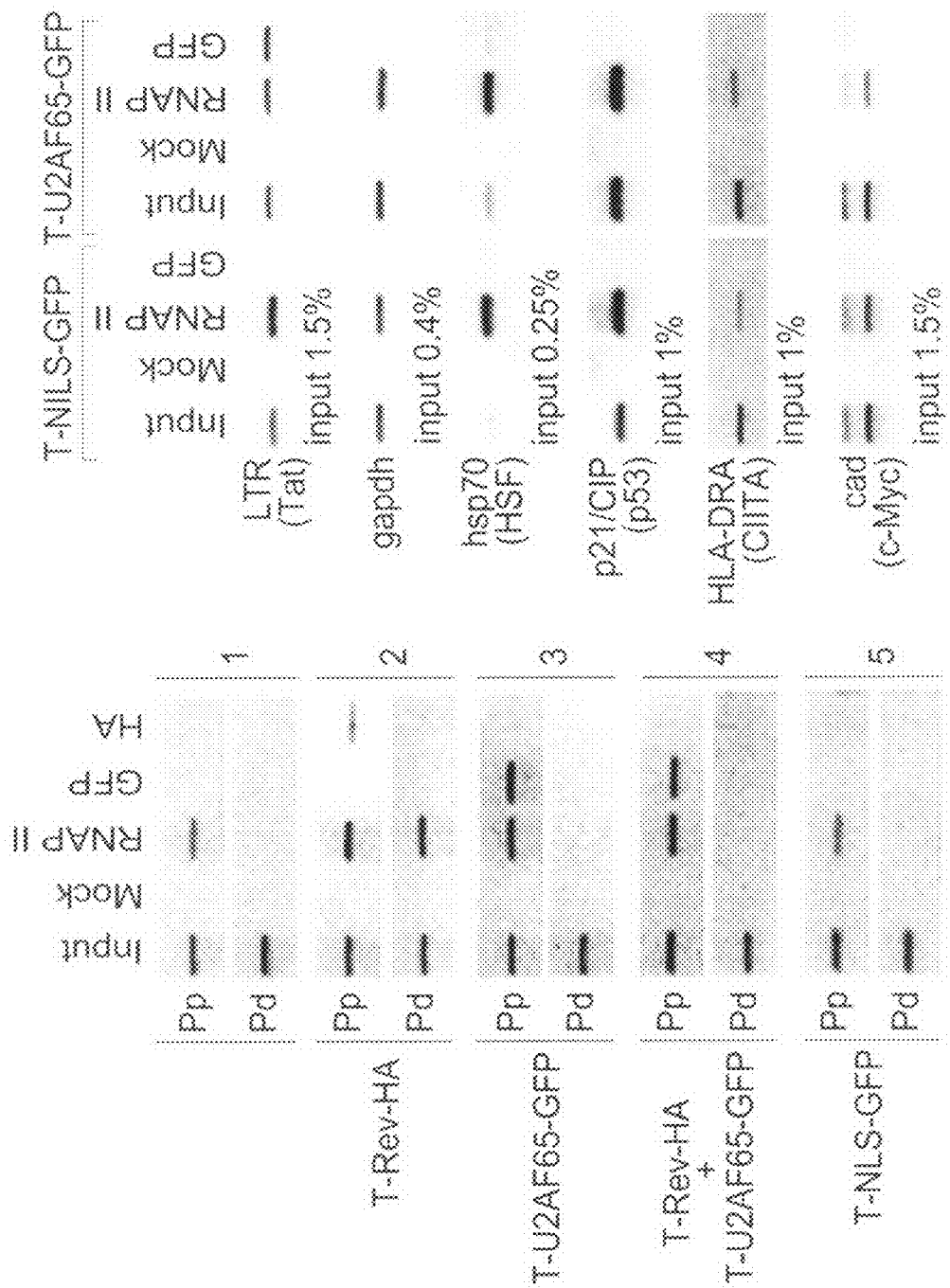

The specificity of dominant negative inhibition for the HIV promoter is clear (FIG. 1d), but the co-localization data (FIG. 3b) suggest that a substantial amount of RNAP II interacts with the inhibitor, prompting us to test whether T-U2AF65 is recruited to other promoters. Of five cellular promoters analyzed by ChIP, including the P-TEFb-dependent MHC class II and hsp70 promoters, only hsp70 showed any detectable T-U2AF65-GFP, unlike the high occupancy observed at the HIV promoter (FIG. 3e). These data indicate that the efficiency of T-U2AF65 recruitment involves interactions other than to RNAP II, likely including interactions with PTEFb and other factors in the transcription machinery.

Example 5

Use of the Tat Dominant Negative to Inhibit HIV Replication

Figure 4A:
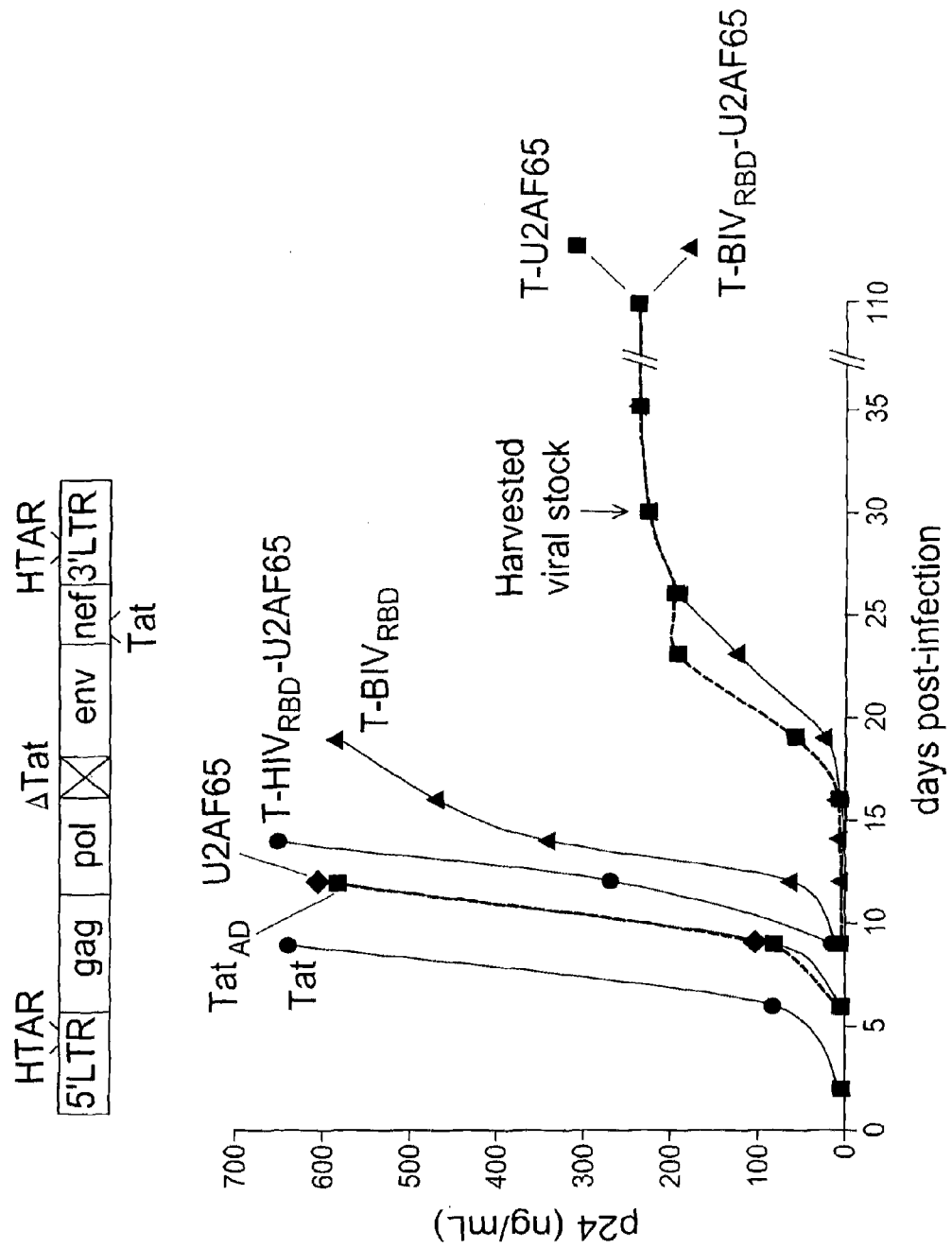
FIG. 4 shows expression of the Tat dominant negative blocks HIV replication and generates a latency-like state. Sup T1 cells stably expressing the Tat domains or fusion proteins indicated were infected with either HIV Tat-TAR-dependent (a) or BIV Tat-TAR-dependent (b) viruses (18) at an m.o.i. of 1 and the kinetics of p24 antigen expression were monitored by ELISA. Viruses emerging from the inhibitor-expressing cell lines were harvested at day 30 (arrows) and used to re-infect the same cell lines from which they were derived, and identical replication rates were observed.
Figure 4B:
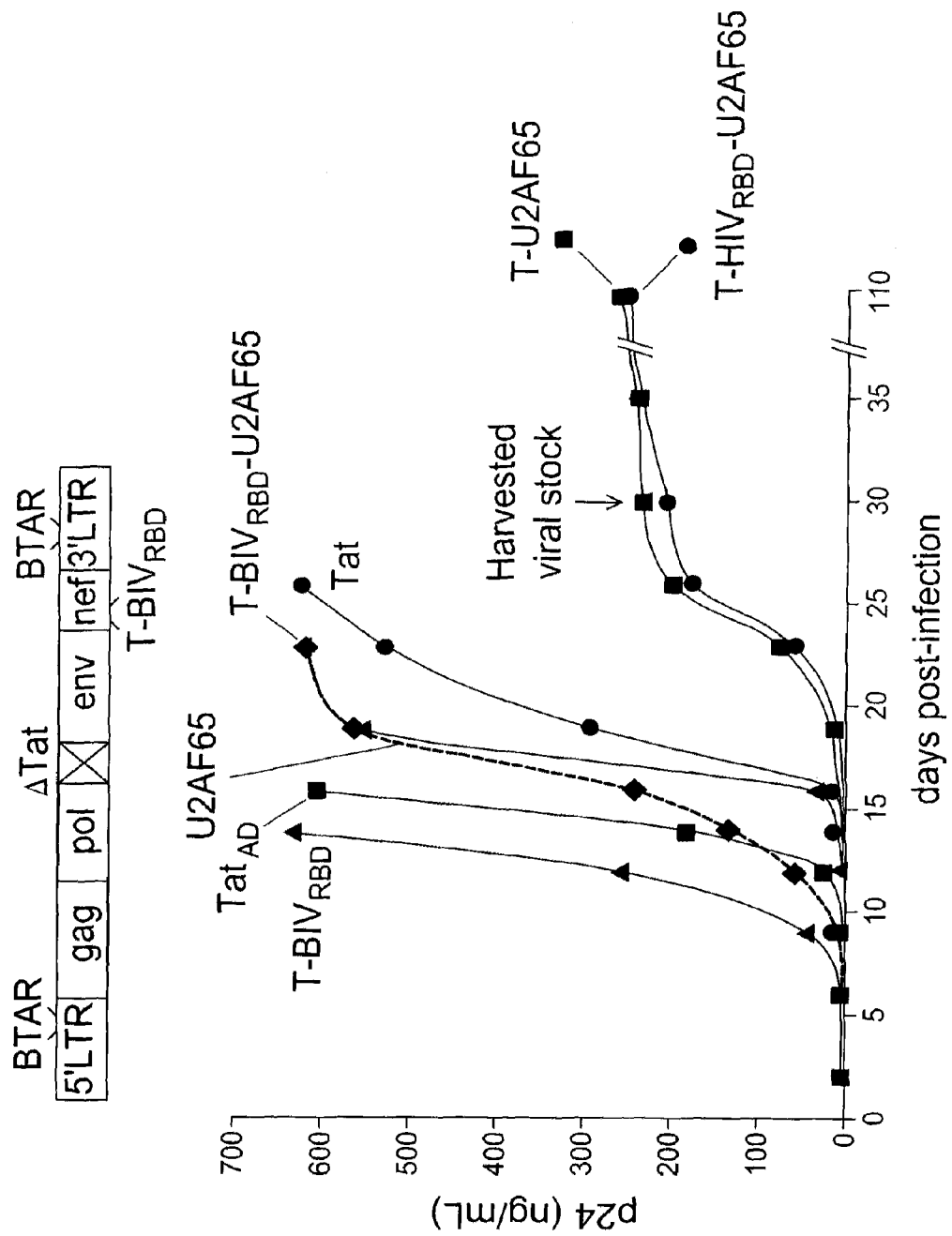

The high potency of the Tat dominant negatives and the requirement of Tat for viral replication suggested that they might be effective HIV inhibitors. To analyze this we generated SupT1 lymphocyte cell lines stably expressing T-U2AF65, T-HIV$_{RBD}$-U2AF65, or T-BIV$_{RBD}$-U2AF65 dominant negatives or the non-fusion controls, Tat$_{AD}$, Tat, T-BIV$_{RBD}$, or U2AF65, and monitored HIV replication rates using viruses dependent on either the HIV or BIV Tat-TAR interactions[18]. We observed striking specificity of the dominant negatives in which replication was inhibited only in viruses driven by a non-cognate RNA-protein interaction. Expression of T-U2AF65, which contains no TAR RNA-binding domain, markedly suppressed replication of both viruses compared to the Tat$_{AD}$ or U2AF65 controls, with no p24 antigen detectable until 18-20 days after infection (FIGS. 4a and 4b). Expression of T-HIV$_{RBD}$-U2AF65 or T-BIV$_{RBD}$-U2AF65 inhibited replication of the non-cognate virus to a similar extent as T-U2AF65 and showed only a slight inhibitory effect on the cognate virus (FIGS. 4a and 4b). Interestingly, expression of the Tat or T-BIV$_{RBD}$ activators actually accelerated replication of the cognate, but not non-cognate viruses, suggesting that Tat levels in these viruses are limiting and/or Tat may benefit viral adaptability. In the inhibitor cell lines, virus that emerged after 18-20 days displayed slow replication kinetics and reached a low plateau of p24 expression that remained constant for at least 110 days (FIGS. 4a and 4b) without producing cytophatic effects. Viral stocks harveted from these cell lines after 30 days displayed identical growth kinetics as the original stock upon re-infection (FIG. 10). Sequencing of integrated viral DNA showed no mutations in the LTR or Tat, indicating that the viruses do not acquire resistance mutations during this time period but rather grow poorly under these conditions of dominant negative inhibitor expression.

Example 6

Tat RBD is Dispensable for Dominant Negative Activity

Figure 5A:
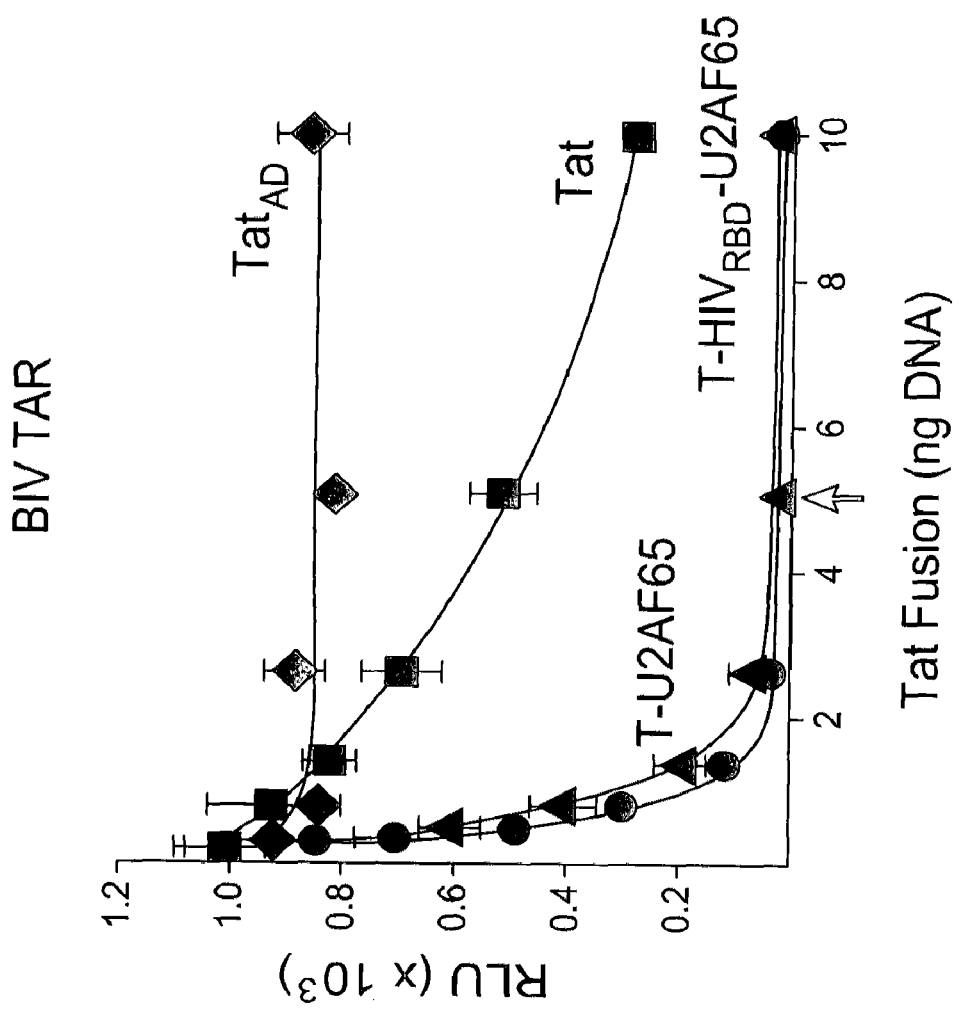
FIG. 5. Tat RBD is dispensable for dominant negative activity. a, Dose response curves showing inhibition of BIV Tat-TAR-mediated activation by Tat$_{AD}$, Tat, T-U2AF65 and T-HIV$_{RBD}$-U2AF65. The arrow indicates the position of stoichiometric DNA concentrations (5 ng) of inhibitor and activator. b, Dose response curves showing inhibition of HIV Tat-TAR-mediated activation by Tat$_{AD}$, T-BIV$_{RBD}$, T-U2AF65 and T-BIV$_{RBD}$-U2AF65.
Figure 5B:
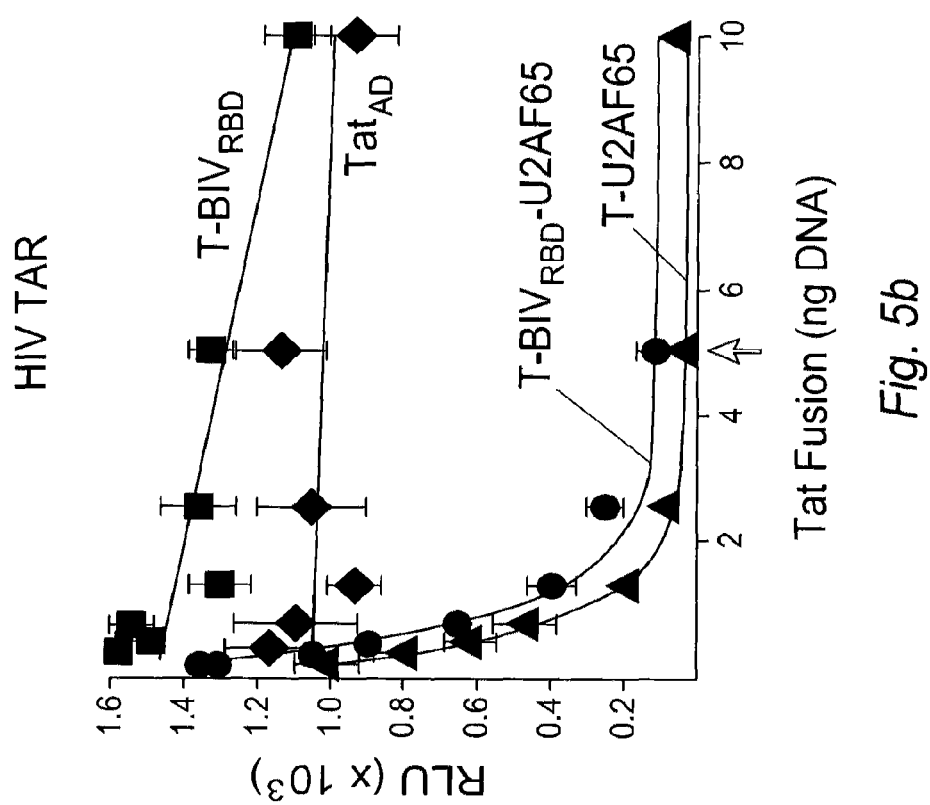

To assess whether the RBD of Tat contributes to the dominant negative activity, we generated U2AF65 fusions to full-length Tat or Tat$_{AD}$ and measured their effects using an LTR-BTAR-RL reporter and Tat-BIV$_{RBD}$ activator. Indeed, both T-HIV$_{RBD}$-U2AF65 and T-U2AF65 inhibited activation more than 10-fold at sub-stoichiometric plasmid DNA levels relative to the activator (FIG. 5a). Tat$_{AD}$ without tethered U2AF65, showed little inhibition. Similarly, full-length Tat is a weak dominant negative inhibitor of BIV Tat-TAR-mediated activation, consistent with a previous report [1]. In a converse experiment, activation of an LTR-HTAR-FFL reporter by Tat-HIV$_{RBD}$ is potently inhibited by T-U2AF65 and T-BIV$_{RBD}$-U2AF65 but not by un-fused Tat$_{AD}$ or T-BIV$_{RBD}$ (FIG. 5b). Additional control experiments showed that T-HIV$_{RBD}$-U2AF65 and T-BIV$_{RBD}$-U2AF65 fusion proteins activated expression of their cognate reporters to about 50% of the un-fused protein levels and that expression of non-Tat fused U2AF65 did not inhibit activation (data not shown).

Example 7

Relative Expression Levels of Tat Activator and Dominant Negative

Immunofluorescence experiments showed that the T-Rev activator and T-U2AF65 dominant negative were expressed similarly and localized to the nucleus (FIG. 2a). We analyzed protein levels more quantitatively by Western blot using HA-tagged proteins and confirmed that stoichiometric plasmid levels express similar amounts of protein (FIG. 6). Thus, the high potency of T-U2AF65 is striking given that the best reported dominant negative Tat inhibitors require more than 5-fold higher inhibitor levels to reduce activation by less than 10-fold [2-4].

Example 8

Inhibition Activities of Other T-Fusions

The potent inhibition observed with T-SF1 and T-U2AF65 prompted us to evaluate whether fusions to other transcription or RNA processing factors might also act as dominant negatives. While T-SF1 was slightly less potent than T-U2AF65, a fusion to the SR-protein 9G8 (T-9G8) was nearly as potent as T-U2AF65 (FIG. 7). Fusions to the CstF1 polyadenylation factor known to be recruited to the CTD [5,6] and to an hnRNP A1 fusion containing RRM RBDs also showed some modest inhibition (about 4 fold). In contrast, fusions to the DNA-binding transcription factors Sp1 or RelA showed relatively little inhibition (about 2 fold), consistent with a previous report showing little inhibitory effect by fusing Tat to other DNA-binding factors[7]. T-TAF8 also showed no inhibition, consistent with the proposal that Tat-activation is exerted through a TFIID-containing TBP complex but independent of TBP-associated factors (TAFs) [8]. All T-fusions were nuclear and expressed at similar levels as judged by indirect immunofluorescence (FIG. 7), except that T-RelA showed more prominent perinuclear localization in the absence of TNF-α activation. Thus, T-fusions to splicing factors containing RS domains (T-U2AF65 and T-9G8) are the most potent inhibitors.

Example 9

Possible Contribution of Subnuclear Localization to Dominant Negative Activity

Deleting the RS domain of T-U2AF65 eliminates dominant negative activity (see T-U2AF65ΔRS in FIG. 2b) and its subcellular localization is strikingly different (FIG. 2b). While T-U2AF65 shows speckle-associated patches typical of splicing factors, U2AF65ΔRS is spread throughout the nucleoplasm. To evaluate whether the Tat or U2AF65 moieties were responsible for these localization patterns, we first compared localization of T-U2AF65-GFP, U2FA65-GFP, and the inactive T(K41A)-U2AF65-GFP variant (FIG. 8). All three are localized similarly in speckles (Spk), implying that U2AF65 drives the localization of the dominant negative and that localization is necessary but not sufficient for inhibition.

An even more striking subnuclear localization pattern is seen for T-RS-GFP bearing only the U2AF65 RS-domain in which only a few (10-30) bright clusters are observed (FIG. 8). Again, the Tat AD K41A mutation does not alter its localization. Interestingly, an RS-GFP fusion lacking the Tat AD is no longer localized to speckles but rather to nucleoli (FIG. 8), suggesting that both the AD and RS domains of T-RS contribute to its speckle localization in this shorter context. Deletion of the RS-domain in both U2AF65 and T-U2AF65 also eliminates localization to speckles and shows a nuclear pattern with nucleolar exclusion (FIG. 8), further highlighting the importance of the RS domain for speckle localization.

Example 10

Dominant Negative Expression Levels and Functional Activity in Stable Supt1 Populations To assess expression levels of the Tat activators (Tat, $Tat_{AD}$ and $T\text{-}BIV_{RBD}$) and dominant negative inhibitors (T-U2AF65, $T\text{-}HIV_{RBD}$-U2AF65, and $T\text{-}BIV_{RBD}$-U2AF65) in the stable SupT1 populations used for the viral replication assays, we first determined mRNA steady-state levels for each protein by quantitative real-time RT-PCR, using two sets of primers that amplify Tat or U2AF65 portions of the mRNAs. While the RNA expression levels varied widely between samples, all were clearly detectable, with the SupT1-Tat population expressing the highest levels (normalized expression level of 370 units), followed by $T\text{-}BIV_{RBD}$ (120 units), $Tat_{AD}$ (100 units), $Tat_{AD}$-U2AF65 and $T\text{-}BIV_{RBD}$-U2AF65 (35 units), and Tat-U2AF65 (7 units). We next characterized expression in a more functional assay in vivo by transfecting each stable cell population with an activatable GFP reporter, depending on the Tat protein expressed, and monitored activity by flow cytometry (data not shown). All stable SupT1 populations expressing the full-length Tat moiety activated an LTR-HTAR-GFP reporter, varying from 9-20 fold, while cell lines expressing $Tat_{AD}$ did not activate. Stable cell populations expressing $T\text{-}BIV_{RBD}$ activated an LTR-BTAR-GFP reporter about 7-9 fold but not an LTR-HTAR-GFP reporter. The $Tat_{AD}$-U2AF65-expressing population weakly activated an LTR-BPS-GFP reporter, through its polypyrimidine tract (PPT) binding site [9]. This weak activity likely reflected the generally lower activation observed with the U2AF65-PPT interaction [9] and, probably, the low transfection efficiency of the SupT1 cells. Thus, expression of each Tat or Tat-fusion protein could be confirmed by RT-PCR and functional assays, but expression levels generally appeared low, as expected for a stable cell population transduced by a retrovirus but not clonally selected [10]. Weak expression was further confirmed by Western blot and immunofluorescence analysis using an anti-Tat antibody where expression was virtually undetectable (data not shown).

Figure 9A:
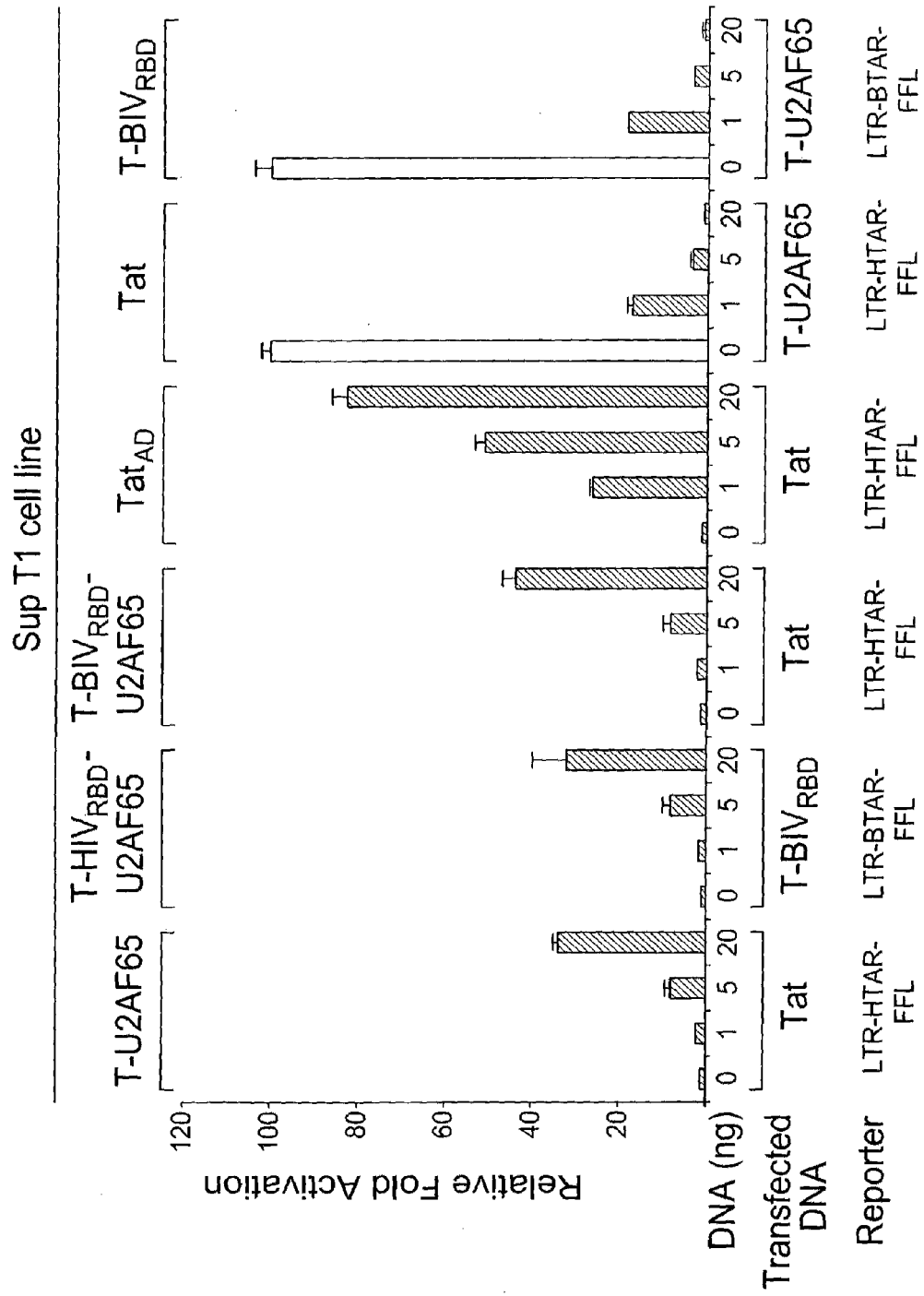
FIG. 9 shows promoter-specificity of the dominant negative. a, Characterization of the SupT1 cell lines by luciferase reporter assays. The indicated SupT1 cell lines were co-transfected with an appropriate activator and reporter pairs as shown. b, Total RNA was extracted from SupT1-Tat$_{AD}$ and SupT1-T-U2AF65 stable cell populations and relative mRNA levels of the nine genes shown were quantitated; β-actin (actin), glyceraldehyde-3-phosphate dehydrogenase (GAPDH), eukaryotic translation elongation factor 1 gamma (EEF1G), heterogeneous nuclear ribonucleoprotein A 1

We also estimated the activities of the integrated dominant negatives in the SupT1 cell lines using functional assays. Cells were co-transfected with a fixed amount of the LTR-HTAR-FFL or LTR-BTAR-FFL reporter and varying concentrations of the corresponding Tat activator and levels of inhibition were measured. For example, SupT1 cells expressing T-U2AF65 and $T\text{-}BIV_{RBD}$-U2AF65 were co-transfected with the LTR-HTAR-FFL reporter and HIV Tat, and no significant activation was observed at low levels (0.1-1 ng) of transfected activator (FIG. 9a). Significant activation was observed with higher (5-20 ng) plasmid amounts, further confirming that the cell lines do not express very large amount of protein and consequently do not block Tat activity completely. It seems probable that more highly expressing dominant negative cell lines can be identified through cloning that would result in even more effective viral inhibition than observed (FIG. 4).

Example 11

Lack of Dominant Negative Activity on Cellular Promoters

Figure 9B:
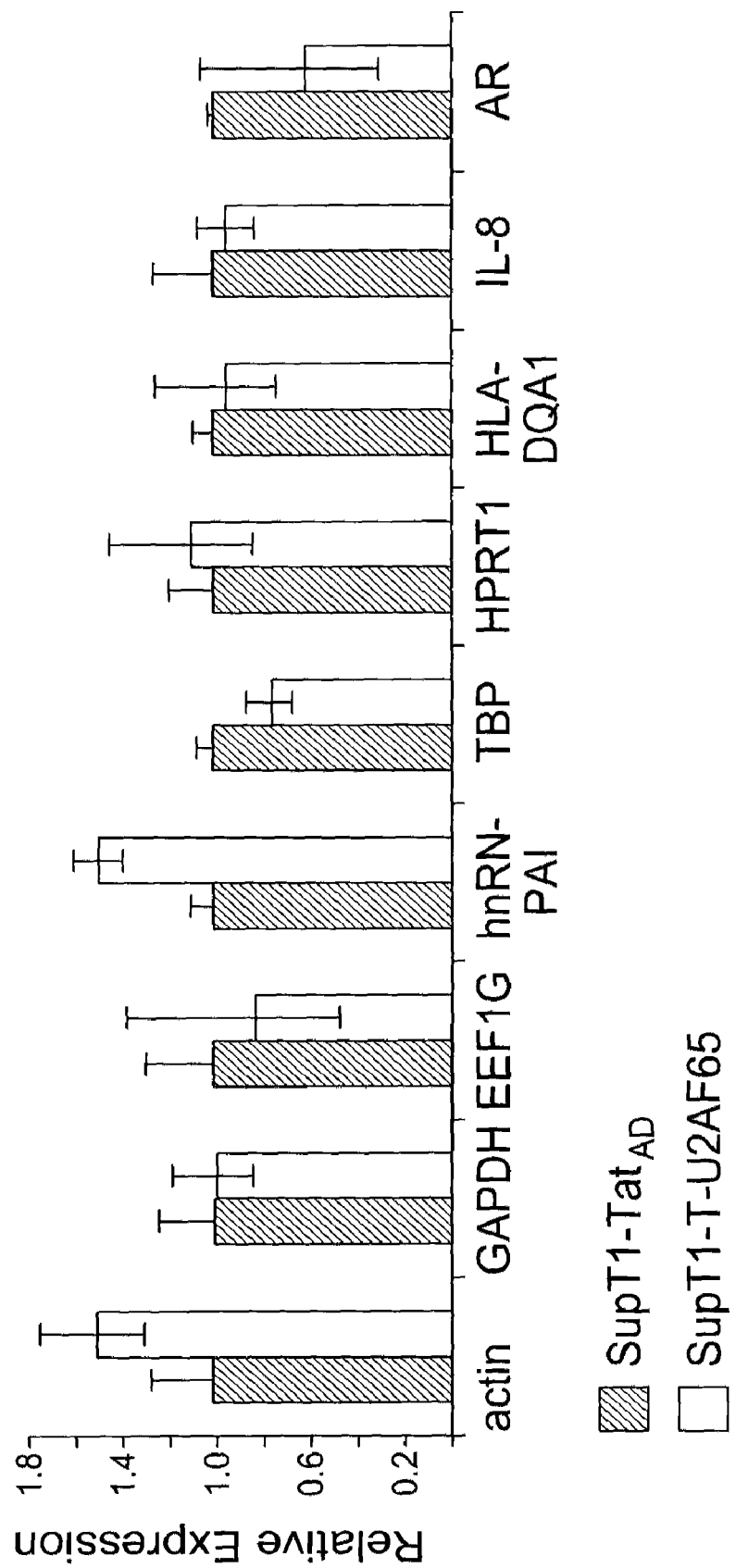

Transcriptional squelching has been described for many dominant negative transcription factors, such as yeast Gal4, and herpes simplex virus VP16, where common components of the transcriptional apparatus become "titrated of" of promoters[11,12]. Typically, these dominant negatives are rather promiscuous because the target co-activators do not need to be bound to the specific promoter. For HIV Tat, for example, it has been shown that Tat over-expression leads to decreased transcription from an MHC class II promoter, because both Tat and the class II transactivator (CIITA) require P-TEFb to function [13]. Because the Tat dominant negatives described here apparently operate via co-transcriptional recruitment to the HIV promoter, we suspected that they might display promoter specificity, unlike the more traditional dominant negatives. Reporter experiments show that T-U2AF65 has specificity for the HIV promoter versus other P-TEFb-regulated promoters (FIG. 1). To further analyze promoter specificity, we compared the relative expression levels of nine endogenous transcripts in the SupT1-$Tat_{AD}$ (non-inhibitor)- and SupT1-T-U2AF65 (inhibitor)-expressing stable cell lines using quantitative RT-PCR and observed no significant differences in RNA levels from any of these promoters (FIG. 9b). The tested genes encode housekeeping proteins (actin, GAPDH, HPRT1), regulatory factors (TBP, hnRNPA1, EEF1G), and include an MHC class II (HLA-DQA1) and two other P-TEFb regulated genes (IL-8 and AR)[14]. Thus, whereas expression of T-U2AF65 effectively blocks Tat activation and HIV replication, it shows no significant effect on cellular promoters.

Example 12

Virus Emerging from the Dominant-Negative-Induced Latency-Like State Behaves as the Original Stock We observed that virus eventually emerged after 18-20 days in the inhibitor-containing cell lines but with low replication kinetics and reaching a low steady-state plateau of p24 expression (FIG. 4). No mutations were found in these emergent viruses in the LTR or Tat coding region (data not shown), suggesting the cellular expression of the dominant negative inhibitor continuously suppressed replication. To test this, we harvested viruses that emerged after 30 days and performed a re-infection experiment to compare the kinetics of the original and emergent viruses. Indeed, identical growth kinetics were observed when the initial or new viral stocks were used to infect the SupT1-T-U2AF65 inhibitor cell line, reaching the same chronic p24-expressing plateau, whereas rapid growth was observed for both stocks in the SupT1-Tat$_{AD}$ control cells (FIG. 10). As expected, inhibitor-expressing cells infected at a high m.o.i. (10 versus 1) showed a cytopathic effect, although again slower replication kinetics was observed than in the control cells (data not shown). Thus, even with low inhibitor expression and a high m.o.i. some protective effect still is seen, highlighting the efficacy of the inhibitor and the balance between activator and inhibitor observed upon transfection of the SupT1 cell lines (FIG. 9a).

Conclusions

The potent Tat dominant negative inhibitors described in this work represent a new mechanistic class in which we hypothesize that a transcription factor AD is efficiently recruited to its promoter via a tethering signal, in this case an RS domain, among other specific contacts with the transcriptional apparatus. Unlike other dominant negatives, these Tat inhibitors function at stoichiometric or even sub-stoichiometric levels and do not require the considerable over-expression typically required for squelching or other simple competition mechanisms[1,19]. We speculate that their specificity and potency is imposed by localization, first at the sub-cellular and sub-nuclear levels and second by efficient recruitment to the promoter. Ptashne and Gann proposed the concept of "regulated localization", where specificity typically is imposed by simple binding interactions between a locator, the transcriptional machinery, and the DNA[20]. We propose that combining localization functions within a single polypeptide can substantially enhance activity. In the case of the T-U2AF65 inhibitor, it appears that the Tat AD provides the dominant negative function, in part through interactions with P-TEFb at the HIV promoter, while the RS domain, provides additional localization and timing functions utilizing co-transcriptional mechanisms that RNA-processing factors, including SR proteins, use to load into transcription complexes[10,11]. This hypothesis is supported by the observations that RS-domain-containing proteins localize to sub-nuclear speckles, which are thought to anchor splicing factors to the nuclear matrix and facilitate assembly with RNAP II,[21] and that Tat and P-TEFb co-localize to nuclear speckles[22]. It remains to be determined if other transcription factors, including those that do not function at the elongation step, can be efficiently localized and assembled into transcription complexes in a similar manner, and if other types of targeting domains may be used.

HIV replication is substantially inhibited by low-level expression of the dominant negative in stable cell lines (FIG. 4), even without optimizing and selecting for lines with high activity (FIG. 9). It is interesting that these cells establish a chronic infection without cytopathic effects, reminiscent of other cellular environments that may resemble latent stages of HIV infection[23]. The balance of Tat clearly affects viral replication rates[24] and also can drive phenotypic diversity[25], and here we show that expression of the dominant negative provides another means to alter the Tat balance. Other dominant negative HIV proteins have been used to suppress HIV replication, including the nuclear export-deficient Rev M10 mutant[26], but resistance mutations have been found[27] and relatively high expression levels are required for inhibition despite the oligomeric nature of Rev[27,28]. It will be interesting to examine mechanisms by which resistance to the Tat dominant negative might arise and to evaluate its therapeutic potential.

Methods and Materials

Transcriptional Activation and Inhibition Reporter Assays

HeLa cells were transfected with GFP or firefly luciferase (FFL) reporter plasmids (typically 25 ng), appropriate amounts of Tat activator and inhibitor plasmids, and 5 ng of a CMV-Renilla luciferase (RL) plasmid using the Polyfect lipid transfection reagent (Qiagen) in a 48-well format. Reporter activity was measured 48 hr post-transfection using a Becton-Dickinson FACS Calibur (FIG. 1a) or Dual-Glo luciferase assay (Promega). All LTR reporter plasmids used contained an internal ribosome entry site (IRES) upstream of the FFL gene to ensure efficient translation irrespective of the 5'UTR sequence used, and RL activity was used to normalize for transfection efficiencies. For experiments presented in FIG. 2, cells were transfected with 10 ng of activator and 2.5 or 10 ng of Tat-fusion plasmids. All activation assays were performed in triplicate, and error bars' represent the SD of the mean.

Microsopy

HeLa or stably-integrated HeLa LTR-RREIIB-FFL cells were grown to 50% confluence on glass cover slips, transfected with 100 ng of plasmid DNAs, fixed in 4% paraformaldehyde in 1× PBS buffer (pH 7.6) 24 hr post-transfection, rinsed twice with PBS, and permeabilized with PBS-Triton 0.5% for 10 min at 4° C. Nonspecific antibody sites were blocked in 1× PBS, 3% goat serum, and 4% BSA for 1 hr at room temperature, cells were incubated with primary antibodies for 1 hr at room temperature, washed three times with PBS, incubated with appropriate Alexa 488- or Alexa 546-coupled secondary antibodies (Molecular Probes) for 1 hr at room temperature, and washed three times with PBS. Cells were mounted on DAPI-containing Vecta-shield slides (Vector Labs). Light microscopy was done using an LSM510 confocal microscope (Zeiss) and images were processed using LSM (Zeiss) software.

Co-Immunoprecipitation

To examine association of dominant negative inhibitors with RNAP II, HeLa cells were transiently transfected with T-U2AF65-GFP, T(K41A)-U2AF65-GFP, or T-NLS-GFP, and nuclear extracts were prepared with RIPA buffer. Half of the extract was used directly for the immunoprecipitation and the remaining half was treated with 1 μg of RNAse A, which was sufficient to quantitatively digest the RNA from $10^6$ HeLa cells. RNAP II was immunoprecipitated using agarose-conjugated to 8WG16 and H14 antibodies overnight at 4° C. with mild shaking. Similarly, GFP-tagged proteins were immunoprecipitated using agarose-conjugated GFP-antibodies. After centrifuging and washing the beads immunocomplexes were dissociated by boiling for 10 min in 2× gel loading buffer, samples were separated by 10% SDSPAGE, transferred to PVDF, and analyzed by Western blot.

RNase Protection Assay

HeLa cells were transfected with the pLTR-HTAR-FFL reporter alone or with activator and inhibitor-expressing plasmids, total RNA was extracted using TRIzol (Invitrogen), and 15 μg of each sample was hybridized with proximal and distal probes corresponding to HIV promoter and luciferase ORF regions, respectively. The antisense probes were synthesized using a T3/T7 MaxiScript kit (Ambion) from plasmid templates linearized at a KpnI site, hybridization was performed with approximately 10,000 cpm of $^{32}$P-CTP-labeled probe (in 80% formamide, 40 mM PIPES, 400 mM NaCl, 1 mM EDTA) incubated at 42° C. overnight, RNase digestion was performed for 1.5 hr at 30° C. (in 10 mM Tris pH 8.0, 300 mM NaCl, 5 mM EDTA, 11 units/ml of RNase A, 11 units/ml RNase T1), samples were treated with proteinase K, extracted with phenol/chloroform, and RNA duplexes were precipitated with ethanol and glycogen carrier. RNAs were separated on a 6% polyacrylamide/8 M urea gel and visualized and quantified using a Typhoon phosphorimager (Molecular Dynamics). Experiments were performed in duplicate, with errors bars representing the SD of the mean.

Selection of a HeLA LTR-RREIIB-FFL Reporter Cell Line and ChIP Assays

HeLa cells were transfected in 6-well plates with a pcDNA3.1-derived plasmid (Invitrogen) bearing the LTR-RREIIB-FFL using Polyfect reagent (Qiagen). Clones were selected over more than four weeks in D-MEM-10% FBS supplemented with 750 μg/ml of G418 (Gibco). Twenty clones were analyzed for activation by pSV-T-Rev-HA by luciferase assays and a single highly active clone was chosen for ChIP analyses. ChIP assays were performed as described[29] with minor modifications. HeLa LTR-RREIIB-FFL reporter cells were transfected with various expressor plasmids (5 μg each) using 30 μl of Lipofectamine 2000 (Invitrogen) per 25 cm culture dish, incubated for 36 hr, and washed in PBS. Chromatin was cross-linked with 1% formaldehyde for 15 min at RT and the reaction stopped by adding glycine to 125 mM. Cells were washed with PBS and harvested in RIPA buffer, and samples were sonicated to generate DNA fragments <500 bp. For immuno-precipitations, 1 mg of protein extract was pre-cleared for 2 hr with 40 μl of a 50% slurry of 50:50 protein A/G-agarose and -then incubated with protein A/G-agarose and the appropriate antibodies overnight at 4° C. preblocked with 1 mg/ml and 0.3 mg/ml of salmon sperm DNA. Immunocomplexes were recovered using anti-rabbit IgG/protein A/G-agarose beads (Santa Cruz), beads were washed twice with RIPA buffer, four times with ChIP wash buffer (100 mM Tris-HCl, pH 8.5, 500 mM LiCL, 1% v/v Nonidet P-40, 1% w/v deoxycholic acid), twice with RIPA buffer, and twice with 1× TE buffer. Immunocomplexes were eluted in 1% SDS for 10 min at 65° C. and cross-linking was reversed by adjusting to 200 mM NaCl and incubating for 5 hr at 65° C. A fraction of purified DNA was used for PCR amplification, with 25-32 cycles performed in the exponential range depending on the particular primers and antibodies. To ensure linearity, control PCR reactions were performed for one cycle using twice and half the amount of sample. PCR products (100-250 bp) were quantified by incorporation of SyBr Green and fluorescence detection (MJ Research) and by visualization on 2% agarose gels stained with ethidium bromide, using PCR products from known input DNAs as standards and IQMac 1.2 for analysis. Primer sequences are provided in Supplementary Information.

Dominant Negative-Expressing SupT1 Cells and Viral Replication Kinetics.

Plasmids expressing $Tat_{AD}$, Tat, T-$BIV_{RBD}$, T-U2AF65, T-$HIV_{RBD}$-U2AF65, T-$BIV_{RBD}$-U2AF65, and U2AF65 were constructed in a pBMN retroviral vector (kindly provided by G. Nolan), using an SV40 promoter to express the Tat or Tat-fusion proteins. Plasmids were transfected into ONX packaging cells using the Polyfect reagent, and the retrovirus-containing supernatant recovered after 48 hr was used to transduce human CD4+ SupT1 cells. Populations of stable integrants were selected by growing cells in 2 mg/ml G418 (Invitrogen) for at least 4 weeks. Relative expression levels for each protein were assessed by real-time RT-PCR, transcriptional activation of transfected reporter plasmids and Western bloting (Supplementary Information). Each stable SupT1 population was infected with an HIV Tat-TAR-dependent (R7HTat/HTAR) or BIV Tat-TAR-dependent (R7 HBTat/BTAR) virus[18] at an m.o.i of 1. Supernatant samples were harvested at different intervals following infection and the amount of viral replication was monitored by p24 antigen expression using ELISA (Immuno Diagnostics, Inc.) over a period of 110 days. Each experiment was performed in duplicate and mean values of p24 were calculated.

RNA Isolation and Expression Levels by Quantitative Real-Time RT-PCR

Total RNA was isolated from cells using the Trizol reagent according to manufacturer instructions (Invitrogen). Randomly primed cDNA was prepared from 1 μg of total RNA using MMULV reverse transcriptase (New England Biolabs). One twentieth of the resultant cDNA was amplified in 35 μl reactions containing 1.25 units of Taq DNA polymerase (ABI), 1.5 mM $MgCl_2$, 300 nM of each primer, 0.5 mM dNTP mix, and 0.2× SYBR green I dye (Molecular Probes) in 1× Taq polymerase buffer. Real-time PCR was performed in an Opticon 2 DNA Engine (MJ Research) and analyzed using the Ct method (Applied Biosystems Prism 7700).

Expression Analysis by Western Blot

To more quantitatively assess relative inhibitor and activator expression levels, HeLa cells were co-transfected with 300 ng of pEGFPN3 (Clontech) and either 1.35 μg of pSV2-T-Rev-HA, 1.35 μg pSV2-T-U2AF65-HA, or both plasmids in 6-well plates. Nuclear extracts were prepared using NE-PER reagents (Pierce), samples were separated on a 12.5% SDS-PAGE gel, transferred to nitrocellulose, and probed with anti-HA, anti-GFP, or anti-nucleolin antibodies.

Functional Analysis of Protein Expression and Activity in SupT1 Cell Lines

Stable SupT1 G418-resistant cell populations ($3\times10^6$ cells) were transfected by electroporation (Bio-Rad, 250V, 0.975 μF) with LTR-HTAR-GFP or LTR-BPS-BTAR-GFP reporters to assess the activities of integrated plasmids expressing Tat or T-fusion proteins. After 48 hours, cells were analyzed by flow cytometry and GFP activity was quantitated using Celquest software (Becton Dickinson). Populations expressing Tat and derivatives were transfected with LTR-HTAR-GFP, populations expressing T-$BIV_{RBD}$ and derivatives were transfected with LTR-BPS-BTAR-GFP, and populations expressing U2AF65 fusions were transfected with LTR-BPS-BTAR-GFP, which contains a BPS and PPT that binds U2AF65 cooperatively with SF1 [9]. For luciferase assays, we used the LTR-HTAR-FFL or LTR-BTAR-FFL reporters and CMV-RL as an internal control for data normalization.

Genomic DNA Extraction from SupT1-Infected Cells and Viral Genome Sequencing

SupT1-T-U2AF65, SupT1-T-$BIV_{RBD}$-U2AF65, and SupT1-T-$HIV_{RBD}$-U2AF65 infected populations (about $1\times10^6$ cells) were harvested 25 days post-infection and genomic DNA was extracted using Flexigene according to manufacturer instructions (Qiagen). DNA was amplified by PCR using Turbo Pfu (Stratagene), with primer pair specific to regions of the HIV LTR promoter and surrounding Tat coding sequence. PCR-amplified DNA was gel purified (Qiagen) and cloned into a TOPO vector (Invitrogen). Eight clones from each cell population were sequenced, and sequences were compared to the original viral isolate, HXB2, using the NCBI BLAST algorithm.

SUPPLEMENTARY REFERENCES

1. Carol, R. et al., *J Virol*, 66:2000-7 (1992).
2. Gren, M. et al., *Cell*, 58:215-23 (1989).
3. Pearson, L. et al., *Proc Natl Acad Sci USA*, 87:5079-83 (1990).
4. Caputo, A. et al., *Gene Ther*, 3:235-45 (1996).
5. McCracken, S. et al., *Nature*, 385:357-61 (1997).
6. Fong, N. & Bentley, D. L., *Gene Dev*, 15:1783-95 (2001).
7. Fraisier, C. et al., *Gene Ther* 5:946-54 (1998).
8. Raha, T. et al., *PLoS Biol*, 3:e44 (2005).
9. Peled-Zehavi et al., *Mol Cell Biol*, 21:5232-41 (2001).
10. Hamm, T. E. et al., *J Virol*, 73:5741-7 (1999).
11. Hope, I. A. & Struhl, K., *Cell*, 46:885-94 (1986).
12. Friedman, A. et al., *Nature*, 335:452-4 (1988).
13. Kanazawa, S. et al., *Immunity*, 12:61-70 (2000).
14. Luecke, H. F. & Yamamoto, K. R., *Gene Dev*, 19:1116-27 (2005).

TABLE 1

Nuclear localized proteins
Last updated: 2006 Feb. 26
nucleus

Accession: GO:0005634
Ontology: cellular_component
Synonyms: None
Definition:
A membrane-bounded organelle of eukaryotic cells in which chromosomes are housed and replicated. In most cells, the nucleus contains all of the cell's chromosomes except the organellar chromosomes, and is the site of RNA synthesis and processing. In some species, or in specialized cell types, RNA metabolism or DNA replication may be absent.
Comment: None
Term Lineage
Graphical View all: all (<167657)
GO:0005575: cellular_component (<105038)
GO:0005623: cell (<75863)
GO:0005622: intracellular (<61387)
GO:0043229: intracellular organelle (<55495)
GO:0043231: intracellular membrane-bound organelle (<51579)
GO:0005634: nucleus (<10723)

TABLE 1-continued

Nuclear localized proteins
Last updated: 2006 Feb. 26
nucleus

GO:0005634: nucleus (<10723)
GO:0043226: organelle (<55511)
GO:0043229: intracellular organelle (<55495)
GO:0043231: intracellular membrane-bound organelle (<51579)
GO:0005634: nucleus (<10723)
GO:0043227: membrane-bound organelle (<51596)
GO:0043231: intracellular membrane-bound organelle (<51579)
GO:0005634: nucleus (<10723)
External References InterPro (333)
MIPS_funcat (1)
Pfam (221)
PRINTS (94)
ProDom (25)
PROSITE (99)
SMART (46)
SP_KW (1)
TIGR_role (1)
All Gene Product Associations (1790 results)
Get ALL associations here:
Direct Associations All Associations All Associations With Terms
Filter Associations
Datasource
AllFlyBaseSGDMGIgenedb_spombeUniProtTAIRdictyBaseWormbaseEnsemblRGDTIGR_CMRTIGRFAMSTIGR_Ath1TIGR_Tba1-Gramenegenedb_tsetsegenedb_tbruceigenedb_pfalciparumgenedb_lmajor-ZFIN
Evidence Code
All Curator ApprovedICIMPIGIIPIISSIDAIEPTASNAS
Species
All *A. japonica A. niger A. platyrhynchos A. thaliana A. trivirgatus B. anthracis* str. Am *B. coronavirus B. indicus B. mori B. taurus C. aethiops C. albicans C. briggsae C. burnetii* RSA 493 *C. carpio C. elegans C. familiaris C. griseus C. jacchus C. jejuni* RM1221 *C. porcellus C. torquatus* atys *D. discoideum D. erecta D. ethenogenes* 195 *D. mauritiana D. melanogaster D. pseudoobscura D. rerio D. sechellia D. simulans D. sp. D. virilis D. yakuba E. caballus F. catus G. gallus G. gorilla G. gorilla gorilla G. sulfurreducens* PCH. lar *H. sapiens L. major L. monocytogenes* str *M. auratus M. capsulatus* str. B *M. fascicularis M. fuscata fuscata M. monax M. mulatta M. musculus M. musculus castaneu M. musculus domestic M. musculus molossin M. musculus musculus M. natalensis M. nemestrina M. parviflora M. unguiculatus O. aries O. cuniculus O. kitabensis O. longistaminata O. mykiss O. nivara O. officinalis O. sativa O. sativa (indica cu O. sativa (japonica O. vulgaris P. anubis P. falciparum P. monodon P. pygmaeus P. sativum P. syringae* pv. *toma P. syringae* pv. *toma P. troglodytes Panicum R. norvegicus R. sp. S. cerevisiae S. coronavirus S. oedipus S. oneidensis S. oneidensis* MR-1 *S. pombe S. pomeroyi* DSS-3 *S. sciureus S. scrofa S. sp.* PCC 6803 *T. brucei T. brucei* TREU927 *T. cambridgei T. vulpecula V. arvensis V. cholerae* O1 biova *V. odorata X. laevis X. tropicalis*

| Qualifier | Symbol Sequence/GOst | Information | Source | Evidence | Reference |
|---|---|---|---|---|---|
| | 2A5D HUMAN | Splice Isoform Delta-1 of Serine/threonine protein phosphatase 2A, 56 kDa regulatory subunit, delta isoform, protein from *Homo sapiens* | UniProt | TAS | PMID: 8703017 |
| | 2A5G HUMAN | Splice Isoform Gamma-3 of Serine/threonine Protein phosphatase 2A, 56 kDa regulatory subunit, gamma isoform, protein from *Homo sapiens* | UniProt | IDA | PMID: 8703017 |

-continued

| Qualifier | Symbol Sequence/GOst | Information | Source | Evidence | Reference |
|---|---|---|---|---|---|
| | 2AAA HUMAN | Serine/threonine protein phosphatase 2A, 65 kDa regulatory subunit A, alpha isoform, protein from *Homo sapiens* | UniProt | NAS | PMID: 11007961 |
| | 2AAB HUMAN | Serine/threonine protein phosphatase 2A, 65 kDa regulatory subunit A, beta isoform, protein from *Homo sapiens* | UniProt | ISS | UniProt: P30154 |
| | 2ACC HUMAN | Protein phosphatase 2, regulatory subunit B", isoform 1, protein from *Homo sapiens* | UniProt | TAS | PMID: 10629059 |
| | 4ET HUMAN | Splice Isoform 1 of Eukaryotic translation initiation factor 4E transporter, protein from *Homo sapiens* | UniProt | TAS | PMID: 10856257 |
| | AATF HUMAN | Protein AATF, protein from *Homo sapiens* | UniProt | IDA | PMID: 12429849 |
| | AB2BP HUMAN | Splice Isoform 1 of Amyloid beta A4 protein-binding family A member 2-binding protein, protein from *Homo sapiens* | UniProt | NAS | PMID: 10833507 |
| | ABCCD HUMAN | Splice Isoform 1 of Putative ATP-binding cassette transporter C13, protein from *Homo sapiens* | UniProt | NAS | UniProt: Q9NSE7 |
| | ABL1 HUMAN | Splice Isoform IA of Proto-oncogene tyrosine-protein kinase ABL1, protein from *Homo sapiens* | UniProt | NAS | PMID: 8242749 |
| | ACINU HUMAN | Splice Isoform 1 of Apoptotic chromatin condensation inducer in the nucleus, protein from *Homo sapiens* | UniProt | IDA | PMID: 10490026 |
| | ACL6B HUMAN | Actin-like protein 6B, protein from *Homo sapiens* | UniProt | IDA | PMID: 10380635 |
| | ACTN4 HUMAN | Alpha-actinin 4, protein from *Homo sapiens* | UniProt | TAS | PMID: 9508771 |
| | ADA10 HUMAN | ADAM 10 precursor, protein from *Homo sapiens* | UniProt | ISS | UniProt: O14672 |
| | ADA2 HUMAN | Transcriptional adapter 2-like, protein from *Homo sapiens* | UniProt | TAS | PMID: 8552087 |
| | AF9 HUMAN | Protein AF-9, protein from *Homo sapiens* | UniProt | TAS | PMID: 8506309 |
| | AFF3 HUMAN | AF4/FMR2 family member 3, protein from *Homo sapiens* | UniProt | TAS | PMID: 8555498 |
| | AHNK HUMAN | Neuroblast differentiation-associated protein AHNAK, protein from *Homo sapiens* | UniProt | NAS | PMID: 1608957 |
| | AHR HUMAN | Aryl hydrocarbon receptor precursor, protein from *Homo sapiens* | UniProt | IDA | PMID: 10395741 |
| | AIF1 HUMAN | Allograft inflammatory factor 1, protein from *Homo sapiens* | UniProt | TAS | PMID: 9614071 |
| | AIPL1 HUMAN | Aryl-hydrocarbon-interacting protein-like 1, protein from *Homo sapiens* | UniProt | IDA | PMID: 12374762 |
| | AIRE HUMAN | Splice Isoform 1 of Autoimmune regulator, protein from *Homo sapiens* | UniProt | NAS | PMID: 9398840 |
| | AKAP8 HUMAN | A-kinase anchor protein 8, protein from *Homo sapiens* | UniProt | TAS | PMID: 9473338 |
| | AKIP HUMAN | Aurora kinase A-interacting protein, protein from *Homo sapiens* | UniProt | IDA | PMID: 12244051 |
| | AKP8L HUMAN | A-kinase anchor protein-like protein 8, protein from *Homo sapiens* | UniProt | TAS | PMID: 10761695 |

| Qualifier | Symbol Sequence/GOst | Information | Source | Evidence | Reference |
|---|---|---|---|---|---|
| | ALP HUMAN | N-acetyltransferase-like protein, protein from *Homo sapiens* | UniProt | NAS | PMID: 11214970 |
| | ALX4 HUMAN | Homeobox protein aristaless-like 4, protein from *Homo sapiens* | UniProt | NAS | PMID: 11137991 |
| | AN32A HUMAN | Acidic leucine-rich nuclear phosphoprotein 32 family member A, protein from *Homo sapiens* | UniProt | IDA | PMID: 11555662 |
| | AN32E HUMAN | Acidic leucine-rich nuclear phosphoprotein 32 family member E, protein from *Homo sapiens* | UniProt | ISS | UniProt: Q9BTT0 |
| | ANDR HUMAN | Androgen receptor, protein from *Homo sapiens* | UniProt | IDA | PMID: 15572661 |
| | ANKR2 HUMAN | Splice Isoform 1 of Ankyrin repeat domain protein 2, protein from *Homo sapiens* | UniProt | ISS | PMID: 1204005 |
| | ANM1 HUMAN | Splice Isoform 1 of Protein arginine N-methyltransferase 1, protein from *Homo sapiens* | UniProt | IDA | PMID: 10749851 |
| | ANM2 HUMAN | Protein arginine N-methyltransferase 2, protein from *Homo sapiens* | UniProt | TAS | PMID: 9545638 |
| | AP2A HUMAN | OTTHUMP00000016011, protein from *Homo sapiens* | UniProt | TAS | PMID: 8321221 |
| | APBB1 HUMAN | Splice Isoform 1 of Amyloid beta A4 precursor protein-binding family B member 1, protein from *Homo sapiens* | UniProt | ISS | UniProt: O00213 |
| | | | | ISS | UniProt: Q96A93 |
| | APBB2 HUMAN | Splice Isoform 1 of Amyloid beta A4 precursor protein-binding family B member 2, protein from *Homo sapiens* | UniProt | ISS | UniProt: Q92870 |
| | APBP2 HUMAN | Amyloid protein-binding protein 2, protein from *Homo sapiens* | UniProt | NAS | PMID: 11742091 |
| | APC HUMAN | Splice Isoform Long of Adenomatous polyposis coli protein, protein from *Homo sapiens* | UniProt | IDA | PMID: 12072559 |
| | APEG1 HUMAN | Hypothetical protein FLJ46856, protein from *Homo sapiens* | UniProt | TAS | PMID: 8663449 |
| | APEX1 HUMAN | DNA-(apurinic or apyrimidinic site) lyase, protein from *Homo sapiens* | UniProt | IDA | PMID: 9119221 |
| | APLP2 HUMAN | Splice Isoform 1 of Amyloid-like protein 2 precursor, protein from *Homo sapiens* | UniProt | IDA | PMID: 7702756 |
| | ARD1H HUMAN | N-terminal acetyltransferase complex ARD1 subunit homolog, protein from *Homo sapiens* | UniProt | IDA | PMID: 15496142 |
| | ARI1A HUMAN | Splice Isoform 1 of AT-rich interactive domain-containing protein 1A, protein from *Homo sapiens* | UniProt | NAS | UniProt: O14497 |
| | ARI2 HUMAN | Ariadne-2 protein homolog, protein from *Homo sapiens* | UniProt | TAS | PMID: 10422847 |
| | ARI3A HUMAN | AT-rich interactive domain-containing protein 3A, protein from *Homo sapiens* | UniProt | NAS | UniProt: Q99856 |
| | ARI4A HUMAN | Splice Isoform I of AT-rich interactive domain-containing protein 4A, protein from *Homo sapiens* | UniProt | TAS | PMID: 8414517 |

-continued

| Qualifier | Symbol Sequence/GOst | Information | Source | Evidence | Reference |
|---|---|---|---|---|---|
| | ARI5B HUMAN | Splice Isoform 1 of AT-rich interactive domain-containing protein 5B, protein from *Homo sapiens* | UniProt | IDA IC | PMID: 11283269 PMID: 15640446 |
| | ARL4A HUMAN | ADP-ribosylation factor-like protein 4A, protein from *Homo sapiens* | UniProt | TAS | PMID: 10462049 |
| | ARL4C HUMAN | ADP ribosylation factor-like protein 7, protein from *Homo sapiens* | UniProt | TAS | PMID: 10462049 |
| | ARNT2 HUMAN | Aryl hydrocarbon receptor nuclear translocator 2, protein from *Homo sapiens* | UniProt | IDA | PMID: 12239177 |
| | ARNT HUMAN | Splice Isoform Long of Aryl hydrocarbon receptor nuclear translocator, protein from *Homo sapiens* | UniProt | TAS | PMID: 1317062 |
| | ASCL2 HUMAN | Achaete-scute homolog 2, protein from *Homo sapiens* | UniProt | NAS | PMID: 8751384 |
| | ASH2L HUMAN | Splice Isoform 1 of Set1/Asb2 histone methyltransferase complex subunit ASH2, protein from *Homo sapiens* | UniProt | IDA | PMID: 15199122 |
| | ASPP1 HUMAN | Apoptosis stimulating of p53 protein 1, protein from *Homo sapiens* | UniProt | IDA | PMID: 11684014 |
| | ATBF1 HUMAN | Splice Isoform A of Alpha-fetoprotein enhancer binding protein, protein from *Homo sapiens* | UniProt | TAS | PMID: 1719379 |
| | ATE1 HUMAN | Splice Isoform ATE1-1 of Arginyl-tRNA--protein transferase 1, protein from *Homo sapiens* | UniProt | IDA | PMID: 9858543 |
| | ATF4 HUMAN | Cyclic AMP-dependent transcription factor ATF-4, protein from *Homo sapiens* | UniProt | ISS | UniProt: P18848 |
| | ATF6B HUMAN | Splice Isoform 1 of Cyclic AMP-dependent transcription factor ATF-6 beta, protein from *Homo sapiens* | UniProt | TAS | PMID: 8586413 |
| | ATN1 HUMAN | Atrophin-1, protein from *Homo sapiens* | UniProt | TAS | PMID: 10814707 |
| | ATRX HUMAN | Splice Isoform 4 of Transcriptional regulator ATRX, protein from *Homo sapiens* | UniProt | TAS | PMID: 7874112 |
| | ATX1 HUMAN | Ataxin-1, protein from *Homo sapiens* | UniProt | TAS | PMID: 7647801 |
| | ATX2 HUMAN | AtAxin 2, protein from *Homo sapiens* | UniProt | TAS | PMID: 10973246 |
| | ATX7 HUMAN | Splice Isoform a of Ataxin-7, protein from *Homo sapiens* | UniProt | TAS | PMID: 10441328 |
| | AURKC HUMAN | Splice Isoform 1 of Serine/threonine-protein kinase 13, protein from *Homo sapiens* | UniProt | TAS | PMID: 10066797 |
| | AXN1 HUMAN | Axin 1, protein from *Homo sapiens* | UniProt | IDA | PMID: 12072559 |
| | AXN2 HUMAN | Axin-2, protein from *Homo sapiens* | UniProt | IDA | PMID: 12072559 |
| | BAP1 HUMAN | Ubiquitin carboxyl-terminal hydrolase BAP1, protein from *Homo sapiens* | UniProt | TAS | PMID: 9528852 |
| | BARD1 HUMAN | BRCA1-associated RING domain protein 1, protein from *Homo sapiens* | UniProt | IMP | PMID: 15632137 |
| | BAZ1B HUMAN | Splice Isoform 1 of Bromodomain adjacent to zinc finger domain protein 1B, protein from *Homo sapiens* | UniProt | IDA NAS | PMID: 15265711 PMID: 11124022 |

-continued

| Qualifier | Symbol Sequence/GOst | Information | Source | Evidence | Reference |
|---|---|---|---|---|---|
| | BC11A HUMAN | Splice Isoform 1 of B-cell lymphoma/leukemia 11A, protein from *Homo sapiens* | UniProt | NAS | UniProt: Q9H165 |
| | BCL6 HUMAN | B-cell lymphoma 6 protein, protein from *Homo sapiens* | UniProt | IDA | PMID: 10898795 |
| | BCLF1 HUMAN | Splice Isoform 1 of Bcl-2-associated transcription factor 1, protein from *Homo sapiens* | UniProt | NAS | UniProt: Q9NYF8 |
| | BCOR HUMAN | Splice Isoform 1 of BCoR protein, protein from *Homo sapiens* | UniProt | IDA | PMID: 10898795 |
| | BHLH2 HUMAN | Class B basic helix-loop-helix protein 2, protein from *Homo sapiens* | UniProt | NAS | PMID: 9240428 |
| | BHLH3 HUMAN | Class B basic helix-loop-helix protein 3, protein from *Homo sapiens* | UniProt | NAS | UniProt: Q9C0J9 |
| | BI1 HUMAN | Bax inhibitor-1, protein from *Homo sapiens* | UniProt | TAS | PMID: 8530040 |
| | BINCA HUMAN | Splice Isoform 1 of Bcl10-interacting CARD protein, protein from *Homo sapiens* | UniProt | NAS | PMID: 15637807 |
| | BLMH HUMAN | Bleomycin hydrolase, protein from *Homo sapiens* | UniProt | TAS | PMID: 8639621 |
| | BNC1 HUMAN | Zinc finger protein basonuclin-1, protein from *Homo sapiens* | UniProt | TAS | PMID: 8034748 |
| | BNIPL HUMAN | Splice Isoform 1 of Bcl-2/adenovirus E1B 19 kDa-interacting protein 2-like protein, protein from *Homo sapiens* | UniProt | IDA | PMID: 11741952 |
| | BRCA1 HUMAN | Breast cancer type 1 susceptibility protein, protein from *Homo sapiens* | UniProt | TAS | PMID: 10918303 |
| | BRCA2 HUMAN | Breast cancer type 2 susceptibility protein, protein from *Homo sapiens* | UniProt | IDA | PMID: 9560268 |
| | BRD1 HUMAN | Bromodomain-containing protein 1, protein from *Homo sapiens* | UniProt | TAS | PMID: 10602503 |
| | BRD3 HUMAN | Splice Isoform 1 of Bromodomain-containing protein 3, protein from *Homo sapiens* | UniProt | NAS | UniProt: Q15059 |
| | BRD8 HUMAN | Splice Isoform 1 of Bromodomain-containing protein 8, protein from *Homo sapiens* | UniProt | NAS | PMID: 8611617 |
| | BRPF1 HUMAN | Peregrin, protein from *Homo sapiens* | UniProt | TAS | PMID: 7906940 |
| | BRSK1 HUMAN | Splice Isoform 1 of BR serine/threonine-protein kinase 1, protein from *Homo sapiens* | UniProt | IDA | PMID: 15150265 |
| | BSN HUMAN | Bassoon protein, protein from *Homo sapiens* | UniProt | TAS | PMID: 9806829 |
| | BT3L2 HUMAN | Transcription factor BTF3 homolog 2, protein from *Homo sapiens* | UniProt | NAS | UniProt: Q13891 |
| | BT3L3 HUMAN | Transcription factor BTF3 homolog 3, protein from *Homo sapiens* | UniProt | NAS | UniProt: Q13892 |
| | BTAF1 HUMAN | TATA-binding-protein-associated factor 172, protein from *Homo sapiens* | UniProt | NAS | UniProt: O14981 |
| | BTG1 HUMAN | BTG1 protein, protein from *Homo sapiens* | UniProt | IMP | PMID: 11420681 |
| | | | | IEP | PMID: 9820826 |
| | CABIN HUMAN | Calcineurin-binding protein Cabin 1, protein from *Homo sapiens* | UniProt | NAS | UniProt: Q9Y6J0 |
| | CAF1B HUMAN | Chromatin assembly factor 1 subunit B, protein from *Homo sapiens* | UniProt | NAS | PMID: 9614144 |

| Qualifier | Symbol Sequence/GOst | Information | Source | Evidence | Reference |
|---|---|---|---|---|---|
| | CARM1 HUMAN | Splice Isoform 1 of Histone-arginine methyltransferase CARM1, protein from *Homo sapiens* | UniProt | IDA | PMID: 15221992 |
| | CASC5 HUMAN | Splice Isoform 1 of Cancer susceptibility candidate gene 5 protein, protein from *Homo sapiens* | UniProt | IDA | PMID: 10980622 |
| | CASL HUMAN | Enhancer of filamentation 1, protein from *Homo sapiens* | UniProt | TAS | PMID: 8668148 |
| | CBP HUMAN | CREB-binding protein, protein from *Homo sapiens* | UniProt | TAS | PMID: 7913207 |
| | CBX2 HUMAN | Splice Isoform 1 of Chromobox protein homolog 2, protein from *Homo sapiens* | UniProt | NAS | UniProt: Q14781 |
| | CBX3 HUMAN | Chromobox protein homolog 3, protein from *Homo sapiens* | UniProt | TAS | PMID: 8663349 |
| | CBX4 HUMAN | Chromobox homolog 4, protein from *Homo sapiens* | UniProt | TAS | PMID: 9315667 |
| | CC14A HUMAN | Splice Isoform 1 of Dual specificity protein phosphatase CDC14A, protein from *Homo sapiens* | UniProt | TAS | PMID: 9367992 |
| | CC14B HUMAN | Splice Isoform 2 of Dual specificity protein phosphatase CDC14B, protein from *Homo sapiens* | UniProt | IDA | PMID: 9367992 |
| | CC45L HUMAN | CDC45-related protein, protein from *Homo sapiens* | UniProt | TAS | PMID: 9660782 |
| | CCNE1 HUMAN | Splice Isoform E1L of G1/S-specific cyclin-E1, protein from *Homo sapiens* | UniProt | NAS | UniProt: P24864 |
| | CCNH HUMAN | Cyclin-H, protein from *Homo sapiens* | UniProt | TAS | PMID: 7936635 |
| | CCP1 HUMAN | Calcipressin 1 large isoform, protein from *Homo sapiens* | UniProt | TAS | PMID: 8595418 |
| | CD2A1 HUMAN | Splice Isoform 1 of Cyclin-dependent kinase inhibitor 2A, isoforms 1/2/3, protein from *Homo sapiens* | UniProt | NR | UniProt: P42771 |
| | CD2L1 HUMAN | Splice Isoform SV9 of PITSLRE serine/threonine-protein kinase CDC2L1, protein from *Homo sapiens* | UniProt | IEP | PMID: 8195233 |
| | CD2L2 HUMAN | Splice Isoform SV6 of PITSLRE serine/threonine-protein kinase CDC2L2, protein from *Homo sapiens* | UniProt | IEP | PMID: 8195233 |
| | CD2L7 HUMAN | Cell division cycle 2-related protein kinase 7, protein from *Homo sapiens* | UniProt | IDA | PMID: 11683387 |
| | CDC2 HUMAN | Hypothetical protein DKFZp686L20222, protein from *Homo sapiens* | UniProt | TAS | PMID: 10767298 |
| | CDC6 HUMAN | Cell division control protein 6 homolog, protein from *Homo sapiens* | UniProt | TAS | PMID: 9566895 |
| | CDC7 HUMAN | Cell division cycle 7-related protein kinase, protein from *Homo sapiens* | UniProt | TAS | PMID: 9250678 |
| | CDCA5 HUMAN | Sororin, protein from *Homo sapiens* | UniProt | ISS | UniProt: Q96FF9 |
| | CDK1 HUMAN | Cyclin-dependent kinase 2-associated protein 1, protein from *Homo sapiens* | UniProt | TAS | PMID: 9506968 |
| | CDK2 HUMAN | Cell division protein kinase 2, protein from *Homo sapiens* | UniProt | TAS | PMID: 10767298 |
| | CDK5 HUMAN | Cell division protein kinase 5, protein from *Homo sapiens* | UniProt | ISS | UNIPROT: Q00535 |
| | CDK7 HUMAN | Cell division protein kinase 7, protein from *Homo sapiens* | UniProt | TAS | PMID: 7936635 |
| | CDK9 HUMAN | Splice Isoform 1 of Cell division protein kinase 9, protein from *Homo sapiens* | UniProt | TAS | PMID: 8170997 |

| Qualifier | Symbol Sequence/GOst | Information | Source | Evidence | Reference |
|---|---|---|---|---|---|
| | CDN1A HUMAN | Cyclin-dependent kinase inhibitor 1, protein from *Homo sapiens* | UniProt | TAS | PMID: 9660939 |
| | CDN1B HUMAN | Cyclin-dependent kinase inhibitor 1B, protein from *Homo sapiens* | UniProt | IDA | PMID: 12093740 |
| | CDN2C HUMAN | Cyclin-dependent kinase 6 inhibitor, protein from *Homo sapiens* | UniProt | NR | UniProt: P42773 |
| | CDN2D HUMAN | Cyclin-dependent kinase 4 inhibitor D, protein from *Homo sapiens* | UniProt | TAS | PMID: 8741839 |
| | CDR2 HUMAN | Cerebellar degeneration-related protein 2, protein from *Homo sapiens* | UniProt | NAS | UniProt: Q13977 |
| | CDT1 HUMAN | DNA replication factor Cdt1, protein from *Homo sapiens* | UniProt | IDA | PMID: 11125146 |
| | CEBPA HUMAN | CCAAT/enhancer binding protein alpha, protein from *Homo sapiens* | UniProt | NAS | PMID: 7575576 |
| | CEBPB HUMAN | CCAAT/enhancer binding protein beta, protein from *Homo sapiens* | UniProt | TAS | PMID: 10821850 |
| | CEBPG HUMAN | CCAAT/enhancer binding protein gamma, protein from *Homo sapiens* | UniProt | ISS | PMID: 7501458 |
| | CEBPZ HUMAN | CCAAT/enhancer binding protein zeta, protein from *Homo sapiens* | UniProt | TAS | PMID: 2247079 |
| | CENA1 HUMAN | Centaurin-alpha 1, protein from *Homo sapiens* | UniProt | IDA | PMID: 10448098 |
| | | | | IDA | PMID: 10333475 |
| | CENG1 HUMAN | Centaurin-gamma 1, protein from *Homo sapiens* | UniProt | ISS | PMID: 11136977 |
| | CENPA HUMAN | Centromere protein A, protein from *Homo sapiens* | UniProt | TAS | PMID: 7962047 |
| | CENPE HUMAN | Centromere protein E, protein from *Homo sapiens* | UniProt | IMP | PMID: 9763420 |
| | CEZ1 HUMAN | Zinc finger protein CeZanne, protein from *Homo sapiens* | UniProt | IDA | PMID: 11463333 |
| | CHD6 HUMAN | Splice Isoform 1 of Chromodomain-helicase-DNA-binding protein 6, protein from *Homo sapiens* | UniProt | NAS | PMID: 12592387 |
| | CHD8 HUMAN | Chromodomain-helicase-DNA-binding protein 8, protein from *Homo sapiens* | UniProt | NAS | UniProt: Q9HCK8 |
| | CHK2 HUMAN | Splice Isoform 1 of Serine/threonine-protein kinase Chk2, protein from *Homo sapiens* | UniProt | NAS | UniProt: O96017 |
| | CITE2 HUMAN | Splice Isoform 2 of Cbp/p300-interacting transactivator 2, protein from *Homo sapiens* | UniProt | NAS | PMID: 10552932 |
| | CIZ1 HUMAN | Splice Isoform 1 of Cip1-interacting zinc finger protein, protein from *Homo sapiens* | UniProt | TAS | PMID: 10529385 |
| | CK001 HUMAN | Protein C11orf1, protein from *Homo sapiens* | UniProt | NAS | PMID: 10873569 |
| | CLAT HUMAN | Splice Isoform M of Choline O-acetyltransferase, protein from *Homo sapiens* | UniProt | TAS | PMID: 10861222 |
| | CLIC2 HUMAN | Chloride intracellular channel protein 2, protein from *Homo sapiens* | UniProt | TAS | PMID: 16130169 |
| | CLIC3 HUMAN | Chloride intracellular channel protein 3, protein from *Homo sapiens* | UniProt | IDA | PMID: 9880541 |
| | CN004 HUMAN | Protein C14orf4, protein from *Homo sapiens* | UniProt | NAS | PMID: 11095982 |
| | CND1 HUMAN | Condensin complex subunit 1, protein from *Homo sapiens* | UniProt | NAS | PMID: 10958694 |
| | CND3 HUMAN | Condensin complex subunit 3, protein from *Homo sapiens* | UniProt | NAS | PMID: 10910072 |

-continued

| Qualifier | Symbol Sequence/GOst | Information | Source | Evidence | Reference |
|---|---|---|---|---|---|
| | CNOT2 HUMAN | Splice Isoform 1 of CCR4-NOT transcription complex subunit 2, protein from *Homo sapiens* | UniProt | NAS | PMID: 10637334 |
| | CNOT7 HUMAN | CCR4-NOT transcription complex subunit 7, protein from *Homo sapiens* | UniProt | IEP | PMID: 9820826 |
| | CNOT8 HUMAN | CCR4-NOT transcription complex subunit 8, protein from *Homo sapiens* | UniProt | NAS | PMID: 10036195 |
| | COF1 HUMAN | Cofilin, non-muscle isoform, protein from *Homo sapiens* | UniProt | TAS | PMID: 16130169 |
| | COT2 HUMAN | COUP transcription factor 2, protein from *Homo sapiens* | UniProt | TAS | PMID: 1899293 |
| | CREB1 HUMAN | Splice Isoform CREB-A of cAMP response element binding protein, protein from *Homo sapiens* | UniProt | TAS | PMID: 10909971 |
| | CREB3 HUMAN | Splice Isoform 1 of Cyclic AMP-responsive element binding protein 3, protein from *Homo sapiens* | UniProt | NAS | PMID: 9271389 |
| | CREB5 HUMAN | Splice Isoform 1 of cAMP response element-binding protein 5, protein from *Homo sapiens* | UniProt | IC | PMID: 8378084 |
| | CREM HUMAN | CAMP responsive element modulator, protein from *Homo sapiens* | UniProt | NAS | UniProt: Q16114 |
| | CRK HUMAN | Splice Isoform Crk-II of Proto-oncogene C-crk, protein from *Homo sapiens* | UniProt | TAS | PMID: 10748058 |
| | CRNL1 HUMAN | Crn, crooked neck-like 1, protein from *Homo sapiens* | UniProt | NAS | UniProt: Q9BZI9 |
| | CRSP2 HUMAN | CRSP complex subunit 2, protein from *Homo sapiens* | UniProt | IDA | PMID: 10235267 |
| | CRSP6 HUMAN | CRSP complex subunit 6, protein from *Homo sapiens* | UniProt | IDA | PMID: 10235267 |
| | CRYAB HUMAN | Alpha crystallin B chain, protein from *Homo sapiens* | UniProt | NR | UniProt: P02511 |
| | CSDC2 HUMAN | Cold shock domain protein C2, protein from *Homo sapiens* | UniProt | NAS | UniProt: Q9Y534 |
| | CSE1 HUMAN | Splice Isoform 1 of Importin-alpha re-exporter, protein from *Homo sapiens* | UniProt | TAS | PMID: 9323134 |
| | CSR2B HUMAN | Splice Isoform 1 of Cysteine-rich protein 2 binding protein, protein from *Homo sapiens* | UniProt | IPI | PMID: 10924333 |
| | CSRP2 HUMAN | Cysteine and glycine-rich protein 2, protein from *Homo sapiens* | UniProt | NAS | PMID: 96215313 |
| | CSTF1 HUMAN | Cleavage stimulation factor, 50 kDa subunit, protein from *Homo sapiens* | UniProt | TAS | PMID: 1358884 |
| | CSTF2 HUMAN | Splice Isoform 1 of Cleavage stimulation factor, 64 kDa subunit, protein from *Homo sapiens* | UniProt | TAS | PMID: 1741396 |
| | CSTF3 HUMAN | Cleavage stimulation factor, 77 kDa subunit, protein from *Homo sapiens* | UniProt | TAS | PMID: 7984242 |
| | CTCF HUMAN | Transcriptional repressor CTCF, protein from *Homo sapiens* | UniProt | IDA | PMID: 9407128 |
| | CTDS1 HUMAN | Carboxy-terminal domain RNA polymerase II polypeptide A small phosphatase 1, protein from *Homo sapiens* | UniProt | TAS | PMID: 10967134 |
| | CTNB1 HUMAN | Splice Isoform 1 of Beta-catenin, protein from *Homo sapiens* | UniProt | TAS | PMID: 9065401 |
| | CTND1 HUMAN | Splice Isoform 1ABC of Catenin delta-1, protein from *Homo sapiens* | UniProt | NAS | PMID: 98317528 |

| Qualifier | Symbol Sequence/GOst | Information | Source | Evidence | Reference |
|---|---|---|---|---|---|
| | CUGB1 HUMAN | Splice Isoform 2 of CUG triplet repeat RNA-binding protein 1, protein from *Homo sapiens* | UniProt | NAS | PMID: 10893231 |
| | CUTL2 HUMAN | Homeobox protein cut-like 2, protein from *Homo sapiens* | UniProt | NAS | UniProt: O14529 |
| | CX4NB HUMAN | Neighbor of COX4, protein from *Homo sapiens* | UniProt | TAS | PMID: 10337626 |
| | CXCC1 HUMAN | CpG binding protein, protein from *Homo sapiens* | UniProt | IDA | PMID: 10688657 |
| | DAPK3 HUMAN | Death-associated protein kinase 3, protein from *Homo sapiens* | UniProt | ISS | UniProt: O43293 |
| | DAXX HUMAN | Splice Isoform 1 of Death domain-associated protein 6, protein from *Homo sapiens* | UniProt | IDA | PMID: 15572661 |
| | DCTN4 HUMAN | Dynactin subunit 4, protein from *Homo sapiens* | UniProt | TAS | PMID: 10671518 |
| | DDX17 HUMAN | Splice Isoform 1 of Probable ATP-dependent RNA helicase DDX17, protein from *Homo sapiens* | UniProt | TAS | PMID: 8871553 |
| | DDX39 HUMAN | ATP-dependent RNA helicase DDX39, protein from *Homo sapiens* | UniProt | ISS | PMID: 15047853 |
| | DDX3X HUMAN | ATP-dependent RNA helicase DDX3X, protein from *Homo sapiens* | UniProt | IDA | PMID: 10329544 |
| | DDX54 HUMAN | ATP-dependent RNA helicase DDX54, protein from *Homo sapiens* | UniProt | ISS | UniProt: Q9BRZ1 |
| | DDX5 HUMAN | Probable ATP-dependent RNA helicase DDX5, protein from *Homo sapiens* | UniProt | NAS | PMID: 2451786 |
| | DEAF1 HUMAN | Splice Isoform 1 of Deformed epidermal autoregulatory factor 1 homolog, protein from *Homo sapiens* | UniProt | TAS | PMID: 9773984 |
| | DEK HUMAN | Protein DEK, protein from *Homo sapiens* | UniProt | TAS | PMID: 9050861 |
| | DFFA HUMAN | Splice Isoform DFF45 of DNA fragmentation factor alpha subunit, protein from *Homo sapiens* | UniProt | IDA | PMID: 15572351 |
| | DFFB HUMAN | Splice Isoform Alpha of DNA fragmentation factor 40 kDa subunit, protein from *Homo sapiens* | UniProt | IDA | PMID: 15572351 |
| | DGC14 HUMAN | DGCR14 protein, protein from *Homo sapiens* | UniProt | ISS | PMID: 8703114 |
| | DGCR8 HUMAN | Splice Isoform 1 of DGCR8 protein, protein from *Homo sapiens* | UniProt | IDA | PMID: 15574589 |
| | DGKI HUMAN | Diacylglycerol kinase, iota, protein from *Homo sapiens* | UniProt | TAS | PMID: 9830018 |
| | DGKZ HUMAN | Splice Isoform Long of Diacylglycerol kinase, zeta, protein from *Homo sapiens* | UniProt | TAS | PMID: 9716136 |
| | DHRS2 HUMAN | Dehydrogenase/reductase, protein from *Homo sapiens* | UniProt | TAS | PMID: 7556196 |
| | DHX15 HUMAN | Putative pre-mRNA splicing factor ATP-dependent RNA helicase DHX15, protein from *Homo sapiens* | UniProt | TAS | PMID: 9388478 |
| | DHX16 HUMAN | Putative pre-mRNA splicing factor ATP-dependent RNA helicase DHX16, protein from *Homo sapiens* | UniProt | TAS | PMID: 9547260 |
| | DHX9 HUMAN | DEAH (Asp-Glu-Ala-His) box polypeptide 9 isoform 1, protein from *Homo sapiens* | UniProt | TAS | PMID: 9111062 |
| | DLG7 HUMAN | Splice Isoform 2 of Discs large homolog 7, protein from *Homo sapiens* | UniProt | IDA | PMID: 12527899 |
| | DLX1 HUMAN | Homeobox protein DLX-1, protein from *Homo sapiens* | UniProt | NAS | UniProt: P56177 |

| Qualifier | Symbol Sequence/GOst | Information | Source | Evidence | Reference |
|---|---|---|---|---|---|
| | DMAP1 HUMAN | DNA methyltransferase 1-associated protein 1, protein from *Homo sapiens* | UniProt | NAS | PMID: 10888872 |
| | DNJC1 HUMAN | DnaJ homolog subfamily C member 1, protein from *Homo sapiens* | UniProt | ISS | UniProt: Q96KC8 |
| | DNL1 HUMAN | DNA ligase I, protein from *Homo sapiens* | UniProt | TAS | PMID: 8696349 |
| | DNL3 HUMAN | Ligase III, DNA, ATP-dependent, isoform alpha, protein from *Homo sapiens* | UniProt | TAS | PMID: 7565692 |
| | DNL4 HUMAN | DNA ligase IV, protein from *Homo sapiens* | UniProt | TAS | PMID: 8798671 |
| | DNM3A HUMAN | DNA, protein from *Homo sapiens* | UniProt | ISS | PMID: 12138111 |
| | DNM3B HUMAN | Splice Isoform 1 of DNA, protein from *Homo sapiens* | UniProt | TAS | PMID: 10433969 |
| | DNM3L HUMAN | DNA (cytosine-5)-methyltransferase 3-like, protein from *Homo sapiens* | UniProt | NAS | PMID: 12202768 |
| | DNMT1 HUMAN | Splice Isoform 1 of DNA, protein from *Homo sapiens* | UniProt | TAS | PMID: 8940105 |
| | DP13A HUMAN | DCC-interacting protein 13 alpha, protein from *Homo sapiens* | UniProt | IDA | PMID: 15016378 |
| | DP13B HUMAN | DCC-interacting protein 13 beta, protein from *Homo sapiens* | UniProt | IDA | PMID: 15016378 |
| | DPF3 HUMAN | Zinc-finger protein DPF3, protein from *Homo sapiens* | UniProt | NAS | UniProt: Q92784 |
| | DPOA2 HUMAN | DNA polymerase alpha subunit B, protein from *Homo sapiens* | UniProt | NAS | UniProt: Q14181 |
| | DPOD2 HUMAN | DNA polymerase delta subunit 2, protein from *Homo sapiens* | UniProt | TAS | PMID: 8530069 |
| | DPOD4 HUMAN | DNA polymerase delta subunit 4, protein from *Homo sapiens* | UniProt | TAS | PMID: 10751307 |
| | DPOE3 HUMAN | DNA polymerase epsilon subunit 3, protein from *Homo sapiens* | UniProt | TAS | PMID: 10801849 |
| | DPOE4 HUMAN | DNA polymerase epsilon subunit 4, protein from *Homo sapiens* | UniProt | TAS | PMID: 10801849 |
| | DPOLA HUMAN | DNA polymerase alpha catalytic subunit, protein from *Homo sapiens* | UniProt | NAS | UniProt: P09884 |
| | DPOLL HUMAN | DNA polymerase lambda, protein from *Homo sapiens* | UniProt | NAS | PMID: 10982892 |
| | DRBP1 HUMAN | Splice Isoform 1 of Developmentally regulated RNA-binding protein 1, protein from *Homo sapiens* | UniProt | IDA | PMID: 12220514 |
| | DRR1 HUMAN | DRR1 protein, protein from *Homo sapiens* | UniProt | IDA | PMID: 10564580 |
| | DSRAD HUMAN | Splice Isoform 1 of Double-stranded RNA-specific adenosine deaminase, protein from *Homo sapiens* | UniProt | TAS | PMID: 7565688 |
| | DTBP1 HUMAN | Splice Isoform 1 of Dystrobrevin-binding protein 1, protein from *Homo sapiens* | UniProt | ISS | UniProt: Q96EV8 |
| | DUS10 HUMAN | Dual specificity protein phosphatase 10, protein from *Homo sapiens* | UniProt | TAS | PMID: 10391943 |
| | DUS11 HUMAN | Splice Isoform 1 of RNA/RNP complex-1 intereracting phosphatase, protein from *Homo sapiens* | UniProt | TAS | PMID: 9685386 |
| | DUS16 HUMAN | Dual specificity protein phosphatase 16, protein from *Homo sapiens* | UniProt | TAS | PMID: 11489891 |

| Qualifier | Symbol Sequence/GOst | Information | Source | Evidence | Reference |
|---|---|---|---|---|---|
| | DUS21 HUMAN | Dual specificity protein phosphatase 21, protein from *Homo sapiens* | UniProt | IDA | PMID: 12408986 |
| | DUS2 HUMAN | Dual specificity protein phosphatase 2, protein from *Homo sapiens* | UniProt | TAS | PMID: 8107850 |
| | DUS4 HUMAN | Dual specificity protein phosphatase 4, protein from *Homo sapiens* | UniProt | TAS | PMID: 7535768 |
| | DUS9 HUMAN | Dual specificity protein phosphatase 9, protein from *Homo sapiens* | UniProt | TAS | PMID: 9030581 |
| | DUT HUMAN | Splice Isoform DUT-M of Deoxyuridine 5'-triphosphate nucleotidohydrolase, mitochondrial precursor, protein from *Homo sapiens* | UniProt | TAS | PMID: 8631816 |
| | DYR1A HUMAN | Splice Isoform Long of Dual specificity tyrosine-phosphorylation regulated kinase 1A, protein from *Homo sapiens* | UniProt | IDA | PMID: 9748265 |
| | DYR1B HUMAN | Splice Isoform 1 of Dual specificity tyrosine-phosphorylation regulated kinase 1B, protein from *Homo sapiens* | UniProt | TAS | PMID: 9918863 |
| | DZIP1 HUMAN | Splice Isoform 1 of Zinc finger protein DZIP1, protein from *Homo sapiens* | UniProt | IDA | PMID: 15081113 |
| | ECM29 HUMAN | PREDICTED: KIAA0368 protein, protein from *Homo sapiens* | UniProt | IDA | PMID: 15496406 |
| | EDD1 HUMAN | Ubiquitin--protein ligase EDD1, protein from *Homo sapiens* | UniProt | IDA | PMID: 12011095 |
| | EDF1 HUMAN | Splice Isoform 1 of Endothelial differentiation-related factor 1, protein from *Homo sapiens* | UniProt | IDA | PMID: 10567391 |
| | EGF HUMAN | Pro-epidermal growth factor precursor, protein from *Homo sapiens* | UniProt | NR | UniProt: P01133 |
| | EGFR HUMAN | Splice Isoform 1 of Epidermal growth factor receptor precursor, protein from *Homo sapiens* | UniProt | IDA | PMID: 12828935 |
| | EGLN2 HUMAN | Egl nine homolog 2, protein from *Homo sapiens* | UniProt | IDA | PMID: 11850811 |
| | EHD2 HUMAN | Similar to EH-domain containing protein 2, protein from *Homo sapiens* | UniProt | TAS | PMID: 10673336 |
| | EHD3 HUMAN | EH-domain containing protein 3, protein from *Homo sapiens* | UniProt | TAS | PMID: 10673336 |
| | EHD4 HUMAN | EH-domain containing protein 4, protein from *Homo sapiens* | UniProt | TAS | PMID: 10673336 |
| | EHMT1 HUMAN | Splice Isoform 2 of Histone-lysine N-methyltransferase, H3 lysine-9 specific 5, protein from *Homo sapiens* | UniProt | IC | PMID: 12004135 |
| | ELF1 HUMAN | ETS-related transcription factor Elf-1, protein from *Homo sapiens* | UniProt | NAS | UniProt: P32519 |
| | ELF2 HUMAN | Splice Isoform 1 of ETS-related transcription factor Elf-2, protein from *Homo sapiens* | UniProt | IC | PMID: 14970218 |
| | ELL3 HUMAN | RNA polymerase II elongation factor ELL3, protein from *Homo sapiens* | UniProt | IDA | PMID: 10882741 |
| | EMX1 HUMAN | Homeobox protein EMX1, protein from *Homo sapiens* | UniProt | NAS | UniProt: Q04741 |

| Qualifier | Symbol Sequence/GOst | Information | Source | Evidence | Reference |
|---|---|---|---|---|---|
| | EMX2 HUMAN | Homeobox protein EMX2, protein from *Homo sapiens* | UniProt | NAS | UniProt: Q04743 |
| | ENC1 HUMAN | Ectoderm-neural cortex 1 protein, protein from *Homo sapiens* | UniProt | TAS | PMID: 9566959 |
| | ENL HUMAN | ENL protein, protein from *Homo sapiens* | UniProt | TAS | PMID: 8080983 |
| | EP300 HUMAN | E1A-associated protein p300, protein from *Homo sapiens* | UniProt | IDA | PMID: 9194565 |
| | EPC1 HUMAN | Splice Isoform 1 of Enhancer of polycomb homolog 1, protein from *Homo sapiens* | UniProt | IDA | PMID: 10976108 |
| | ERCC2 HUMAN | TFIIH basal transcription factor complex helicase subunit, protein from *Homo sapiens* | UniProt | NAS | UniProt: P18074 |
| | ERCC3 HUMAN | TFIIH basal transcription factor complex helicase XPB subunit, protein from *Homo sapiens* | UniProt | TAS | PMID: 8663148 |
| | ERG HUMAN | Splice Isoform ERG-2 of Transcriptional regulator ERG, protein from *Homo sapiens* | UniProt | TAS | PMID: 8502479 |
| | ERR1 HUMAN | Steroid hormone receptor ERR1, protein from *Homo sapiens* | UniProt | TAS | PMID: 9286700 |
| | ERR3 HUMAN | Splice Isoform 1 of Estrogen-related receptor gamma, protein from *Homo sapiens* | UniProt | ISS | UniProt: P62508 |
| | ESR2 HUMAN | Splice Isoform 1 of Estrogen receptor beta, protein from *Homo sapiens* | UniProt | TAS | PMID: 11181953 |
| | ETV3 HUMAN | Splice Isoform 1 of ETS translocation variant 3, protein from *Homo sapiens* | UniProt | NAS | UniProt: P41162 |
| | ETV4 HUMAN | ETS translocation variant 4, protein from *Homo sapiens* | UniProt | NAS | UniProt: P43268 |
| | ETV7 HUMAN | Splice Isoform B of Transcription factor ETV7, protein from *Homo sapiens* | UniProt | TAS | PMID: 10828014 |
| | EVI1 HUMAN | Splice Isoform 1 of Ecotropic virus integration 1 site protein, protein from *Homo sapiens* | UniProt | NAS | UniProt: Q03112 |
| | EVX2 HUMAN | Homeobox even-skipped homolog protein 2, protein from *Homo sapiens* | UniProt | NAS | UniProt: Q03828 |
| | EXOS2 HUMAN | Exosome complex exonuclease RRP4, protein from *Homo sapiens* | UniProt | TAS | PMID: 8600032 |
| | FA50A HUMAN | Protein FAM50A, protein from *Homo sapiens* | UniProt | TAS | PMID: 9339379 |
| | FAF1 HUMAN | Splice Isoform Long of FAS-associated factor 1, protein from *Homo sapiens* | UniProt | IDA | PMID: 15596450 |
| | FALZ HUMAN | Fetal Alzheimer antigen, protein from *Homo sapiens* | UniProt | IDA | PMID: 10727212 |
| | FANCA HUMAN | Splice Isoform 1 of Fanconi anemia group A protein, protein from *Homo sapiens* | UniProt | TAS | PMID: 9398857 |
| | FANCC HUMAN | Fanconi anemia group C protein, protein from *Homo sapiens* | UniProt | TAS | PMID: 9398857 |
| | FANCE HUMAN | Fanconi anemia group E protein, protein from *Homo sapiens* | UniProt | NAS | PMID: 11001585 |
| | FANCJ HUMAN | Splice Isoform 1 of Fanconi anemia group J protein, protein from *Homo sapiens* | UniProt | NAS | PMID: 11301010 |
| | FGF10 HUMAN | Fibroblast growth factor 10 precursor, protein from *Homo sapiens* | UniProt | IDA | PMID: 11923311 |
| | FHL2 HUMAN | FHL2 isoform 5, protein from *Homo sapiens* | UniProt | TAS | PMID: 9150430 |

| Qualifier | Symbol Sequence/GOst | Information | Source | Evidence | Reference |
|---|---|---|---|---|---|
| | FHOD1 HUMAN | FH1/FH2 domain-containing protein, protein from *Homo sapiens* | UniProt | TAS | PMID: 10352228 |
| | FIBP HUMAN | Splice Isoform Short of Acidic fibroblast growth factor intracellular binding protein, protein from *Homo sapiens* | UniProt | TAS | PMID: 9806903 |
| | FIZ1 HUMAN | Flt3-interacting zinc finger protein 1, protein from *Homo sapiens* | UniProt | ISS | UniProt: Q96SL8 |
| | FMR1 HUMAN | Splice Isoform 6 of Fragile X mental retardation 1 protein, protein from *Homo sapiens* | UniProt | TAS | PMID: 8515814 |
| | FOS HUMAN | Proto-oncogene protein c-fos, protein from *Homo sapiens* | UniProt | TAS | PMID: 9443941 |
| | FOSL1 HUMAN | Fos-related antigen 1, protein from *Homo sapiens* | UniProt | TAS | PMID: 10918580 |
| | FOSL2 HUMAN | Fos-related antigen 2, protein from *Homo sapiens* | UniProt | TAS | PMID: 8954781 |
| | FOXC1 HUMAN | Forkhead box protein C1, protein from *Homo sapiens* | UniProt | NAS | UniProt: Q9BYM1 |
| | FOXD3 HUMAN | Forkhead box protein D3, protein from *Homo sapiens* | UniProt | ISS | UniProt: Q9UJU5 |
| | FOXD4 HUMAN | Forkhead box protein D4, protein from *Homo sapiens* | UniProt | NAS | UniProt: O43638 |
| | FOXE3 HUMAN | Forkhead box protein E3, protein from *Homo sapiens* | UniProt | NAS | UniProt: Q13461 |
| | FOXF1 HUMAN | Forkhead box protein F1, protein from *Homo sapiens* | UniProt | TAS | PMID: 9722567 |
| | FOXF2 HUMAN | Forkhead box protein F2, protein from *Homo sapiens* | UniProt | TAS | PMID: 9722567 |
| | FOXGC HUMAN | Forkhead box protein G1C, protein from *Homo sapiens* | UniProt | NAS | UniProt: Q14488 |
| | FOXI1 HUMAN | Forkhead box I1 isoForm a, protein from *Homo sapiens* | UniProt | NAS | UniProt: Q12951 |
| | FOXJ1 HUMAN | Forkhead box protein J1, protein from *Homo sapiens* | UniProt | TAS | PMID: 9073514 |
| | FOXK2 HUMAN | Splice Isoform 1 of Forkhead box protein K2, protein from *Homo sapiens* | UniProt | TAS | PMID: 1909027 |
| | FOXL1 HUMAN | Forkhead box protein L1, protein from *Homo sapiens* | UniProt | NAS | UniProt: Q12952 |
| | FOXL2 HUMAN | FOXL2, protein from *Homo sapiens* | UniProt | NAS | UniProt: P58012 |
| | FOXN1 HUMAN | Forkhead box protein N1, protein from *Homo sapiens* | UniProt | TAS | PMID: 10767081 |
| | FOXO3 HUMAN | Forkhead box protein O3A, protein from *Homo sapiens* | UniProt | TAS | PMID: 10102273 |
| | FOXO4 HUMAN | Splice Isoform 1 of Putative fork head domain transcription factor AFX1, protein from *Homo sapiens* | UniProt | TAS | PMID: 9010221 |
| | FOXP3 HUMAN | Splice Isoform 1 of Forkhead box protein P3, protein from *Homo sapiens* | UniProt | NAS | UniProt: Q9BZS1 |
| | FREA HUMAN | Forkhead-related transcription factor 10, protein from *Homo sapiens* | UniProt | NAS | UniProt: O43638 |
| | FRK HUMAN | Tyrosine-protein kinase FRK, protein from *Homo sapiens* | UniProt | TAS | PMID: 7696183 |
| | FUBP3 HUMAN | Splice Isoform 2 of Far upstream element-binding protein 3, protein from *Homo sapiens* | UniProt | NAS | PMID: 8940189 |
| | FUS HUMAN | Fus-like protein, protein from *Homo sapiens* | UniProt | TAS | PMID: 8510758 |
| | FUSIP HUMAN | Splice Isoform 1 of FUS-interacting serine-arginine-rich protein 1, protein from *Homo sapiens* | UniProt | ISS | UniProt: Q96P17 |
| | FXL10 HUMAN | Splice Isoform 1 of F-box/LRR-repeat protein 10, protein from *Homo sapiens* | UniProt | IC NAS | PMID: 9774382 PMID: 10799292 |

| Qualifier | Symbol Sequence/GOst | Information | Source | Evidence | Reference |
|---|---|---|---|---|---|
| | FXR2 HUMAN | Fragile X mental retardation syndrome-related protein 2, protein from *Homo sapiens* | UniProt | TAS | PMID: 10888599 |
| | FYB HUMAN | Splice Isoform FYB-120 of FYN-binding protein, protein from *Homo sapiens* | UniProt | TAS | PMID: 9207119 |
| | G10 HUMAN | G10 protein homolog, protein from *Homo sapiens* | UniProt | TAS | PMID: 7841202 |
| | G3BP HUMAN | Ras-GTPase-activating protein binding protein 1, protein from *Homo sapiens* | UniProt | TAS | PMID: 9889278 |
| | GA45A HUMAN | Growth arrest and DNA-damage-inducible protein GADD45 alpha, protein from *Homo sapiens* | UniProt | TAS | PMID: 7798274 |
| | GABP2 HUMAN | Splice Isoform 1 of GA binding protein beta chain, protein from *Homo sapiens* | UniProt | TAS | PMID: 9016666 |
| | GABPA HUMAN | GA binding protein alpha chain, protein from *Homo sapiens* | UniProt | TAS | PMID: 9016666 |
| | GATA1 HUMAN | Splice Isoform 1 of Erythroid transcription factor, protein from *Homo sapiens* | UniProt | TAS | PMID: 2300555 |
| | GATA2 HUMAN | Endothelial transcription factor GATA-2, protein from *Homo sapiens* | UniProt | TAS | PMID: 1370462 |
| | GATA4 HUMAN | Transcription factor GATA-4, protein from *Homo sapiens* | UniProt | NAS | PMID: 12845333 |
| | GCFC HUMAN | Splice Isoform A of GC-rich sequence DNA-binding factor homolog, protein from *Homo sapiens* | UniProt | NAS | UniProt: Q9Y5B6 |
| | GCM1 HUMAN | Chorion-specific transcription factor GCMa, protein from *Homo sapiens* | UniProt | TAS | PMID: 8962155 |
| | GCM2 HUMAN | Chorion-specific transcription factor GCMb, protein from *Homo sapiens* | UniProt | TAS | PMID: 9928992 |
| | GCR HUMAN | Splice Isoform Alpha of Glucocorticoid receptor, protein from *Homo sapiens* | UniProt | TAS | PMID: 9873044 |
| | GLI3 HUMAN | Zinc finger protein GLI3, protein from *Homo sapiens* | UniProt | TAS | PMID: 10077605 |
| | GLI4 HUMAN | Zinc finger protein GLI4, protein from *Homo sapiens* | UniProt | NAS | UniProt: P10075 |
| | GLIS1 HUMAN | Zinc finger protein GLIS1, protein from *Homo sapiens* | UniProt | ISS | UniProt: Q8NBF1 |
| | GLIS3 HUMAN | Zinc finger protein GLIS3, protein from *Homo sapiens* | UniProt | ISS | UniProt: Q8NEA6 |
| | GLRX2 HUMAN | Splice Isoform 1 of Glutaredoxin-2, mitochondrial precursor, protein from *Homo sapiens* | UniProt | IEP | PMID: 11297543 |
| | GMEB1 HUMAN | Splice Isoform 1 of Glucocorticoid modulatory element-binding protein 1, protein from *Homo sapiens* | UniProt | TAS | PMID: 10386584 |
| | GMEB2 HUMAN | Glucocorticoid modulatory element-binding protein 2, protein from *Homo sapiens* | UniProt | TAS | PMID: 10523663 |
| | GNEFR HUMAN | Splice Isoform 2 of Guanine nucleotide exchange factor-related protein, protein from *Homo sapiens* | UniProt | IDA | PMID: 10571079 |
| | GNL3 HUMAN | Splice Isoform 1 of Guanine nucleotide binding protein-like 3, protein from *Homo sapiens* | UniProt | ISS | UniProt: Q9BVP2 |
| | GO45 HUMAN | Splice Isoform 1 of Golgin 45, protein from *Homo sapiens* | UniProt | NAS | PMID: 9129147 |
| | GRAA HUMAN | Granzyme A precursor, protein from *Homo sapiens* | UniProt | TAS | PMID: 11909973 |
| | GRAB HUMAN | Endogenous granzyme B, protein from *Homo sapiens* | UniProt | TAS | PMID: 11909973 |

-continued

| Qualifier | Symbol Sequence/GOst | Information | Source | Evidence | Reference |
|---|---|---|---|---|---|
| | GRLF1 HUMAN | Glucocorticoid receptor DNA bindinG factor 1 isoform b, protein from *Homo sapiens* | UniProt | IC | PMID: 1894621 |
| | GRP78 HUMAN | 78 kDa glucose-regulated protein precursor, protein from *Homo sapiens* | UniProt | IDA | PMID: 12665508 |
| | GSC HUMAN | Homeobox protein goosecoid, protein from *Homo sapiens* | UniProt | NAS | UniProt: P56915 |
| | GT2D1 HUMAN | Splice Isoform 1 of General transcription factor II-I repeat domain-containing protein 1, protein from *Homo sapiens* | UniProt | NAS | PMID: 11438732 |
| | H2AFX HUMAN | Histone H2A.x, protein from *Homo sapiens* | UniProt | IDA | PMID: 15604234 |
| | HAIR HUMAN | Splice Isoform 1 of Hairless protein, protein from *Homo sapiens* | UniProt | IDA NAS | PMID: 11331621 PMID: 9445480 |
| | HASP HUMAN | Splice Isoform 1 of Serine/threonine-protein kinase Haspin, protein from *Homo sapiens* | UniProt | IEP | PMID: 11228240 |
| | HAT1 HUMAN | Histone acetyltransferase type B catalytic subunit, protein from *Homo sapiens* | UniProt | TAS | PMID: 9427644 |
| | HBXAP HUMAN | Remodeling and spacing factoR 1, protein from *Homo sapiens* | UniProt | IDA | PMID: 12972596 |
| | HCC1 HUMAN | Nuclear protein Hcc-1, protein from *Homo sapiens* | UniProt | IDA NAS | PMID: 11788598 PMID: 11356193 |
| | HCFC1 HUMAN | Splice Isoform 1 of Host cell factor, protein from *Homo sapiens* | UniProt | IDA | PMID: 7876203 |
| | HCFC2 HUMAN | Host cell factor 2, protein from *Homo sapiens* | UniProt | IDA | PMID: 10196288 |
| | HDA10 HUMAN | Splice Isoform 1 of Histone deacetylase 10, protein from *Homo sapiens* | UniProt | IDA | PMID: 11861901 |
| | HDA11 HUMAN | Histone deacetylase 11, protein from *Homo sapiens* | UniProt | IDA | PMID: 11948178 |
| | HDAC1 HUMAN | Histone deacetylase 1, protein from *Homo sapiens* | UniProt | TAS | PMID: 12711221 |
| | HDAC2 HUMAN | Histone deacetylase 2, protein from *Homo sapiens* | UniProt | TAS | PMID: 12711221 |
| | HDAC3 HUMAN | Splice Isoform 1 of Histone deacetylase 3, protein from *Homo sapiens* | UniProt | TAS | PMID: 12711221 |
| | HDAC4 HUMAN | Histone deacetylase 4, protein from *Homo sapiens* | UniProt | NAS | UniProt: P56524 |
| | HDAC5 HUMAN | Splice Isoform 1 of Histone deacetylase 5, protein from *Homo sapiens* | UniProt | TAS | PMID: 12711221 |
| | HDAC6 HUMAN | Histone deacetylase 6, protein from *Homo sapiens* | UniProt | NAS | UNIPROT: Q9UBN7 |
| | HDAC7 HUMAN | Histone deacetylase, protein from *Homo sapiens* | UniProt | TAS | PMID: 12711221 |
| | HDAC9 HUMAN | Splice Isoform 1 of Histone deacetylase 9, protein from *Homo sapiens* | UniProt | NAS | UniProt: Q9UKV0 |
| | HDGR3 HUMAN | Hepatoma-derived growth factor-related protein 3, protein from *Homo sapiens* | UniProt | IDA | PMID: 10581169 |
| | HD HUMAN | Huntingtin, protein from *Homo sapiens* | UniProt | TAS | PMID: 9778247 |
| | HELI HUMAN | Splice Isoform 1 of Zinc finger protein Helios, protein from *Homo sapiens* | UniProt | NAS | UniProt: Q9UKS7 |
| | HIC1 HUMAN | Splice Isoform 2 of Hypermethylated in cancer 1 protein, protein from *Homo sapiens* | UniProt | NAS | UniProt: Q14526 |
| | HIC2 HUMAN | Splice Isoform 1 of Hypermethylated in cancer 2 protein, protein from *Homo sapiens* | UniProt | IEP | PMID: 11554746 |
| | HIF1A HUMAN | Hypoxia-inducible factor 1 alpha, protein from *Homo sapiens* | UniProt | IDA | PMID: 15261140 |

| Qualifier | Symbol Sequence/GOst | Information | Source | Evidence | Reference |
|---|---|---|---|---|---|
| | HINT1 HUMAN | Histidine triad nucleotide-binding protein 1, protein from *Homo sapiens* | UniProt | TAS | PMID: 9770345 |
| | HIPK2 HUMAN | Splice Isoform 1 of Homeodomain-interacting protein kinase 2, protein from *Homo sapiens* | UniProt | IDA | PMID: 12220523 |
| | HIPK3 HUMAN | Splice Isoform 1 of Homeodomain-interacting protein kinase 3, protein from *Homo sapiens* | UniProt | IDA | PMID: 11034606 |
| | HIRA HUMAN | Splice Isoform Long of HIRA protein, protein from *Homo sapiens* | UniProt | TAS | PMID: 9710638 |
| | HIRP3 HUMAN | Splice Isoform 1 of HIRA-interacting protein 3, protein from *Homo sapiens* | UniProt | TAS | PMID: 9710638 |
| | HKR1 HUMAN | Krueppel-related zinc finger protein 1, protein from *Homo sapiens* | UniProt | NAS | UniProt: P10072 |
| | HKR2 HUMAN | Krueppel-related zinc finger protein 2, protein from *Homo sapiens* | UniProt | NAS | UniProt: P10073 |
| | HLF HUMAN | Hepatic leukemia factor, protein from *Homo sapiens* | UniProt | TAS | PMID: 1386162 |
| | HLXB9 HUMAN | Homeobox protein HB9, protein from *Homo sapiens* | UniProt | NAS | UniProt: P50219 |
| | HM20B HUMAN | SWI/SNF-related matrix-associated actin-dependent regulator of chromatin subfamily E member 1-related, protein from *Homo sapiens* | UniProt | NAS NAS | UniProt: Q9Y648 UniProt: Q9P0W2 |
| | HM2L1 HUMAN | High mobility group protein 2-like 1, protein from *Homo sapiens* | UniProt | NAS | UniProt: Q9UGU5 |
| | HMG17 HUMAN | Nonhistone chromosomal protein HMG-17, protein from *Homo sapiens* | UniProt | NAS | UniProt: P05204 |
| | HMG1 HUMAN | High mobility group protein 1, protein from *Homo sapiens* | UniProt | TAS | PMID: 16130169 |
| | HMGN3 HUMAN | High mobility group nucleosome binding domain 3, protein from *Homo sapiens* | UniProt | NAS | UniProt: Q15651 |
| | HNF1B HUMAN | Splice Isoform A of Hepatocyte nuclear factor 1-beta, protein from *Homo sapiens* | UniProt | TAS | PMID: 1677179 |
| | HNF3G HUMAN | Hepatocyte nuclear factor 3-gamma, protein from *Homo sapiens* | UniProt | TAS | PMID: 7739897 |
| | HNF4A HUMAN | Hepatocyte nuclear factor 4 alpHa isoform b, protein from *Homo sapiens* | UniProt | TAS | PMID: 9048927 |
| | HNF6 HUMAN | Hepatocyte nuclear factor 6, protein from *Homo sapiens* | UniProt | NAS | UniProt: Q9UBC0 |
| | HNRPD HUMAN | Splice Isoform 1 of Heterogeneous nuclear ribonucleoprotein D0, protein from *Homo sapiens* | UniProt | NAS | PMID: 1433497 |
| | HNRPQ HUMAN | Splice Isoform 1 of Heterogeneous nuclear ribonucleoprotein Q, protein from *Homo sapiens* | UniProt | TAS | PMID: 9847309 |
| | HRX HUMAN | Splice Isoform 1 of Zinc finger protein HRX, protein from *Homo sapiens* | UniProt | IDA | PMID: 11313484 |
| | HS74L HUMAN | Heat shock 70 kDa protein 4L, protein from *Homo sapiens* | UniProt | ISS | UniProt: O95757 |
| | HSBP1 HUMAN | Heat shock factor binding protein 1, protein from *Homo sapiens* | UniProt | TAS | PMID: 9649501 |

-continued

| Qualifier | Symbol Sequence/GOst | Information | Source | Evidence | Reference |
|---|---|---|---|---|---|
| | HSP71 HUMAN | Heat shock 70 kDa protein 1, protein from *Homo sapiens* | UniProt | TAS | PMID: 10205060 |
| | HTRA2 HUMAN | Splice Isoform 1 of Serine protease HTRA2, mitochondrial precursor, protein from *Homo sapiens* | UniProt | TAS | PMID: 10971580 |
| | HUWE1 HUMAN | Splice Isoform 1 of HECT, UBA and WWE domain containing protein 1, protein from *Homo sapiens* | UniProt | ISS | UniProt: Q7Z6Z7 |
| | HXA5 HUMAN | Homeobox protein Hox-A5, protein from *Homo sapiens* | UniProt | NAS | UniProt: P20719 |
| | HXB1 HUMAN | Homeobox protein Hox-B1, protein from *Homo sapiens* | UniProt | NAS | UniProt: P14653 |
| | HXB4 HUMAN | Homeobox protein Hox-B4, protein from *Homo sapiens* | UniProt | NAS | UniProt: P17483 |
| | HXB6 HUMAN | Splice Isoform 1 of Homeobox protein Hox-B6, protein from *Homo sapiens* | UniProt | NAS | UniProt: P17509 |
| | HXB7 HUMAN | Homeobox protein Hox-B7, protein from *Homo sapiens* | UniProt | NAS | PMID: 1678287 |
| | HXB8 HUMAN | Homeobox protein Hox-B8, protein from *Homo sapiens* | UniProt | NAS | UniProt: P17481 |
| | HXB9 HUMAN | Homeobox protein Hox-B9, protein from *Homo sapiens* | UniProt | NAS | UniProt: P17482 |
| | HXC13 HUMAN | Homeobox protein Hox-C13, protein from *Homo sapiens* | UniProt | NAS | UniProt: P31276 |
| | HXC4 HUMAN | Homeobox protein Hox-C4, protein from *Homo sapiens* | UniProt | NAS | UniProt: P09017 |
| | HXC8 HUMAN | Homeobox protein Hox-C8, protein from *Homo sapiens* | UniProt | NAS | UniProt: P31273 |
| | HXD11 HUMAN | Homeobox protein Hox-D11, protein from *Homo sapiens* | UniProt | NAS | UniProt: P31277 |
| | HXD4 HUMAN | Homeobox protein Hox-D4, protein from *Homo sapiens* | UniProt | NAS | UniProt: P09016 |
| | HXD8 HUMAN | Homeobox protein Hox-D8, protein from *Homo sapiens* | UniProt | NAS | PMID: 2568311 |
| | IASPP HUMAN | Splice Isoform 1 of RelA-associated inhibitor, protein from *Homo sapiens* | UniProt | TAS | PMID: 10336463 |
| | IF16 HUMAN | Splice Isoform 2 of Gamma-interferon-inducible protein Ifi-16, protein from *Homo sapiens* | UniProt | IDA | PMID: 7536752 |
| | IF6 HUMAN | Eukaryotic translation initiation factor 6, protein from *Homo sapiens* | UniProt | TAS | PMID: 9374518 |
| | IKBA HUMAN | NF-kappaB inhibitor alpha, protein from *Homo sapiens* | UniProt | IDA | PMID: 7679069 |
| | ILF2 HUMAN | Interleukin enhancer-binding factor 2, protein from *Homo sapiens* | UniProt | IDA | PMID: 7519613 |
| | ILF3 HUMAN | Splice Isoform 1 of Interleukin enhancer-binding factor 3, protein from *Homo sapiens* | UniProt | IDA | PMID: 11739746 |
| | | | | NAS | PMID: 10400669 |
| | IMA2 HUMAN | Importin alpha-2 subunit, protein from *Homo sapiens* | UniProt | TAS | PMID: 9020106 |
| | IMB3 HUMAN | Importin beta-3, protein from *Homo sapiens* | UniProt | TAS | PMID: 9114010 |
| | IMUP HUMAN | Similar to Immortalization-upregulated protein, protein from *Homo sapiens* | UniProt | TAS | PMID: 11080599 |
| | IN35 HUMAN | Splice Isoform 1 of Interferon-induced 35 kDa protein, protein from *Homo sapiens* | UniProt | IDA | PMID: 8288566 |
| | ING1 HUMAN | Splice Isoform 1 of Inhibitor of growth protein 1, protein from *Homo sapiens* | UniProt | NAS | PMID: 10866301 |
| | ING2 HUMAN | Inhibitor of growth protein 2, protein from *Homo sapiens* | UniProt | IEP | PMID: 15243141 |
| | ING4 HUMAN | Splice Isoform 1 of Inhibitor of growth protein 4, protein from *Homo sapiens* | UniProt | IDA | PMID: 15029197 |

| Qualifier | Symbol Sequence/GOst | Information | Source | Evidence | Reference |
|---|---|---|---|---|---|
| | IP6K1 HUMAN | Inositol hexaphosphate kinase 1, protein from *Homo sapiens* | UniProt | TAS | PMID: 11502751 |
| | IP6K2 HUMAN | Splice Isoform 1 of Inositol hexakisphosphate kinase 2, protein from *Homo sapiens* | UniProt | ISS | UniProt: Q9UHH9 |
| | IP6K3 HUMAN | Inositol hexaphosphate kinase 3, protein from *Homo sapiens* | UniProt | IDA | PMID: 11502751 |
| | | | | ISS | UniProt: Q96PC2 |
| | IRF4 HUMAN | Splice Isoform 1 of Interferon regulatory factor 4, protein from *Homo sapiens* | UniProt | IC | PMID: 12374808 |
| | IRF7 HUMAN | Splice Isoform A of Interferon regulatory factor 7, protein from *Homo sapiens* | UniProt | ISS | UniProt: Q92985 |
| | IRS1 HUMAN | Insulin receptor substrate 1, protein from *Homo sapiens* | UniProt | ISS | UniProt: P35568 |
| | IRTF HUMAN | Transcriptional regulator ISGF3 gamma subunit, protein from *Homo sapiens* | UniProt | TAS | PMID: 1630447 |
| | ITF2 HUMAN | Splice Isoform SEF2-1B of Transcription factor 4, protein from *Homo sapiens* | UniProt | TAS | PMID: 1681116 |
| | JAD1A HUMAN | Jumonji/ARID domain-containing protein 1A, protein from *Homo sapiens* | UniProt | TAS | PMID: 8414517 |
| | JERKL HUMAN | Jerky homolog-like, protein from *Homo sapiens* | UniProt | TAS | PMID: 9240447 |
| | KCY HUMAN | UMP-CMP kinase, protein from *Homo sapiens* | UniProt | TAS | PMID: 10462544 |
| | KIF22 HUMAN | Kinesin-like protein KIF22, protein from *Homo sapiens* | UniProt | TAS | PMID: 8599929 |
| | KLF10 HUMAN | Transforming growth factor-beta-inducible early growth response protein 1, protein from *Homo sapiens* | UniProt | TAS | PMID: 9748269 |
| | KLF11 HUMAN | Transforming growth factor-beta-inducible early growth response protein 2, protein from *Homo sapiens* | UniProt | TAS | PMID: 9748269 |
| | KLF2 HUMAN | Kruppel-like factor 2, protein from *Homo sapiens* | UniProt | NAS | UniProt: Q9Y5W3 |
| | KLF4 HUMAN | Kruppel-like factor 4, protein from *Homo sapiens* | UniProt | ISS | PMID: 9422764 |
| | KLF6 HUMAN | Splice Isoform 1 of Core promoter element-binding protein, protein from *Homo sapiens* | UniProt | TAS | PMID: 9689109 |
| | KNTC1 HUMAN | Kinetochore-associated protein 1, protein from *Homo sapiens* | UniProt | NAS | PMID: 11146660 |
| | KPCI HUMAN | Protein kinase C, iota type, protein from *Homo sapiens* | UniProt | ISS | UniProt: P41743 |
| | KR18 HUMAN | Zinc finger protein Kr18, protein from *Homo sapiens* | UniProt | NAS | UniProt: Q9HCG1 |
| | KS6A2 HUMAN | Ribosomal protein S6 kinase alpha 2, protein from *Homo sapiens* | UniProt | TAS | PMID: 7623830 |
| | KS6A4 HUMAN | Ribosomal protein S6 kinase alpha 4, protein from *Homo sapiens* | UniProt | IEP | PMID: 9792677 |
| | | | | ISS | UniProt: O75585 |
| | | | | IDA | PMID: 11035004 |
| | KS6A5 HUMAN | Ribosomal protein S6 kinase alpha 5, protein from *Homo sapiens* | UniProt | IEP | PMID: 9687510 |
| | KU70 HUMAN | ATP-dependent DNA helicase II, 70 kDa subunit, protein from *Homo sapiens* | UniProt | TAS | PMID: 10508516 |
| | KU86 HUMAN | ATP-dependent DNA helicase II 80 kDa subunit, protein from *Homo sapiens* | UniProt | TAS | PMID: 7957065 |
| | LANC2 HUMAN | LanC-like protein 2, protein from *Homo sapiens* | UniProt | IDA | PMID: 12566319 |

-continued

| Qualifier | Symbol Sequence/GOst | Information | Source | Evidence | Reference |
|---|---|---|---|---|---|
| | LAP2 HUMAN | Splice Isoform 1 of LAP2 protein, protein from *Homo sapiens* | UniProt | ISS | PMID: 11375975 |
| | | | | IDA | PMID: 11375975 |
| | LATS2 HUMAN | Serine/threonine-protein kinase LATS2, protein from *Homo sapiens* | UniProt | NAS | PMID: 10673337 |
| | LDOC1 HUMAN | Protein LDOC1, protein from *Homo sapiens* | UniProt | TAS | PMID: 10403563 |
| | LEG3 HUMAN | LGALS3 protein, protein from *Homo sapiens* | UniProt | IDA | PMID: 14961764 |
| | LHX3 HUMAN | Splice Isoform A of LIM/homeobox protein Lhx3, protein from *Homo sapiens* | UniProt | TAS | PMID: 10598593 |
| | LIMK2 HUMAN | Splice Isoform LIMK2a of LIM domain kinase 2, protein from *Homo sapiens* | UniProt | TAS | PMID: 8954941 |
| | LMBL2 HUMAN | Splice Isoform 1 of Lethal(3)malignant brain tumor-like 2 protein, protein from *Homo sapiens* | UniProt | NAS | UniProt: Q969R5 |
| | LMBL3 HUMAN | Splice Isoform 1 of Lethal(3)malignant brain tumor-like 3 protein, protein from *Homo sapiens* | UniProt | NAS | UniProt: Q96JM7 |
| | LMO7 HUMAN | Splice Isoform 3 of LIM domain only protein 7, protein from *Homo sapiens* | UniProt | TAS | PMID: 9826547 |
| | LMX1B HUMAN | Splice Isoform Short of LIM homeobox transcription factor 1 beta, protein from *Homo sapiens* | UniProt | NAS | UniProt: O60663 |
| | | | | IDA | PMID: 10767331 |
| | LPIN1 HUMAN | Lipin-1, protein from *Homo sapiens* | UniProt | ISS | PMID: 11138012 |
| | LPPRC HUMAN | 130 kDa leucine-rich protein, protein from *Homo sapiens* | UniProt | IDA | PMID: 12832482 |
| | | | | ISS | UniProt: P42704 |
| | LSM1 HUMAN | U6 snRNA-associated Sm-like protein LSm1, protein from *Homo sapiens* | UniProt | TAS | PMID: 10369684 |
| | LSM2 HUMAN | U6 snRNA-associated Sm-like protein LSm2, protein from *Homo sapiens* | UniProt | NAS | UniProt: Q9Y333 |
| | LSM3 HUMAN | U6 snRNA-associated Sm-like protein LSm3, protein from *Homo sapiens* | UniProt | TAS | PMID: 10369684 |
| | LSM5 HUMAN | U6 snRNA-associated Sm-like protein LSm5, protein from *Homo sapiens* | UniProt | TAS | PMID: 10369684 |
| | LSM7 HUMAN | U6 snRNA-associated Sm-like protein LSm7, protein from *Homo sapiens* | UniProt | NAS | UNIPROT: Q9UK45 |
| | LSM8 HUMAN | U6 snRNA-associated Sm-like protein LSm8, protein from *Homo sapiens* | UniProt | NAS | UniProt: O95777 |
| | LZTS1 HUMAN | Leucine zipper, putative tumor suppressor 1, protein from *Homo sapiens* | UniProt | NAS | UniProt: Q9Y5V7 |
| | | | | NAS | UniProt: Q9Y5W2 |
| | | | | NAS | UniProt: Q9Y5W1 |
| | | | | NAS | UniProt: Q9Y5W0 |
| | | | | NAS | UniProt: Q9Y5V8 |
| | MAD HUMAN | MAD protein, protein from *Homo sapiens* | UniProt | TAS | PMID: 8425218 |
| | MAFB HUMAN | Transcription factor MafB, protein from *Homo sapiens* | UniProt | TAS | PMID: 8001130 |
| | MAGC2 HUMAN | Melanoma-associated antigen C2, protein from *Homo sapiens* | UniProt | IDA | PMID: 12920247 |
| | MAGE1 HUMAN | Melanoma-associated antigen E1, protein from *Homo sapiens* | UniProt | ISS | PMID: 14623885 |
| | MAML1 HUMAN | Mastermind-like protein 1, protein from *Homo sapiens* | UniProt | IDA | PMID: 11101851 |
| | MAML2 HUMAN | MasterMind-like 2, protein from *Homo sapiens* | UniProt | IDA | PMID: 12370315 |

| Qualifier | Symbol Sequence/GOst | Information | Source | Evidence | Reference |
|---|---|---|---|---|---|
| | MAML3 HUMAN | MasterMind-like 3, protein from *Homo sapiens* | UniProt | IDA | PMID: 12370315 |
| | MAPK2 HUMAN | Splice Isoform 1 of MAP kinase-activated protein kinase 2, protein from *Homo sapiens* | UniProt | TAS | PMID: 8280084 |
| | MAPK3 HUMAN | MAP kinase-activated protein kinase 3, protein from *Homo sapiens* | UniProt | TAS | PMID: 10781029 |
| | MBB1A HUMAN | Splice Isoform 1 of Myb-binding protein 1A, protein from *Homo sapiens* | UniProt | ISS | UniProt: Q9BQG0 |
| | MBD1 HUMAN | Splice Isoform 1 of Methyl-CpG-binding domain protein 1, protein from *Homo sapiens* | UniProt | NAS | PMID: 10454587 |
| | MBD2 HUMAN | Splice Isoform 1 of Methyl-CpG-binding domain protein 2, protein from *Homo sapiens* | UniProt | NAS | PMID: 10441743 |
| | MBD4 HUMAN | Splice Isoform 1 of Methyl-CpG-binding domain protein 4, protein from *Homo sapiens* | UniProt | TAS | PMID: 9774669 |
| | MBNL HUMAN | Splice Isoform EXP35 of Muscleblind-like protein, protein from *Homo sapiens* | UniProt | IDA | PMID: 10970838 |
| | MCA3 HUMAN | Eukaryotic translation elongation factor 1 epsilon-1, protein from *Homo sapiens* | UniProt | ISS | UniProt: O43324 |
| | MCE1 HUMAN | Splice Isoform 1 of mRNA capping enzyme, protein from *Homo sapiens* | UniProt | TAS | PMID: 9473487 |
| | MCM2 HUMAN | DNA replication licensing factor MCM2, protein from *Homo sapiens* | UniProt | TAS | PMID: 8175912 |
| | MCM3A HUMAN | 80 kda MCM3-associated protein, protein from *Homo sapiens* | UniProt | TAS | PMID: 9712829 |
| | MCM4 HUMAN | DNA replication licensing factor MCM4, protein from *Homo sapiens* | UniProt | NAS | PMID: 8265339 |
| | MCM5 HUMAN | DNA replication licensing factor MCM5, protein from *Homo sapiens* | UniProt | TAS | PMID: 8751386 |
| | MCM6 HUMAN | DNA replication licensing factor MCM6, protein from *Homo sapiens* | UniProt | NAS | PMID: 9286856 |
| | MD2BP HUMAN | MAD2L1 binding protein, protein from *Homo sapiens* | UniProt | IDA | PMID: 10942595 |
| | MDC1 HUMAN | Splice Isoform 1 of Mediator of DNA damage checkpoint protein 1, protein from *Homo sapiens* | UniProt | IDA | PMID: 15604234 |
| | MDM4 HUMAN | Mdm4 protein, protein from *Homo sapiens* | UniProt | NAS | PMID: 9226370 |
| | MDN1 HUMAN | Midasin, protein from *Homo sapiens* | UniProt | NAS | PMID: 12102729 |
| | MECP HUMAN | Methyl-CpG-binding protein 2, protein from *Homo sapiens* | UniProt | TAS | PMID: 10773092 |
| | MECT1 HUMAN | Splice Isoform 1 of Mucoepidermoid carcinoma translocated protein 1, protein from *Homo sapiens* | UniProt | IDA | PMID: 14506290 |
| | MED12 HUMAN | Mediator of RNA polymerase II transcription subunit 12, protein from *Homo sapiens* | UniProt | IDA | PMID: 10235267 |
| | MED4 HUMAN | Mediator complex subunit 4, protein from *Homo sapiens* | UniProt | IDA | PMID: 10235267 |
| | MED6 HUMAN | RNA polymerase transcriptional regulation mediator, subunit 6 homolog, protein from *Homo sapiens* | UniProt | TAS | PMID: 10024883 |

| Qualifier | Symbol Sequence/GOst | Information | Source | Evidence | Reference |
|---|---|---|---|---|---|
| | MEF2A HUMAN | Splice Isoform MEF2 of Myocyte-specific enhancer factor 2A, protein from *Homo sapiens* | UniProt | TAS | PMID: 1516833 |
| | MEF2B HUMAN | Myocyte-specific enhancer factor 2B, protein from *Homo sapiens* | UniProt | TAS | PMID: 1516833 |
| | MEFV HUMAN | Splice Isoform 1 of Pyrin, protein from *Homo sapiens* | UniProt | IDA | PMID: 11115844 |
| | MEN1 HUMAN | Splice Isoform 1 of Menin, protein from *Homo sapiens* | UniProt | IDA | PMID: 15199122 |
| | MERL HUMAN | Splice Isoform 1 of Merlin, protein from *Homo sapiens* | UniProt | IDA | PMID: 10401006 |
| | MGMT HUMAN | Methylated-DNA--protein-cysteine methyltransferase, protein from *Homo sapiens* | UniProt | TAS | PMID: 2188979 |
| | MGN HUMAN | Mago nashi protein homolog, protein from *Homo sapiens* | UniProt | NAS | UniProt: P61326 |
| | MITF HUMAN | Splice Isoform A2 of Microphthalmia-associated transcription factor, protein from *Homo sapiens* | UniProt | NAS | PMID: 9647758 |
| | | | | NAS | PMID: 10578055 |
| | MK14 HUMAN | Mitogen-activated protein kinase 14 isoforM 2, protein from *Homo sapiens* | UniProt | ISS | UniProt: Q16539 |
| | MKL2 HUMAN | Splice Isoform 1 of MKL/myocardin-like protein 2, protein from *Homo sapiens* | UniProt | IC | PMID: 14565952 |
| | MLH3 HUMAN | Splice Isoform 1 of DNA mismatch repair protein Mlh3, protein from *Homo sapiens* | UniProt | TAS | PMID: 10615123 |
| | MLL2 HUMAN | Splice Isoform 1 of Myeloid/lymphoid or mixed-lineage leukemia protein 2, protein from *Homo sapiens* | UniProt | NAS | PMID: 9247308 |
| | MLL4 HUMAN | Splice Isoform 1 of Myeloid/lymphoid or mixed-lineage leukemia protein 4, protein from *Homo sapiens* | UniProt | NAS | UniProt: Q9UMN6 |
| | MLX HUMAN | Splice Isoform Gamma of MAx-like protein X, protein from *Homo sapiens* | UniProt | IDA | PMID: 10918583 |
| | MLZE HUMAN | Melanoma-derived leucine zipper-containing extranuclear factor, protein from *Homo sapiens* | UniProt | NAS | PMID: 11223543 |
| | MO4L1 HUMAN | Similar to Testis expressed gene 189, protein from *Homo sapiens* | UniProt | NAS | UniProt: Q9UBU8 |
| | MO4L2 HUMAN | Mortality factor 4-like protein 2, protein from *Homo sapiens* | UniProt | NAS | UniProt: Q15014 |
| | MOL1A HUMAN | Mps one binder kinase activator-like 1A, protein from *Homo sapiens* | UniProt | IDA | PMID: 15067004 |
| | MOS1A HUMAN | Splice Isoform 1 of Molybdenum cofactor biosynthesis protein 1 A, protein from *Homo sapiens* | UniProt | NAS | PMID: 9731530 |
| | MPP8 HUMAN | M-phase phosphoprotein 8, protein from *Homo sapiens* | UniProt | IDA | PMID: 8885239 |
| | MRE11 HUMAN | Splice Isoform 1 of Double-strand break repair protein MRE11A, protein from *Homo sapiens* | UniProt | TAS | PMID: 10802669 |
| | MS3L1 HUMAN | Splice Isoform 1 of Male-specific lethal 3-like 1, protein from *Homo sapiens* | UniProt | TAS | PMID: 10395802 |

| Qualifier | Symbol Sequence/GOst | Information | Source | Evidence | Reference |
|---|---|---|---|---|---|
| | MSH2 HUMAN | DNA mismatch repair protein Msh2, protein from *Homo sapiens* | UniProt | NAS | PMID: 7923193 |
| | MSH4 HUMAN | MutS protein homolog 4, protein from *Homo sapiens* | UniProt | TAS | PMID: 9299235 |
| | MSMB HUMAN | Splice Isoform PSP94 of Beta-microseminoprotein precursor, protein from *Homo sapiens* | UniProt | TAS | PMID: 7566962 |
| | MTA70 HUMAN | Splice Isoform 1 of N6-adenosine-methyltransferase 70 kDa subunit, protein from *Homo sapiens* | UniProt | IDA | PMID: 9409616 |
| | MTF1 HUMAN | Metal-regulatory transcription factor 1, protein from *Homo sapiens* | UniProt | TAS | PMID: 3208749 |
| | MTMR2 HUMAN | Myotubularin-related protein 2, protein from *Homo sapiens* | UniProt | IDA | PMID: 12837694 |
| | MUSC HUMAN | Musculin, protein from *Homo sapiens* | UniProt | TAS | PMID: 9584154 |
| | MUTYH HUMAN | Splice Isoform Alpha-1 of A/G-specific adenine DNA glycosylase, protein from *Homo sapiens* | UniProt | TAS | PMID: 7823963 |
| | MVP HUMAN | Major vault protein, protein from *Homo sapiens* | UniProt | TAS | PMID: 7585126 |
| | MX2 HUMAN | Interferon-induced GTP-binding protein Mx2, protein from *Homo sapiens* | UniProt | TAS | PMID: 8798556 |
| | MXI1 HUMAN | Splice Isoform 1 of MAX interacting protein 1, protein from *Homo sapiens* | UniProt | TAS | PMID: 8425219 |
| | MYBA HUMAN | Myb-related protein A, protein from *Homo sapiens* | UniProt | NAS | PMID: 8058310 |
| | MYC HUMAN | Myc proto-oncogene protein, protein from *Homo sapiens* | UniProt | IDA | PMID: 15994933 |
| | MYCBP HUMAN | C-Myc binding protein, protein from *Homo sapiens* | UniProt | TAS | PMID: 9797456 |
| | MYCN HUMAN | N-myc proto-oncogene protein, protein from *Homo sapiens* | UniProt | TAS | PMID: 3796607 |
| | MYF6 HUMAN | Myogenic factor 6, protein from *Homo sapiens* | UniProt | TAS | PMID: 2311584 |
| | MYOD1 HUMAN | Myoblast determination protein 1, protein from *Homo sapiens* | UniProt | TAS | PMID: 3175662 |
| | MYST2 HUMAN | Histone acetyltransferase MYST2, protein from *Homo sapiens* | UniProt | TAS | PMID: 10438470 |
| | MYT1 HUMAN | Myelin transcription factor 1, protein from *Homo sapiens* | UniProt | NAS | PMID: 1280325 |
| | NAB1 HUMAN | Splice Isoform Long of NGFI-A binding protein 1, protein from *Homo sapiens* | UniProt | NAS | PMID: 8668170 |
| | NARG1 HUMAN | Splice Isoform 1 of NMDA receptor regulated protein 1, protein from *Homo sapiens* | UniProt | IDA | PMID: 12145306 |
| | NARGL HUMAN | Splice Isoform 1 of NMDA receptor regulated 1-like protein, protein from *Homo sapiens* | UniProt | IDA ISS | PMID: 12140756 UniProt: Q6N069 |
| | NASP HUMAN | Splice Isoform 1 of Nuclear autoantigenic sperm protein, protein from *Homo sapiens* | UniProt | TAS | PMID: 1426632 |
| | NCBP2 HUMAN | Nuclear cap binding protein subunit 2, protein from *Homo sapiens* | UniProt | NAS | PMID: 7651522 |
| | NCOA1 HUMAN | Splice Isoform 1 of Nuclear receptor coactivator 1, protein from *Homo sapiens* | UniProt | TAS | PMID: 9223431 |
| | NCOA2 HUMAN | Nuclear receptor coactivator 2, protein from *Homo sapiens* | UniProt | NAS | UniProt: Q15596 |

| Qualifier | Symbol Sequence/GOst | Information | Source | Evidence | Reference |
|---|---|---|---|---|---|
| | NCOA3 HUMAN | Splice Isoform 1 of Nuclear receptor coactivator 3, protein from *Homo sapiens* | UniProt | NAS | PMID: 97410321 |
| | | | | NAS | UniProt: Q9UPC9 |
| | NCOA4 HUMAN | Splice Isoform Alpha of Nuclear receptor coactivator 4, protein from *Homo sapiens* | UniProt | TAS | PMID: 8643607 |
| | NCOA6 HUMAN | Nuclear receptor coactivator 6, protein from *Homo sapiens* | UniProt | IDA | PMID: 11443112 |
| | | | | NAS | PMID: 10567404 |
| | NCOR2 HUMAN | Nuclear receptor co-repressor 2, protein from *Homo sapiens* | UniProt | TAS | PMID: 10097068 |
| | NDKA HUMAN | Nucleoside diphosphate kinase A, protein from *Homo sapiens* | UniProt | NAS | UniProt: P15531 |
| | | | | TAS | PMID: 16130169 |
| | NDKB HUMAN | Nucleoside diphosphate kinase B, protein from *Homo sapiens* | UniProt | NAS | UniProt: P22392 |
| | NEDD8 HUMAN | NEDD8 precursor, protein from *Homo sapiens* | UniProt | TAS | PMID: 9353319 |
| | NEK1 HUMAN | Splice Isoform 1 of Serine/threonine-protein kinase Nek1, protein from *Homo sapiens* | UniProt | IDA | PMID: 15604234 |
| | NEK3 HUMAN | Serine/threonine-protein kinase Nek3, protein from *Homo sapiens* | UniProt | NAS | PMID: 7522034 |
| | NELFE HUMAN | Splice Isoform 1 of Negative elongation factor E, protein from *Homo sapiens* | UniProt | NAS | PMID: 2119325 |
| | NFAC2 HUMAN | Splice Isoform C of Nuclear factor of activated T-cells, cytoplasmic 2, protein from *Homo sapiens* | UniProt | TAS | PMID: 8668213 |
| | NFAT5 HUMAN | Splice Isoform C of Nuclear factor of activated T cells 5, protein from *Homo sapiens* | UniProt | TAS | PMID: 10051678 |
| | NFE2 HUMAN | Transcription factor NF-E2 45 kDa subunit, protein from *Homo sapiens* | UniProt | TAS | PMID: 7774011 |
| | NFIA HUMAN | Nuclear factor 1 A-type, protein from *Homo sapiens* | UniProt | NAS | PMID: 7590749 |
| | NFIB HUMAN | Splice Isoform 1 of Nuclear factor 1 B-type, protein from *Homo sapiens* | UniProt | TAS | PMID: 7590749 |
| | NFKB2 HUMAN | Splice Isoform 1 of Nuclear factor NF-kappa-B p100 subunit, protein from *Homo sapiens* | UniProt | IDA | PMID: 15677444 |
| | NFS1 HUMAN | Cysteine desulfurase, mitochondrial precursor, protein from *Homo sapiens* | UniProt | TAS | PMID: 9885568 |
| | NFYA HUMAN | Splice Isoform Long of Nuclear transcription factor Y subunit alpha, protein from *Homo sapiens* | UniProt | IDA | PMID: 15243141 |
| | NFYB HUMAN | Nuclear transcription factor Y subunit beta, protein from *Homo sapiens* | UniProt | IEP | PMID: 15243141 |
| | NFYC HUMAN | Splice Isoform 3 of Nuclear transcription factor Y subunit gamma, protein from *Homo sapiens* | UniProt | IEP | PMID: 15243141 |
| | NHRF2 HUMAN | Splice Isoform 1 of Na(+)/H(+) exchange regulatory cofactor NHE-RF2, protein from *Homo sapiens* | UniProt | TAS | PMID: 9054412 |
| | NKRF HUMAN | NF-kappa-B-repressing factor, protein from *Homo sapiens* | UniProt | IDA | PMID: 10562553 |
| | NKX31 HUMAN | Splice Isoform 1 of Homeobox protein Nkx-3.1, protein from *Homo sapiens* | UniProt | NAS | PMID: 11137288 |
| | NLK HUMAN | Serine/threonine kinase NLK, protein from *Homo sapiens* | UniProt | ISS | UniProt: Q9UBE8 |

| Qualifier | Symbol Sequence/GOst | Information | Source | Evidence | Reference |
|---|---|---|---|---|---|
| | NMES1 HUMAN | Normal mucosa of esophagus-specific gene 1 protein, protein from *Homo sapiens* | UniProt | IDA | PMID: 12209954 |
| | NMNA1 HUMAN | Nicotinamide mononucleotide adenylyltransferase 1, protein from *Homo sapiens* | UniProt | IDA | PMID: 11248244 |
| | NNP1 HUMAN | NNP-1 protein, protein from *Homo sapiens* | UniProt | TAS | PMID: 9192856 |
| | NOCT HUMAN | Nocturnin, protein from *Homo sapiens* | UniProt | TAS | PMID: 10521507 |
| | NOG2 HUMAN | Nucleolar GTP-binding protein 2, protein from *Homo sapiens* | UniProt | TAS | PMID: 8822211 |
| | NONO HUMAN | Non-POU domain-containing octamer-binding protein, protein from *Homo sapiens* | UniProt | TAS | PMID: 9360842 |
| | NOTC1 HUMAN | Neurogenic locus notch homolog protein 1 precursor, protein from *Homo sapiens* | UniProt | TAS | PMID: 10713164 |
| | NOTC2 HUMAN | Neurogenic locus notch homolog protein 2 precursor, protein from *Homo sapiens* | UniProt | IDA | PMID: 1303260 |
| | NOTC4 HUMAN | Splice Isoform 1 of Neurogenic locus notch homolog protein 4 precursor, protein from *Homo sapiens* | UniProt | TAS | PMID: 8681805 |
| | NP1L2 HUMAN | Nucleosome assembly protein 1-like 2, protein from *Homo sapiens* | UniProt | TAS | PMID: 8789438 |
| | NPM2 HUMAN | Nucleoplasmin-2, protein from *Homo sapiens* | UniProt | IEP | PMID: 12714744 |
| | NPM HUMAN | Nucleophosmin, protein from *Homo sapiens* | UniProt | IDA | PMID: 12080348 |
| | | | | TAS | PMID: 16130169 |
| | NR1D1 HUMAN | Orphan nuclear receptor NR1D1, protein from *Homo sapiens* | UniProt | TAS | PMID: 8622974 |
| | NR1D2 HUMAN | Orphan nuclear receptor NR1D2, protein from *Homo sapiens* | UniProt | TAS | PMID: 7997240 |
| | NR1H2 HUMAN | Oxysterols receptor LXR-beta, protein from *Homo sapiens* | UniProt | TAS | PMID: 7926814 |
| | NR1H3 HUMAN | Splice Isoform 1 of Oxysterols receptor LXR-alpha, protein from *Homo sapiens* | UniProt | TAS | PMID: 7744246 |
| | NR2E3 HUMAN | Splice Isoform Long of Photoreceptor-specific nuclear receptor, protein from *Homo sapiens* | UniProt | TAS | PMID: 10220376 |
| | NR4A2 HUMAN | Orphan nuclear receptor NR4A2, protein from *Homo sapiens* | UniProt | TAS | PMID: 7877627 |
| | NR4A3 HUMAN | Nuclear receptor subfamily 4, group A, member 3 isoform b, protein from *Homo sapiens* | UniProt | NAS | PMID: 8634690 |
| | NR5A2 HUMAN | Splice Isoform 2 of Orphan nuclear receptor NR5A2, protein from *Homo sapiens* | UniProt | TAS | PMID: 9786908 |
| | NRIF3 HUMAN | Splice Isoform 2 of Nuclear receptor-interacting factor 3, protein from *Homo sapiens* | UniProt | TAS | PMID: 10490654 |
| | NRIP1 HUMAN | Nuclear receptor-interacting protein 1, protein from *Homo sapiens* | UniProt | IDA | PMID: 7641693 |
| | | | | IDA | PMID: 12773562 |
| | | | | IDA | PMID: 11266503 |
| | NRL HUMAN | Neural retina-specific leucine zipper protein, protein from *Homo sapiens* | UniProt | TAS | PMID: 8939891 |

| Qualifier | Symbol Sequence/GOst | Information | Source | Evidence | Reference |
|---|---|---|---|---|---|
| | NSBP1 HUMAN | Nucleosomal binding protein 1, protein from *Homo sapiens* | UniProt | NAS | PMID: 11161810 |
| | NSG1 HUMAN | Neuron-specific protein family member 1, protein from *Homo sapiens* | UniProt | TAS | PMID: 9013775 |
| | NT5C HUMAN | Splice Isoform 1 of 5'(3')-deoxyribonucleotidase, cytosolic type, protein from *Homo sapiens* | UniProt | TAS | PMID: 10702291 |
| | NTHL1 HUMAN | Endonuclease III-like protein 1, protein from *Homo sapiens* | UniProt | IDA | PMID: 12531031 |
| | NUMA1 HUMAN | Splice Isoform 1 of Nuclear mitotic apparatus protein 1, protein from *Homo sapiens* | UniProt | TAS | PMID: 1541636 |
| | NUPL2 HUMAN | Splice Isoform 1 of Nucleoporin-like 2, protein from *Homo sapiens* | UniProt | TAS | PMID: 10358091 |
| | NUPR1 HUMAN | Nuclear protein 1, protein from *Homo sapiens* | UniProt | IDA | PMID: 10092851 |
| | NVL HUMAN | Splice Isoform 1 of Nuclear valosin-containing protein-like, protein from *Homo sapiens* | UniProt | TAS | PMID: 9286697 |
| | NXF2 HUMAN | Nuclear RNA export factor 2, protein from *Homo sapiens* | UniProt | ISS | UniProt: Q9GZY0 |
| | NXF3 HUMAN | Nuclear RNA export factor 3, protein from *Homo sapiens* | UniProt | IDA | PMID: 11545741 |
| | NXF5 HUMAN | Splice Isoform A of Nuclear RNA export factor 5, protein from *Homo sapiens* | UniProt | IDA | PMID: 11566096 |
| | O00290 | Adenovirus E3-14.7K interacting protein 1, protein from *Homo sapiens* | UniProt | IDA | PMID: 11073942 |
| | O00366 | Putative p150, protein from *Homo sapiens* | UniProt | ISS | UniProt: O00366 |
| | O14777 | Retinoblastoma-associated protein HEC, protein from *Homo sapiens* | UniProt | TAS | PMID: 9315664 |
| | O14789 | Testis-specific BRDT protein, protein from *Homo sapiens* | UniProt | TAS | PMID: 9367677 |
| | O15125 | Alternative spliced form of p15 CDK inhibitor, protein from *Homo sapiens* | UniProt | IDA | PMID: 9230210 |
| | O15150 | Cerebrin-50, protein from *Homo sapiens* | UniProt | TAS | PMID: 9373037 |
| | O15183 | Trinucleotide repeat DNA binding protein p20-CGGBP, protein from *Homo sapiens* | UniProt | TAS | PMID: 8626781 |
| | O15415 | CAGH3, protein from *Homo sapiens* | UniProt | TAS | PMID: 9225980 |
| | O43148 | MRNA (Guanine-7-) methyltransferase, protein from *Homo sapiens* | UniProt | TAS | PMID: 9705270 |
| | O43245 | Protein p65, protein from *Homo sapiens* | UniProt | NAS | PMID: 8706045 |
| | O43663 | Protein regulating cytokinesis 1, protein from *Homo sapiens* | UniProt | TAS | PMID: 9885575 |
| | O43719 | HIV TAT specific factor 1, protein from *Homo sapiens* | UniProt | TAS | PMID: 10454543 |
| | O43809 | Pre-mRNA cleavage factor I 25 kDa subunit, protein from *Homo sapiens* | UniProt | TAS | PMID: 9659921 |
| | O43812 | Homeobox protein DUX3, protein from *Homo sapiens* | UniProt | TAS | PMID: 9736770 |
| | O60519 | Cre binding protein-like 2, protein from *Homo sapiens* | UniProt | TAS | PMID: 9693048 |
| | O60592 | Arg/Abl-interacting protein ArgBP2a, protein from *Homo sapiens* | UniProt | TAS | PMID: 9211900 |
| | O60593 | SORBS2 protein, protein from *Homo sapiens* | UniProt | NAS | PMID: 9211900 |
| | O60671 | Cell cycle checkpoint protein Hrad1, protein from *Homo sapiens* | UniProt | IC | PMID: 9660799 |
| | O60870 | Kin17 protein, protein from *Homo sapiens* | UniProt | TAS | PMID: 1923796 |

| Qualifier | Symbol Sequence/GOst | Information | Source | Evidence | Reference |
|---|---|---|---|---|---|
| | O75525 | T-Star, protein from Homo sapiens | UniProt | TAS | PMID: 10332027 |
| | O75530 | Embryonic ectoderm development protein homolog, protein from Homo sapiens | UniProt | NAS | PMID: 9584199 |
| | O75766 | TRIP protein, protein from Homo sapiens | UniProt | TAS | PMID: 9705290 |
| | O75799 | Transcription repressor, protein from Homo sapiens | UniProt | NAS | PMID: 9705290 |
| | O75805 | HOXA-9A, protein from Homo sapiens | UniProt | NAS | UniProt: O75805 |
| | O75806 | HOXA-9B, protein from Homo sapiens | UniProt | NAS | UniProt: O75806 |
| | O94992 | HEXIM1 protein, protein from Homo sapiens | UniProt | IDA | PMID: 12581153 |
| | O95082 | EH-binding protein, protein from Homo sapiens | UniProt | TAS | PMID: 10644451 |
| | O95133 | SOX-29 protein, protein from Homo sapiens | UniProt | NAS | UniProt: O95133 |
| | O95268 | Origin recognition complex subunit ORC5T, protein from Homo sapiens | UniProt | NAS | PMID: 9765232 |
| | O95273 | D-type cyclin-interacting protein 1, protein from Homo sapiens | UniProt | IDA | PMID: 12437976 |
| | O95391 | Step II splicing factor SLU7, protein from Homo sapiens | UniProt | NR | UNIPROT: O95391 |
| | O95443 | AT rich interactive domain 3B (BRIGHT-like) protein, protein from Homo sapiens | UniProt | NAS | PMID: 10446990 |
| | O95480 | Hypothetical protein, protein from Homo sapiens | UniProt | NAS | UniProt: O95480 |
| | O95926 | Hypothetical protein DKFZp564O2082, protein from Homo sapiens | UniProt | NAS | PMID: 11118353 |
| | OGT1 HUMAN | Splice Isoform 2 of UDP-N-acetylglucosamine--peptide N-acetylglucosaminyltransferase 110 kDa subunit, protein from Homo sapiens | UniProt | TAS | PMID: 9083067 |
| | OI106 HUMAN | Splice Isoform 1 of 106 kDA O-GlcNAc transferase-interacting protein, protein from Homo sapiens | UniProt | ISS | UniProt: Q9UPV9 |
| | ORC1 HUMAN | Origin recognition complex subunit 1, protein from Homo sapiens | UniProt | TAS | PMID: 7502077 |
| | ORC2 HUMAN | Origin recognition complex subunit 2, protein from Homo sapiens | UniProt | TAS | PMID: 8808289 |
| | ORC4 HUMAN | Origin recognition complex subunit 4, protein from Homo sapiens | UniProt | TAS | PMID: 9353276 |
| | ORC5 HUMAN | Origin recognition complex subunit 5, protein from Homo sapiens | UniProt | TAS | PMID: 9765232 |
| | OTX1 HUMAN | Homeobox protein OTX1, protein from Homo sapiens | UniProt | NAS | UniProt: P32242 |
| | OTX2 HUMAN | Homeobox protein OTX2, protein from Homo sapiens | UniProt | NAS | UniProt: P32243 |
| | OVOL1 HUMAN | Putative transcription factor Ovo-like 1, protein from Homo sapiens | UniProt | NAS | UniProt: O14753 |
| | OZF HUMAN | Zinc finger protein OZF, protein from Homo sapiens | UniProt | TAS | PMID: 8665923 |
| | P53 HUMAN | Splice Isoform 1 of Cellular tumor antigen p53, protein from Homo sapiens | UniProt | IDA | PMID: 7720704 |
| | P66A HUMAN | Splice Isoform 1 of Transcriptional repressor p66 alpha, protein from Homo sapiens | UniProt | IDA | PMID: 12183469 |

| Qualifier | Symbol Sequence/GOst | Information | Source | Evidence | Reference |
|---|---|---|---|---|---|
| | P73L HUMAN | Splice Isoform 1 of Tumor protein p73-like, protein from Homo sapiens | UniProt | ISS IDA | UniProt: Q96F28 PMID: 12446779 |
| | P78365 | Polyhomeotic 2 homolog, protein from Homo sapiens | UniProt | TAS | PMID: 9121482 |
| | P80C HUMAN | Coilin, protein from Homo sapiens | UniProt | TAS | PMID: 7971277 |
| | PA2G4 HUMAN | Proliferation-associated protein 2G4, protein from Homo sapiens | UniProt | IDA | PMID: 15073182 |
| | PAPOA HUMAN | Poly(A) Polymerase alPha, protein from Homo sapiens | UniProt | TAS | PMID: 8302877 |
| | PAR6A HUMAN | Splice Isoform 1 of Partitioning defective 6 homolog alpha, protein from Homo sapiens | UniProt | ISS | UniProt: Q9NPB6 |
| | PARK7 HUMAN | Protein DJ-1, protein from Homo sapiens | UniProt | IDA | PMID: 12446870 |
| | PARN HUMAN | Poly(A)-specific ribonuclease PARN, protein from Homo sapiens | UniProt | TAS | PMID: 9736620 |
| | PARP1 HUMAN | Poly [ADP-ribose] polymerase 1, protein from Homo sapiens | UniProt | TAS | PMID: 2513174 |
| | PARP4 HUMAN | Poly [ADP-ribose] polymerase 4, protein from Homo sapiens | UniProt | NAS | PMID: 10644454 |
| | PARP9 HUMAN | Splice Isoform 1 of Poly [ADP-ribose] polymerase 9, protein from Homo sapiens | UniProt | TAS | PMID: 11110709 |
| | PAWR HUMAN | PRKC apoptosis WT1 regulator protein, protein from Homo sapiens | UniProt | NAS | UniProt: Q96IZ0 |
| | PAX8 HUMAN | Splice Isoform 1 of Paired box protein Pax-8, protein from Homo sapiens | UniProt | NAS | UniProt: Q16339 |
| | PAX9 HUMAN | Paired box protein Pax-9, protein from Homo sapiens | UniProt | NAS | UniProt: P55771 |
| | PBX1 HUMAN | Splice Isoform PBX1a of Pre-B-cell leukemia transcription factor 1, protein from Homo sapiens | UniProt | ISS | UniProt: P40424 |
| | PBX3 HUMAN | Splice Isoform PBX3a of Pre-B-cell leukemia transcription factor 3, protein from Homo sapiens | UniProt | ISS | UniProt: P40426 |
| | PBX4 HUMAN | Pre-B-cell leukemia transcriPtion factor 4, protein from Homo sapiens | UniProt | ISS | UniProt: Q9BYU1 |
| | PCAF HUMAN | Histone acetyltransferase PCAF, protein from Homo sapiens | UniProt | TAS | PMID: 10891508 |
| | PCBP1 HUMAN | Poly(rC)-binding protein 1, protein from Homo sapiens | UniProt | NAS | UNIPROT: Q15365 |
| | PCBP2 HUMAN | Poly(rC)-binding protein 2, protein from Homo sapiens | UniProt | NAS | UniProt: Q15366 |
| | PDCD8 HUMAN | Splice Isoform 1 of Programmed cell death protein 8, mitochondrial precursor, protein from Homo sapiens | UniProt | TAS | PMID: 9989411 |
| | PDZK3 HUMAN | Splice Isoform 1 of PDZ domain containing protein 3, protein from Homo sapiens | UniProt | ISS | PMID: 12671685 |
| | PEPP1 HUMAN | Paired-like homeobox protein PEPP-1, protein from Homo sapiens | UniProt | IDA | PMID: 11980563 |
| | PERM HUMAN | Splice Isoform H17 of Myeloperoxidase precursor, protein from Homo sapiens | UniProt | TAS | PMID: 2829220 |
| | PFD5 HUMAN | Prefoldin subunit 5, protein from Homo sapiens | UniProt | TAS | PMID: 9792694 |
| | PFTK1 HUMAN | Splice Isoform 1 of Serine/threonine-protein kinase PFTAIRE-1, protein from Homo sapiens | UniProt | TAS | PMID: 9202329 |

| Qualifier | Symbol Sequence/GOst | Information | Source | Evidence | Reference |
|---|---|---|---|---|---|
| | PGEA1 HUMAN | Chibby protein, protein from *Homo sapiens* | UniProt | IDA | PMID: 12712206 |
| | PGH1 HUMAN | Cyclooxygenase 1b3, protein from *Homo sapiens* | UniProt | ISS | UniProt: P23219 |
| | PGH2 HUMAN | Prostaglandin G/H synthase 2 precursor, protein from *Homo sapiens* | UniProt | ISS | UniProt: P35354 |
| | PHB HUMAN | Prohibitin, protein from *Homo sapiens* | UniProt | TAS | PMID: 16130169 |
| | PHC1 HUMAN | Polyhomeotic-like protein 1, protein from *Homo sapiens* | UniProt | TAS | PMID: 9121482 |
| | PHF12 HUMAN | Splice Isoform 2 of PHD finger protein 12, protein from *Homo sapiens* | UniProt | IDA | PMID: 11390640 |
| | PHF2 HUMAN | PHD finger protein 2, protein from *Homo sapiens* | UniProt | TAS | PMID: 10051327 |
| | PIAS1 HUMAN | Protein inhibitor of activated STAT protein 1, protein from *Homo sapiens* | UniProt | TAS | PMID: 9724754 |
| | PIAS4 HUMAN | Protein inhibitor of activated STAT protein 4, protein from *Homo sapiens* | UniProt | IDA | PMID: 11248056 |
| | | | | NAS | PMID: 9724754 |
| | PIN1 HUMAN | Peptidyl-prolyl cis-trans isomerase NIMA-interacting 1, protein from *Homo sapiens* | UniProt | TAS | PMID: 8606777 |
| | PIR HUMAN | Pirin, protein from *Homo sapiens* | UniProt | TAS | PMID: 9079676 |
| | PKP1 HUMAN | Splice Isoform 2 of Plakophilin-1, protein from *Homo sapiens* | UniProt | NAS | PMID: 9369526 |
| | PKP2 HUMAN | Splice Isoform 2 of Plakophilin-2, protein from *Homo sapiens* | UniProt | NAS | PMID: 8922383 |
| | PLCB1 HUMAN | Splice Isoform A of 1-phosphatidylinositol-4,5-bisphosphate phosphodiesterase beta 1, protein from *Homo sapiens* | UniProt | NAS | PMID: 10760467 |
| | PML HUMAN | Splice Isoform PML-1 of Probable transcription factor PML, protein from *Homo sapiens* | UniProt | IDA | PMID: 9294197 |
| | PMS1 HUMAN | PMS1 protein homolog 1, protein from *Homo sapiens* | UniProt | TAS | PMID: 8072530 |
| | PMS2 HUMAN | Postmeiotic segregation increased 2 nirs variant 2, protein from *Homo sapiens* | UniProt | TAS | PMID: 8072530 |
| | PNKP HUMAN | Bifunctional polynucleotide phosphatase/kinase, protein from *Homo sapiens* | UniProt | IDA | PMID: 10446193 |
| | PNRC1 HUMAN | Proline-rich nuclear receptor coactivator 1, protein from *Homo sapiens* | UniProt | TAS | PMID: 7578250 |
| | PO2F1 HUMAN | Splice Isoform 1 of POU domain, class 2, transcription factor 1, protein from *Homo sapiens* | UniProt | IDA | PMID: 11891224 |
| | PO5FL HUMAN | POU domain, class 5, transcription factor 1-like protein 1, protein from *Homo sapiens* | UniProt | TAS | UniProt: Q06416 |
| | PO6F2 HUMAN | Splice Isoform 1 of POU domain, class 6, transcription factor 2, protein from *Homo sapiens* | UniProt | IC | PMID: 8601806 |
| | POLS HUMAN | DNA polymerase sigma, protein from *Homo sapiens* | UniProt | IDA | PMID: 10066793 |
| | POP7 HUMAN | Ribonuclease P protein subunit p20, protein from *Homo sapiens* | UniProt | TAS | PMID: 9630247 |
| | PP2AA HUMAN | Serine/threonine protein phosphatase 2A, catalytic subunit, alpha isoform, protein from *Homo sapiens* | UniProt | NAS | PMID: 11007961 |

-continued

| Qualifier | Symbol Sequence/GOst | Information | Source | Evidence | Reference |
|---|---|---|---|---|---|
| | PP2CD HUMAN | Protein phosphatase 2C isoform delta, protein from *Homo sapiens* | UniProt | TAS | PMID: 9177166 |
| | PP2CE HUMAN | Splice Isoform 1 of Protein phosphatase 2C isoform eta, protein from *Homo sapiens* | UniProt | ISS | UniProt: Q96MI6 |
| | PP2CG HUMAN | Protein phosphatase 2C isoform gamma, protein from *Homo sapiens* | UniProt | TAS | PMID: 9271424 |
| | PP4C HUMAN | Serine/threonine protein phosphatase 4 catalytic subunit, protein from *Homo sapiens* | UniProt | NAS | UniProt: P60510 |
| | PPARA HUMAN | Peroxisome proliferator-activated receptor alpha, protein from *Homo sapiens* | UniProt | TAS | PMID: 16271724 |
| | PPARB HUMAN | Splice Isoform 1 of Peroxisome proliferator-activated receptor delta, protein from *Homo sapiens* | UniProt | NAS | PMID: 11551955 |
| | PPIE HUMAN | Splice Isoform A of Peptidyl-prolyl cis-trans isomerase E, protein from *Homo sapiens* | UniProt | IDA | PMID: 11313484 |
| | PPIG HUMAN | Splice Isoform 1 of Peptidyl-prolyl cis-trans isomerase G, protein from *Homo sapiens* | UniProt | TAS | PMID: 9153302 |
| | PPIL2 HUMAN | Splice Isoform 1 of Peptidyl-prolyl cis-trans isomerase-like 2, protein from *Homo sapiens* | UniProt | TAS | PMID: 8660300 |
| | PPP5 HUMAN | Serine/threonine protein phosphatase 5, protein from *Homo sapiens* | UniProt | TAS | PMID: 7925273 |
| | PPRB HUMAN | Splice Isoform 1 of Peroxisome proliferator-activated receptor-binding protein, protein from *Homo sapiens* | UniProt | IDA | PMID: 10235267 |
| | PQBP1 HUMAN | Splice Isoform 1 of Polyglutamine-binding protein 1, protein from *Homo sapiens* | UniProt | TAS | PMID: 10198427 |
| | PRD15 HUMAN | PR-domain zinc finger protein 15, protein from *Homo sapiens* | UniProt | NAS | UniProt: P57071 |
| | PRD16 HUMAN | Splice Isoform 1 of PR-domain zinc finger protein 16, protein from *Homo sapiens* | UniProt | IC | PMID: 11050005 |
| | PRDM2 HUMAN | Splice Isoform 1 of PR-domain zinc finger protein 2, protein from *Homo sapiens* | UniProt | NAS | PMID: 7590293 |
| | | | | NAS | PMID: 7538672 |
| | PREB HUMAN | Prolactin regulatory element-binding protein, protein from *Homo sapiens* | UniProt | TAS | PMID: 10194769 |
| | PRGC1 HUMAN | Peroxisome proliferator-activated receptor gamma coactivator 1-alpha, protein from *Homo sapiens* | UniProt | TAS | PMID: 12588810 |
| | PRP16 HUMAN | Pre-mRNA splicing factor ATP-dependent RNA helicase PRP16, protein from *Homo sapiens* | UniProt | NAS | PMID: 9524131 |
| | PRS6A HUMAN | 26S protease regulatory subunit 6A, protein from *Homo sapiens* | UniProt | TAS | PMID: 2194290 |
| | PSA1 HUMAN | Splice Isoform Short of Proteasome subunit alpha type 1, protein from *Homo sapiens* | UniProt | TAS | PMID: 7681138 |
| | PSA3 HUMAN | Proteasome subunit alpha type 3, protein from *Homo sapiens* | UniProt | TAS | PMID: 16130169 |

| Qualifier | Symbol Sequence/GOst | Information | Source | Evidence | Reference |
|---|---|---|---|---|---|
| | PSB4 HUMAN | Proteasome subunit beta type 4 precursor, protein from *Homo sapiens* | UniProt | TAS | PMID: 16130169 |
| | PSF1 HUMAN | DNA replication complex GINS protein PSF1, protein from *Homo sapiens* | UniProt | IDA | PMID: 10942595 |
| | PTDSR HUMAN | Splice Isoform 1 of Protein PTDSR, protein from *Homo sapiens* | UniProt | IDA | PMID: 14729065 |
| | PTHR1 HUMAN | Parathyroid hormone/parathyroid hormone-related peptide receptor precursor, protein from *Homo sapiens* | UniProt | TAS | PMID: 10709993 |
| | PTMA HUMAN | Prothymosin alpha, protein from *Homo sapiens* | UniProt | TAS | PMID: 10854063 |
| | PTMS HUMAN | Parathymosin, protein from *Homo sapiens* | UniProt | TAS | PMID: 10854063 |
| | PTTG1 HUMAN | Securin, protein from *Homo sapiens* | UniProt | TAS | PMID: 9811450 |
| | PTTG HUMAN | Pituitary tumor-transforming gene 1 protein-interacting protein precursor, protein from *Homo sapiens* | UniProt | IDA | PMID: 10781616 |
| | PWP1 HUMAN | Periodic tryptophan protein 1 homolog, protein from *Homo sapiens* | UniProt | TAS | PMID: 7828893 |
| | Q02313 | Kruppel-related zinc finger protein, protein from *Homo sapiens* | UniProt | NAS | UniProt: Q02313 |
| | Q03989 | ARID5A protein, protein from *Homo sapiens* | UniProt | IC | PMID: 15640446 |
| | Q12771 | P37 AUF1, protein from *Homo sapiens* | UniProt | NAS | PMID: 8246982 |
| | Q12869 | R kappa B, protein from *Homo sapiens* | UniProt | NR | UniProt: Q12869 |
| | Q13028 | Homeo box protein, protein from *Homo sapiens* | UniProt | NAS | PMID: 7647458 |
| | Q13051 | Nuclear factor I, protein from *Homo sapiens* | UniProt | NAS | PMID: 8799200 |
| | Q13127 | REST protein, protein from *Homo sapiens* | UniProt | TAS | PMID: 7697725 |
| | Q13137 | NDP52, protein from *Homo sapiens* | UniProt | TAS | PMID: 7540613 |
| | Q13395 | TAR RNA loop binding protein, protein from *Homo sapiens* | UniProt | TAS | PMID: 8846792 |
| | Q13826 | Autoantigen, protein from *Homo sapiens* | UniProt | IDA | PMID: 7520377 |
| | Q13862 | DNA-binding protein, protein from *Homo sapiens* | UniProt | TAS | PMID: 7887923 |
| | Q13901 | Hypothetical protein C1D, protein from *Homo sapiens* | UniProt | TAS | PMID: 9469821 |
| | Q14211 | E4BP4 protein, protein from *Homo sapiens* | UniProt | TAS | PMID: 7565758 |
| | Q14333 | Facioscapulohumeral muscular dystrophy, protein from *Homo sapiens* | UniProt | NAS | UniProt: Q14333 |
| | Q14501 | HCREM 1alpha protein, protein from *Homo sapiens* | UniProt | NAS | PMID: 8206879 |
| | Q14503 | HCREM 2beta-a protein, protein from *Homo sapiens* | UniProt | NAS | PMID: 8206879 |
| | Q14548 | HOX2.8 protein, protein from *Homo sapiens* | UniProt | IDA | PMID: 1871139 |
| | Q14561 | HPX-5 protein, protein from *Homo sapiens* | UniProt | NAS | PMID: 7518789 |
| | Q14655 | C-MYC promoter-binding protein IRLB, protein from *Homo sapiens* | UniProt | NAS | UniProt: Q14655 |
| | Q14820 | ZFM1 protein, alternatively spliced product, protein from *Homo sapiens* | UniProt | NAS | PMID: 7912130 |
| | Q14869 | MSSP-2 protein, protein from *Homo sapiens* | UniProt | NAS | PMID: 7838710 |
| | Q14901 | Myc protein, protein from *Homo sapiens* | UniProt | NAS | PMID: 2834731 |

-continued

| Qualifier | Symbol Sequence/GOst | Information | Source | Evidence | Reference |
|---|---|---|---|---|---|
| | Q15156 | PML-RAR protein, protein from *Homo sapiens* | UniProt | NAS | UniProt: Q15156 |
| | Q15170 | Pp21 protein, protein from *Homo sapiens* | UniProt | TAS | PMID: 7971997 |
| | Q15270 | HPX-153 protein, protein from *Homo sapiens* | UniProt | NAS | UniProt: Q15270 |
| | Q15288 | No distinctive protein motifs; ORF, protein from *Homo sapiens* | UniProt | NAS | PMID: 8543184 |
| | Q15299 | RARB protein, protein from *Homo sapiens* | UniProt | IDA | PMID: 2177841 |
| | Q15325 | DNA-binding protein, protein from *Homo sapiens* | UniProt | TAS | PMID: 3174636 |
| | Q15327 | Nuclear protein, protein from *Homo sapiens* | UniProt | TAS | PMID: 7730328 |
| | Q15361 | Transcription factor, protein from *Homo sapiens* | UniProt | NAS | PMID: 7597036 |
| | Q15376 | Y-chromosome RNA recognition motif protein, protein from *Homo sapiens* | UniProt | NAS | PMID: 9598316 |
| | Q15381 | Y-chromosome RNA recognition motif protein, protein from *Homo sapiens* | UniProt | TAS | PMID: 9598316 |
| | Q15435 | Yeast sds22 homolog, protein from *Homo sapiens* | UniProt | TAS | PMID: 7498485 |
| | Q15552 | CACCC box-binding protein, protein from *Homo sapiens* | UniProt | TAS | PMID: 8355710 |
| | Q15574 | Hypothetical protein TAF1B, protein from *Homo sapiens* | UniProt | NAS | PMID: 7801123 |
| | Q15736 | Zinc finger protein 223, protein from *Homo sapiens* | UniProt | NAS | UniProt: Q9UMW0 |
| | Q15936 | Zinc-finger protein, protein from *Homo sapiens* | UniProt | NAS | UniProt: Q15936 |
| | Q16247 | Histone H1 transcription factor large subunit 2A, protein from *Homo sapiens* | UniProt | NAS | PMID: 7969168 |
| | Q16365 | GATA-4 transcription factor, protein from *Homo sapiens* | UniProt | NAS | PMID: 7791790 |
| | Q16464 | Chromosome 17q21 mRNA clone 694:2., protein from *Homo sapiens* | UniProt | NAS | UniProt: Q16464 |
| | Q16624 | Long overlapping ORF, protein from *Homo sapiens* | UniProt | NAS | PMID: 3265124 |
| | Q16630 | HPBRII-4 mRNA, protein from *Homo sapiens* | UniProt | TAS | PMID: 9659921 |
| | Q16670 | Transcriptional regulator SCAN domain containing protein, protein from *Homo sapiens* | UniProt | NAS | PMID: 1569959 |
| | Q5W1B6 | OTTHUMP00000028668, protein from *Homo sapiens* | UniProt | ISS | UniProt: Q5W1B6 |
| | Q6ZNA8 | Hypothetical protein FLJ16262, protein from *Homo sapiens* | UniProt | ISS | UniProt: Q6ZNA8 |
| | Q7RTV3 | ZNF367, protein from *Homo sapiens* | UniProt | IDA | PMID: 15344908 |
| | Q86T11 | Discs large homolog 7; *Drosophila* Discs large-1 tumor suppressor-like; hepatoma up-regulateD protein, protein from *Homo sapiens* | UniProt | ISS | UniProt: Q86T11 |
| | Q86TP4 | TCFL5 protein, protein from *Homo sapiens* | UniProt | ISS | UniProt: Q86TP4 |
| | Q86XB9 | BRUNOL4 protein, protein from *Homo sapiens* | UniProt | ISS | UniProt: Q86XB9 |
| | Q86XF5 | DNA cytosine methyltransferase 3 alpha, isoform a, protein from *Homo sapiens* | UniProt | ISS | PMID: 12138111 |
| | Q86XW5 | P621, protein from *Homo sapiens* | UniProt | IDA | PMID: 12665582 |
| | Q86YN6 | Peroxisome proliferator-activated receptor gamma coactivator 1beta-1a, protein from *Homo sapiens* | UniProt | ISS | UniProt: Q86YN6 |

-continued

| Qualifier | Symbol Sequence/GOst | Information | Source | Evi-dence | Refer-ence |
|---|---|---|---|---|---|
| | Q8IWR7 | CGI-121 L1 isoform, protein from *Homo sapiens* | UniProt | NAS | PMID: 12659830 |
| | Q8IXI0 | Early hematopoietic zinc finger, protein from *Homo sapiens* | UniProt | IDA | PMID: 12393497 |
| | Q8IZV0 | DNA cytosine methyltransferase 3 alpha isoform b, protein from *Homo sapiens* | UniProt | IDA | PMID: 12138111 |
| | Q8N717 | KLF4 protein, protein from *Homo sapiens* | UniProt | ISS | UniProt: Q8N717 |
| | Q8N9B5 | Hypothetical protein FLJ37870, protein from *Homo sapiens* | UniProt | ISS | UniProt: Q8N9B5 |
| | Q8NFW5 | Homeoprotein MBX-L, protein from *Homo sapiens* | UniProt | ISS | UniProt: Q8NFW5 |
| | Q8NFW6 | Homeoprotein MBX-S, protein from *Homo sapiens* | UniProt | ISS | UniProt: Q8NFW6 |
| | Q8NHW3 | V-maf musculoaponeurotic fibrosarcoma oncogene homolog A, protein from *Homo sapiens* | UniProt | IDA | PMID: 12368292 |
| | Q8TAL0 | PPARGC1B protein, protein from *Homo sapiens* | UniProt | ISS | UniProt: Q8TAL0 |
| | Q8TD23 | TRAF6-binding zinc finger protein, protein from *Homo sapiens* | UniProt | IDA | PMID: 11751921 |
| | Q8TDE4 | PGC-1-related estrogen receptor alpha coactivator short isoform, protein from *Homo sapiens* | UniProt | ISS | PMID: 10713165 |
| | | | | IDA | PMID: 11854298 |
| | Q8TEY4 | Adaptor protein FE65a2, protein from *Homo sapiens* | UniProt | ISS | UniProt: Q8TEY4 |
| | Q8WX93 | Myoneurin, protein from *Homo sapiens* | UniProt | IDA | PMID: 11598191 |
| | Q8WYA4 | Brain-muscle-ARNT-like transcription factor 2a, protein from *Homo sapiens* | UniProt | IDA | PMID: 12055078 |
| | Q92657 | HP8 peptide, protein from *Homo sapiens* | UniProt | NAS | PMID: 8758458 |
| | Q92728 | RB1 protein, protein from *Homo sapiens* | UniProt | NAS | PMID: 3413073 |
| | Q96BU1 | S100P binding protein Riken, isoform a, protein from *Homo sapiens* | UniProt | IDA | PMID: 15632002 |
| | Q96BX9 | Hypothetical protein FLJ32915, protein from *Homo sapiens* | UniProt | IDA | PMID: 15843405 |
| | Q96C70 | Transcription factor RAM2 splice variant c, protein from *Homo sapiens* | UniProt | IDA | PMID: 15994933 |
| | Q96HR3 | TRAP/Mediator complex component TRAP25, protein from *Homo sapiens* | UniProt | IDA | PMID: 10235267 |
| | Q96JL8 | JADE1L protein, protein from *Homo sapiens* | UniProt | ISS | UniProt: Q96JL8 |
| | Q96L96 | Muscle alpha-kinase, protein from *Homo sapiens* | UniProt | ISS | UniProt: Q96L96 |
| | Q96MH2 | Hypothetical protein FLJ32384, protein from *Homo sapiens* | UniProt | ISS | UniProt: Q96MH2 |
| | Q96S66 | Mid-1-related chloride channel 1, protein from *Homo sapiens* | UniProt | ISS | PMID: 11279057 |
| | Q96SQ1 | Hypothetical protein FLJ14714, protein from *Homo sapiens* | UniProt | IDA | PMID: 12169691 |
| | Q99419 | ICSAT transcription factor, protein from *Homo sapiens* | UniProt | ISS | UniProt: Q99419 |
| | Q99638 | RAD9A protein, protein from *Homo sapiens* | UniProt | TAS | PMID: 8943031 |
| | Q99718 | ESE-1a, protein from *Homo sapiens* | UniProt | NAS | PMID: 9234700 |
| | Q9BRV3 | LOC55974 protein, protein from *Homo sapiens* | UniProt | IC | PMID: 8630032 |

| Qualifier | Symbol Sequence/GOst | Information | Source | Evidence | Reference |
|---|---|---|---|---|---|
| | Q9BXX3 | Breast cancer antigen NY-BR-1, protein from *Homo sapiens* | UniProt | NAS | PMID: 11280766 |
| | Q9BYE0 | BHLH factor Hes7, protein from *Homo sapiens* | UniProt | NAS | PMID: 11260262 |
| | Q9BYG9 | Nucleophosmin/B23.2, protein from *Homo sapiens* | UniProt | ISS | UniProt: Q9BYG9 |
| | Q9BYU3 | MORF/CBP protein, protein from *Homo sapiens* | UniProt | NAS | PMID: 11157802 |
| | Q9BZ95 | Putative chromatin modulator, protein from *Homo sapiens* | UniProt | NAS | UniProt: Q9BZ95 |
| | Q9BZC1 | Bruno-like 4, RNA Binding protein; RNA-Binding protein BRUNOL-5; CUG-BP and ETR-3 like factor 4, protein from *Homo sapiens* | UniProt | ISS | UniProt: Q9BZC1 |
| | Q9BZC2 | Trinucleotide repeat containing 4, protein from *Homo sapiens* | UniProt | NAS | PMID: 11158314 |
| | Q9BZS0 | Kappa B and V(D)J recombination signal sequences binding protein, protein from *Homo sapiens* | UniProt | NAS | UniProt: Q9BZS0 |
| | Q9C056 | NK6 transcription factor related, locus 2, protein from *Homo sapiens* | UniProt | NAS | PMID: 11210186 |
| | Q9H2G4 | CTCL tumor antigen se20-4, protein from *Homo sapiens* | UniProt | IDA | PMID: 11395479 |
| | Q9H2M1 | Estrogen receptor alpha, protein from *Homo sapiens* | UniProt | NAS | UniProt: Q9H2M1 |
| | Q9H2M4 | Cycle-like factor CLIF, protein from *Homo sapiens* | UniProt | NAS | PMID: 11018023 |
| | Q9H2S9 | Zinc finger transcription factor Eos, protein from *Homo sapiens* | UniProt | TAS | PMID: 10978333 |
| | Q9H315 | ARTS protein, protein from *Homo sapiens* | UniProt | NAS | PMID: 11146656 |
| | Q9H4E3 | Probable ATP-dependent RNA helicase DDX47, protein from *Homo sapiens* | UniProt | NAS | PMID: 11024137 |
| | Q9H509 | DJ875K15.1.1, protein from *Homo sapiens* | UniProt | ISS | UniProt: Q9H509 |
| | Q9HB90 | GTPase-interacting protein 2, protein from *Homo sapiens* | UniProt | IDA | PMID: 11073942 |
| | Q9HBE0 | Beta protein 1 BP1, protein from *Homo sapiens* | UniProt | NAS | PMID: 11069021 |
| | Q9HBU2 | Lim-homeobox transcription factor LHX3, protein from *Homo sapiens* | UniProt | NAS | UniProt: Q9HBU2 |
| | Q9HD85 | Pre-B-cell leukemia transcription factor interacting protein 1, protein from *Homo sapiens* | UniProt | NAS | PMID: 10825160 |
| | Q9NP66 | High-mobility group 20A variant, protein from *Homo sapiens* | UniProt | NAS | PMID: 10773667 |
| | Q9NPE2 | Mesenchymal stem cell protein DSC92, protein from *Homo sapiens* | UniProt | NAS | PMID: 11118320 |
| | Q9NQL2 | OTTHUMP00000016853, protein from *Homo sapiens* | UniProt | IDA | PMID: 11073942 |
| | Q9NQL9 | Doublesex and mab-3 related transcription factor 3, protein from *Homo sapiens* | UniProt | NAS | UniProt: Q9NQL9 |
| | Q9NR48 | Ash1, protein from *Homo sapiens* | UniProt | TAS | PMID: 10860993 |
| | Q9NR55 | Jun dimerization protein p21SNFT, protein from *Homo sapiens* | UniProt | TAS | PMID: 10878360 |
| | Q9NS72 | K562 cell-derived leucine-zipper-like protein 1, protein from *Homo sapiens* | UniProt | NAS | PMID: 10873651 |
| | Q9NX07 | Hypothetical protein FLJ20503, protein from *Homo sapiens* | UniProt | ISS | UniProt: Q9NX07 |

| Qualifier | Symbol Sequence/GOst | Information | Source | Evidence | Reference |
|---|---|---|---|---|---|
| | Q9NYW8 | RB-associated KRAB repressor, protein from *Homo sapiens* | UniProt | TAS | PMID: 10702291 |
| | Q9NZC4 | Ets domain transcription factor, protein from *Homo sapiens* | UniProt | ISS | UniProt: Q9NZC4 |
| | Q9P016 | THY28 protein, protein from *Homo sapiens* | UniProt | ISS | PMID: 14601557 |
| | Q9P112 | Chromosome 16 open reading frame 5, protein from *Homo sapiens* | UniProt | NAS | PMID: 10570909 |
| | Q9P1Z2 | KIAA1536 protein, protein from *Homo sapiens* | UniProt | ISS | UniProt: Q9P1Z2 |
| | Q9P2R9 | SRp25 nuclear protein isoform 2, protein from *Homo sapiens* | UniProt | TAS | PMID: 10708573 |
| | Q9P2S7 | Hypothetical protein FLJ11063, protein from *Homo sapiens* | UniProt | NR | UniProt: Q9P2S7 |
| | Q9UC05 | 22 Kruppel-related zinc finger protein, protein from *Homo sapiens* | UniProt | NAS | UniProt: Q9UC05 |
| | Q9UCY6 | Nuclear receptor subfamily 5, group A, member 1, protein from *Homo sapiens* | UniProt | NAS | PMID: 7479914 |
| | Q9UD04 | GHDTA = GROWTH hormone gene-derived transcriptional activator/hepatic nuclear factor-1 alpha homolog, protein from *Homo sapiens* | UniProt | NAS | PMID: 7642589 |
| | Q9UD29 | Surfactant protein B-binding protein, protein from *Homo sapiens* | UniProt | NAS | PMID: 7887923 |
| | Q9UD78 | LBP-1A transcription factor protein, protein from *Homo sapiens* | UniProt | TAS | PMID: 8114710 |
| | Q9UD83 | ATF-A0 transcription factor protein, protein from *Homo sapiens* | UniProt | NAS | PMID: 8288576 |
| | Q9UEP1 | Cell cycle checkpoint protein, protein from *Homo sapiens* | UniProt | ISS | UniProt: Q9UEP1 |
| | Q9UGK6 | Putative secreted ligand, protein from *Homo sapiens* | UniProt | NR | UniProt: Q9UGK6 |
| | Q9UGL1 | RB-binding protein, protein from *Homo sapiens* | UniProt | TAS | PMID: 12657635 |
| | Q9UH59 | Bromodomain protein CELTIX1, protein from *Homo sapiens* | UniProt | TAS | PMID: 10526152 |
| | Q9UHK0 | Nuclear fragile X mental retardation protein interacting protein 1, protein from *Homo sapiens* | UniProt | TAS | PMID: 10556305 |
| | Q9ULW3 | Basal transcriptional activator hABT1, protein from *Homo sapiens* | UniProt | TAS | PMID: 10648625 |
| | Q9UMC5 | Zinc finger protein 2, isoform a, protein from *Homo sapiens* | UniProt | NAS | UniProt: Q9UMC5 |
| | Q9Y294 | ASF1A protein, protein from *Homo sapiens* | UniProt | NAS | PMID: 10759893 |
| | Q9Y2A1 | P53TG1-B, protein from *Homo sapiens* | UniProt | NAS | UniProt: Q9Y2A1 |
| | Q9Y2A2 | P53TG1-C, protein from *Homo sapiens* | UniProt | NAS | UniProt: Q9Y2A2 |
| | Q9Y2A3 | P53TG1-D, protein from *Homo sapiens* | UniProt | NAS | UniProt: Q9Y2A3 |
| | Q9Y2Y4 | Testis zinc finger protein, protein from *Homo sapiens* | UniProt | TAS | PMID: 10572087 |
| | Q9Y310 | CGI-21 protein, protein from *Homo sapiens* | UniProt | NR | UniProt: Q9Y310 |
| | Q9Y3C4 | My019 protein, protein from *Homo sapiens* | UniProt | IDA | PMID: 12659830 |
| | Q9Y451 | Androgen-induced prostate proliferative shutoff associated protein, protein from *Homo sapiens* | UniProt | TAS | PMID: 10215036 |

| Qualifier | Symbol Sequence/GOst | Information | Source | Evidence | Reference |
|---|---|---|---|---|---|
| | Q9Y474 | Zinc-finger motif-enhancer binding-protein-1, protein from *Homo sapiens* | UniProt | TAS | PMID: 9305772 |
| | Q9Y489 | Centrosomal protein 1, protein from *Homo sapiens* | UniProt | TAS | PMID: 10359848 |
| | Q9Y4I0 | Zinc-finger helicase, protein from *Homo sapiens* | UniProt | NAS | PMID: 9688266 |
| | Q9Y586 | MAB21L2 protein, protein from *Homo sapiens* | UniProt | NR | UniProt: Q9Y586 |
| | Q9Y655 | Splice Isoform 1 of Myelin expression factor 2, protein from *Homo sapiens* | UniProt | TAS | PMID: 2601707 |
| | Q9Y664 | Actin-associated protein 2E4/kaptin, protein from *Homo sapiens* | UniProt | TAS | PMID: 1372044 |
| | Q9Y675 | SNRPN upstream reading frame protein, protein from *Homo sapiens* | UniProt | NAS | PMID: 10318933 |
| | Q9Y6B2 | PTD014, protein from *Homo sapiens* | UniProt | IDA | PMID: 11073990 |
| | Q9Y6D4 | MORC1 protein, protein from *Homo sapiens* | UniProt | TAS | PMID: 10369865 |
| | Q9Y6R2 | HUEL, protein from *Homo sapiens* | UniProt | IDA | PMID: 10409434 |
| | Q9Y6Z7 | Collectin sub-family member 10, protein from *Homo sapiens* | UniProt | ISS | PMID: 12450124 |
| | R51A1 HUMAN | Splice Isoform 1 of RAD51-associated protein 1, protein from *Homo sapiens* | UniProt | IC | PMID: 9396801 |
| | RA51B HUMAN | Splice Isoform 2 of DNA repair protein RAD51 homolog 2, protein from *Homo sapiens* | UniProt | TAS | PMID: 9512535 |
| | RA51C HUMAN | DNA repair protein RAD51 homolog 3, protein from *Homo sapiens* | UniProt | TAS | PMID: 9469824 |
| | RA51D HUMAN | Splice Isoform 1 of DNA repair protein RAD51 homolog 4, protein from *Homo sapiens* | UniProt | TAS | PMID: 9570954 |
| | RAB3I HUMAN | Splice Isoform 2 of RAB3A-interacting protein, protein from *Homo sapiens* | UniProt | IDA | PMID: 12007189 |
| | RAD18 HUMAN | Postreplication repair protein RAD18, protein from *Homo sapiens* | UniProt | NAS | PMID: 10884424 |
| | RAD51 HUMAN | Splice Isoform 1 of DNA repair protein RAD51 homolog 1, protein from *Homo sapiens* | UniProt | ISS | UniProt: Q06609 |
| | | | | IDA | PMID: 12442171 |
| | RAD52 HUMAN | RAD52 homolog isoform alpha, protein from *Homo sapiens* | UniProt | TAS | PMID: 7774919 |
| | RAD54 HUMAN | DNA repair and recombination protein RAD54-like, protein from *Homo sapiens* | UniProt | TAS | PMID: 8805304 |
| | RAE1L HUMAN | mRNA-associated protein mrnp 41, protein from *Homo sapiens* | UniProt | TAS | PMID: 9370289 |
| | RAG2 HUMAN | V(D)J recombination-activating protein 2, protein from *Homo sapiens* | UniProt | NAS | UniProt: P55895 |
| | RANB3 HUMAN | Splice Isoform 1 of Ran-binding protein 3, protein from *Homo sapiens* | UniProt | TAS | PMID: 9637251 |
| | RANB9 HUMAN | Splice Isoform 1 of Ran-binding protein 9, protein from *Homo sapiens* | UniProt | IDA | PMID: 12220523 |
| | RANG HUMAN | Ran-specific GTPase-activating protein, protein from *Homo sapiens* | UniProt | TAS | PMID: 16130169 |
| | RASF1 HUMAN | Splice Isoform D of Ras association domain family 1, protein from *Homo sapiens* | UniProt | IEP | PMID: 14743218 |

| Qualifier | Symbol Sequence/GOst | Information | Source | Evidence | Reference |
|---|---|---|---|---|---|
| | RASF7 HUMAN | Splice Isoform 1 of Ras association domain protein 7, protein from *Homo sapiens* | UniProt | NAS | UniProt: Q02833 |
| | RB HUMAN | Retinoblastoma-associated protein, protein from *Homo sapiens* | UniProt | TAS | PMID: 3657987 |
| | RBBP4 HUMAN | Chromatin assembly factor 1 subunit C, protein from *Homo sapiens* | UniProt | TAS | PMID: 8350924 |
| | RBBP5 HUMAN | Retinoblastoma-binding protein 5, protein from *Homo sapiens* | UniProt | IDA | PMID: 15199122 |
| | RBBP8 HUMAN | RBBP8 protein, protein from *Homo sapiens* | UniProt | TAS | PMID: 10764811 |
| | RBM10 HUMAN | RNA binding motif protein 10, isoform 1, protein from *Homo sapiens* | UniProt | NAS | UniProt: P98175 |
| | RBM5 HUMAN | RNA-binding protein 5, protein from *Homo sapiens* | UniProt | TAS | PMID: 10352938 |
| | RBM6 HUMAN | RNA-binding protein 6, protein from *Homo sapiens* | UniProt | TAS | PMID: 10352938 |
| | RBM8A HUMAN | Splice Isoform 1 of RNA-binding protein 8A, protein from *Homo sapiens* | UniProt | NAS | PMID: 11013075 |
| | | | | NAS | PMID: 11030346 |
| | RBM9 HUMAN | Splice Isoform 1 of RNA-binding protein 9, protein from *Homo sapiens* | UniProt | IDA | PMID: 11875103 |
| | RBX2 HUMAN | Splice Isoform 1 of RING-box protein 2, protein from *Homo sapiens* | UniProt | NAS | PMID: 10082581 |
| | RBY1A HUMAN | RNA-binding motif protein, Y chromosome, family 1 member A1, protein from *Homo sapiens* | UniProt | TAS | PMID: 9598316 |
| | RCL HUMAN | c-Myc-responsive protein Rcl, protein from *Homo sapiens* | UniProt | TAS | PMID: 9271375 |
| | RD23B HUMAN | UV excision repair protein RAD23 homolog B, protein from *Homo sapiens* | UniProt | TAS | PMID: 8168482 |
| | RECQ1 HUMAN | ATP-dependent DNA helicase Q1, protein from *Homo sapiens* | UniProt | TAS | PMID: 7961977 |
| | RED1 HUMAN | Splice Isoform 1 of Double-stranded RNA-specific editase 1, protein from *Homo sapiens* | UniProt | TAS | PMID: 8995285 |
| | REN3A HUMAN | Splice Isoform 1 of Regulator of nonsense transcripts 3A, protein from *Homo sapiens* | UniProt | NAS | PMID: 11163187 |
| | REN3B HUMAN | Splice Isoform 1 of Regulator of nonsense transcripts 3B, protein from *Homo sapiens* | UniProt | NAS | PMID: 11163187 |
| | RERE HUMAN | Splice Isoform 1 of Arginine-glutamic acid dipeptide repeats protein, protein from *Homo sapiens* | UniProt | NAS | PMID: 10814707 |
| | RERG HUMAN | Ras-related and estrogen-regulated growth inhibitor, protein from *Homo sapiens* | UniProt | IDA | PMID: 11533059 |
| | REXO4 HUMAN | Splice Isoform 1 of RNA exonuclease 4, protein from *Homo sapiens* | UniProt | NAS | PMID: 10908561 |
| | RFX3 HUMAN | Splice Isoform 1 of Transcription factor RFX3, protein from *Homo sapiens* | UniProt | IC | PMID: 12411430 |
| | RFX5 HUMAN | DNA-binding protein RFX5, protein from *Homo sapiens* | UniProt | TAS | PMID: 9806546 |
| | RHOB HUMAN | Rho-related GTP-binding protein RhoB, protein from *Homo sapiens* | UniProt | ISS | UniProt: P62745 |

| Qualifier | Symbol Sequence/GOst | Information | Source | Evidence | Reference |
|---|---|---|---|---|---|
| | RING1 HUMAN | Polycomb complex protein RING1, protein from *Homo sapiens* | UniProt | IDA | PMID: 9199346 |
| | RM19 HUMAN | 39S ribosomal protein L19, mitochondrial precursor, protein from *Homo sapiens* | UniProt | IDA | PMID: 10942595 |
| | RM40 HUMAN | 39S ribosomal protein L40, mitochondrial precursor, protein from *Homo sapiens* | UniProt | TAS | PMID: 9790763 |
| | RMP HUMAN | RNA polymerase II subunit 5-mediating protein, protein from *Homo sapiens* | UniProt | TAS | PMID: 9878255 |
| | RNF14 HUMAN | RING finger protein 14, protein from *Homo sapiens* | UniProt | IDA | PMID: 11322894 |
| | RNF4 HUMAN | RING finger protein 4, protein from *Homo sapiens* | UniProt | TAS | PMID: 9710597 |
| | RNPS1 HUMAN | Splice Isoform 1 of RNA-binding protein with serine-rich domain 1, protein from *Homo sapiens* | UniProt | TAS | PMID: 9580558 |
| | RP14 HUMAN | Ribonuclease P protein subunit p14, protein from *Homo sapiens* | UniProt | TAS | PMID: 10024167 |
| | RP30 HUMAN | Ribonuclease P protein subunit p30, protein from *Homo sapiens* | UniProt | TAS | PMID: 9630247 |
| | RPB1 HUMAN | DNA-directed RNA polymerase II largest subunit, protein from *Homo sapiens* | UniProt | NAS | PMID: 7622068 |
| | RPB8 HUMAN | DNA-directed RNA polymerases I, II, and III 17.1 kDa polypeptide, protein from *Homo sapiens* | UniProt | TAS | UniProt: P52434 |
| | RPGF5 HUMAN | Splice Isoform 1 of Rap guanine nucleotide exchange factor 5, protein from *Homo sapiens* | UniProt | IDA | PMID: 10486569 |
| | RPP38 HUMAN | Ribonuclease P protein subunit p38, protein from *Homo sapiens* | UniProt | TAS | PMID: 9630247 |
| | RPP40 HUMAN | Ribonuclease P protein subunit p40, protein from *Homo sapiens* | UniProt | TAS | PMID: 9630247 |
| | RRP5 HUMAN | RRP5 protein homolog, protein from *Homo sapiens* | UniProt | IDA | PMID: 14624448 |
| | RSSA HUMAN | 40S ribosomal protein SA, protein from *Homo sapiens* | UniProt | TAS | PMID: 16130169 |
| | RUNX1 HUMAN | Splice Isoform AML-1B of Runt-related transcription factor 1, protein from *Homo sapiens* | UniProt | NAS | UniProt: O60473 |
| | RUNX3 HUMAN | Splice Isoform 1 of Runt-related transcription factor 3, protein from *Homo sapiens* | UniProt | NAS | UniProt: Q13761 |
| | RUVB1 HUMAN | RuvB-like 1, protein from *Homo sapiens* | UniProt | IDA | PMID: 9843967 |
| | RUVB2 HUMAN | RuvB-like 2, protein from *Homo sapiens* | UniProt | IDA | PMID: 10524211 |
| | S100P HUMAN | S-100P protein, protein from *Homo sapiens* | UniProt | IDA | PMID: 15632002 |
| | S10AB HUMAN | Calgizzarin, protein from *Homo sapiens* | UniProt | TAS | PMID: 10851017 |
| | S14L2 HUMAN | Splice Isoform 1 of SEC14-like protein 2, protein from *Homo sapiens* | UniProt | NAS | PMID: 11444841 |
| | S2A4R HUMAN | Splice Isoform 1 of GLUT4 enhancer factor DNA binding domain, protein from *Homo sapiens* | UniProt | NAS | PMID: 10825161 |
| | SAFB1 HUMAN | Scaffold attachment factor B, protein from *Homo sapiens* | UniProt | TAS | PMID: 1324173 |
| | SALL2 HUMAN | Sal-like protein 2, protein from *Homo sapiens* | UniProt | NAS | UniProt: Q9Y467 |

| Qualifier | Symbol Sequence/GOst | Information | Source | Evidence | Reference |
|---|---|---|---|---|---|
| | SAM68 HUMAN | Splice Isoform 1 of KH domain containing, RNA binding, signal transduction associated protein 1, protein from *Homo sapiens* | UniProt | IDA | PMID: 1374686 |
| | SAS10 HUMAN | Something about silencing protein 10, protein from *Homo sapiens* | UniProt | ISS | UniProt: Q9NQZ2 |
| | SATB1 HUMAN | DNA-binding protein SATB1, protein from *Homo sapiens* | UniProt | TAS | PMID: 1505028 |
| | SCMH1 HUMAN | Splice Isoform 1 of Polycomb protein SCMH1, protein from *Homo sapiens* | UniProt | IC | PMID: 10524249 |
| | SCND1 HUMAN | SCAN domain-containing protein 1, protein from *Homo sapiens* | UniProt | ISS | UniProt: P57086 |
| | SCRN1 HUMAN | Secernin-1, protein from *Homo sapiens* | UniProt | IDA | PMID: 10942595 |
| | SCRT1 HUMAN | Transcriptional repressor scratch 1, protein from *Homo sapiens* | UniProt | NAS | UniProt: Q9BWW7 |
| | SDCB1 HUMAN | Syntenin-1, protein from *Homo sapiens* | UniProt | NAS | PMID: 11179419 |
| | SELB HUMAN | Selenocysteine-specific elongation factor, protein from *Homo sapiens* | UniProt | NAS | UniProt: P57772 |
| | SENP1 HUMAN | Sentrin/SUMO-specific protease 1, protein from *Homo sapiens* | UniProt | TAS | PMID: 10652325 |
| | SENP7 HUMAN | Similar to SUMO-1-specific protease, protein from *Homo sapiens* | UniProt | ISS | PMID: 10652325 |
| | SEPT2 HUMAN | Septin-2, protein from *Homo sapiens* | UniProt | IDA | PMID: 10942595 |
| | SEPT7 HUMAN | Septin-7, protein from *Homo sapiens* | UniProt | IDA | PMID: 15485874 |
| | SESN1 HUMAN | Splice Isoform T1 of Sestrin-1, protein from *Homo sapiens* | UniProt | TAS | PMID: 9926927 |
| | SET7 HUMAN | Histone-lysine N-methyltransferase, H3 lysine-4 specific SET7, protein from *Homo sapiens* | UniProt | NAS | UniProt: Q8WTS6 |
| | SET HUMAN | Splice Isoform 1 of SET protein, protein from *Homo sapiens* | UniProt | IDA | PMID: 11555662 |
| | SFR11 HUMAN | Splicing factor arginine/serine-rich 11, protein from *Homo sapiens* | UniProt | TAS | PMID: 1896467 |
| | SFRS2 HUMAN | Splicing factor, arginine/serine-rich 2, protein from *Homo sapiens* | UniProt | IDA | PMID: 15652350 |
| | SFRS4 HUMAN | Splicing factor, arginine/serine-rich 4, protein from *Homo sapiens* | UniProt | TAS | PMID: 8321209 |
| | SFRS7 HUMAN | Splice Isoform 1 of Splicing factor, arginine/serine-rich 7, protein from *Homo sapiens* | UniProt | TAS | PMID: 8013463 |
| | SH3L1 HUMAN | SH3 domain-binding glutamic acid-rich-like protein, protein from *Homo sapiens* | UniProt | TAS | PMID: 16130169 |
| | SIN3A HUMAN | Paired amphipathic helix protein Sin3a, protein from *Homo sapiens* | UniProt | ISS | UniProt: Q96ST3 |
| | SIP1 HUMAN | Zinc finger homeobox protein 1b, protein from *Homo sapiens* | UniProt | IC | PMID: 9853615 |
| | SIPA1 HUMAN | Signal-induced proliferation-associated protein 1, protein from *Homo sapiens* | UniProt | IC | PMID: 9183624 |
| | SIRT6 HUMAN | Splice Isoform 1 of Mono-ADP-ribosyltransferase sirtuin-6, protein from *Homo sapiens* | UniProt | ISS | UniProt: Q8N6T7 |
| | SKI HUMAN | Ski oncogene, protein from *Homo sapiens* | UniProt | NAS | UniProt: P12755 |

| Qualifier | Symbol Sequence/GOst | Information | Source | Evidence | Reference |
|---|---|---|---|---|---|
| | SKIL HUMAN | Splice Isoform SNON of Ski-like protein, protein from *Homo sapiens* | UniProt | ISS | UniProt: P12757 |
| | SLUG HUMAN | Zinc finger protein SLUG, protein from *Homo sapiens* | UniProt | TAS | PMID: 10866665 |
| | SMAD1 HUMAN | Mothers against decapentaplegic homolog 1, protein from *Homo sapiens* | UniProt | ISS | UniProt: Q15797 |
| | | | | NAS | PMID: 9759503 |
| | SMAD2 HUMAN | Splice Isoform Long of Mothers against decapentaplegic homolog 2, protein from *Homo sapiens* | UniProt | ISS | UniProt: Q15796 |
| | SMAD4 HUMAN | Mothers against decapentaplegic homolog 4, protein from *Homo sapiens* | UniProt | TAS | PMID: 10980615 |
| | SMAD5 HUMAN | Mothers against decapentaplegic homolog 5, protein from *Homo sapiens* | UniProt | NAS | PMID: 9759503 |
| | SMC1A HUMAN | Structural maintenance of chromosome 1-like 1 protein, protein from *Homo sapiens* | UniProt | IDA | PMID: 11076961 |
| | SMC2 HUMAN | Splice Isoform 1 of Structural maintenance of chromosome 2-like 1 protein, protein from *Homo sapiens* | UniProt | TAS | PMID: 9789013 |
| | SMC4 HUMAN | Splice Isoform 1 of Structural maintenance of chromosomes 4-like 1 protein, protein from *Homo sapiens* | UniProt | TAS | PMID: 11850403 |
| | SMCA1 HUMAN | SWI/SNF related, matrix associated, actin dependent regulator of chromatin, subfamily a, member 1, protein from *Homo sapiens* | UniProt | TAS | PMID: 1408766 |
| | SMCA4 HUMAN | Possible global transcription activator SNF2L4, protein from *Homo sapiens* | UniProt | TAS | PMID: 8232556 |
| | SMCA5 HUMAN | SWI/SNF-related matrix associated actin dependent regulator of chromatin subfamily A member 5, protein from *Homo sapiens* | UniProt | IDA | PMID: 12972596 |
| | SMRA3 HUMAN | SWI/SNF-related matrix-associated actin-dependent regulator of chromatin subfamily A member 3, protein from *Homo sapiens* | UniProt | TAS | PMID: 7876228 |
| | SMRD3 HUMAN | Splice Isoform 1 of SWI/SNF-related matrix-associated actin-dependent regulator of chromatin subfamily D member 3, protein from *Homo sapiens* | UniProt | IDA | PMID: 14701856 |
| | SMUF2 HUMAN | Smad ubiquitination regulatory factor 2, protein from *Homo sapiens* | UniProt | NAS | PMID: 11163210 |
| | SND1 HUMAN | Staphylococcal nuclease domain-containing protein 1, protein from *Homo sapiens* | UniProt | TAS | PMID: 7651391 |
| | SNPC2 HUMAN | snRNA-activating protein complex subunit 2, protein from *Homo sapiens* | UniProt | TAS | PMID: 7715707 |
| | SNPC3 HUMAN | snRNA-activating protein complex subunit 3, protein from *Homo sapiens* | UniProt | TAS | PMID: 7715707 |
| | SNPC5 HUMAN | Splice Isoform 1 of snRNA-activating protein complex subunit 5, protein from *Homo sapiens* | UniProt | TAS | PMID: 9732265 |
| | SOX15 HUMAN | SOX-15 protein, protein from *Homo sapiens* | UniProt | NAS | PMID: 8332506 |
| | SOX1 HUMAN | SOX-1 protein, protein from *Homo sapiens* | UniProt | NAS | PMID: 9337405 |
| | SOX21 HUMAN | Transcription factor SOX-21, protein from *Homo sapiens* | UniProt | NAS | PMID: 1614875 |

-continued

| Qualifier | Symbol Sequence/GOst | Information | Source | Evidence | Reference |
|---|---|---|---|---|---|
| | SOX2 HUMAN | Transcription factor SOX-2, protein from *Homo sapiens* | UniProt | NAS | PMID: 7849401 |
| | SOX6 HUMAN | HMG1/2 (high mobility group) box family protein, protein from *Homo sapiens* | UniProt | NAS | PMID: 1614875 |
| | SOX9 HUMAN | Transcription factor SOX-9, protein from *Homo sapiens* | UniProt | TAS | PMID: 10805756 |
| | SP100 HUMAN | Splice Isoform Sp100-HMG of Nuclear autoantigen Sp-100, protein from *Homo sapiens* | UniProt | TAS | PMID: 2258622 |
| | SP110 HUMAN | Splice Isoform 1 of Sp110 nuclear body protein, protein from *Homo sapiens* | UniProt | TAS | PMID: 7693701 |
| | SP1 HUMAN | Transcription factor Sp1, protein from *Homo sapiens* | UniProt | NAS | UniProt: P08047 |
| | SP3 HUMAN | Transcription factor Sp3, protein from *Homo sapiens* | UniProt | NAS | UniProt: Q02447 |
| | SPAST HUMAN | Splice Isoform 1 of Spastin, protein from *Homo sapiens* | UniProt | TAS | PMID: 10610178 |
| | SPNXA HUMAN | Sperm protein associated with the nucleus on the X chromosome A, protein from *Homo sapiens* | UniProt | TAS | PMID: 10906052 |
| | SPNXB HUMAN | Sperm protein associated with the nucleus on the X chromosome B/F, protein from *Homo sapiens* | UniProt | TAS | PMID: 10906052 |
| | SPNXC HUMAN | Sperm protein associated with the nucleus on the X chromosome C, protein from *Homo sapiens* | UniProt | TAS | PMID: 10626816 |
| | SPOP HUMAN | Speckle-type POZ protein, protein from *Homo sapiens* | UniProt | TAS | PMID: 9414087 |
| | SPT6H HUMAN | Splice Isoform 1 of Transcription elongation factor SPT6, protein from *Homo sapiens* | UniProt | NAS | PMID: 8786132 |
| | SRBS1 HUMAN | Splice Isoform 1 of Sorbin and SH3 domain-containing protein 1, protein from *Homo sapiens* | UniProt | IDA | PMID: 11371513 |
| | SRF HUMAN | Serum response factor, protein from *Homo sapiens* | UniProt | TAS | PMID: 3203386 |
| | SRPK1 HUMAN | Splice Isoform 1 of Serine/threonine-protein kinase SRPK1, protein from *Homo sapiens* | UniProt | IDA | PMID: 11509566 |
| | SRPK2 HUMAN | Serine/threonine-protein kinase SRPK2, protein from *Homo sapiens* | UniProt | IDA | PMID: 9472028 |
| | SRY HUMAN | Sex-determining region Y protein, protein from *Homo sapiens* | UniProt | NAS | PMID: 8265659 |
| | | | | NAS | PMID: 1425584 |
| | SSBP2 HUMAN | Single-stranded DNA-binding protein 2, protein from *Homo sapiens* | UniProt | NAS | UniProt: P81877 |
| | SSBP3 HUMAN | Splice Isoform 1 of Single-stranded DNA-binding protein 3, protein from *Homo sapiens* | UniProt | ISS | UniProt: Q9BWW4 |
| | SSF1 HUMAN | Splice Isoform 1 of Suppressor of SWI4 1 homolog, protein from *Homo sapiens* | UniProt | IDA | PMID: 15302935 |
| | SSNA1 HUMAN | Sjogren's syndrome nuclear autoantigen 1, protein from *Homo sapiens* | UniProt | TAS | PMID: 9430706 |
| | SSX1 HUMAN | Protein SSX1, protein from *Homo sapiens* | UniProt | TAS | PMID: 10072425 |
| | SSXT HUMAN | Splice Isoform 1 of SSXT protein, protein from *Homo sapiens* | UniProt | TAS | PMID: 10072425 |
| | ST17A HUMAN | Serine/threonine-protein kinase 17A, protein from *Homo sapiens* | UniProt | IEP | PMID: 9786912 |

| Qualifier | Symbol Sequence/GOst | Information | Source | Evidence | Reference |
|---|---|---|---|---|---|
| | ST17B HUMAN | Serine/threonine-protein kinase 17B, protein from *Homo sapiens* | UniProt | IEP | PMID: 9786912 |
| | ST65G HUMAN | Splice Isoform 1 of STAGA complex 65 gamma subunit, protein from *Homo sapiens* | UniProt | NAS | PMID: 10987294 |
| | STABP HUMAN | STAM-binding protein, protein from *Homo sapiens* | UniProt | TAS | PMID: 10383417 |
| | STAG1 HUMAN | Cohesin subunit SA-1, protein from *Homo sapiens* | UniProt | TAS | PMID: 9305759 |
| | STAG2 HUMAN | Cohesin subunit SA-2, protein from *Homo sapiens* | UniProt | TAS | PMID: 9305759 |
| | STAG3 HUMAN | Splice Isoform 1 of Cohesin subunit SA-3, protein from *Homo sapiens* | UniProt | TAS | PMID: 10698974 |
| | STAT1 HUMAN | Splice Isoform Alpha of Signal transducer and activator of transcription 1-alpha/beta, protein from *Homo sapiens* | UniProt | TAS | PMID: 10820245 |
| | STAT3 HUMAN | Splice Isoform 1 of Signal transducer and activator of transcription 3, protein from *Homo sapiens* | UniProt | TAS | PMID: 7512451 |
| | STF1 HUMAN | Steroidogenic factor 1, protein from *Homo sapiens* | UniProt | IDA | PMID: 10567391 |
| | STIP1 HUMAN | Stress-induced-phosphoprotein 1, protein from *Homo sapiens* | UniProt | TAS | PMID: 16130169 |
| | STK19 HUMAN | Splice Isoform 1 of Serine/threonine-protein kinase 19, protein from *Homo sapiens* | UniProt | TAS | PMID: 9812991 |
| | STK38 HUMAN | Serine/threonine-protein kinase 38, protein from *Homo sapiens* | UniProt | IDA | PMID: 12493777 |
| | STK39 HUMAN | STE20/SPS1-related proline-alanine-rich protein kinase, protein from *Homo sapiens* | UniProt | NAS | PMID: 10980603 |
| | STK6 HUMAN | Serine/threonine-protein kinase 6, protein from *Homo sapiens* | UniProt | TAS | PMID: 9153231 |
| | STRN3 HUMAN | Splice Isoform Alpha of Striatin-3, protein from *Homo sapiens* | UniProt | IDA | PMID: 7910562 |
| | SUFU HUMAN | Splice Isoform 1 of Suppressor of fused homolog, protein from *Homo sapiens* | UniProt | TAS | PMID: 10559945 |
| | SUH HUMAN | Splice Isoform APCR-2 of Recombining binding protein suppressor of hairless, protein from *Homo sapiens* | UniProt | NAS | UniProt: Q06330 |
| | SUPT3 HUMAN | Splice Isoform 1 of Transcription initiation protein SPT3 homolog, protein from *Homo sapiens* | UniProt | IDA IEP | PMID: 9874765 PMID: 9726987 |
| | SUV91 HUMAN | Histone-lysine N-methyltransferase, H3 lysine-9 specific 1, protein from *Homo sapiens* | UniProt | TAS | PMID: 10949293 |
| | SVIL HUMAN | Splice Isoform 1 of Supervillin, protein from *Homo sapiens* | UniProt | IDA | PMID: 12711699 |
| | SYCP2 HUMAN | Synaptonemal complex protein 2, protein from *Homo sapiens* | UniProt | NAS | PMID: 10341103 |
| | TAD3L HUMAN | Splice Isoform 1 of Transcriptional adapter 3-like, protein from *Homo sapiens* | UniProt | TAS | PMID: 9674425 |
| | TADBP HUMAN | TAR DNA-binding protein 43, protein from *Homo sapiens* | UniProt | TAS | PMID: 7745706 |

-continued

| Qualifier | Symbol Sequence/GOst | Information | Source | Evidence | Reference |
|---|---|---|---|---|---|
| | TAF1 HUMAN | Splice Isoform 1 of Transcription initiation factor TFIID subunit 1, protein from *Homo sapiens* | UniProt | TAS | PMID: 7680771 |
| | TAF1L HUMAN | Transcription initiation factor TFIID 210 kDa subunit, protein from *Homo sapiens* | UniProt | ISS | PMID: 12217962 |
| | TAF4B HUMAN | PREDICTED: TAF4b RNA polymerase II, TATA box binding protein (TBP)-associated factor, 105 kDa, protein from *Homo sapiens* | UniProt | NAS | UniProt: Q92750 |
| | TB182 HUMAN | 182 kDa tankyrase 1-binding protein, protein from *Homo sapiens* | UniProt | NAS | PMID: 11854288 |
| | TBX18 HUMAN | T-box transcription factor TBX18, protein from *Homo sapiens* | UniProt | NAS | UniProt: O95935 |
| | TBX21 HUMAN | T-box transcription factor TBX21, protein from *Homo sapiens* | UniProt | NAS | UniProt: Q9UL17 |
| | TBX22 HUMAN | T-box transcription factor TBX22, protein from *Homo sapiens* | UniProt | NAS | UniProt: Q9Y458 |
| | TBX4 HUMAN | T-box transcription factor TBX4, protein from *Homo sapiens* | UniProt | NAS | UniProt: P57082 |
| | TCF20 HUMAN | Splice Isoform 1 of Transcription factor 20, protein from *Homo sapiens* | UniProt | NAS | PMID: 10995766 |
| | TCFL5 HUMAN | TranscripTion facTor-like 5 proTein, protein from *Homo sapiens* | UniProt | IDA | PMID: 9763657 |
| | TCRG1 HUMAN | Transcription elongation regulator 1, protein from *Homo sapiens* | UniProt | TAS | PMID: 9315662 |
| | TEAD2 HUMAN | Transcriptional enhancer factor TEF-4, protein from *Homo sapiens* | UniProt | NAS | PMID: 8702974 |
| | TERA HUMAN | Transitional endoplasmic reticulum ATPase, protein from *Homo sapiens* | UniProt | IDA | PMID: 10855792 |
| | | | | TAS | PMID: 16130169 |
| | TERF1 HUMAN | Splice Isoform TRF1 of Telomeric repeat binding factor 1, protein from *Homo sapiens* | UniProt | NAS | PMID: 9739097 |
| | | | | NAS | PMID: 7502076 |
| | TESK2 HUMAN | Splice Isoform 1 of Dual specificity testis-specific protein kinase 2, protein from *Homo sapiens* | UniProt | ISS | UniProt: Q96S53 |
| | TF65 HUMAN | Splice Isoform 1 of Transcription factor p65, protein from *Homo sapiens* | UniProt | IDA | PMID: 3140380 |
| | TF7L1 HUMAN | Transcription factor 7-like 1, protein from *Homo sapiens* | UniProt | NAS | PMID: 11085512 |
| | | | | NAS | PMID: 1741298 |
| | TF7L2 HUMAN | Splice Isoform 1 of Transcription factor 7-like 2, protein from *Homo sapiens* | UniProt | NAS | PMID: 10919662 |
| | TFE2 HUMAN | Splice Isoform E12 of Transcription factor E2-alpha, protein from *Homo sapiens* | UniProt | NAS | PMID: 2493990 |
| | TFEB HUMAN | Splice Isoform 1 of Transcription factor EB, protein from *Homo sapiens* | UniProt | NAS | PMID: 2115126 |
| | TGIF2 HUMAN | Homeobox protein TGIF2, protein from *Homo sapiens* | UniProt | TAS | PMID: 11006116 |
| | THB1 HUMAN | Thyroid hormone receptor beta-1, protein from *Homo sapiens* | UniProt | TAS | PMID: 1618799 |
| | THB2 HUMAN | Thyroid hormone receptor beta-2, protein from *Homo sapiens* | UniProt | TAS | PMID: 1618799 |

-continued

| Qualifier | Symbol Sequence/GOst | Information | Source | Evidence | Reference |
|---|---|---|---|---|---|
| | THOC1 HUMAN | THO complex subunit 1, protein from *Homo sapiens* | UniProt | TAS | PMID: 7525595 |
| | TIAF1 HUMAN | TGFB1-induced anti-apoptotic factor 1, protein from *Homo sapiens* | UniProt | NAS | PMID: 9918798 |
| | TIF1A HUMAN | Splice Isoform Long of Transcription intermediary factor 1-alpha, protein from *Homo sapiens* | UniProt | TAS | PMID: 9115274 |
| | TIF1G HUMAN | Splice Isoform Alpha of Transcription intermediary factor 1-gamma, protein from *Homo sapiens* | UniProt | NAS | UniProt: Q9UPN9 |
| | TIM HUMAN | Splice Isoform 1 of Timeless homolog, protein from *Homo sapiens* | UniProt | IC | PMID: 9856465 |
| | TIP60 HUMAN | Splice Isoform 1 of Histone acetyltransferase HTATIP, protein from *Homo sapiens* | UniProt | TAS | PMID: 8607265 |
| | TITF1 HUMAN | Splice Isoform 1 of Thyroid transcription factor 1, protein from *Homo sapiens* | UniProt | NAS | UniProt: P43699 |
| | TLE1 HUMAN | Transducin-like enhancer protein 1, protein from *Homo sapiens* | UniProt | TAS | PMID: 1303260 |
| | TLE2 HUMAN | Transducin-like enhancer protein 2, protein from *Homo sapiens* | UniProt | TAS | PMID: 1303260 |
| | TLE3 HUMAN | Splice Isoform 1 of Transducin-like enhancer protein 3, protein from *Homo sapiens* | UniProt | TAS | PMID: 1303260 |
| | TLE4 HUMAN | TLE4 protein, protein from *Homo sapiens* | UniProt | NAS | PMID: 1303260 |
| | TLK1 HUMAN | Splice Isoform 1 of Serine/threonine-protein kinase tousled-like 1, protein from *Homo sapiens* | UniProt | IEP | PMID: 10523312 |
| | | | | TAS | PMID: 9427565 |
| | TLK2 HUMAN | Splice Isoform 1 of Serine/threonine-protein kinase tousled-like 2, protein from *Homo sapiens* | UniProt | IEP | PMID: 9427565 |
| | | | | NAS | PMID: 98087437 |
| | TNAP3 HUMAN | Tumor necrosis factor, alpha-induced protein 3, protein from *Homo sapiens* | UniProt | IDA | PMID: 11463333 |
| | TNPO1 HUMAN | Importin beta-2 subunit, protein from *Homo sapiens* | UniProt | TAS | PMID: 9144189 |
| | TNPO2 HUMAN | Splice Isoform 1 of Transportin-2, protein from *Homo sapiens* | UniProt | TAS | PMID: 9298975 |
| | TOB2 HUMAN | Tob2 protein, protein from *Homo sapiens* | UniProt | TAS | PMID: 10602502 |
| | TOP2A HUMAN | Splice Isoform 1 of DNA topoisomerase 2-alpha, protein from *Homo sapiens* | UniProt | TAS | PMID: 6267071 |
| | TOP3A HUMAN | Splice Isoform Long of DNA topoisomerase III alpha, protein from *Homo sapiens* | UniProt | TAS | PMID: 8622991 |
| | TOP3B HUMAN | Splice Isoform 1 of DNA topoisomerase III beta-1, protein from *Homo sapiens* | UniProt | TAS | PMID: 9786843 |
| | TOPB1 HUMAN | DNA topoisomerase II binding protein 1, protein from *Homo sapiens* | UniProt | TAS | PMID: 9461304 |
| | TPX2 HUMAN | Targeting protein for Xklp2, protein from *Homo sapiens* | UniProt | TAS | PMID: 9207457 |
| | TR100 HUMAN | Thyroid hormone receptor-associated protein complex 100 kDa component, protein from *Homo sapiens* | UniProt | IDA | PMID: 10235267 |
| | TR150 HUMAN | Thyroid hormone receptor-associated protein complex 150 kDa component, protein from *Homo sapiens* | UniProt | IDA | PMID: 10235267 |

| Qualifier | Symbol Sequence/GOst | Information | Source | Evidence | Reference |
|---|---|---|---|---|---|
| | TR240 HUMAN | Thyroid hormone receptor-associated protein complex 240 kDa component, protein from *Homo sapiens* | UniProt | IDA | PMID: 10235267 |
| | TR95 HUMAN | Splice Isoform 1 of Thyroid hormone receptor-associated protein complex 95 kDa component, protein from *Homo sapiens* | UniProt | NAS | PMID: 10198638 |
| | TRA2A HUMAN | Splice Isoform Long of Transformer-2 protein homolog, protein from *Homo sapiens* | UniProt | IDA | PMID: 9546399 |
| | TRA2B HUMAN | Splice Isoform 1 of Arginine/serine-rich splicing factor 10, protein from *Homo sapiens* | UniProt | IDA | PMID: 9546399 |
| | TRABD HUMAN | TRABID protein, protein from *Homo sapiens* | UniProt | IDA | PMID: 11463333 |
| | TRAF4 HUMAN | Splice Isoform 1 of TNF receptor-associated factor 4, protein from *Homo sapiens* | UniProt | TAS | PMID: 7592751 |
| | TRBP2 HUMAN | TAR RNA-binding protein 2, protein from *Homo sapiens* | UniProt | TAS | PMID: 2011739 |
| | TREF1 HUMAN | Splice Isoform 1 of Transcriptional-regulating factor 1, protein from *Homo sapiens* | UniProt | IDA | PMID: 11349124 |
| | TRI22 HUMAN | Splice Isoform 1 of Tripartite motif protein 22, protein from *Homo sapiens* | UniProt | TAS | PMID: 7797467 |
| | TRI32 HUMAN | Tripartite motif protein 32, protein from *Homo sapiens* | UniProt | TAS | PMID: 7778269 |
| | TRIB3 HUMAN | Tribbles homolog 3, protein from *Homo sapiens* | UniProt | ISS | UniProt: Q96RU7 |
| | TRIP4 HUMAN | Activating signal cointegrator 1, protein from *Homo sapiens* | UniProt | IDA | PMID: 10454579 |
| | TRP13 HUMAN | Splice Isoform 1 of Thyroid receptor-interacting protein 13, protein from *Homo sapiens* | UniProt | TAS | PMID: 7776974 |
| | TRRAP HUMAN | Splice Isoform 1 of Transformation/transcription domain-associated protein, protein from *Homo sapiens* | UniProt | IDA | PMID: 9708738 |
| | TRUA HUMAN | tRNA pseudouridine synthase A, protein from *Homo sapiens* | UniProt | NAS | UniProt: Q9Y606 |
| | TSN HUMAN | Translin, protein from *Homo sapiens* | UniProt | TAS | PMID: 7663511 |
| | TUB HUMAN | Tubby protein homolog, protein from *Homo sapiens* | UniProt | TAS | PMID: 11000483 |
| | TULP3 HUMAN | Tubby related protein 3, protein from *Homo sapiens* | UniProt | NAS | PMID: 11375483 |
| | TWST2 HUMAN | Twist-related protein 2, protein from *Homo sapiens* | UniProt | IDA | PMID: 11062344 |
| | TYDP1 HUMAN | Tyrosyl-DNA phosphodiesterase 1, protein from *Homo sapiens* | UniProt | NAS | PMID: 10521354 |
| | U2AFL HUMAN | U2 small nuclear ribonucleoprotein auxiliary factor 35 kDa subunit related-protein 1, protein from *Homo sapiens* | UniProt | NAS | UniProt: Q15695 |
| | U360 HUMAN | Hypothetical protein DKFZp586N0222, protein from *Homo sapiens* | UniProt | NAS | PMID: 10873569 |
| | UB2R1 HUMAN | Ubiquitin-conjugating enzyme E2-32 kDa complementing, protein from *Homo sapiens* | UniProt | NAS | PMID: 8248134 |
| | UB2V1 HUMAN | Splice Isoform 1 of Ubiquitin-conjugating enzyme E2 variant 1, protein from *Homo sapiens* | UniProt | TAS | PMID: 9305758 |

| Qualifier | Symbol Sequence/GOst | Information | Source | Evidence | Reference |
|---|---|---|---|---|---|
| | UB7I1 HUMAN | Splice Isoform 1 of E3 ubiquitin ligase TRIAD3, protein from *Homo sapiens* | UniProt | NR | UniProt: Q9NWF9 |
| | UBIQ HUMAN | Ubiquitin, protein from *Homo sapiens* | UniProt | IC | PMID: 14528304 |
| | UBP18 HUMAN | Ubl carboxyl-terminal hydrolase 18, protein from *Homo sapiens* | UniProt | TAS | PMID: 10777664 |
| | UBP4 HUMAN | Splice Isoform UNPEL of Ubiquitin carboxyl-terminal hydrolase 4, protein from *Homo sapiens* | UniProt | TAS | PMID: 8183569 |
| | UBP7 HUMAN | Ubiquitin carboxyl-terminal hydrolase 7, protein from *Homo sapiens* | UniProt | TAS | PMID: 9130697 |
| | UBQL4 HUMAN | Ubiquilin-4, protein from *Homo sapiens* | UniProt | IDA | PMID: 11001934 |
| | UGTAP HUMAN | Splice Isoform 1 of UGA suppressor tRNA-associated protein, protein from *Homo sapiens* | UniProt | ISS | UniProt: Q9HD40 |
| | UHMK1 HUMAN | Splice Isoform 1 of Serine/threonine-protein kinase Kist, protein from *Homo sapiens* | UniProt | ISS | UniProt: Q8TAS1 |
| | UK14 HUMAN | Ribonuclease UK114, protein from *Homo sapiens* | UniProt | TAS | PMID: 8530410 |
| | ULE1A HUMAN | Ubiquitin-like 1-activating enzyme E1A, protein from *Homo sapiens* | UniProt | NAS | PMID: 10187858 |
| | | | | ISS | UniProt: O95717 |
| | | | | ISS | UniProt: Q9P020 |
| | UNG HUMAN | Splice Isoform 2 of Uracil-DNA glycosylase, protein from *Homo sapiens* | UniProt | NAS | PMID: 9016624 |
| | USF1 HUMAN | Upstream stimulatory factor 1, protein from *Homo sapiens* | UniProt | TAS | PMID: 2249772 |
| | UTP11 HUMAN | Probable U3 small nucleolar RNA-associated protein 11, protein from *Homo sapiens* | UniProt | IDA | PMID: 12559088 |
| | VAV HUMAN | Vav proto-oncogene, protein from *Homo sapiens* | UniProt | NR | UniProt: P15498 |
| | VCX1 HUMAN | Variable charge X-linked protein 1, protein from *Homo sapiens* | UniProt | IDA | PMID: 12826317 |
| | VCX3 HUMAN | Variable charge X-linked protein 3, protein from *Homo sapiens* | UniProt | ISS | UniProt: Q9NNX9 |
| | VCXC HUMAN | VCX-C protein, protein from *Homo sapiens* | UniProt | ISS | UniProt: Q9H321 |
| | VGLL1 HUMAN | Transcription cofactor vestigial-like protein 1, protein from *Homo sapiens* | UniProt | NAS | PMID: 10518497 |
| | VHL HUMAN | Splice Isoform 1 of Von Hippel-Lindau disease tumor suppressor, protein from *Homo sapiens* | UniProt | TAS | PMID: 7604013 |
| | WBP11 HUMAN | WW domain-binding protein 11, protein from *Homo sapiens* | UniProt | TAS | PMID: 10593949 |
| | WDFY1 HUMAN | WD repeat and FYVE domain containing protein 1, protein from *Homo sapiens* | UniProt | IDA | PMID: 11739631 |
| | WDR33 HUMAN | WD-repeat protein 33, protein from *Homo sapiens* | UniProt | IDA | PMID: 11162572 |
| | WDR3 HUMAN | WD-repeat protein 3, protein from *Homo sapiens* | UniProt | TAS | PMID: 10395803 |
| | WDR50 HUMAN | WD-repeat protein 50, protein from *Homo sapiens* | UniProt | IDA | PMID: 15199122 |
| | WEE1 HUMAN | Wee1-like protein kinase, protein from *Homo sapiens* | UniProt | TAS | PMID: 8348613 |
| | WRB HUMAN | Tryptophan-rich protein, protein from *Homo sapiens* | UniProt | TAS | PMID: 9544840 |
| | WRIP1 HUMAN | Splice Isoform 1 of ATPase WRNIP1, protein from *Homo sapiens* | UniProt | ISS | UniProt: Q96S55 |

| Qualifier | Symbol Sequence/GOst | Information | Source | Evidence | Reference |
|---|---|---|---|---|---|
| | WRN HUMAN | Werner syndrome ATP-dependent helicase, protein from *Homo sapiens* | UniProt | TAS | PMID: 9288107 |
| | WT1 HUMAN | Wilms tumor 1 isoform D, protein from *Homo sapiens* | UniProt | NAS | UniProt: Q16256 |
| | WTAP HUMAN | Splice Isoform 2 of Wilms' tumor 1-associating protein, protein from *Homo sapiens* | UniProt | NAS IDA | UniProt: P19544 PMID: 10942595 |
| | WWTR1 HUMAN | WW domain containing transcription regulator protein 1, protein from *Homo sapiens* | UniProt | NAS | PMID: 11118213 |
| | XAB2 HUMAN | XPA-binding protein 2, protein from *Homo sapiens* | UniProt | IC | PMID: 10944529 |
| | XPA HUMAN | DNA-repair protein complementing XP-A cells, protein from *Homo sapiens* | UniProt | TAS | PMID: 1601884 |
| | XPO7 HUMAN | Exportin-7, protein from *Homo sapiens* | UniProt | IDA | PMID: 11071879 |
| | XRN2 HUMAN | 5'-3' exoribonuclease 2, protein from *Homo sapiens* | UniProt | ISS | UniProt: Q9H0D6 |
| | YAF2 HUMAN | Splice Isoform 2 of YY1-associated factor 2, protein from *Homo sapiens* | UniProt | IDA | PMID: 11593398 |
| | YBOX1 HUMAN | Nuclease sensitive element binding protein 1, protein from *Homo sapiens* | UniProt | NAS | UniProt: P67809 |
| | YBOX2 HUMAN | Y-box binding protein 2, protein from *Homo sapiens* | UniProt | TAS | PMID: 10100484 |
| | YETS4 HUMAN | YEATS domain-containing protein 4, protein from *Homo sapiens* | UniProt | TAS | PMID: 9302258 |
| | YL1 HUMAN | Protein YL-1, protein from *Homo sapiens* | UniProt | TAS | PMID: 7702631 |
| | YYY1 HUMAN | Hypothetical protein, protein from *Homo sapiens* | UniProt | TAS | PMID: 8121495 |
| | ZBT16 HUMAN | Splice Isoform PLZFB of Zinc finger and BTB domain-containing protein 16, protein from *Homo sapiens* | UniProt | IDA | PMID: 9294197 |
| | ZBT38 HUMAN | Zinc finger and BTB domain-containing protein 38, protein from *Homo sapiens* | UniProt | ISS | UniProt: Q8NAP3 |
| | ZBT7A HUMAN | Zinc finger and BTB domain-containing protein 7A, protein from *Homo sapiens* | UniProt | ISS | PMID: 15337766 |
| | ZCSL2 HUMAN | Splice Isoform 1 of CSL-type zinc finger-containing protein 2, protein from *Homo sapiens* | UniProt | IDA | PMID: 14980502 |
| | ZEP1 HUMAN | Zinc finger protein 40, protein from *Homo sapiens* | UniProt | TAS | PMID: 2106471 |
| | ZEP2 HUMAN | Human immunodeficiency virus type I enHancer binding protein 2, protein from *Homo sapiens* | UniProt | NAS | UniProt: P31629 |
| | ZF161 HUMAN | Zinc finger protein 161 homolog, protein from *Homo sapiens* | UniProt | TAS | PMID: 9177479 |
| | ZFP37 HUMAN | Zinc finger protein 37 homolog, protein from *Homo sapiens* | UniProt | NAS | UniProt: Q9Y6Q3 |
| | ZFP38 HUMAN | Hypothetical protein DKFZp686H10254, protein from *Homo sapiens* | UniProt | NAS | UniProt: Q9Y5A6 |
| | ZFP95 HUMAN | Zinc finger protein 95 homolog, protein from *Homo sapiens* | UniProt | NAS | PMID: 10585779 |
| | ZFPL1 HUMAN | Splice Isoform 1 of Zinc finger protein-like 1, protein from *Homo sapiens* | UniProt | NAS | PMID: 9653652 |
| | ZHANG HUMAN | Host cell factor-binding transcription factor Zhangfei, protein from *Homo sapiens* | UniProt | IDA | PMID: 15705566 |

-continued

| Qualifier | Symbol Sequence/GOst | Information | Source | Evidence | Reference |
|---|---|---|---|---|---|
| | ZHX1 HUMAN | Zinc fingers and homeoboxes protein 1, protein from *Homo sapiens* | UniProt | IDA | PMID: 12237128 |
| | ZHX2 HUMAN | Zinc fingers and homeoboxes protein 2, protein from *Homo sapiens* | UniProt | IDA | PMID: 12741956 |
| | ZHX3 HUMAN | Zinc fingers and homeoboxes protein 3, protein from *Homo sapiens* | UniProt | IDA | PMID: 12659632 |
| | ZIC1 HUMAN | Zinc finger protein ZIC 1, protein from *Homo sapiens* | UniProt | IDA | PMID: 8542595 |
| | ZKSC1 HUMAN | Zinc finger with KRAB and SCAN domain-containing protein 1, protein from *Homo sapiens* | UniProt | NAS | PMID: 7557990 |
| | ZMY11 HUMAN | Zinc finger MYND domain containing protein 11, protein from *Homo sapiens* | UniProt | TAS | PMID: 7621829 |
| | ZN117 HUMAN | Zinc finger protein 117, protein from *Homo sapiens* | UniProt | NAS | UniProt: Q03924 |
| | ZN11A HUMAN | Zinc finger protein 11A, protein from *Homo sapiens* | UniProt | NAS | PMID: 8464732 |
| | ZN11B HUMAN | Zinc finger protein 11B, protein from *Homo sapiens* | UniProt | NAS | UniProt: Q06732 |
| | ZN123 HUMAN | Zinc finger protein 123, protein from *Homo sapiens* | UniProt | NAS | PMID: 1339395 |
| | ZN125 HUMAN | Zinc finger protein 125, protein from *Homo sapiens* | UniProt | NAS | PMID: 1339395 |
| | ZN126 HUMAN | Zinc finger protein 126, protein from *Homo sapiens* | UniProt | NAS | PMID: 1339395 |
| | ZN131 HUMAN | Splice Isoform 1 of Zinc finger protein 131, protein from *Homo sapiens* | UniProt | NAS | PMID: 7557990 |
| | ZN134 HUMAN | Zinc finger protein 134, protein from *Homo sapiens* | UniProt | NAS | PMID: 7557990 |
| | ZN135 HUMAN | Similar to Zinc finger protein 135, protein from *Homo sapiens* | UniProt | NAS | PMID: 7557990 |
| | ZN138 HUMAN | Zinc finger protein 138, protein from *Homo sapiens* | UniProt | NAS | PMID: 7557990 |
| | ZN154 HUMAN | Zinc finger protein 154, protein from *Homo sapiens* | UniProt | NAS | PMID: 7557990 |
| | ZN165 HUMAN | Zinc finger protein 165, protein from *Homo sapiens* | UniProt | NAS | UniProt: P49910 |
| | ZN169 HUMAN | KRAB box family protein, protein from *Homo sapiens* | UniProt | NAS | UniProt: Q14929 |
| | ZN184 HUMAN | Zinc finger protein 184, protein from *Homo sapiens* | UniProt | NAS | UniProt: Q99676 |
| | ZN195 HUMAN | Hypothetical protein DKFZp666D035, protein from *Homo sapiens* | UniProt | NAS | UniProt: O14628 |
| | ZN200 HUMAN | Zinc finger protein 200, protein from *Homo sapiens* | UniProt | NAS | UniProt: P98182 |
| | ZN205 HUMAN | Zinc finger protein 205, protein from *Homo sapiens* | UniProt | NAS | UniProt: O95201 |
| | ZN207 HUMAN | Splice Isoform 1 of Zinc finger protein 207, protein from *Homo sapiens* | UniProt | NAS | PMID: 9799612 |
| | ZN208 HUMAN | Zinc finger protein 208, protein from *Homo sapiens* | UniProt | NAS | UNIPROT: O43345 |
| | ZN211 HUMAN | Zinc finger protein 211 isoform 2, protein from *Homo sapiens* | UniProt | NAS | UniProt: Q13398 |
| | ZN212 HUMAN | Zinc finger protein 212, protein from *Homo sapiens* | UniProt | NAS | UniProt: Q9UDV6 |
| | ZN214 HUMAN | Zinc finger protein 214, protein from *Homo sapiens* | UniProt | NAS | UniProt: Q9UL59 |
| | ZN215 HUMAN | Zinc finger protein 215, protein from *Homo sapiens* | UniProt | NAS | UniProt: Q9UL58 |
| | ZN219 HUMAN | Zinc finger protein 219, protein from *Homo sapiens* | UniProt | TAS | PMID: 10819330 |
| | ZN236 HUMAN | Similar to Mszf28, protein from *Homo sapiens* | UniProt | NAS | UniProt: Q9UL36 |
| | ZN253 HUMAN | Zinc finger protein 253, protein from *Homo sapiens* | UniProt | NAS | UniProt: O75346 |

| Qualifier | Symbol Sequence/GOst | Information | Source | Evidence | Reference |
|---|---|---|---|---|---|
| | ZN257 HUMAN | Zinc finger protein 257, protein from *Homo sapiens* | UniProt | NAS | UniProt: Q9Y2Q1 |
| | ZN265 HUMAN | Splice Isoform ZIS-1 of Zinc finger protein 265, protein from *Homo sapiens* | UniProt | TAS | PMID: 9931435 |
| | ZN268 HUMAN | Splice Isoform A of Zinc finger protein 268, protein from *Homo sapiens* | UniProt | NAS | PMID: 11311945 |
| | ZN277 HUMAN | Zinc finger protein 277, protein from *Homo sapiens* | UniProt | NAS | UniProt: Q9NRM2 |
| | ZN278 HUMAN | Splice Isoform 1 of Zinc finger protein 278, protein from *Homo sapiens* | UniProt | TAS | PMID: 10713105 |
| | ZN282 HUMAN | Zinc finger protein 282, protein from *Homo sapiens* | UniProt | NAS | UniProt: Q9UDV7 |
| | ZN297 HUMAN | Zinc finger protein 297, protein from *Homo sapiens* | UniProt | TAS | PMID: 9545376 |
| | ZN331 HUMAN | Zinc finger protein 331, protein from *Homo sapiens* | UniProt | NAS | UniProt: Q9NQX6 |
| | ZN33A HUMAN | Zinc finger protein 33A, protein from *Homo sapiens* | UniProt | NAS | UniProt: Q06730 |
| | ZN33B HUMAN | Zinc finger protein 33B, protein from *Homo sapiens* | UniProt | NAS | UniProt: Q06731 |
| | ZN346 HUMAN | Splice Isoform 1 of Zinc finger protein 346, protein from *Homo sapiens* | UniProt | TAS | PMID: 10488071 |
| | ZN37A HUMAN | Zinc finger protein 37A, protein from *Homo sapiens* | UniProt | NAS | PMID: 8464732 |
| | ZN396 HUMAN | Splice Isoform 1 of Zinc finger protein 396, protein from *Homo sapiens* | UniProt | IMP | UniProt: Q96N95 |
| | ZN398 HUMAN | Splice Isoform 1 of Zinc finger protein 398, protein from *Homo sapiens* | UniProt | NAS | PMID: 11779858 |
| | ZN482 HUMAN | Zinc finger protein 482, protein from *Homo sapiens* | UniProt | TAS | PMID: 7958847 |
| | ZNF19 HUMAN | Zinc finger protein 19, protein from *Homo sapiens* | UniProt | NAS | PMID: 7557990 |
| | ZNF22 HUMAN | Zinc finger protein 22, protein from *Homo sapiens* | UniProt | ISS | UniProt: P17026 |
| | ZNF24 HUMAN | Zinc finger protein 24, protein from *Homo sapiens* | UniProt | IC | PMID: 10585455 |
| | ZNF38 HUMAN | KRAB box family protein, protein from *Homo sapiens* | UniProt | IC | PMID: 2288909 |
| | | | | NAS | UniProt: Q9NNX8 |
| | ZNF41 HUMAN | Splice Isoform 1 of Zinc finger protein 41, protein from *Homo sapiens* | UniProt | NAS | UniProt: P51814 |
| | ZNF69 HUMAN | Zinc finger protein 69, protein from *Homo sapiens* | UniProt | NAS | UniProt: Q9UC07 |
| | ZNF70 HUMAN | Zinc finger protein 70, protein from *Homo sapiens* | UniProt | NAS | UniProt: Q9UC06 |
| | ZNF71 HUMAN | Endothelial zinc finger protein induced by tumor necrosis factor alpha, protein from *Homo sapiens* | UniProt | NAS | UniProt: Q9UC09 |
| | ZNF73 HUMAN | Zinc finger protein 73, protein from *Homo sapiens* | UniProt | NAS | UniProt: O43830 |
| | ZNF75 HUMAN | Hypothetical protein DKFZp667L2223, protein from *Homo sapiens* | UniProt | NAS | UniProt: P51815 |
| | ZNF79 HUMAN | Zinc finger protein 79, protein from *Homo sapiens* | UniProt | NAS | UniProt: Q15937 |
| | ZNF80 HUMAN | Zinc finger protein 80, protein from *Homo sapiens* | UniProt | NAS | UniProt: P51504 |
| | ZNF81 HUMAN | Zinc finger protein 81, protein from *Homo sapiens* | UniProt | NAS | UniProt: P51508 |
| | ZNF83 HUMAN | Zinc finger protein 83, protein from *Homo sapiens* | UniProt | NAS | UniProt: P51522 |
| | ZNF84 HUMAN | Zinc finger protein 84, protein from *Homo sapiens* | UniProt | NAS | UniProt: P51523 |
| | ZNF85 HUMAN | Zinc finger protein 85, protein from *Homo sapiens* | UniProt | TAS | PMID: 9839802 |
| | ZNF8 HUMAN | Zinc finger protein 8, protein from *Homo sapiens* | UniProt | NAS | UniProt: P17098 |
| | ZNF90 HUMAN | Zinc finger protein 90, protein from *Homo sapiens* | UniProt | NAS | UniProt: Q03938 |

| Qualifier | Symbol Sequence/GOst | Information | Source | Evidence | Reference |
|---|---|---|---|---|---|
| | ZNF91 HUMAN | Zinc finger protein 91, protein from *Homo sapiens* | UniProt | NAS | UniProt: Q05481 |
| | ZNF92 HUMAN | Splice Isoform 1 of Zinc finger protein 92, protein from *Homo sapiens* | UniProt | NAS | UniProt: Q03936 |
| | ZNF93 HUMAN | Splice Isoform 1 of Zinc finger protein 93, protein from *Homo sapiens* | UniProt | NAS | UniProt: P35789 |
| | ZPR1 HUMAN | Zinc-finger protein ZPR1, protein from *Homo sapiens* | UniProt | TAS | PMID: 8650580 |
| | ZRF1 HUMAN | Zuotin-related factor 1, protein from *Homo sapiens* | UniProt | NAS | UniProt: Q99543 |
| | ZW10 HUMAN | Centromere/kinetochore protein zw10 homolog, protein from *Homo sapiens* | UniProt | NAS | PMID: 11146660 |
| | ZWIA HUMAN | ZW10 interactor, antisense, protein from *Homo sapiens* | UniProt | IDA | PMID: 8885239 |
| | ZXDA HUMAN | Zinc finger X-linked protein ZXDA, protein from *Homo sapiens* | UniProt | NAS | UniProt: P98168 |
| | ZXDB HUMAN | Zinc finger X-linked protein ZXDB, protein from *Homo sapiens* | UniProt | NAS | UniProt: P98169 |
| | ACF HUMAN | Splice Isoform 1 of APOBEC1 complementation factor, protein from *Homo sapiens* | UniProt | IDA | PMID: 10781591 |
| | HILS1 HUMAN | Spermatid-specific linker histone H1-like protein, protein from *Homo sapiens* | UniProt | IDA | PMID: 12920187 |
| | HNRH1 HUMAN | Heterogeneous nuclear ribonucleoprotein H1, protein from *Homo sapiens* | UniProt | TAS | PMID: 7499401 |
| | HNRH2 HUMAN | Heterogeneous nuclear ribonucleoprotein H', protein from *Homo sapiens* | UniProt | TAS | PMID: 7499401 |
| | HNRH3 HUMAN | Splice Isoform 1 of Heterogeneous nuclear ribonucleoprotein H3, protein from *Homo sapiens* | UniProt | NAS | PMID: 10858537 |
| | HNRPC HUMAN | Full-length cDNA clone CS0DA009YK08 of Neuroblastoma of *Homo sapiens*, protein from *Homo sapiens* | UniProt | NR | UniProt: P07910 |
| | HNRPF HUMAN | Heterogeneous nuclear ribonucleoprotein F, protein from *Homo sapiens* | UniProt | TAS | PMID: 7499401 |
| | HNRPG HUMAN | Heterogeneous nuclear ribonucleoprotein G, protein from *Homo sapiens* | UniProt | NAS | PMID: 7692398 |
| | HNRPL HUMAN | Heterogeneous nuclear ribonucleoprotein L isoform a, protein from *Homo sapiens* | UniProt | TAS | PMID: 2687284 |
| | HNRPR HUMAN | Heterogeneous nuclear ribonucleoprotein R, protein from *Homo sapiens* | UniProt | TAS | PMID: 9421497 |
| | HNRPU HUMAN | Splice Isoform Long of Heterogenous nuclear ribonucleoprotein U, protein from *Homo sapiens* | UniProt | TAS | PMID: 7509195 |
| | HNRU2 HUMAN | Heterogeneous nuclear ribonucleoprotein UP2, protein from *Homo sapiens* | UniProt | NAS | UniProt: P07029 |
| | O14979 | JKTBP2, protein from *Homo sapiens* | UniProt | TAS | PMID: 9538234 |
| | O76022 | E1B-55 kDa-associated protein, protein from *Homo sapiens* | UniProt | TAS | PMID: 9733834 |
| | PTBP1 HUMAN | Splice Isoform 1 of Polypyrimidine tract-binding protein 1, protein from *Homo sapiens* | UniProt | TAS | PMID: 1641332 |
| | Q9UCE7 | D(TTAGGG)N-binding protein B37 = TYPE A-B heterogeneous nuclear | UniProt | TAS | PMID: 8321232 |

-continued

| Qualifier | Symbol Sequence/GOst | Information | Source | Evidence | Reference |
|---|---|---|---|---|---|
| | | ribonucleoprotein homolog, protein from *Homo sapiens* | | | |
| | RALY HUMAN | RNA binding protein, protein from *Homo sapiens* | UniProt | TAS | PMID: 9376072 |
| | ROA0 HUMAN | Heterogeneous nuclear ribonucleoprotein A0, protein from *Homo sapiens* | UniProt | TAS | PMID: 7585247 |
| | ROA1 HUMAN | Heterogeneous nuclear ribonucleoprotein A1 isoform b, protein from *Homo sapiens* | UniProt | TAS | PMID: 8521471 |
| | ROA2 HUMAN | Splice Isoform B1 of Heterogeneous nuclear ribonucleoproteins A2/B1, protein from *Homo sapiens* | UniProt | TAS | PMID: 7789969 |
| | O60934 | Nibrin, protein from *Homo sapiens* | UniProt | IDA | PMID: 9590181 |
| | Q63HR6 | Hypothetical protein DKFZp686G19151, protein from *Homo sapiens* | UniProt | ISS | UniProt: Q63HR6 |
| | RAD50 HUMAN | Splice Isoform 1 of DNA repair protein RAD50, protein from *Homo sapiens* | UniProt | TAS | PMID: 15279769 |
| | BARX1 HUMAN | Homeobox protein BarH-like 1, protein from *Homo sapiens* | UniProt | NAS | UniProt: Q9HBU1 |
| | GBX1 HUMAN | Homeobox protein GBX-1, protein from *Homo sapiens* | UniProt | NAS | UniProt: Q14549 |
| | HDAC8 HUMAN | Splice Isoform 3 of Histone deacetylase 8, protein from *Homo sapiens* | UniProt | TAS | PMID: 10748112 |
| | HMG2 HUMAN | High mobility group protein 2, protein from *Homo sapiens* | UniProt | TAS | PMID: 1551873 |
| | HXD12 HUMAN | Homeo box D12, protein from *Homo sapiens* | UniProt | NAS | UniProt: P35452 |
| | JUN HUMAN | Transcription factor AP-1, protein from *Homo sapiens* | UniProt | TAS | PMID: 10918580 |
| | PRRX2 HUMAN | Paired mesoderm homeobox protein 2, protein from *Homo sapiens* | UniProt | NAS | UniProt: Q99811 |
| | SMC3 HUMAN | Structural maintenance of chromosome 3, protein from *Homo sapiens* | UniProt | NR | UniProt: Q9UQE7 |
| | SMCE1 HUMAN | Splice Isoform 1 of SWI/SNF-related matrix-associated actin-dependent regulator of chromatin subfamily E member 1, protein from *Homo sapiens* | UniProt | TAS | PMID: 9435219 |
| | TE2IP HUMAN | Telomeric repeat binding factor 2 interacting protein 1, protein from *Homo sapiens* | UniProt | TAS | PMID: 10850490 |
| | ZBED1 HUMAN | Zinc finger BED domain containing protein 1, protein from *Homo sapiens* | UniProt | TAS | PMID: 9887332 |
| | ZN238 HUMAN | Zinc finger protein 238, protein from *Homo sapiens* | UniProt | TAS | PMID: 9756912 |
| | CHK1 HUMAN | Serine/threonine-protein kinase Chk1, protein from *Homo sapiens* | UniProt | TAS | PMID: 9382850 |
| | CHM1A HUMAN | Splice Isoform 1 of Charged multivesicular body protein 1a, protein from *Homo sapiens* | UniProt | IDA | PMID: 11559747 |
| | DMC1 HUMAN | Meiotic recombination protein DMC1/LIM15 homolog, protein from *Homo sapiens* | UniProt | TAS | PMID: 8602360 |
| | MCP33 HUMAN | Metaphase chromosomal protein 1, protein from *Homo sapiens* | UniProt | IDA | PMID: 9543011 |
| | MK67I HUMAN | MKI67 FHA domain-interacting nucleolar phosphoprotein, protein from *Homo sapiens* | UniProt | IDA | PMID: 11342549 |
| | NOL6 HUMAN | Splice Isoform 1 of Nucleolar protein 6, protein from *Homo sapiens* | UniProt | ISS | PMID: 11895476 |

-continued

| Qualifier | Symbol Sequence/GOst | Information | Source | Evidence | Reference |
|---|---|---|---|---|---|
| | Q8WZ42 | Titin, protein from *Homo sapiens* | UniProt | ISS | PMID: 9548712 |
| | | | | TAS | PMID: 10481174 |
| | RCC1 HUMAN | RCC1 protein, protein from *Homo sapiens* | UniProt | IDA | PMID: 15014043 |
| | RGS12 HUMAN | Splice Isoform 1 of Regulator of G-protein signaling 12, protein from *Homo sapiens* | UniProt | TAS | PMID: 10869340 |
| | SMC1A HUMAN | Structural maintenance of chromosome 1-like 1 protein, protein from *Homo sapiens* | UniProt | TAS | PMID: 7757074 |
| | SUV91 HUMAN | Histone-lysine N-methyltransferase, H3 lysine-9 specific 1, protein from *Homo sapiens* | UniProt | TAS | PMID: 10202156 |
| | TBG1 HUMAN | Tubulin gamma-1 chain, protein from *Homo sapiens* | UniProt | ISS | UNIPROT: P23258 |
| | NO55 HUMAN | Nucleolar autoantigen No55, protein from *Homo sapiens* | UniProt | TAS | PMID: 8862517 |
| | Q6ZNA8 | Hypothetical protein FLJ16262, protein from *Homo sapiens* | UniProt | ISS | UniProt: Q6ZNA8 |
| | RAD51 HUMAN | Splice Isoform 1 of DNA repair protein RAD51 homolog 1, protein from *Homo sapiens* | UniProt | ISS | UniProt: Q06609 |
| | STAG3 HUMAN | Splice Isoform 1 of Cohesin subunit SA-3, protein from *Homo sapiens* | UniProt | TAS | PMID: 10698974 |
| | SYCP2 HUMAN | Synaptonemal complex protein 2, protein from *Homo sapiens* | UniProt | NAS | PMID: 10341103 |
| | | | | NAS | PMID: 9592139 |
| | Q6PIF2 | PREDICTED: hypothetical protein XP_497609, protein from *Homo sapiens* | UniProt | ISS | PMID: 15944401 |
| | Q8N0S2 | Conserved hypothetical protein, protein from *Homo sapiens* | UniProt | ISS | PMID: 15944401 |
| | SYCP1 HUMAN | Synaptonemal complex protein 1, protein from *Homo sapiens* | UniProt | ISS | PMID: 15944401 |
| | NPM2 HUMAN | Nucleoplasmin-2, protein from *Homo sapiens* | UniProt | IDA | PMID: 12714744 |
| | Q8N7S8 | Hypothetical protein FLJ40400, protein from *Homo sapiens* | UniProt | ISS | UniProt: Q8N7S8 |
| | Q96GH7 | KLHDC3 protein, protein from *Homo sapiens* | UniProt | ISS | UniProt: Q96GH7 |
| | RCC1 HUMAN | RCC1 protein, protein from *Homo sapiens* | UniProt | IDA | PMID: 15014043 |
| | ATRX HUMAN | Splice Isoform 4 of Transcriptional regulator ATRX, protein from *Homo sapiens* | UniProt | TAS | PMID: 10570185 |
| | CBX1 HUMAN | Chromobox protein homolog 1, protein from *Homo sapiens* | UniProt | TAS | PMID: 9169582 |
| | CBX5 HUMAN | Chromobox protein homolog 5, protein from *Homo sapiens* | UniProt | TAS | PMID: 8663349 |
| | Q9Y654 | Heterochromatin-specific nonhistone protein, protein from *Homo sapiens* | UniProt | ISS | UniProt: Q9Y654 |
| | TB182 HUMAN | 182 kDa tankyrase 1-binding protein, protein from *Homo sapiens* | UniProt | NAS | PMID: 11854288 |
| | H2AW HUMAN | Core histone macro-H2A.2, protein from *Homo sapiens* | UniProt | IDA | PMID: 11331621 |
| | H2AY HUMAN | H2A histone family, member Y, isoform 3, protein from *Homo sapiens* | UniProt | IDA | PMID: 11331621 |
| | Q96AP0 | 24432 protein, protein from *Homo sapiens* | UniProt | IDA | PMID: 15181449 |
| | O95268 | Origin recognition complex subunit ORC5T, protein from *Homo sapiens* | UniProt | NAS | PMID: 9765232 |
| | Q9NZH2 | Replication initiator 1, protein from *Homo sapiens* | UniProt | TAS | PMID: 10606657 |

| Qualifier | Symbol Sequence/GOst | Information | Source | Evidence | Reference |
|---|---|---|---|---|---|
| | MCM3 HUMAN | DNA replication licensing factor MCM3, protein from *Homo sapiens* | UniProt | TAS | PMID: 1549468 |
| | DPOD3 HUMAN | DNA polymerase delta subunit 3, protein from *Homo sapiens* | UniProt | NAS | PMID: 10219083 |
| | PCNA HUMAN | Proliferating cell nuclear antigen, protein from *Homo sapiens* | UniProt | TAS | PMID: 2565339 |
| | RFC3 HUMAN | Activator 1 38 kDa subunit, protein from *Homo sapiens* | UniProt | TAS | PMID: 7774928 |
| | RFC4 HUMAN | Activator 1 37 kDa subunit, protein from *Homo sapiens* | UniProt | TAS | PMID: 7774928 |
| | RFC5 HUMAN | Activator 1 36 kDa subunit, protein from *Homo sapiens* | UniProt | NAS | PMID: 8999859 |
| | RFA1 HUMAN | Replication protein A 70 kDa DNA-binding subunit, protein from *Homo sapiens* | UniProt | TAS | PMID: 8756712 |
| | RFA2 HUMAN | Replication protein A 32 kDa subunit, protein from *Homo sapiens* | UniProt | TAS | PMID: 2406247 |
| | RFA3 HUMAN | Replication protein A 14 kDa subunit, protein from *Homo sapiens* | UniProt | TAS | PMID: 8454588 |
| | RFA4 HUMAN | Replication protein A 30 kDa subunit, protein from *Homo sapiens* | UniProt | TAS | PMID: 7760808 |
| | CHRC1 HUMAN | Chromatin accessibility complex protein 1, protein from *Homo sapiens* | UniProt | NAS | PMID: 10880450 |
| | Q9P288 | TOK-1alpha, protein from *Homo sapiens* | UniProt | IDA | PMID: 10878006 |
| | AKAP6 HUMAN | A-kinase anchor protein 6, protein from *Homo sapiens* | UniProt | IDA | PMID: 10413680 |
| | ANX11 HUMAN | Annexin A11, protein from *Homo sapiens* | UniProt | NAS | PMID: 12577318 |
| | ATF6A HUMAN | Cyclic AMP-dependent transcription factor ATF-6 alpha, protein from *Homo sapiens* | UniProt | TAS | PMID: 10866666 |
| | CBX5 HUMAN | Chromobox protein homolog 5, protein from *Homo sapiens* | UniProt | TAS | PMID: 8663349 |
| | CENPF HUMAN | CENP-F kinetochore protein, protein from *Homo sapiens* | UniProt | IDA | PMID: 12154071 |
| | CLIC1 HUMAN | Chloride intracellular channel protein 1, protein from *Homo sapiens* | UniProt | IDA | PMID: 9139710 |
| | EMD HUMAN | Emerin, protein from *Homo sapiens* | UniProt | TAS | PMID: 8589715 |
| | GNAZ HUMAN | Guanine nucleotide-binding protein G(z), alpha subunit, protein from *Homo sapiens* | UniProt | TAS | PMID: 2117645 |
| | HAX1 HUMAN | HS1-associating protein X-1, protein from *Homo sapiens* | UniProt | TAS | PMID: 9058808 |
| | LAP2A HUMAN | Lamina-associated polypeptide 2 isoform alpha, protein from *Homo sapiens* | UniProt | TAS | PMID: 8530026 |
| | LAP2B HUMAN | ThymopoieTin isoform beTa, protein from *Homo sapiens* | UniProt | TAS | PMID: 8530026 |
| | LIS1 HUMAN | Platelet-activating factor acetylhydrolase IB alpha subunit, protein from *Homo sapiens* | UniProt | IDA | PMID: 11940666 |
| | LY10 HUMAN | Splice Isoform LYSp100-B of Nuclear body protein SP140, protein from *Homo sapiens* | UniProt | TAS | PMID: 8695863 |
| | MYOF HUMAN | Splice Isoform 1 of Myoferlin, protein from *Homo sapiens* | UniProt | TAS | PMID: 10607832 |
| | PE2R3 HUMAN | Splice Isoform EP3A of Prostaglandin E2 receptor, EP3 subtype, protein from *Homo sapiens* | UniProt | TAS | PMID: 10336471 |
| | PTGDS HUMAN | Prostaglandin-H2 D-isomerase precursor, protein from *Homo sapiens* | UniProt | ISS | UniProt: P41222 |

| Qualifier | Symbol Sequence/GOst | Information | Source | Evidence | Reference |
|---|---|---|---|---|---|
| | Q86UU5 | Gametogenetin protein 1a, protein from *Homo sapiens* | UniProt | ISS | UniProt: Q86UU5 |
| | Q9UN92 | Nurim, protein from *Homo sapiens* | UniProt | TAS | PMID: 10402458 |
| | RTN4 HUMAN | Splice Isoform 1 of Reticulon-4, protein from *Homo sapiens* | UniProt | IDA | PMID: 11126360 |
| | S10A6 HUMAN | Calcyclin, protein from *Homo sapiens* | UniProt | NAS | PMID: 12577318 |
| | SRBP1 HUMAN | Sterol regulatory element binding transcription factor 1, isoform a, protein from *Homo sapiens* | UniProt | TAS | PMID: 8156598 |
| | SYNE1 HUMAN | Splice Isoform 1 of Nesprin-1, protein from *Homo sapiens* | UniProt | IDA | PMID: 11792814 |
| | TIP30 HUMAN | Conserved hypothetical protein, protein from *Homo sapiens* | UniProt | IDA | PMID: 15282309 |
| | TREX1 HUMAN | Splice Isoform 1 of Three prime repair exonuclease 1, protein from *Homo sapiens* | UniProt | ISS | UniProt: Q9Y4X2 |
| | | | | ISS | UniProt: Q8TEU2 |
| | | | | NAS | PMID: 10391904 |
| | UN84B HUMAN | Sad1/unc-84-like protein 2, protein from *Homo sapiens* | UniProt | TAS | PMID: 10375507 |
| | LMNB2 HUMAN | Lamin B2, protein from *Homo sapiens* | UniProt | NAS | UniProt: Q03252 |
| | Q9UHQ1 | Nuclear prelamin A recognition factor, protein from *Homo sapiens* | UniProt | TAS | PMID: 10514485 |
| | LMNA HUMAN | Splice Isoform A of Lamin A/C, protein from *Homo sapiens* | UniProt | TAS | PMID: 10080180 |
| | LMNB1 HUMAN | Lamin B1, protein from *Homo sapiens* | UniProt | TAS | PMID: 7557986 |
| | Q9BWC6 | Nuclear prelamin A recognition factor, isoform b, protein from *Homo sapiens* | UniProt | IDA | PMID: 10514485 |
| | RM19 HUMAN | 39S ribosomal protein L19, mitochondrial precursor, protein from *Homo sapiens* | UniProt | IDA | PMID: 10942595 |
| | SCRN1 HUMAN | Secernin-1, protein from *Homo sapiens* | UniProt | IDA | PMID: 10942595 |
| | TAGL2 HUMAN | Transgelin-2, protein from *Homo sapiens* | UniProt | IDA | PMID: 10942595 |
| | WTAP HUMAN | Splice Isoform 2 of Wilms' tumor 1-associating protein, protein from *Homo sapiens* | UniProt | IDA | PMID: 10942595 |
| | AT11B HUMAN | Probable phospholipid-transporting ATPase IF, protein from *Homo sapiens* | UniProt | NAS | PMID: 11790799 |
| | MATR3 HUMAN | Matrin-3, protein from *Homo sapiens* | UniProt | TAS | PMID: 2033075 |
| | LBR HUMAN | Lamin-B receptor, protein from *Homo sapiens* | UniProt | TAS | PMID: 8157662 |
| | MAN1 HUMAN | Inner nuclear membrane protein Man1, protein from *Homo sapiens* | UniProt | TAS | PMID: 10671519 |
| | PSN1 HUMAN | Splice Isoform 1 of Presenilin-1, protein from *Homo sapiens* | UniProt | TAS | PMID: 9298903 |
| | PSN2 HUMAN | Splice Isoform 1 of Presenilin-2, protein from *Homo sapiens* | UniProt | TAS | PMID: 9298903 |
| | DHCR7 HUMAN | 7-dehydrocholesterol reductase, protein from *Homo sapiens* | UniProt | IDA | PMID: 9878250 |
| | GUC2D HUMAN | Retinal guanylyl cyclase 1 precursor, protein from *Homo sapiens* | UniProt | TAS | PMID: 7777544 |
| | GUC2F HUMAN | Retinal guanylyl cyclase 2 precursor, protein from *Homo sapiens* | UniProt | TAS | PMID: 7777544 |
| | Q6NUM9 | All-trans-13,14-dihydroretinol saturase, protein from *Homo sapiens* | UniProt | ISS | PMID: 15358783 |

| Qualifier | Symbol Sequence/GOst | Information | Source | Evidence | Reference |
|---|---|---|---|---|---|
| | RAE1L HUMAN | mRNA-associated protein mrnp 41, protein from *Homo sapiens* | UniProt | TAS | PMID: 9256445 |
| colocalizes_with | AAAS HUMAN | Aladin, protein from *Homo sapiens* | UniProt | IDA | PMID: 12730363 |
| | DD19B HUMAN | Splice Isoform 1 of ATP-dependent RNA helicase DDX19B, protein from *Homo sapiens* | UniProt | TAS | PMID: 10428971 |
| | RAE1L HUMAN | mRNA-associated protein mrnp 41, protein from *Homo sapiens* | UniProt | TAS | PMID: 9256445 |
| | IMA1 HUMAN | Importin alpha-1 subunit, protein from *Homo sapiens* | UniProt | TAS | PMID: 8052633 |
| | IMA3 HUMAN | Importin alpha-3 subunit, protein from *Homo sapiens* | UniProt | TAS | PMID: 9154134 |
| | IMB1 HUMAN | Importin beta-1 subunit, protein from *Homo sapiens* | UniProt | TAS | PMID: 7627554 |
| | IMB3 HUMAN | Importin beta-3, protein from *Homo sapiens* | UniProt | TAS | PMID: 9271386 |
| colocalizes_with | IPO4 HUMAN | Splice Isoform 1 of Importin-4, protein from *Homo sapiens* | UniProt | NAS | PMID: 11823430 |
| | IPO7 HUMAN | Importin-7, protein from *Homo sapiens* | UniProt | TAS | PMID: 9214382 |
| | NU107 HUMAN | Nuclear pore complex protein Nup107, protein from *Homo sapiens* | UniProt | IDA | PMID: 11564755 |
| | | | | IDA | PMID: 11684705 |
| | NU133 HUMAN | Nuclear pore complex protein Nup133, protein from *Homo sapiens* | UniProt | IDA | PMID: 11684705 |
| | | | | IDA | PMID: 11564755 |
| | NU153 HUMAN | Nuclear pore complex protein Nup153, protein from *Homo sapiens* | UniProt | TAS | PMID: 8110839 |
| | NU160 HUMAN | NucleoporiN 160 kDa, protein from *Homo sapiens* | UniProt | IDA | PMID: 11564755 |
| | | | | IDA | PMID: 11684705 |
| | NU205 HUMAN | Nuclear pore complex protein Nup205, protein from *Homo sapiens* | UniProt | NAS | PMID: 9348540 |
| | NU214 HUMAN | Nuclear pore complex protein Nup214, protein from *Homo sapiens* | UniProt | TAS | PMID: 8108440 |
| | NUP50 HUMAN | Nucleoporin 50 kDa, protein from *Homo sapiens* | UniProt | TAS | PMID: 10449902 |
| | NUP54 HUMAN | Nucleoporin 54 kDa variant, protein from *Homo sapiens* | UniProt | TAS | PMID: 870784 |
| | NUP62 HUMAN | Nuclear pore glycoprotein p62, protein from *Homo sapiens* | UniProt | IDA | PMID: 1915414 |
| | NUP88 HUMAN | Nuclear pore complex protein Nup88, protein from *Homo sapiens* | UniProt | TAS | PMID: 9049309 |
| | NUP98 HUMAN | Splice Isoform 1 of Nuclear pore complex protein Nup98-Nup96 precursor, protein from *Homo sapiens* | UniProt | IDA | PMID: 9348540 |
| | | | | NAS | PMID: 10087256 |
| | NUPL HUMAN | Nucleoporin-like protein RIP, protein from *Homo sapiens* | UniProt | TAS | PMID: 7637788 |
| | NXT1 HUMAN | NTF2-related export protein 1, protein from *Homo sapiens* | UniProt | TAS | PMID: 10567585 |
| | O75761 | Ranbp3 protein, protein from *Homo sapiens* | UniProt | NAS | PMID: 9637251 |
| | Q6GTM2 | Nucleoporin 62 kDa, protein from *Homo sapiens* | UniProt | ISS | UniProt: Q6GTM2 |
| | RAE1L HUMAN | mRNA-associated protein mrnp 41, protein from *Homo sapiens* | UniProt | TAS | PMID: 9256445 |
| | RAN HUMAN | GTP-binding nuclear protein RAN, protein from *Homo sapiens* | UniProt | NAS | PMID: 8421051 |
| | RBP17 HUMAN | Ran-binding protein 17, protein from *Homo sapiens* | UniProt | NAS | PMID: 11024021 |

-continued

| Qualifier | Symbol Sequence/GOst | Information | Source | Evidence | Reference |
|---|---|---|---|---|---|
| | RBP23 HUMAN | Ran-binding protein 2-like 3, protein from *Homo sapiens* | UniProt | NAS | PMID: 9480752 |
| | RBP2 HUMAN | Ran-binding protein 2, protein from *Homo sapiens* | UniProt | TAS | PMID: 7603572 |
| | RGP1 HUMAN | Ran GTPase-activating protein 1, protein from *Homo sapiens* | UniProt | TAS | PMID: 8978815 |
| | RNUT1 HUMAN | SNURPORTIN1, protein from *Homo sapiens* | UniProt | TAS | PMID: 9670026 |
| | SENP2 HUMAN | Sentrin-specific protease 2, protein from *Homo sapiens* | UniProt | IDA | PMID: 12192048 |
| | TPR HUMAN | Translocated promoter region, protein from *Homo sapiens* | UniProt | TAS | PMID: 7798308 |
| | XPO7 HUMAN | Exportin-7, protein from *Homo sapiens* | UniProt | IDA | PMID: 11024021 |
| | EXOS3 HUMAN | Exosome complex exonuclease RRP40, protein from *Homo sapiens* | UniProt | IDA | PMID: 11110791 |
| | EXOS9 HUMAN | Polymyositis/scleroderma autoantigen 1, protein from *Homo sapiens* | UniProt | NAS | PMID: 11879549 |
| | O60934 | Nibrin, protein from *Homo sapiens* | UniProt | IDA | PMID: 12447371 |
| | Q63HR6 | Hypothetical protein DKFZp686G19151, protein from *Homo sapiens* | UniProt | ISS | UniProt: Q63HR6 |
| | Q9BWC6 | Nuclear prelamin A recognition factor, isoform b, protein from *Homo sapiens* | UniProt | IDA | PMID: 10514485 |
| | CENPF HUMAN | CENP-F kinetochore protein, protein from *Homo sapiens* | UniProt | IDA | PMID: 7542657 |
| | CHM1A HUMAN | Splice Isoform 1 of Charged multivesicular body protein 1a, protein from *Homo sapiens* | UniProt | IDA | PMID: 11559747 |
| | DNM3A HUMAN | DNA, protein from *Homo sapiens* | UniProt | ISS | PMID: 12138111 |
| | ERCC8 HUMAN | Splice Isoform 1 of DNA excision repair protein ERCC-8, protein from *Homo sapiens* | UniProt | IDA | PMID: 11782547 |
| | MYB HUMAN | Splice Isoform 1 of Myb proto-oncogene protein, protein from *Homo sapiens* | UniProt | NAS | PMID: 3014652 |
| | P53 HUMAN | Splice Isoform 1 of Cellular tumor antigen p53, protein from *Homo sapiens* | UniProt | IDA | PMID: 11080164 |
| | PML HUMAN | Splice Isoform PML-1 of Probable transcription factor PML, protein from *Homo sapiens* | UniProt | TAS | PMID: 9294197 |
| | Q86XF5 | DNA cytosine methyltransferase 3 alpha, isoform a, protein from *Homo sapiens* | UniProt | ISS | PMID: 12138111 |
| | Q8IZV0 | DNA cytosine methyltransferase 3 alpha isoform b, protein from *Homo sapiens* | UniProt | IDA | PMID: 12138111 |
| | SMC3 HUMAN | Structural maintenance of chromosome 3, protein from *Homo sapiens* | UniProt | IDA | PMID: 11590136 |
| | SMRCD HUMAN | SWI/SNF-related, matrix associated, actin-dependent regulator of chromatin subfamily A containing DEAD/H box 1, protein from *Homo sapiens* | UniProt | NAS | PMID: 11031099 |
| | SPTN4 HUMAN | Splice Isoform 1 of Spectrin beta chain, brain 3, protein from *Homo sapiens* | UniProt | IDA | PMID: 11294830 |
| | TEP1 HUMAN | Splice Isoform 1 of Telomerase protein component 1, protein from *Homo sapiens* | UniProt | IDA | PMID: 7876352 |

-continued

| Qualifier | Symbol Sequence/GOst | Information | Source | Evidence | Reference |
|---|---|---|---|---|---|
| | ARSA1 HUMAN | Arsenical pump-driving ATPase, protein from *Homo sapiens* | UniProt | TAS | PMID: 9736449 |
| | EXOS9 HUMAN | Polymyositis/scleroderma autoantigen 1, protein from *Homo sapiens* | UniProt | TAS | PMID: 2007859 |
| | P53 HUMAN | Splice Isoform 1 of Cellular tumor antigen p53, protein from *Homo sapiens* | UniProt | IDA | PMID: 12080348 |
| | DDX21 HUMAN | Splice Isoform 2 of Nucleolar RNA helicase 2, protein from *Homo sapiens* | UniProt | TAS | PMID: 8614622 |
| | DDX54 HUMAN | ATP-dependent RNA helicase DDX54, protein from *Homo sapiens* | UniProt | ISS | UniProt: Q9BRZ1 |
| | DDX56 HUMAN | Probable ATP-dependent RNA helicase DDX56, protein from *Homo sapiens* | UniProt | TAS | PMID: 10749921 |
| | DEDD2 HUMAN | Splice Isoform 1 of DNA-binding death effector domain-containing protein 2, protein from *Homo sapiens* | UniProt | IDA | PMID: 11741985 |
| | DEDD HUMAN | Splice Isoform 1 of Death effector domain-containing protein, protein from *Homo sapiens* | UniProt | ISS | UniProt: O75618 |
| | DKC1 HUMAN | H/ACA ribonucleoprotein complex subunit 4, protein from *Homo sapiens* | UniProt | TAS | PMID: 10556300 |
| | DNJB9 HUMAN | DnaJ homolog subfamily B member 9, protein from *Homo sapiens* | UniProt | ISS | UniProt: Q9UBS3 |
| | EXOS1 HUMAN | 3'-5' exoribonuclease CSL4 homolog, protein from *Homo sapiens* | UniProt | IDA | PMID: 11812149 |
| | EXOS4 HUMAN | Exosome complex exonuclease RRP41, protein from *Homo sapiens* | UniProt | NAS | PMID: 11110791 |
| | EXOS5 HUMAN | Exosome complex exonuclease RRP46, protein from *Homo sapiens* | UniProt | NAS | PMID: 11110791 |
| | EXOS9 HUMAN | Polymyositis/scleroderma autoantigen 1, protein from *Homo sapiens* | UniProt | TAS | PMID: 2007859 |
| | EXOSX HUMAN | Splice Isoform 1 of Exosome component 10, protein from *Homo sapiens* | UniProt | TAS | PMID: 1383382 |
| | FXR1 HUMAN | Fragile X mental retardation syndrome-related protein 1, protein from *Homo sapiens* | UniProt | TAS | PMID: 10888599 |
| | GEMI4 HUMAN | Component of gems 4, protein from *Homo sapiens* | UniProt | TAS | PMID: 10725331 |
| | GNL3 HUMAN | Splice Isoform 1 of Guanine nucleotide binding protein-like 3, protein from *Homo sapiens* | UniProt | ISS | UniProt: Q9BVP2 |
| | IF16 HUMAN | Splice Isoform 2 of Gamma-interferon-inducible protein Ifi-16, protein from *Homo sapiens* | UniProt | IDA | PMID: 14654789 |
| | ILF2 HUMAN | Interleukin enhancer-binding factor 2, protein from *Homo sapiens* | UniProt | IDA | PMID: 11790298 |
| | IMP3 HUMAN | U3 small nucleolar ribonucleoprotein protein IMP3, protein from *Homo sapiens* | UniProt | IDA | PMID: 12655004 |
| | IMP4 HUMAN | U3 small nucleolar ribonucleoprotein protein IMP4, protein from *Homo sapiens* | UniProt | IDA | PMID: 12655004 |
| | KI67 HUMAN | Splice Isoform Long of Antigen KI-67, protein from *Homo sapiens* | UniProt | NR | UniProt: P46013 |
| | MBB1A HUMAN | Splice Isoform 1 of Myb-binding protein 1A, protein from *Homo sapiens* | UniProt | ISS | UniProt: Q9BQG0 |

-continued

| Qualifier | Symbol Sequence/GOst | Information | Source | Evidence | Reference |
|---|---|---|---|---|---|
| | MDM2 HUMAN | Splice Isoform Mdm2 of Ubiquitin-protein ligase E3 Mdm2, protein from *Homo sapiens* | UniProt | IDA | PMID: 10707090 |
| | MK67I HUMAN | MKI67 FHA domain-interacting nucleolar phosphoprotein, protein from *Homo sapiens* | UniProt | IDA | PMID: 11342549 |
| | MO4L2 HUMAN | Mortality factor 4-like protein 2, protein from *Homo sapiens* | UniProt | IDA | PMID: 10942595 |
| | NEK11 HUMAN | Splice Isoform 1 of Serine/threonine-protein kinase Nek11, protein from *Homo sapiens* | UniProt | IDA | PMID: 15161910 |
| | NHPX HUMAN | NHP2-like protein 1, protein from *Homo sapiens* | UniProt | TAS | PMID: 10593953 |
| | NO55 HUMAN | Nucleolar autoantigen No55, protein from *Homo sapiens* | UniProt | TAS | PMID: 8862517 |
| | NOL1 HUMAN | Proliferating-cell nucleolar antigen p120, protein from *Homo sapiens* | UniProt | TAS | PMID: 1394192 |
| | NOL3 HUMAN | Splice Isoform 1 of Nucleolar protein 3, protein from *Homo sapiens* | UniProt | TAS | PMID: 10196175 |
| | NOL4 HUMAN | Splice Isoform 1 of Nucleolar protein 4, protein from *Homo sapiens* | UniProt | TAS | PMID: 9813152 |
| | NOL6 HUMAN | Splice Isoform 1 of Nucleolar protein 6, protein from *Homo sapiens* | UniProt | ISS | PMID: 11895476 |
| | NOLC1 HUMAN | Nucleolar and coiled-body phosphoprotein 1, protein from *Homo sapiens* | UniProt | TAS | PMID: 7657714 |
| | NOP56 HUMAN | Nucleolar protein Nop56, protein from *Homo sapiens* | UniProt | TAS | PMID: 9372940 |
| | NOP5 HUMAN | Nucleolar protein NOP5, protein from *Homo sapiens* | UniProt | TAS | PMID: 10925205 |
| | NPA1P HUMAN | Nucleolar preribosomal-associated protein 1, protein from *Homo sapiens* | UniProt | NAS | PMID: 12429849 |
| | NPM HUMAN | Nucleophosmin, protein from *Homo sapiens* | UniProt | IDA | PMID: 12080348 |
| | NUCL HUMAN | Nucleolin, protein from *Homo sapiens* | UniProt | TAS | PMID: 2394707 |
| | O00366 | Putative p150, protein from *Homo sapiens* | UniProt | ISS | UniProt: O00366 |
| | OASL HUMAN | Splice Isoform p56 of 59 kDa 2'-5'-oligoadenylate synthetase-like protein, protein from *Homo sapiens* | UniProt | TAS | PMID: 9826176 |
| | P53 HUMAN | Splice Isoform 1 of Cellular tumor antigen p53, protein from *Homo sapiens* | UniProt | IDA | PMID: 12080348 |
| | PNMA1 HUMAN | Paraneoplastic antigen Ma1, protein from *Homo sapiens* | UniProt | TAS | PMID: 10050892 |
| | PTBP1 HUMAN | Splice Isoform 1 of Polypyrimdine tract-binding protein 1, protein from *Homo sapiens* | UniProt | TAS | PMID: 1641332 |
| | Q76D35 | Nop132, protein from *Homo sapiens* | UniProt | IDA | PMID: 14660641 |
| | Q8WYJ1 | MDM2 protein, protein from *Homo sapiens* | UniProt | ISS | UniProt: Q8WYJ1 |
| | Q8WYJ2 | MDM2 protein, protein from *Homo sapiens* | UniProt | ISS | UniProt: Q8WYJ2 |
| | Q96Q89 | M-phase phosphoprotein 1, protein from *Homo sapiens* | UniProt | IDA | PMID: 11470801 |
| | Q9H2G4 | CTCL tumor antigense 20-4, protein from *Homo sapiens* | UniProt | IDA | PMID: 11395479 |
| | Q9P1T7 | HIC protein isoform p40, protein from *Homo sapiens* | UniProt | NAS | PMID: 10671520 |
| | Q9UFR5 | M-phase phosphoprotein 1, protein from *Homo sapiens* | UniProt | ISS | UniProt: Q9UFR5 |
| | RCL1 HUMAN | RNA 3'-terminal phosphate cyclase-like protein, protein from *Homo sapiens* | UniProt | NAS | UniProt: Q9Y2P8 |

-continued

| Qualifier | Symbol Sequence/GOst | Information | Source | Evidence | Reference |
|---|---|---|---|---|---|
| | DKC1 HUMAN | H/ACA ribonucleoprotein complex subunit 4, protein from *Homo sapiens* | UniProt | TAS | PMID: 10556300 |
| | IF16 HUMAN | Splice Isoform 2 of Gamma-interferon-inducible protein Ifi-16, protein from *Homo sapiens* | UniProt | IDA | PMID: 14654789 |
| | RL35 HUMAN | 60S ribosomal protein L35, protein from *Homo sapiens* | UniProt | TAS | PMID: 2891103 |
| | RL3 HUMAN | 60S ribosomal protein L3, protein from *Homo sapiens* | UniProt | TAS | PMID: 2891103 |
| | RPF1 HUMAN | Ribosome production factor 1, protein from *Homo sapiens* | UniProt | IDA | PMID: 12429849 |
| | RS7 HUMAN | 40S ribosomal protein S7, protein from *Homo sapiens* | UniProt | IDA | PMID: 11823430 |
| | S29A2 HUMAN | Solute carrier family 29 (Nucleoside transporters), member 2, protein from *Homo sapiens* | UniProt | TAS | PMID: 7639753 |
| | SRP68 HUMAN | Splice Isoform 1 of Signal recognition particle 68 kDa protein, protein from *Homo sapiens* | UniProt | TAS | PMID: 10618370 |
| | SUH HUMAN | Splice Isoform APCR-2 of Recombining binding protein suppressor of hairless, protein from *Homo sapiens* | UniProt | IDA | PMID: 9874765 |
| | TCOF HUMAN | Treacle protein, protein from *Homo sapiens* | UniProt | IDA | PMID: 15249688 |
| | UBF1 HUMAN | Splice Isoform UBF1 of Nucleolar transcription factor 1, protein from *Homo sapiens* | UniProt | TAS | PMID: 2330041 |
| | VCX1 HUMAN | Variable charge X-linked protein 1, protein from *Homo sapiens* | UniProt | IEP | PMID: 12826317 |
| | VCX3 HUMAN | Variable charge X-linked protein 3, protein from *Homo sapiens* | UniProt | ISS | UniProt: Q9NNX9 |
| | VCXC HUMAN | VCX-C protein, protein from *Homo sapiens* | UniProt | ISS | UniProt: Q9H321 |
| | ZN239 HUMAN | Zinc finger protein 239, protein from *Homo sapiens* | UniProt | NR | UniProt: Q16600 |
| | ZN274 HUMAN | Splice Isoform 1 of Zinc finger protein 274, protein from *Homo sapiens* | UniProt | TAS | PMID: 10777669 |
| | ZN330 HUMAN | Zinc finger protein 330, protein from *Homo sapiens* | UniProt | IDA | PMID: 10593942 |
| | ZN346 HUMAN | Splice Isoform 1 of Zinc finger protein 346, protein from *Homo sapiens* | UniProt | TAS | PMID: 10488071 |
| | ZPR1 HUMAN | Zinc-finger protein ZPR1, protein from *Homo sapiens* | UniProt | TAS | PMID: 9763455 |
| | RPA1 HUMAN | DNA-directed RNA polymerase I largest subunit, protein from *Homo sapiens* | UniProt | NAS | UniProt: O95602 |
| | RPA5 HUMAN | Splice Isoform 1 of DNA-directed RNA polymerase I 40 kDa polypeptide, protein from *Homo sapiens* | UniProt | TAS | PMID: 9540830 |
| | SURF6 HUMAN | Surfeit locus protein 6, protein from *Homo sapiens* | UniProt | ISS | UniProt: O75683 |
| | POP1 HUMAN | Ribonucleases P/MRP protein subunit POP1, protein from *Homo sapiens* | UniProt | IDA | PMID: 8918471 |
| | POP7 HUMAN | Ribonuclease P protein subunit p20, protein from *Homo sapiens* | UniProt | TAS | PMID: 9630247 |
| | RP30 HUMAN | Ribonuclease P protein subunit p30, protein from *Homo sapiens* | UniProt | TAS | PMID: 9630247 |
| | RPP38 HUMAN | Ribonuclease P protein subunit p38, protein from *Homo sapiens* | UniProt | TAS | PMID: 9630247 |
| | RPP40 HUMAN | Ribonuclease P protein subunit p40, protein from *Homo sapiens* | UniProt | TAS | PMID: 9630247 |

-continued

| Qualifier | Symbol Sequence/GOst | Information | Source | Evidence | Reference |
|---|---|---|---|---|---|
| | BAZ2A HUMAN | Hypothetical protein DKFZp781B109, protein from Homo sapiens | UniProt | NAS | PMID: 10662543 |
| | POP1 HUMAN | Ribonucleases P/MRP protein subunit POP1, protein from Homo sapiens | UniProt | IDA | PMID: 8918471 |
| | RP29 HUMAN | Ribonuclease P protein subunit p29, protein from Homo sapiens | UniProt | TAS | PMID: 10352175 |
| | O15446 | Nucleolar fibrillar center protein, protein from Homo sapiens | UniProt | TAS | PMID: 9426281 |
| | MPP10 HUMAN | U3 small nucleolar ribonucleoprotein protein MPP10, protein from Homo sapiens | UniProt | NAS | PMID: 9450966 |
| | NOLA2 HUMAN | H/ACA ribonucleoprotein complex subunit 2, protein from Homo sapiens | UniProt | ISS | UniProt: Q9NX24 |
| | NOLA3 HUMAN | H/ACA ribonucleoprotein complex subunit 3, protein from Homo sapiens | UniProt | TAS | PMID: 9843512 |
| | U3IP2 HUMAN | U3 small nucleolar RNA-interacting protein 2, protein from Homo sapiens | UniProt | TAS | PMID: 9418896 |
| | 3MG HUMAN | Splice Isoform 1 of DNA-3-methyladenine glycosylase, protein from Homo sapiens | UniProt | TAS | PMID: 10854423 |
| | ANX11 HUMAN | Annexin A11, protein from Homo sapiens | UniProt | NAS | PMID: 12577318 |
| | ATF6A HUMAN | Cyclic AMP-dependent transcription factor ATF-6 alpha, protein from Homo sapiens | UniProt | TAS | PMID: 10866666 |
| | ATX3 HUMAN | Splice Isoform 1 of Machado-Joseph disease protein 1, protein from Homo sapiens | UniProt | TAS | PMID: 9580663 |
| | CB80 HUMAN | 80 kDa nuclear cap binding protein, protein from Homo sapiens | UniProt | TAS | PMID: 7937105 |
| | CBX1 HUMAN | Chromobox protein homolog 1, protein from Homo sapiens | UniProt | TAS | PMID: 9169582 |
| | CPSF3 HUMAN | Cleavage and polyadenylation specificity factor, 73 kDa subunit, protein from Homo sapiens | UniProt | TAS | PMID: 7969155 |
| | DKC1 HUMAN | H/ACA ribonucleoprotein complex subunit 4, protein from Homo sapiens | UniProt | TAS | PMID: 10556300 |
| | DPOQ HUMAN | DNA polymerase theta, protein from Homo sapiens | UniProt | TAS | PMID: 10395804 |
| | FMR1 HUMAN | Splice Isoform 6 of Fragile X mental retardation 1 protein, protein from Homo sapiens | UniProt | TAS | PMID: 10888599 |
| | FUSIP HUMAN | Splice Isoform 1 of FUS-interacting serine-arginine-rich protein 1, protein from Homo sapiens | UniProt | IDA | PMID: 11684676 |
| | GIT2 HUMAN | Splice Isoform 2 of ARF GTPase-activating protein GIT2, protein from Homo sapiens | UniProt | IDA | PMID: 10942595 |
| | HNRPL HUMAN | Heterogeneous nuclear ribonucleoprotein L isoform a, protein from Homo sapiens | UniProt | TAS | PMID: 2687284 |
| | HSP1 HUMAN | Sperm protamine P1, protein from Homo sapiens | UniProt | TAS | PMID: 2081589 |
| | IF16 HUMAN | Splice Isoform 2 of Gamma-interferon-inducible protein Ifi-16, protein from Homo sapiens | UniProt | IDA | PMID: 14654789 |
| | IMA2 HUMAN | Importin alpha-2 subunit, protein from Homo sapiens | UniProt | TAS | PMID: 7565597 |

-continued

| Qualifier | Symbol Sequence/GOst | Information | Source | Evidence | Reference |
|---|---|---|---|---|---|
| | ISG20 HUMAN | Splice Isoform 1 of Interferon-stimulated gene 20 kDa protein, protein from *Homo sapiens* | UniProt | TAS | PMID: 9235947 |
| | LY10 HUMAN | Splice Isoform LYSp100-B of Nuclear body protein SP140, protein from *Homo sapiens* | UniProt | TAS | PMID: 8695863 |
| | MCRS1 HUMAN | Splice Isoform 1 of Microspherule protein 1, protein from *Homo sapiens* | UniProt | TAS | PMID: 9765390 |
| | MDM2 HUMAN | Splice Isoform Mdm2 of Ubiquitin-protein ligase E3 Mdm2, protein from *Homo sapiens* | UniProt | IDA | PMID: 10707090 |
| | MK67I HUMAN | MKI67 FHA domain-interacting nucleolar phosphoprotein, protein from *Homo sapiens* | UniProt | IDA | PMID: 11342549 |
| | MRE11 HUMAN | Splice Isoform 1 of Double-strand break repair protein MRE11A, protein from *Homo sapiens* | UniProt | TAS | PMID: 9651580 |
| | NB6M HUMAN | Cell death-regulatory protein GRIM19, protein from *Homo sapiens* | UniProt | IDA | PMID: 10924506 |
| | NUP54 HUMAN | Nucleoporin 54 kDa variant, protein from *Homo sapiens* | UniProt | TAS | PMID: 8707840 |
| | NUP98 HUMAN | Splice Isoform 1 of Nuclear pore complex protein Nup98-Nup96 precursor, protein from *Homo sapiens* | UniProt | TAS | PMID: 7736573 |
| | OGG1 HUMAN | Splice Isoform 2A of N-glycosylase/DNA lyase, protein from *Homo sapiens* | UniProt | TAS | PMID: 9223305 |
| | P53 HUMAN | Splice Isoform 1 of Cellular tumor antigen p53, protein from *Homo sapiens* | UniProt | IDA | PMID: 11080164 |
| | | | | IDA | PMID: 12915590 |
| | PHB HUMAN | Prohibitin, protein from *Homo sapiens* | UniProt | IDA | PMID: 12466959 |
| | PML HUMAN | Splice Isoform PML-1 of Probable transcription factor PML, protein from *Homo sapiens* | UniProt | IDA | PMID: 12915590 |
| | | | | TAS | PMID: 9294197 |
| | POLH HUMAN | Splice Isoform 1 of DNA polymerase eta, protein from *Homo sapiens* | UniProt | TAS | PMID: 10385124 |
| | POLI HUMAN | DNA polymerase iota, protein from *Homo sapiens* | UniProt | TAS | PMID: 10458907 |
| | PPIG HUMAN | Splice Isoform 1 of Peptidyl-prolyl cis-trans isomerase G, protein from *Homo sapiens* | UniProt | TAS | PMID: 9153302 |
| | PRM2 HUMAN | Protamine-2, protein from *Homo sapiens* | UniProt | TAS | PMID: 2081589 |
| | PTBP1 HUMAN | Splice Isoform 1 of Polypyrimidine tract-binding protein 1, protein from *Homo sapiens* | UniProt | TAS | PMID: 1641332 |
| | Q8WYJ1 | MDM2 protein, protein from *Homo sapiens* | UniProt | ISS | UniProt: Q8WYJ1 |
| | | | | IDA | PMID: 12915590 |
| | Q8WYJ2 | MDM2 protein, protein from *Homo sapiens* | UniProt | ISS | UniProt: Q8WYJ2 |
| | Q96Q89 | M-phase phosphoprotein 1, protein from *Homo sapiens* | UniProt | IDA | PMID: 11470801 |
| | Q96SB3 | Neurabin II protein, protein from *Homo sapiens* | UniProt | IMP | PMID: 11278317 |
| | Q9UFR5 | M-phase phosphoprotein 1, protein from *Homo sapiens* | UniProt | ISS | UniProt: Q9UFR5 |
| | Q9Y654 | Heterochromatin-specific nonhistone protein, protein from *Homo sapiens* | UniProt | ISS | UniProt: Q9Y654 |

-continued

| Qualifier | Symbol Sequence/GOst | Information | Source | Evidence | Reference |
|---|---|---|---|---|---|
| | RECQ5 HUMAN | Splice Isoform Alpha of ATP-dependent DNA helicase Q5, protein from *Homo sapiens* | UniProt | NAS | PMID: 10710432 |
| | RNPC2 HUMAN | Splice Isoform 2 of RNA-binding region containing protein 2, protein from *Homo sapiens* | UniProt | TAS | PMID: 8227358 |
| | ROA1 HUMAN | Heterogeneous nuclear ribonucleoprotein A1 isoform b, protein from *Homo sapiens* | UniProt | TAS | PMID: 8521471 |
| | RTC1 HUMAN | Splice Isoform 1 of RNA 3'-terminal phosphate cyclase, protein from *Homo sapiens* | UniProt | TAS | PMID: 9184239 |
| | SMCA2 HUMAN | Splice Isoform Long of Possible global transcription activator SNF2L2, protein from *Homo sapiens* | UniProt | TAS | PMID: 8670841 |
| | SMCA4 HUMAN | Possible global transcription activator SNF2L4, protein from *Homo sapiens* | UniProt | TAS | PMID: 8208605 |
| | SMCA5 HUMAN | SWI/SNF-related matrix associated actin dependent regulator of chromatin subfamily A member 5, protein from *Homo sapiens* | UniProt | TAS | PMID: 9730600 |
| | SMRC1 HUMAN | SWI/SNF-related matrix-associated actin-dependent regulator of chromatin subfamily C member 1, protein from *Homo sapiens* | UniProt | TAS | PMID: 8804307 |
| | SMRD2 HUMAN | Splice Isoform 1 of SWI/SNF-related matrix-associated actin-dependent regulator of chromatin subfamily D member 2, protein from *Homo sapiens* | UniProt | TAS | PMID: 8804307 |
| | SMRD3 HUMAN | Splice Isoform 1 of SWI/SNF-related matrix-associated actin-dependent regulator of chromatin subfamily D member 3, protein from *Homo sapiens* | UniProt | TAS | PMID: 8804307 |
| | SNF5 HUMAN | Splice Isoform A of SWI/SNF related, matrix associated, actin dependent regulator of chromatin subfamily B member 1, protein from *Homo sapiens* | UniProt | TAS | PMID: 7801128 |
| | SRR35 HUMAN | OTTHUMP00000016846, protein from *Homo sapiens* | UniProt | ISS | PMID: 11684676 |
| | SYMPK HUMAN | Splice Isoform 1 of Symplekin, protein from *Homo sapiens* | UniProt | IDA | PMID: 8769423 |
| | TDG HUMAN | G/T mismatch-specific thymine DNA glycosylase, protein from *Homo sapiens* | UniProt | TAS | PMID: 9489705 |
| | TP53B HUMAN | Tumor suppressor p53-binding protein 1, protein from *Homo sapiens* | UniProt | IDA | PMID: 9748285 |
| | UNG2 HUMAN | Uracil-DNA glycosylase 2, protein from *Homo sapiens* | UniProt | IDA | PMID: 12161446 |
| | WDHD1 HUMAN | WD repeat and HMG-box DNA binding protein 1, protein from *Homo sapiens* | UniProt | TAS | PMID: 9175701 |
| | XPO1 HUMAN | Exportin-1, protein from *Homo sapiens* | UniProt | TAS | PMID: 9368044 |
| | ZN638 HUMAN | Splice Isoform 1 of Zinc finger protein 638, protein from *Homo sapiens* | UniProt | TAS | PMID: 8647861 |
| | ESR1 HUMAN | Splice Isoform Long of Estrogen receptor, protein from *Homo sapiens* | UniProt | NAS | PMID: 12351687 |
| | Q9Y294 | ASF1A protein, protein from *Homo sapiens* | UniProt | IDA | PMID: 10759893 |

-continued

| Qualifier | Symbol Sequence/GOst | Information | Source | Evidence | Reference |
|---|---|---|---|---|---|
| | SMRD1 HUMAN | Splice Isoform 1 of SWI/SNF-related matrix-associated actin-dependent regulator of chromatin subfamily D member 1, protein from *Homo sapiens* | UniProt | NAS | PMID: 9693044 |
| | CHRC1 HUMAN | Chromatin accessibility complex protein 1, protein from *Homo sapiens* | UniProt | NAS | PMID: 10880450 |
| | CAF1A HUMAN | Chromatin assembly factor 1, subunit A, protein from *Homo sapiens* | UniProt | TAS | PMID: 7600578 |
| | CAF1B HUMAN | Chromatin assembly factor 1 subunit B, protein from *Homo sapiens* | UniProt | TAS | PMID: 7600578 |
| | NP1L1 HUMAN | Nucleosome assembly protein 1-like 1, protein from *Homo sapiens* | UniProt | TAS | PMID: 8297347 |
| | NP1L2 HUMAN | Nucleosome assembly protein 1-like 2, protein from *Homo sapiens* | UniProt | TAS | PMID: 8789438 |
| | NP1L3 HUMAN | Nucleosome assembly protein 1-like 3, protein from *Homo sapiens* | UniProt | TAS | PMID: 8976385 |
| | NP1L4 HUMAN | Nucleosome assembly protein 1-like 4, protein from *Homo sapiens* | UniProt | TAS | PMID: 9325046 |
| | SIRT2 HUMAN | Splice Isoform 1 of NAD-dependent deacetylase sirtuin-2, protein from *Homo sapiens* | UniProt | NAS | PMID: 12697818 |
| | HBXAP HUMAN | Remodeling and spacing factoR 1, protein from *Homo sapiens* | UniProt | IPI | PMID: 9836642 |
| | SMCA5 HUMAN | SWI/SNF-related matrix associated actin dependent regulator of chromatin subfamily A member 5, protein from *Homo sapiens* | UniProt | IPI | PMID: 9836642 |
| | ACL6B HUMAN | Actin-like protein 6B, protein from *Homo sapiens* | UniProt | ISS | UniProt: O94805 |
| | ARI1A HUMAN | Splice Isoform 1 of AT-rich interactive domain-containing protein 1A, protein from *Homo sapiens* | UniProt | ISS | UniProt: O14497 |
| | | | | IDA | PMID: 9584200 |
| | ARI1B HUMAN | Splice Isoform 1 of AT-rich interactive domain-containing protein 1B, protein from *Homo sapiens* | UniProt | IDA | PMID: 11734557 |
| | NCTR1 HUMAN | Splice Isoform 1 of Natural cytotoxicity triggering receptor 1 precursor, protein from *Homo sapiens* | UniProt | ISS | UniProt: O76036 |
| | SMRC1 HUMAN | SWI/SNF-related matrix-associated actin-dependent regulator of chromatin subfamily C member 1, protein from *Homo sapiens* | UniProt | IDA | PMID: 10078207 |
| | SMRC2 HUMAN | Splice Isoform 1 of SWI/SNF-related matrix-associated actin-dependent regulator of chromatin subfamily C member 2, protein from *Homo sapiens* | UniProt | IDA | PMID: 10078207 |
| | SMRD3 HUMAN | Splice Isoform 1 of SWI/SNF-related matrix-associated actin-dependent regulator of chromatin subfamily D member 3, protein from *Homo sapiens* | UniProt | NAS | PMID: 14701856 |
| | HCLS1 HUMAN | Hematopoietic lineage cell-specific protein, protein from *Homo sapiens* | UniProt | TAS | PMID: 2587259 |
| | MED21 HUMAN | Mediator of RNA polymerase II transcription subunit 21, protein from *Homo sapiens* | UniProt | TAS | PMID: 8598913 |

-continued

| Qualifier | Symbol Sequence/GOst | Information | Source | Evidence | Reference |
|---|---|---|---|---|---|
| | PRGC1 HUMAN | Peroxisome proliferator-activated receptor gamma coactivator 1-alpha, protein from *Homo sapiens* | UniProt | TAS | PMID: 12588810 |
| | Q15161 | POLR2 protein, protein from *Homo sapiens* | UniProt | NAS | PMID: 3145407 |
| | Q99590 | SRrp129 protein, protein from *Homo sapiens* | UniProt | TAS | PMID: 9224939 |
| | RMP HUMAN | RNA polymerase II subunit 5-mediating protein, protein from *Homo sapiens* | UniProt | TAS | PMID: 9819440 |
| | RPB11 HUMAN | RPB11a protein, protein from *Homo sapiens* | UniProt | TAS | PMID: 8797801 |
| | RPB1 HUMAN | DNA-directed RNA polymerase II largest subunit, protein from *Homo sapiens* | UniProt | TAS | PMID: 2999107 |
| | RPB2 HUMAN | DNA-directed RNA polymerase II 140 kDa polypeptide, protein from *Homo sapiens* | UniProt | TAS | PMID: 1518060 |
| | RPB3 HUMAN | DNA-directed RNA polymerase II 33 kDa polypeptide, protein from *Homo sapiens* | UniProt | NR | UniProt: P19387 |
| | RPB4 HUMAN | DNA-directed RNA polymerase II 16 kDa polypeptide, protein from *Homo sapiens* | UniProt | IC | PMID: 9528765 |
| | RPB5 HUMAN | DNA-directed RNA polymerase II 23 kDa polypeptide, protein from *Homo sapiens* | UniProt | TAS | PMID: 7828586 |
| | RPB9 HUMAN | DNA-directed RNA polymerase II 14.5 kDa polypeptide, protein from *Homo sapiens* | UniProt | NR | UniProt: P36954 |
| | RPC10 HUMAN | DNA-directed RNA polymerases I, II, and III 7.0 kDa polypeptide, protein from *Homo sapiens* | UniProt | NR | UniProt: P53803 |
| | ZN148 HUMAN | Zinc finger protein 148, protein from *Homo sapiens* | UniProt | TAS | PMID: 8355710 |
| | ZN281 HUMAN | Zinc finger protein 281, protein from *Homo sapiens* | UniProt | TAS | PMID: 10448078 |
| | BCL6 HUMAN | B-cell lymphoma 6 protein, protein from *Homo sapiens* | UniProt | NR | UniProt: P41182 |
| | CDK8 HUMAN | Cell division protein kinase 8, protein from *Homo sapiens* | UniProt | IDA | PMID: 14638676 |
| | CRSP2 HUMAN | CRSP complex subunit 2, protein from *Homo sapiens* | UniProt | IDA | PMID: 10198638 |
| | CRSP6 HUMAN | CRSP complex subunit 6, protein from *Homo sapiens* | UniProt | IDA | PMID: 10198638 |
| | MED12 HUMAN | Mediator of RNA polymerase II transcription subunit 12, protein from *Homo sapiens* | UniProt | IDA | PMID: 10198638 |
| | MED21 HUMAN | Mediator of RNA polymerase II transcription subunit 21, protein from *Homo sapiens* | UniProt | IDA | PMID: 12037571 |
| | MED4 HUMAN | Mediator complex subunit 4, protein from *Homo sapiens* | UniProt | IEP | PMID: 10882111 |
| | MED6 HUMAN | RNA polymerase transcriptional regulation mediator, subunit 6 homolog, protein from *Homo sapiens* | UniProt | IDA | PMID: 14638676 |
| | | | | IDA | PMID: 12037571 |
| | MED8 HUMAN | Splice Isoform 1 of Mediator of RNA polymerase II transcription subunit 8 homolog, protein from *Homo sapiens* | UniProt | IDA | PMID: 14638676 |
| | PPRB HUMAN | Splice Isoform 1 of Peroxisome proliferator-activated receptor-binding protein, protein from *Homo sapiens* | UniProt | IDA | PMID: 10198638 |
| | Q5XX09 | Intersex-like protein, protein from *Homo sapiens* | UniProt | IDA | PMID: 14638676 |

| Qualifier | Symbol Sequence/GOst | Information | Source | Evidence | Reference |
|---|---|---|---|---|---|
| | Q8TDE4 | PGC-1-related estrogen receptor alpha coactivator short isoform, protein from *Homo sapiens* | UniProt | IDA | PMID: 11854298 |
| | Q96HR3 | TRAP/Mediator complex component TRAP25, protein from *Homo sapiens* | UniProt | IDA | PMID: 10198638 |
| | Q9BUE0 | MED18 protein, protein from *Homo sapiens* | UniProt | IDA | PMID: 14638676 |
| | Q9P086 | Similar to HSPC296, protein from *Homo sapiens* | UniProt | IDA | PMID: 14638676 |
| | RBM14 HUMAN | Splice Isoform 1 of RNA-binding protein 14, protein from *Homo sapiens* | UniProt | NAS | PMID: 11443112 |
| | SURF5 HUMAN | Splice Isoform Surf5A of Surfeit locus protein 5, protein from *Homo sapiens* | UniProt | IDA | PMID: 14638676 |
| | TR100 HUMAN | Thyroid hormone receptor-associated protein complex 100 kDa component, protein from *Homo sapiens* | UniProt | NAS | PMID: 9653119 |
| | TR150 HUMAN | Thyroid hormone receptor-associated protein complex 150 kDa component, protein from *Homo sapiens* | UniProt | IDA | PMID: 10198638 |
| | TR240 HUMAN | Thyroid hormone receptor-associated protein complex 240 kDa component, protein from *Homo sapiens* | UniProt | IDA | PMID: 10198638 |
| | TR95 HUMAN | Splice Isoform 1 of Thyroid hormone receptor-associated protein complex 95 kDa component, protein from *Homo sapiens* | UniProt | IDA | PMID: 10198638 |
| | TRFP HUMAN | TRF-proximal protein homolog, protein from *Homo sapiens* | UniProt | NAS | PMID: 9933582 |
| | T2AG HUMAN | Transcription initiation factor IIA gamma chain, protein from *Homo sapiens* | UniProt | NAS | PMID: 7958900 |
| | TF2AA HUMAN | Transcription initiation factor IIA subunit 1, protein from *Homo sapiens* | UniProt | NR | UniProt: P52655 |
| colocalizes_with | EDF1 HUMAN | Splice Isoform 1 of Endothelial differentiation-related factor 1, protein from *Homo sapiens* | UniProt | IDA | PMID: 12040021 |
| | O43604 | Cofactor of initiator function, protein from *Homo sapiens* | UniProt | TAS | PMID: 9418870 |
| | Q7Z7C8 | OTTHUMP00000016392, protein from *Homo sapiens* | UniProt | IDA | PMID: 14580349 |
| | Q9BQS9 | TAF3 RNA polymerase II, TATA box binding protein, protein from *Homo sapiens* | UniProt | IDA | PMID: 11438666 |
| | RBP56 HUMAN | Splice Isoform Long of TATA-binding protein associated factor 2N, protein from *Homo sapiens* | UniProt | NR | UnitProt: Q92804 |
| | TAF10 HUMAN | Transcription initiation factor TFIID subunit 10, protein from *Homo sapiens* | UniProt | IDA | PMID: 14580349 |
| | TAF11 HUMAN | Transcription initiation factor TFIID subunit 11, protein from *Homo sapiens* | UniProt | IDA | PMID: 14580349 |
| | TAF12 HUMAN | Transcription initiation factor TFIID subunit 12, protein from *Homo sapiens* | UniProt | IDA | PMID: 14580349 |
| | TAF13 HUMAN | Transcription initiation factor TFIID subunit 13, protein from *Homo sapiens* | UniProt | TAS | PMID: 7729427 |
| | TAF1 HUMAN | Splice Isoform 1 of Transcription initiation factor TFIID subunit 1, protein from *Homo sapiens* | UniProt | TAS | PMID: 7680771 |
| | TAF1L HUMAN | Transcription initiation factor TFIID 210 kDa subunit, protein from *Homo sapiens* | UniProt | ISS | PMID: 12217962 |

-continued

| Qualifier | Symbol Sequence/GOst | Information | Source | Evidence | Reference |
|---|---|---|---|---|---|
| | TAF4 HUMAN | Transcription initiation factor TFIID subunit 4, protein from *Homo sapiens* | UniProt | IDA | PMID: 14580349 |
| | TAF5 HUMAN | Splice Isoform Long of Transcription initiation factor TFIID subunit 5, protein from *Homo sapiens* | UniProt | IDA | PMID: 14580349 |
| | TAF6 HUMAN | Transcription initiation factor TFIID subunit 6, protein from *Homo sapiens* | UniProt | IDA | PMID: 14580349 |
| | TAF7 HUMAN | Transcription initiation factor TFIID subunit 7, protein from *Homo sapiens* | UniProt | IDA | PMID: 14580349 |
| | TAF9 HUMAN | Transcription initiation factor TFIID subunit 9, protein from *Homo sapiens* | UniProt | IDA | PMID: 14580349 |
| | TBP HUMAN | TATA-box binding protein, protein from *Homo sapiens* | UniProt | IDA | PMID: 14580349 |
| | TAF6 HUMAN | Transcription initiation factor TFIID subunit 6, protein from *Homo sapiens* | UniProt | TAS | PMID: 7667268 |
| | T2FA HUMAN | Transcription initiation factor IIF alpha subunit, protein from *Homo sapiens* | UniProt | TAS | PMID: 1734283 |
| | ERCC2 HUMAN | TFIIH basal transcription factor complex helicase subunit, protein from *Homo sapiens* | UniProt | TAS | PMID: 7663514 |
| | ERCC3 HUMAN | TFIIH basal transcription factor complex helicase XPB subunit, protein from *Homo sapiens* | UniProt | TAS | PMID: 7663514 |
| | TF2H1 HUMAN | TFIIH basal transcription factor complex p62 subunit, protein from *Homo sapiens* | UniProt | TAS | PMID: 9118947 |
| | TF2H2 HUMAN | TFIIH basal transcription factor complex p44 subunit, protein from *Homo sapiens* | UniProt | NR | UniProt: Q13888 |
| | TF2H3 HUMAN | TFIIH basal transcription factor complex p34 subunit, protein from *Homo sapiens* | UniProt | NAS | UniProt: Q13889 |
| | TF2H4 HUMAN | TFIIH basal transcription factor complex p52 subunit, protein from *Homo sapiens* | UniProt | TAS | PMID: 9118947 |
| | RPC10 HUMAN | DNA-directed RNA polymerases I, II, and III 7.0 kDa polypeptide, protein from *Homo sapiens* | UniProt | NR | UniProt: P53803 |
| | RPC11 HUMAN | DNA-directed RNA polymerases III 12.5 kDa polypeptide, protein from *Homo sapiens* | UniProt | TAS | PMID: 9869639 |
| | RPC1 HUMAN | DNA-directed RNA polymerase III largest subunit, protein from *Homo sapiens* | UniProt | NAS | UniProt: O14802 |
| | RPC62 HUMAN | DNA-directed RNA polymerase III 62 kDa polypeptide, protein from *Homo sapiens* | UniProt | TAS | PMID: 9171375 |
| | RPC6 HUMAN | DNA-directed RNA polymerase III 39 kDa polypeptide, protein from *Homo sapiens* | UniProt | NAS | PMID: 10623476 |
| | RPC7 HUMAN | DNA-directed RNA polymerase III 32 kDa polypeptide, protein from *Homo sapiens* | UniProt | TAS | PMID: 9171375 |
| | RPC8 HUMAN | Splice Isoform 1 of DNA-directed RNA polymerase III subunit 22.9 kDa polypeptide, protein from *Homo sapiens* | UniProt | IDA | PMID: 12391170 |
| | MEN1 HUMAN | Splice Isoform 1 of Menin, protein from *Homo sapiens* | UniProt | IDA | PMID: 14992727 |
| | NSD1 HUMAN | Splice Isoform 1 of Histone-lysine N-methyltransferase, H3 | UniProt | ISS | UniProt: Q96L73 |

| Qualifier | Symbol Sequence/GOst | Information | Source | Evidence | Reference |
|---|---|---|---|---|---|
| | | lysine-36 and H4 lysine-20 specific, protein from *Homo sapiens* | | | |
| | PCF11 HUMAN | Pre-mRNA cleavage comPlex II Protein Pcf11, protein from *Homo sapiens* | UniProt | NAS | PMID: 11060040 |
| | CPSF1 HUMAN | Cleavage and polyadenylation specificity factor, 160 kDa subunit, protein from *Homo sapiens* | UniProt | IDA | PMID: 7590244 |
| | GEMI5 HUMAN | Gem-associated protein 5, protein from *Homo sapiens* | UniProt | IDA | PMID: 11714716 |
| | GEMI6 HUMAN | Gem-associated protein 6, protein from *Homo sapiens* | UniProt | IDA | PMID: 11748230 |
| | GEMI7 HUMAN | Gem-associated protein 7, protein from *Homo sapiens* | UniProt | IDA | PMID: 12065586 |
| | HIPK2 HUMAN | Splice Isoform 1 of Homeodomain-interacting protein kinase 2, protein from *Homo sapiens* | UniProt | TAS | PMID: 14626429 |
| | Q9Y474 | Zinc-finger motif-enhancer binding-protein-1, protein from *Homo sapiens* | UniProt | TAS | PMID: 9305772 |
| | Q8WWY3 | U4/U6 snRNP-associated 61 kDa protein, protein from *Homo sapiens* | UniProt | IDA | PMID: 11867543 |
| | SMN HUMAN | Splice Isoform SMN of Survival motor neuron protein, protein from *Homo sapiens* | UniProt | NAS | PMID: 9845364 |
| | | | | NAS | PMID: 8670859 |
| | U2AF1 HUMAN | Splicing factor U2AF 35 kDa subunit, protein from *Homo sapiens* | UniProt | TAS | PMID: 1388271 |
| | Q8WWY3 | U4/U6 snRNP-associated 61 kDa protein, protein from *Homo sapiens* | UniProt | IDA | PMID: 11867543 |
| | ZBT16 HUMAN | Splice Isoform PLZFB of Zinc finger and BTB domain-containing protein 16, protein from *Homo sapiens* | UniProt | IDA | PMID: 8541544 |
| | ELF4 HUMAN | ETS-related transcription factor Elf-4, protein from *Homo sapiens* | UniProt | IDA | PMID: 14970218 |
| | HIPK3 HUMAN | Splice Isoform 1 of Homeodomain-interacting protein kinase 3, protein from *Homo sapiens* | UniProt | IDA | PMID: 11034606 |
| | ISG20 HUMAN | Splice Isoform 1 of Interferon-stimulated gene 20 kDa protein, protein from *Homo sapiens* | UniProt | IDA | PMID: 9235947 |
| colocalizes_with | PML HUMAN | Splice Isoform PML-1 of Probable transcription factor PML, protein from *Homo sapiens* | UniProt | IDA | PMID: 10910364 |
| | | | | TAS | PMID: 9294197 |
| not | SFRS2 HUMAN | Splicing factor, arginine/serine-rich 2, protein from *Homo sapiens* | UniProt | IDA | PMID: 15652350 |
| | SP100 HUMAN | Splice Isoform Sp100-HMG of Nuclear autoantigen Sp-100, protein from *Homo sapiens* | UniProt | TAS | PMID: 9230084 |
| | SPTN4 HUMAN | Splice Isoform 1 of Spectrin beta chain, brain 3, protein from *Homo sapiens* | UniProt | IDA | PMID: 11294830 |
| | NXF2 HUMAN | Nuclear RNA export factor 2, protein from *Homo sapiens* | UniProt | NAS | PMID: 11073998 |
| | NXF3 HUMAN | Nuclear RNA export factor 3, protein from *Homo sapiens* | UniProt | IDA | PMID: 11545741 |
| | CDK9 HUMAN | Splice Isoform 1 of Cell division protein kinase 9, protein from *Homo sapiens* | UniProt | TAS | PMID: 10866664 |
| | ELL2 HUMAN | RNA polymerase II elongation factor ELL2, protein from *Homo sapiens* | UniProt | TAS | PMID: 9108030 |

-continued

| Qualifier | Symbol Sequence/GOst | Information | Source | Evidence | Reference |
|---|---|---|---|---|---|
| | ELL3 HUMAN | RNA polymerase II elongation factor ELL3, protein from *Homo sapiens* | UniProt | NAS | PMID: 10882741 |
| | TCEA2 HUMAN | Transcription elongation factor A protein 2, protein from *Homo sapiens* | UniProt | NAS | PMID: 8566795 |
| | CRSP3 HUMAN | Splice Isoform 1 of CRSP complex subunit 3, protein from *Homo sapiens* | UniProt | IDA | PMID: 9989412 |
| | CRSP6 HUMAN | CRSP complex subunit 6, protein from *Homo sapiens* | UniProt | IDA | PMID: 9989412 |
| | CSP9 HUMAN | Cofactor required for Sp1 transcriptional activation subunit 9, protein from *Homo sapiens* | UniProt | IDA | PMID: 9989412 |
| | FOXE3 HUMAN | Forkhead box protein E3, protein from *Homo sapiens* | UniProt | IDA | PMID: 10652278 |
| | FOXF1 HUMAN | Forkhead box protein F1, protein from *Homo sapiens* | UniProt | TAS | PMID: 9722567 |
| | FOXF2 HUMAN | Forkhead box protein F2, protein from *Homo sapiens* | UniProt | TAS | PMID: 9722567 |
| | HES6 HUMAN | Splice Isoform 1 of Transcription cofactor HES-6, protein from *Homo sapiens* | UniProt | ISS | PMID: 10851137 |
| | KU70 HUMAN | ATP-dependent DNA helicase II, 70 kDa subunit, protein from *Homo sapiens* | UniProt | IDA | PMID: 12145306 |
| | LMO4 HUMAN | LIM domain transcription factor LMO4, protein from *Homo sapiens* | UniProt | ISS | UniProt: P61968 |
| | NARG1 HUMAN | Splice Isoform 1 of NMDA receptor regulated protein 1, protein from *Homo sapiens* | UniProt | IDA | PMID: 12145306 |
| | NARGL HUMAN | Splice Isoform 1 of NMDA receptor regulated 1-like protein, protein from *Homo sapiens* | UniProt | ISS | UniProt: Q6N069 |
| | NCOA6 HUMAN | Nuclear receptor coactivator 6, protein from *Homo sapiens* | UniProt | TAS | PMID: 11443112 |
| | NKX2S HUMAN | Homeobox protein Nkx-2.5, protein from *Homo sapiens* | UniProt | ISS | UniProt: P52952 |
| | Q9UBQ3 | Polyamine-modulated factor 1, protein from *Homo sapiens* | UniProt | TAS | PMID: 10419538 |
| | Q9UKB0 | High mobility group protein-R, protein from *Homo sapiens* | UniProt | TAS | PMID: 10428834 |
| | Q9Y6Y0 | Influenza vIrus NS1A binding protein; NS1-binding protein; likely ortholog of mouse kelch family protein Nd1, protein from *Homo sapiens* | UniProt | TAS | PMID: 9696811 |
| | RBM14 HUMAN | Splice Isoform 1 of RNA-binding protein 14, protein from *Homo sapiens* | UniProt | IPI | PMID: 11443112 |
| | SMAD2 HUMAN | Splice Isoform Long of Mothers against decapentaplegic homolog 2, protein from *Homo sapiens* | UniProt | ISS | UniProt: Q15796 |
| | TCP4 HUMAN | Activated RNA polymerase II transcriptional coactivator p15, protein from *Homo sapiens* | UniProt | IDA | PMID: 8062391 |
| | TF65 HUMAN | Splice Isoform 1 of Transcription factor p65, protein from *Homo sapiens* | UniProt | IDA | PMID: 12048232 |
| | WBS14 HUMAN | Splice Isoform 1 of Williams-Beuren syndrome chromosome region 14 protein, protein from *Homo sapiens* | UniProt | NAS | PMID: 11230181 |
| | ING2 HUMAN | Inhibitor of growth protein 2, protein from *Homo sapiens* | UniProt | IDA | PMID: 15243141 |
| | NFYA HUMAN | Splice Isoform Long of Nuclear transcription factor Y subunit alpha, protein from *Homo sapiens* | UniProt | IDA | PMID: 15243141 |

-continued

| Qualifier | Symbol Sequence/GOst | Information | Source | Evidence | Reference |
|---|---|---|---|---|---|
| | NFYB HUMAN | Nuclear transcription factor Y subunit beta, protein from *Homo sapiens* | UniProt | IDA | PMID: 15243141 |
| | NFYC HUMAN | Splice Isoform 3 of Nuclear transcription factor Y subunit gamma, protein from *Homo sapiens* | UniProt | IDA | PMID: 15243141 |
| | CNOT7 HUMAN | CCR4-NOT transcription complex subunit 7, protein from *Homo sapiens* | UniProt | NAS | PMID: 9820826 |
| | TRRAP HUMAN | Splice Isoform 1 of Transformation/transcription domain-associated protein, protein from *Homo sapiens* | UniProt | NAS | PMID: 9885574 |
| | ACL6A HUMAN | Splice Isoform 1 of Actin-like protein 6A, protein from *Homo sapiens* | UniProt | IDA | PMID: 10966108 |
| | ACTB HUMAN | Actin, cytoplasmic 1, protein from *Homo sapiens* | UniProt | IDA | PMID: 10966108 |
| | RUVB1 HUMAN | RuvB-like 1, protein from *Homo sapiens* | UniProt | IDA | PMID: 10966108 |
| | RUVB2 HUMAN | RuvB-like 2, protein from *Homo sapiens* | UniProt | IDA | PMID: 10966108 |
| | TIP60 HUMAN | Splice Isoform 1 of Histone acetyltransferase HTATIP, protein from *Homo sapiens* | UniProt | IDA | PMID: 10966108 |
| | TRRAP HUMAN | Splice Isoform 1 of Transformation/transcription domain-associated protein, protein from *Homo sapiens* | UniProt | IDA | PMID: 10966108 |
| | HDA10 HUMAN | Splice Isoform 1 of Histone deacetylase 10, protein from *Homo sapiens* | UniProt | IDA | PMID: 11861901 |
| | HDA11 HUMAN | Histone deacetylase 11, protein from *Homo sapiens* | UniProt | IDA | PMID: 11948178 |
| | HDAC1 HUMAN | Histone deacetylase 1, protein from *Homo sapiens* | UniProt | TAS | PMID: 12711221 |
| | HDAC2 HUMAN | Histone deacetylase 2, protein from *Homo sapiens* | UniProt | TAS | PMID: 12711221 |
| | HDAC3 HUMAN | Splice Isoform 1 of Histone deacetylase 3, protein from *Homo sapiens* | UniProt | TAS | PMID: 12711221 |
| | HDAC4 HUMAN | Histone deacetylase 4, protein from *Homo sapiens* | UniProt | TAS | PMID: 12711221 |
| | HDAC5 HUMAN | Splice Isoform 1 of Histone deacetylase 5, protein from *Homo sapiens* | UniProt | TAS | PMID: 12711221 |
| | HDAC6 HUMAN | Histone deacetylase 6, protein from *Homo sapiens* | UniProt | IDA | PMID: 11948178 |
| | HDAC7 HUMAN | Histone deacetylase, protein from *Homo sapiens* | UniProt | TAS | PMID: 12711221 |
| | HDAC8 HUMAN | Splice Isoform 3 of Histone deacetylase 8, protein from *Homo sapiens* | UniProt | TAS | PMID: 12711221 |
| | HDAC9 HUMAN | Splice Isoform 1 of Histone deacetylase 9, protein from *Homo sapiens* | UniProt | TAS | PMID: 12711221 |
| | MTA2 HUMAN | Metastasis-associated protein MTA2, protein from *Homo sapiens* | UniProt | TAS | PMID: 10444591 |
| | SAP18 HUMAN | Sin3 associated polypeptide p18, protein from *Homo sapiens* | UniProt | TAS | PMID: 9150135 |
| | SAP30 HUMAN | Histone deacetylase complex subunit SAP30, protein from *Homo sapiens* | UniProt | TAS | PMID: 9651585 |
| | TAF6L HUMAN | TAF6-like RNA polymerase II p300/CBP-associated factor-associated factor 65 kDa subunit 6L, protein from *Homo sapiens* | UniProt | TAS | PMID: 9674425 |
| colocalizes_with | DP13A HUMAN | DCC-interacting protein 13 alpha, protein from *Homo sapiens* | UniProt | IDA | PMID: 15016378 |
| colocalizes_with | DP13B HUMAN | DCC-interacting protein 13 beta, protein from *Homo sapiens* | UniProt | IDA | PMID: 15016378 |

| Qualifier | Symbol Sequence/GOst | Information | Source | Evidence | Reference |
|---|---|---|---|---|---|
| | P66A HUMAN | Splice Isoform 1 of Transcriptional repressor p66 alpha, protein from *Homo sapiens* | UniProt | IDA | PMID: 12183469 |
| | | | | ISS | UniProt: Q96F28 |
| | SDS3 HUMAN | Sin3 histone deacetylase corepressor complex component SDS3, protein from *Homo sapiens* | UniProt | ISS | PMID: 11909966 |
| | Q16219 | Insulin activator factor, protein from *Homo sapiens* | UniProt | NAS | PMID: 7935390 |
| | TF3B HUMAN | Splice Isoform 1 of Transcription factor IIIB 90 kDa subunit, protein from *Homo sapiens* | UniProt | NAS | PMID: 20380946 |
| | | | | NAS | PMID: 8943358 |
| | TF3C1 HUMAN | Splice Isoform 1 of General transcription factor 3C polypeptide 1, protein from *Homo sapiens* | UniProt | NR | UniProt: Q12789 |
| | TF3C2 HUMAN | G-protein beta WD-40 repeat containing protein, protein from *Homo sapiens* | UniProt | NR | UniProt: Q8WUA4 |
| | TF3C3 HUMAN | Splice Isoform 1 of General transcription factor 3C polypeptide 3, protein from *Homo sapiens* | UniProt | TAS | PMID: 10373544 |
| | TF3C4 HUMAN | General transcription factor 3C polypeptide 4, protein from *Homo sapiens* | UniProt | TAS | PMID: 10523658 |
| | TF3C5 HUMAN | Splice Isoform 1 of General transcription factor 3C polypeptide 5, protein from *Homo sapiens* | UniProt | TAS | PMID: 10373544 |
| | ARI4A HUMAN | Splice Isoform I of AT-rich interactive domain-containing protein 4A, protein from *Homo sapiens* | UniProt | IPI | PMID: 12724404 |
| | | | | IDA | PMID: 11283269 |
| | JAZF1 HUMAN | Splice Isoform 1 of Juxtaposed with another zinc finger protein 1, protein from *Homo sapiens* | UniProt | IDA | PMID: 15302918 |
| | PHF12 HUMAN | Splice Isoform 2 of PHD finger protein 12, protein from *Homo sapiens* | UniProt | IDA | PMID: 11390640 |
| | Q9HAQ4 | Zinc finger protein 350, protein from *Homo sapiens* | UniProt | IDA | PMID: 11090615 |
| | RNF12 HUMAN | RING finger protein 12, protein from *Homo sapiens* | UniProt | NAS | PMID: 11013082 |
| | SMCE1 HUMAN | Splice Isoform 1 of SWI/SNF-related matrix-associated actin-dependent regulator of chromatin subfamily E member 1, protein from *Homo sapiens* | UniProt | IPI | PMID: 12192000 |
| colocalizes_with | SMRC2 HUMAN | Splice Isoform 1 of SWI/SNF-related matrix-associated actin-dependent regulator of chromatin subfamily C member 2, protein from *Homo sapiens* | UniProt | IPI | PMID: 12192000 |
| | ZBT16 HUMAN | Splice Isoform PLZFB of Zinc finger and BTB domain-containing protein 16, protein from *Homo sapiens* | UniProt | IDA | PMID: 12802276 |
| | DPOLZ HUMAN | DNA polymerase zeta catalytic subunit, protein from *Homo sapiens* | UniProt | NR | UNIPROT: O60673 |
| | ANC4 HUMAN | Splice Isoform 1 of Anaphase promoting complex subunit 4, protein from *Homo sapiens* | UniProt | TAS | PMID: 9469815 |
| | ANC5 HUMAN | Splice Isoform 1 of Anaphase promoting complex subunit 5, protein from *Homo sapiens* | UniProt | TAS | PMID: 9469815 |

| Qualifier | Symbol Sequence/GOst | Information | Source | Evidence | Reference |
|---|---|---|---|---|---|
| | APC10 HUMAN | Anaphase promoting complex subunit 10, protein from *Homo sapiens* | UniProt | NAS | PMID: 10318877 |
| | APC11 HUMAN | Splice Isoform 1 of Anaphase promoting complex subunit 11, protein from *Homo sapiens* | UniProt | IDA | PMID: 11739784 |
| | APC7 HUMAN | Anaphase promoting complex subunit 7, protein from *Homo sapiens* | UniProt | NR | UniProt: Q9UJX3 |
| | BUB1B HUMAN | Mitotic checkpoint serine/threonine-protein kinase BUB1 beta, protein from *Homo sapiens* | UniProt | TAS | PMID: 10477750 |
| | CDC23 HUMAN | Splice Isoform 1 of Cell division cycle protein 23 homolog, protein from *Homo sapiens* | UniProt | IDA | PMID: 14657031 |
| | CDC27 HUMAN | Protein CDC27Hs, protein from *Homo sapiens* | UniProt | NR | UniProt: P30260 |
| | CUL7 HUMAN | Cullin-7, protein from *Homo sapiens* | UniProt | NAS | PMID: 12481031 |
| | FZR HUMAN | Splice Isoform 1 of Fizzy-related protein homolog, protein from *Homo sapiens* | UniProt | TAS | PMID: 9734353 |
| | Q8NHZ8 | CDC26 subunit of anaphase promoting complex, protein from *Homo sapiens* | UniProt | IDA | PMID: 10922056 |
| | BARD1 HUMAN | BRCA1-associated RING domain protein 1, protein from *Homo sapiens* | UniProt | IDA | PMID: 15265711 |
| | BRCA1 HUMAN | Breast cancer type 1 susceptibility protein, protein from *Homo sapiens* | UniProt | IDA | PMID: 15265711 |
| | ERCC1 HUMAN | DNA excision repair protein ERCC-1, protein from *Homo sapiens* | UniProt | IDA | PMID: 3290851 |
| | ERCC4 HUMAN | Excision rEpair cross-complEmEnting rodEntr Epair dEficiEncy, complEmEntation group 4, protein from *Homo sapiens* | UniProt | IDA | PMID: 10644440 |
| | ERCC8 HUMAN | Splice Isoform 1 of DNA excision repair protein ERCC-8, protein from *Homo sapiens* | UniProt | IDA | PMID: 12732143 |
| | CSN2 HUMAN | Splice Isoform 1 of COP9 signalosome complex subunit 2, protein from *Homo sapiens* | UniProt | IDA | PMID: 9535219 |
| | GEMI4 HUMAN | Component of gems 4, protein from *Homo sapiens* | UniProt | TAS | PMID: 10725331 |
| | LSM6 HUMAN | U6 snRNA-associated Sm-like protein LSm6, protein from *Homo sapiens* | UniProt | TAS | PMID: 10523320 |
| | RSMB HUMAN | Splice Isoform SM-B' of Small nuclear ribonucleoprotein associated proteins B and B', protein from *Homo sapiens* | UniProt | TAS | PMID: 2531083 |
| | RUXE HUMAN | Small nuclear ribonucleoprotein E, protein from *Homo sapiens* | UniProt | NAS | PMID: 2974536 |
| | RSMB HUMAN | Splice Isoform SM-B' of Small nuclear ribonucleoprotein associated proteins B and B', protein from *Homo sapiens* | UniProt | TAS | PMID: 2531083 |
| | RUXE HUMAN | Small nuclear ribonucleoprotein E, protein from *Homo sapiens* | UniProt | NAS | PMID: 2974536 |
| | RUXG HUMAN | Small nuclear ribonucleoprotein G, protein from *Homo sapiens* | UniProt | NAS | PMID: 7744013 |
| | SF3A2 HUMAN | Splicing factor 3A subunit 2, protein from *Homo sapiens* | UniProt | TAS | PMID: 8211113 |
| | SF3B3 HUMAN | Splicing factor 3B subunit 3, protein from *Homo sapiens* | UniProt | TAS | PMID: 10490618 |

| Qualifier | Symbol Sequence/GOst | Information | Source | Evidence | Reference |
|---|---|---|---|---|---|
| | U3IP2 HUMAN | U3 small nucleolar RNA-interacting protein 2, protein from *Homo sapiens* | UniProt | TAS | PMID: 9418896 |
| | RU1C HUMAN | U1 small nuclear ribonucleoprotein C, protein from *Homo sapiens* | UniProt | TAS | PMID: 2971157 |
| | SNRPA HUMAN | U1 small nuclear ribonucleoprotein A, protein from *Homo sapiens* | UniProt | NR | UniProt: P09012 |
| | PHF5A HUMAN | PHD finger-like domain protein 5A, protein from *Homo sapiens* | UniProt | IDA | PMID: 12234937 |
| | RU2A HUMAN | U2 small nuclear ribonucleoprotein A', protein from *Homo sapiens* | UniProt | TAS | PMID: 2928112 |
| | RU2B HUMAN | U2 small nuclear ribonucleoprotein B", protein from *Homo sapiens* | UniProt | TAS | PMID: 2951739 |
| | LSM4 HUMAN | U6 snRNA-associated Sm-like protein LSm4, protein from *Homo sapiens* | UniProt | TAS | PMID: 10369684 |
| | Q8WWY3 | U4/U6 snRNP-associated 61 kDa protein, protein from *Homo sapiens* | UniProt | IDA | PMID: 11867543 |
| | API5 HUMAN | Splice Isoform 1 of Apoptosis inhibitor 5, protein from *Homo sapiens* | UniProt | ISS | PMID: 11555636 |
| | BCAS2 HUMAN | Breast carcinoma amplified sequence 2, protein from *Homo sapiens* | UniProt | IDA | PMID: 12169396 |
| | DHX8 HUMAN | ATP-dependent RNA helicase DHX8, protein from *Homo sapiens* | UniProt | TAS | PMID: 7935475 |
| | GEMI2 HUMAN | Splice Isoform 1 of Survival of motor neuron protein-interacting protein 1, protein from *Homo sapiens* | UniProt | TAS | PMID: 9323129 |
| | PPIH HUMAN | Peptidyl-prolyl cis-trans isomerase H, protein from *Homo sapiens* | UniProt | TAS | PMID: 9570313 |
| | PRP17 HUMAN | Pre-mRNA splicing factor PRP17, protein from *Homo sapiens* | UniProt | TAS | PMID: 9524131 |
| | PRP18 HUMAN | Splice Isoform 1 of Pre-mRNA splicing factor 18, protein from *Homo sapiens* | UniProt | TAS | PMID: 9000057 |
| | PRP4 HUMAN | Splice Isoform 1 of U4/U6 small nuclear ribonucleoprotein Prp4, protein from *Homo sapiens* | UniProt | NAS | PMID: 9328476 |
| | PRPF3 HUMAN | Splice Isoform 1 of U4/U6 small nuclear ribonucleoprotein Prp3, protein from *Homo sapiens* | UniProt | NAS | PMID: 9328476 |
| | PRPU HUMAN | U5 snRNP-associated 102 kDa protein, protein from *Homo sapiens* | UniProt | NAS | PMID: 10788320 |
| | Q9Y6Y0 | Influenza vIrus NS1A binding protein; NS1-binding protein; likely ortholog of mouse kelch family protein Nd1, protein from *Homo sapiens* | UniProt | TAS | PMID: 9696811 |
| | RSMB HUMAN | Splice Isoform SM-B' of Small nuclear ribonucleoprotein associated proteins B and B', protein from *Homo sapiens* | UniProt | TAS | PMID: 2531083 |
| | RUXE HUMAN | Small nuclear ribonucleoprotein E, protein from *Homo sapiens* | UniProt | NAS | PMID: 2974536 |
| | RUXG HUMAN | Small nuclear ribonucleoprotein G, protein from *Homo sapiens* | UniProt | TAS | PMID: 7744013 |
| | SF3A2 HUMAN | Splicing factor 3A subunit 2, protein from *Homo sapiens* | UniProt | TAS | PMID: 8211113 |

| Qualifier | Symbol Sequence/GOst | Information | Source | Evidence | Reference |
|---|---|---|---|---|---|
| | SF3A3 HUMAN | Splicing factor 3A subunit 3, protein from *Homo sapiens* | UniProt | TAS | PMID: 8022796 |
| | SF3B1 HUMAN | Splicing factor 3B subunit 1, protein from *Homo sapiens* | UniProt | NAS | PMID: 9585501 |
| | SF3B2 HUMAN | Splicing factor 3B Subunit 2, protein from *Homo sapiens* | UniProt | TAS | PMID: 8566756 |
| | SF3B3 HUMAN | Splicing factor 3B subunit 3, protein from *Homo sapiens* | UniProt | TAS | PMID: 10490618 |
| | SF3B4 HUMAN | Splicing factor 3B subunit 4, protein from *Homo sapiens* | UniProt | TAS | PMID: 7958871 |
| | SNW1 HUMAN | Nuclear protein Skip, protein from *Homo sapiens* | UniProt | IDA | PMID: 15194481 |
| | SPF30 HUMAN | Survival of motor neuron-related splicing factor 30, protein from *Homo sapiens* | UniProt | TAS | PMID: 9731529 |
| | TXN4A HUMAN | Thioredoxin-like protein 4A, protein from *Homo sapiens* | UniProt | TAS | PMID: 10610776 |
| | U520 HUMAN | U5 small nuclear ribonucleoprotein 200 kDa helicase, protein from *Homo sapiens* | UniProt | IDA | PMID: 8670905 |
| | U5S1 HUMAN | 116 kDa U5 small nuclear ribonucleoprotein component, protein from *Homo sapiens* | UniProt | TAS | PMID: 9233818 |
| | DKC1 HUMAN | H/ACA ribonucleoprotein complex subunit 4, protein from *Homo sapiens* | UniProt | IDA | PMID: 12135483 |
| | TEBP HUMAN | Telomerase-binding protein p23, protein from *Homo sapiens* | UniProt | IDA | PMID: 12135483 |
| | TEP1 HUMAN | Splice Isoform 1 of Telomerase protein component 1, protein from *Homo sapiens* | UniProt | IDA | PMID: 12135483 |
| | TERT HUMAN | Telomerase reverse transcriptase, protein from *Homo sapiens* | UniProt | IDA | PMID: 12135483 |

TABLE 2

Proteins With a Known Function in Splicing and RNA Processing

| Acc. no.a | Name | Comments |
|---|---|---|
| snRNP core proteins | | |
| SWISS-PROT: Q15357a | Sm G | |
| SWISS-PROT: Q15356 | Sm F | |
| SWISS-PROT: P08578 | Sm E | |
| SWISS-PROT: P13641 | Sm D1 | |
| SWISS-PROT: P43330 | Sm D2 | |
| SWISS-PROT: P43331 | Sm D3 | |
| SWISS-PROT: P14678 | Sm B/B' | |
| U1 snRNP | | |
| SWISS-PROT: P09234 | U1 snRNP C | |
| SWISS-PROT: P09012 | U1 snRNP A | |
| SWISS-PROT: P08621 | U1 snRNP 70 kDa | |
| U2 snRNP | | |
| SWISS-PROT: Q15427 | SAP 49 | |
| SWISS-PROT: Q12874 | SAP 61 | |
| SWISS-PROT: Q15428 | SAP 62 | |
| SWISS-PROT: Q15459 | SAP 114 | |
| SWISS-PROT: Q15393 | SAP 130 | |
| SWISS-PROT: Q13435 | SAP 145 | |
| SWISS-PROT: O75533 | SAP 155 | |
| SWISS-PROT: Q01081 | U2AF 35 kDa | |
| SWISS-PROT: P26368 | U2AF 65 kDa | |
| SWISS-PROT: P09661 | U2 snRNP A' | |
| SWISS-PROT: P08579 | U2 snRNP B" | |
| U5 snRNP | | |
| ENSP00000263694, Q96D17 | U5 snRNP 40 kDa | |
| ENSP00000261905, Q9BUQ8 | U5 snRNP 100 kDa | |

TABLE 2-continued

Proteins With a Known Function in Splicing and RNA Processing

| Acc. no.a | Name | Comments |
|---|---|---|
| ENSP00000266079, O94906 | U5 snRNP 102 kDa | |
| SWISS-PROT: Q15029 | U5 snRNP 116 kDa | |
| SWISS-PROT: O75643 | U5 snRNP 200 kDa | |
| ENSP00000254706, Q6P2Q9 | U5 snRNP 220 kDa | |
| U6 snRNP | | |
| SWISS-PROT: Q9Y333 | LSm2 | |
| SWISS-PROT: Q9Y4Z1 | LSm3 | |
| SWISS-PROT: Q9Y4Z0 | LSm4 | |
| SWISS-PROT: Q9Y4Y8 | LSm6 | |
| SWISS-PROT: Q9UK45 | LSm7 | |
| SWISS-PROT: O95777 | LSm8 | |
| U4/U6 snRNP | | |
| ENSP00000259401 | U4/U6 snRNP hPrp4 | |
| ENSP00000236015, O43395 | U4/U6 snRNP hPrp3 | |
| ENSP00000291763 | U4/U6 snRNP 61 kDa | |
| U4/U6.U5 snRNP | | |
| SWISS-PROT: P55769 | U4/U6.snRNP 15.5 kDa | |
| ENSP00000263858 | U4/U6.U5 snRNP 65 kDa | |
| ENSP00000256313 | SART-1 = U4/U6.U5 snRNP 110 kDa | |
| SR proteins | | |
| SWISS-PROT: Q07955 | SF2 | |
| SWISS-PROT: Q16629 | 9G8 | |
| SWISS-PROT: Q01130 | SC35 | |
| SWISS-PROT: P23152 | SRp20 | |
| SWISS-PROT: Q13242 | SRp30C | |
| SWISS-PROT: Q05519 | SRp54 | |
| SWISS-PROT: Q13247 | SRp55 | |
| TREMBL: Q8WXA9 | Splicing factor, arginine/serine-rich 12 | |
| ENSP00000255590 | Ser/Arg-related nuclear matrix protein | |
| Other splicing factors | | |
| ENSP00000227503 | SF1 | |
| ENSP00000235397 | SPF27 | |
| ENSP00000239010 | SPF30 | |
| ENSP00000263697 | SPF31 | |
| TREMBL: O75939; Q96GY6 | SPF45 | |
| ENSP00000265414 | CDC5-related protein | |
| SWISS-PROT: Q13573 | SKIP | |
| TREMBL: Q9NZA0 | PUF60 | |
| TREMBL: O43660 | Pleiotropic regulator 1 | |
| ENSP00000253363 | CC1.3 | |
| ENSP00000296702 | CA150 | |
| SWISS-PROT: Q14562 | DEAH-box protein 8 | |
| SWISS-PROT: O43143 | DEAD/H-box-15 | |
| SWISS-PROT: O60231 | DEAD/H-box-16 | |
| ENSP00000268482 | hPRP16 | |
| SWISS-PROT: O60508 | hPRP17 | |
| ENSP00000198939 (+ENSP00000248044) | ERPROT 213-21 (+N-terminal extension of ERPROT) | |
| ENSP00000290341 | IGE-II mRNA-binding protein 1 | |
| SWISS-PROT: P23246 | PTB-associated splicing factor | |
| ENSP00000266611 | IK factor | |
| ENSP00000257528 | SLU7 | |
| ENSP00000216727 | poly(A)-binding protein II | |
| ENSP00000293531 | KH-type splicing regulatory protein | |
| ENSP00000294623 | far upstream element-binding protein 1 | |
| ENSP00000227524 | nuclear matrix protein NMP200 | |
| TREMBL: Q96HB0 | HCNP protein | |
| ENSP00000278799 | crooked neck-like 1 | |
| SWISS-PROT: Q9Y3B4 | pre-mRNA branch site protein p14 | |
| ENSP00000292123 | scaffold attachment factor B | |
| ENSP00000261167 | SH3 domain-binding protein SNP70 | |
| hnRNP | | |
| ENSP00000257767 | GRY-RBP | |
| SWISS-PROT: Q13151 | hnRNP A0 | |

TABLE 2-continued

Proteins With a Known Function in Splicing and RNA Processing

| Acc. no.a | Name | Comments |
|---|---|---|
| SWISS-PROT: P09651 | hnRNP A1 | |
| SWISS-PROT: P22626 | hnRNP A2/hnRNP B1 | |
| ENSP00000298069 | hnRNP A3 | |
| ENSP00000261952 | hnRNP AB, isoform a | |
| SWISS-PROT: P07910 | hnRNP C | |
| SWISS-PROT: Q14103 | hnRNP D | |
| ENSP00000295469 | hnRNP D-like | |
| SWISS-PROT: P52597 | hnRNP F | |
| SWISS-PROT: P38159 | hnRNP G | |
| SWISS-PROT: P31943 | hnRNP H | |
| ENSP00000265866 | hnRNP H3 | |
| SWISS-PROT: P26599 | Polypyrimidine tract-binding protein; hnRNP I | |
| ENSP00000297818 | hnRNP K | |
| SWISS-PROT: P14866 | hnRNP L | |
| SWISS-PROT: P52272 | hnRNP M | |
| SWISS-PROT: O43390 | hnRNP R | |
| Q00839 | hnRNP U | |
| TREMBL: O76022 | E1B-55kDa-associated protein 5 | |
| RNA processing | | |
| SWISS-PROT: P52298 | CBP 20 kDa | |
| SWISS-PROT: Q09161 | CBP 80 kDa | |
| SWISS-PROT: P17844 | DEAD/H-box-5; RNA helicase p68 | |
| SWISS-PROT: P35637 | RNA-binding protein FUS | |
| SWISS-PROT: Q01844 | RNA-binding protein EWS | |
| SWISS-PROT: Q12906 | Interleukin enhancer-binding factor 3 | |
| ENSP00000270794 | TLS-associated serine-arginine protein 2 | |
| RNA processing | | |
| ENSP00000269407 | Aly | |
| SWISS-PROT: Q9UBU9 | Tap | |
| ENSP00000261600 | hHpr1 | |
| SWISS-PROT: Q08211 | RNA helicase A | |
| ENSP00000264073 | ELAV-like protein 1 (Hu-antigen R) | |
| SWISS-PROT: P43243 | matrin 3 | |
| SWISS-PROT: P55265 | Double-stranded RNA-specific adenosine deaminase (DRADA) | |
| ENSP00000300291 | CPSF 25 kDa | |
| ENSP00000292476 | CPSF 30 kDa | |
| ENSP00000266679 | similar to CPSF 68 kDa | |
| SWISS-PROT: Q9UKF6 | CPSF 73 kDa | |
| SWISS-PROT: Q9P2I0 | CPSF 100 kDa | |
| SWISS-PROT: Q10570 | CPSF 160 kDa | |
| ENSP00000227158 | cleavage stimulation factor subunit 3 | |
| SWISS-PROT: P05455 | Lupus La protein: Sjogren syndrome type B antigen | |
| SWISS-PROT: Q06265 | Polymyositis/scleroderma autoantigen 1 | |
| SWISS-PROT: Q01780 | Polymyositis/scleroderma autoantigen 2 | |
| SWISS-PROT: Q9Y2L1 | Exosome complex exonuclease RRP44 | |
| SWISS-PROT: Q9NPD3 | Exosome complex exonuclease RRP41 | |
| ENSP00000262489 | Dhm1-like protein | | a SWISS-PROT or ENSEMBL accession numbers are given at http://srs.embl-heidelberg.de:8000/srs5/ and http://www.ensembl.org.

TABLE 2-continued

Proteins With a Known Function in Splicing and RNA Processing

| Acc. no.a | Name | Comments |
|---|---|---|
| Novel Proteins | | |
| Novel proteins and proteins with unclear functions with sequence similarities implicating them in splicing/mRNA processing | | |
| ENSP00000295270 | Hypothetical protein | Similar to U5 snRNP 200 kDa |
| ENSP00000272417 | CDNA FLJ13778 fis | Similar to U5 snRNP 200 kDa |
| ENSP00000301345 | Hypothetical protein | Similar to U5 snRNP 220 kDa |
| TREMBL: Q9NUY0 | CDNA FLJ11063 fis | Similar to arginine/serine-rich 4 |
| SWISS-PROT: Q13523 | Serine/threonine-protein kinase | Ser/Thr protein kinase family, similar to S. pombe PRP4 |
| ENSP00000296630 | Hypothetical protein | RRM domain, bipartite NLS, similar to arginine/serine-rich 11 |
| ENSP00000266057 | CDNA FLJ10998 fis | Similar to RNA lariat debranching enzyme |
| ENSP00000273541 | Hypothetical protein | Similar to Isy 1p, a potential splice factor in yeast |
| XP_013029 | Hypothetical protein | Similar to U2 snRNP A' |
| ENSP00000286032 | Hypothetical protein | Similar to hnRNP A3 |
| ENSP00000301786 | Hypothetical protein | Similar to hnRNP U |
| ENSP000000301784 | Hypothetical protein | Similar to hnRNP U |
| ENSP00000261832 | Hypothetical protein DKFZp434E2220 | BASIC, basic domain in HLH proteins of MYOD family, PSP, proline-rich domain in spliceosome-associated proteins, zinc finger CCHC, zinc knuckle |
| ENSP00000244367 | CGI-124 protein | Cyclophilin-type peptidyl-prolyl cis-trans isomerase |
| ENSP00000215824 | CYP-60 | Cyclophilin-type peptidyl-prolyl cis-trans isomerase |
| ENSP00000234288 | PPIL3b | Cyclophilin-type peptidyl-prolyl cis-trans isomerase |
| ENSP00000282972 | Serologically defined colon cancer antigen 10 | Cyclophilin-type peptidyl-prolyl cis-trans isomerase bipartite NLS |
| SWISS-PROT: Q9UNP9 | Cyclophilin E | Cyclophilin-type peptidyl-prolyl cis-trans isomerase RRM domain |
| ENSP00000261308 | KIAA0073 protein | Cyclophilin-type peptidyl-prolyl cis-trans isomerase G-protein beta WD-40 repeats |
| SWISS-PROT: Q92841 | Probable RNA-dependent helicase p72 | DEAD/DEAH-box helicase |
| ENSP00000274514 | RNA helicase | DEAD/DEAH-box helicase |
| ENSP00000242776 | Hypothetical protein | Similar to nuclear RNA helicase, DECD variant of DEAD-box helicase family |
| SWISS-PROT: Q92499 | DDX1 | DEAD/DEAH-box helicase, SPRY domain |
| SWISS-PROT: Q9NR30 | DDX21 | DEAD/DEAH-box helicase, bipartite NLS |
| SWISS-PROT: Q9UJV9 | DEAD-box protein abstract homolog | DEAD/DEAH-box helicase, zinc finger CCHC type |
| ENSP00000218971 | DDX26 | DEAD-box, von Willebrand factor type A domain |
| SWISS-PROT: P38919 | Eukaryotic initiation | DEAD-box helicase factor 4A-like NUK-34 |
| ENSP00000297920 | Hypothetical protein FLJ11307 | Double-stranded RNA-binding domain (DsRBD) |
| ENSP00000263115 | Hypothetical protein | G-patch domain |
| ENSP00000277477 | Far upstream element (FUSE) binding protein 3 | KH domain |
| ENSP00000295749 | KIAA 1604 protein | MIF4G, middle domain of eukaryotic initiation factor 4G and MA3 domain, bipartite NLS |
| ENSP00000298643 | PRO1777 | PWI domain |
| SWISS-PROT: Q9Y580 | RNA-binding protein 7 | RRM domain |
| SWISS-PROT: O43251 | RNA-binding protein 9 | RRM domain |
| ENSP00000295971 | Hypothetical protein FLJ20273 | RRM domain |
| ENSP00000266301 | KIAA 1649 protein | RRM domain |
| SWISS-PROT: Q9Y388 | Hypothetical protein CGI-79.B | RRM domain |

TABLE 2-continued

| Proteins With a Known Function in Splicing and RNA Processing | | |
|---|---|---|
| Acc. no.a | Name | Comments |
| SWISS-PROT: Q02040 | B-lymphocyte antigen precursor | RRM domain |
| ENSP00000262632 | Hypothetical 47.4 kDa | RRM domain, ATP/GTP-binding site motif A (P-loop) |
| ENSP00000293677 | Hypothetical protein | RRM domain, Bipartite NLS |
| SWISS-PROT: Q9BXP5 | Arsenite-resistance protein 2 | RRM domain, Bipartite NLS |
| ENSP00000220496 | Hypothetical protein FLJ10634 | RRM domain, DNAJ heat shock protein, bipartite NLS |
| TREMBL: O00425 | Putative RNA-binding protein KOC | RRM domain, KH domain |
| ENSP00000262710 | KIAA0670 protein | RRM domain, SAP domain |
| TREMBL: Q96SC6 | OTT-MAL | RRM domain, SAP domain |
| ENSP00000295996 | K1AA0332 protein | RRM domain, Surp domain Bipartite NLS |
| ENSP00000199814 | Hypothetical protein FLJ10290 | RRM domain, Zinc finger C-x8-C-x5-C-x3-H type |
| SWISS-PROT: P98175 | RNA-binding protein 10 | RRM domain, C2H2 type zinc finger, bipartite NLS |
| ENSP00000261972 (+ENSP00000261973) | Hypothetical protein S164 (+N-terminal extension: CDNA: FLJ22454 fis, clone HRC09703) | RRM domain, PWI domain, bipartite NLS, Spectrin repeat (ENSP00000261973 encodes the N-terminal extension of ENSP00000261972) |
| TREMBL: Q9UQ35 | RNA-binding protein | RS domain |
| ENSP00000247001 | F23858_1 | Surp domain, G-patch domain |
| ENSP00000299951 | Hypothetical protein | U1-like zinc finger, bipartite NLS |
| ENSP00000281372 | HsKin17 protein | C2H2 zinc finger |
| TREMBL: Q96KR1 | Putative Zinc finger protein | C2H2 zinc finger |
| ENSP00000239893 | OPA-interacting protein OIP2 | 3' exoribonuclease family |
| Novel proteins without similarities implicating them in splicing/mRNA processing | | |
| SWISS-PROT: Q9C0J8 | WDC146 | G-protein beta WD-40 repeats |
| ENSP00000253952 | Hypothetical 34.8 kDa protein | G-protein beta WD-40 repeats |
| ENSP00000263222 | Hypothetical 57.5 kDa protein | G-protein beta WD-40 repeats |
| ENSP00000156471 | K1AA0560 protein | ATP/GTP-binding site motif A (P-loop) |
| SWISS-PROT: Q9UH06 | Hypothetical 12.4 kDa protein | PHD-finger (C4HC3 zinc finger) |
| ENSP00000216252 | BK223H9 | belongs to the UPF0123 family of hypothetical proteins |
| ENSP00000260210 | Hypothetical protein MGC13125 | Bipartite NLS, ankyrin similarity |
| ENSP00000257181 | Hypothetical protein FLJ14936 | Bipartite NLS, similar to unknowns |
| ENSP00000290008 | Hypothetical protein | Bipartite NLS |
| SWISS-PROT: Q9NZB2 | C9orf10 protein | Bipartite NLS, similar to unknowns |
| ENSP00000247026 | Hypothetical 66.4 kDa protein | Bipartite NLS |
| ENSP00000236273 | GCIP-interacting protein p29 | Bipartite NLS, similar to unknowns |
| ENSP00000292314 | Hypothetical protein | Bipartite NLS, similar to unknowns |
| ENSP00000266923 | C21orf70 | Bipartite NLS, similar to unknowns |
| NSP00000221899 | NY-REN-24 antigen | Bipartite NLS, Ezrin/radixin/moesin family; similar to Drosophila cactin |
| SWISS-PROT: Q14331 | FRG1 protein (FSHD region gene 1 protein) | Bipartite NLS, Lipocalin-related protein and Bos/Can/Equ allergen domain |
| SWISS-PROT: P42285 | KIAA0052 protein | SKI2 helicase family |
| ENSP00000221413 | CGI-46 protein | DnaB helicase family |
| ENSP00000222969 | G10 protein homolog (EDG-2) | G10 protein family |
| ENSP00000279839 | Adrenal gland protein AD-002 | GTP-binding signal recognition particle (SRP54) G-domain |
| ENSP00000278702 | Similar to nuclear mitotic apparatus protein 1 | Involucrin repeat, G-protein gamma subunit, DNA gyrase/topoisomerase IV, subunit A, M protein repeat, bZIP (Basic-leucine zipper) transcription factor family |
| SWISS- PROT: Q92733 | Proline-rich protein PRCC | Proline-rich extension |
| ENSP00000263905 | KIAA1461 protein | PWWP domain, Methyl-CpG binding domain |
| XP_089514 | Hypothetical protein | Similar to nucleophosmin |
| ENSP00000258457 | Hypothetical 25.9 kDa protein | Similar to Xenopus ashwin |
| TREMBL: Q8WYA6 | Nuclear associated protein | Similar to Bos taurus P14 |
| TREMBL: Q13769 | Hypothetical protein | Similarity to intermediate filament b [*Dugesia japonica*] |

TABLE 2-continued

Proteins With a Known Function in Splicing and RNA Processing

| Acc. no.a | Name | Comments |
|---|---|---|
| SWISS-PROT: Q9Y5B6 | GC-rich sequence DNA-binding factor homolog | Similar to C-TERMINAL OF GCF/TCF9 and other putative transcription factors |
| SWISS-PROT: Q9Y224 | Hypothetical protein CGI-99 | Similarity to putative transcription factors |
| ENSP00000216038 | Hypothetical 55.2 kDa protein | Uncharacterized protein family UPFOO27 |
| ENSP00000289509 | Hypothetical 80.5 kDa protein | Similar to unknowns |
| ENSP00000245838 | Hypothetical protein L0C57187 | Similar to unknowns |
| ENSP00000289996 | Hypothetical protein | Similar to unknowns |
| ENSP00000252137 | DiGeorge syndrome critical region gene DGSI protein | Similar to unknowns |
| ENSP00000256579 | Hypothetical protein FLJ10330 | Similar to unknowns |
| ENSP00000245651 | C20orf158 protein | Similar to unknowns |
| SWISS-PROT: Q9BWJ5 | Hypothetical protein MGC3133 | Similar to unknowns |
| ENSP00000272091 | Hypothetical protein XP_089191 | Similar to unknowns |
| ENSP00000297526 | KIAA1440 protein | Similar to unknowns |
| ENSP00000271942 | Hypothetical protein FLJ21919 | Similar to unknowns |
| TREMBL: Q9BTU2 | Hypothetical 31.5 kDa protein | Similar to unknowns |
| TREMBL: Q8WVN3 | Hypothetical protein | Similar to unknowns | a SWISS-PROT or ENSEMBL accession numbers are given at http://srs.embl-heidelberg.de:8000 and http://www.ensembl.org.
b Domains: RRM: RNA recognition motive; Bipartite NLS: Bipartite Nuclear Localization Signal; SPRY: SP1a/RY anodine receptor SPRY domain; G-patch: named after seven highly conserved glycines; KH: hnRNP K homology domain; PWI: proline-tryptophan-isoleucine motifs; SAP: SAF-A/B, Acinus and PIAS motif; RS: Arginine-Serine repeats; Surp: Suppressor-of-white-apricot splicing regulator domain.

TABLE 3

Proteins Involved in Transcription, Translation, and Other Functions

| Acc. no. a | Name | Comments |
|---|---|---|
| SWISS-PROT: P16991 | CCAAT-binding transcription factor I subunit A | |
| ENSP00000271939 | Interleukin enhancer binding factor 2, 45 kD | |
| TREMBL: O15043 | Death associated transcription factor 1 | |
| ENSP00000266071 | Death associated transcription factor-1 isoform b | |
| SWISS-PROT: P16383 | GC-rich sequence DNA binding factor | |
| SWISS-PROT: P78347 | general transcription factor II | |
| ENSP00000228251 | Cold shock domain protein A | |
| NP_005325 | host cell factor CI | |
| SWISS-PROT: P49848 | Transcription initiation factor TFIID 70 kD subunit | |
| SWISS-PROT: P12956 | ATP-dependent DNA helicase II, 70 kD subunit | |
| ENSP00000283131 | SWI/SNF related, matrix associated, actin dependent regulator of chromatin subfamily a, member 6 | |
| SWISS-PROT: P30876 | DNA-directed RNA polymerase II 140 kD | |
| SWISS-PROT: P24928 | DNA-directed RNA polymerase II largest subunit | |
| SWISS-PROT: P02261 | Histone H2A- | |
| SWISS-PROT: P20670 | H2A histone family member O | |
| SWISS-PROT: Q93080 | H2B histone family several members possible | |

TABLE 3-continued

Proteins Involved in Transcription, Translation, and Other Functions

| Acc. no. a | Name | Comments |
|---|---|---|
| SWISS-PROT: P09429 | High-mobility group protein 1 | |
| SWISS-PROT: O15347 | High mobility group box 4 | |
| ENSP00000275182 | Histone deacetylase 2 | |
| SWISS-PROT: Q16576 | Histone acetyltransferase type B subunit 2 | |
| SWISS-PROT: P23396 | 40S ribosomal protein S3 | |
| NP_000997 | 40S ribosomal protein S3A | |
| SWISS-PROT: P12750 | 40S ribosomal protein S4 | |
| SWISS-PROT: P22090 | 40S ribosomal protein S4Y isoform | |
| SWISS-PROT: P46782 | 40S ribosomal protein S5 | |
| SWISS-PROT: P23821 | 40S ribosomal protein S7 | |
| SWISS-PROT: P09058 | 40S ribosomal protein S8 | |
| SWISS-PROT: P46781 | 40S ribosomal protein S9 | |
| SWISS-PROT: P46783 | 40S ribosomal protein S10 | |
| ENSP00000237131 | 40S ribosomal protein S12 | |
| SWISS-PROT: Q02546 | 40S ribosomal protein S13 | |
| SWISS-PROT: P11174 | 40S ribosomal protein S15 | |
| SWISS-PROT: P39027 | 40S ribosomal protein S15a | |
| SWISS-PROT: P17008 | 40S ribosomal protein S16 | |
| SWISS-PROT: P08708 | 40S ribosomal protein S17 | |
| SWISS-PROT: P25232 | 40S ribosomal protein S18 | |
| SWISS-PROT: P39019 | 40S ribosomal protein S19 | |
| SWISS-PROT: P25111 | 40S ribosomal protein S25 | |
| SWISS-PROT: P30054 | 40S ribosomal protein S29 | |
| SWISS-PROT: Q05472 | 40S ribosomal protein S30 | |
| SWISS-PROT: P04643 | 40S ribosomal protein S11 | |
| SWISS-PROT: P46777 | 60S ribosomal protein L5 | |
| SWISS-PROT: P35268 | 60S ribosomal protein L22 | |
| SWISS-PROT: P29316 | 60S ribosomal protein L23a | |
| SWISS-PROT: P12947 | 60S ribosomal protein L31 | |
| TREMBL Q8WT0 | Signal recognition particle 9 kD | |
| SWISS-PROT: P09132 | Signal recognition particle 19 kD | |
| SWISS-PROT: Q9UHB9 | Signal recognition particle 68 kD | |
| TREMBL: Q8WUK2 | Signal recognition particle 68 kD isoform | |
| SWISS-PROT: Q76094 | Signal recognition particle 72 kD | |
| SWISS-PROT: P04720 | Elongation factor 1 | |
| SWISS-PROT: P12270 | Nucleoprotein TPR | |
| SWISS-PROT: P46940 | Ras GTPase-activating-like protein IQGAP1 (P195) | |
| ENSP00000268182 | | |
| SWISS-PROT: P52292 | Importin alpha-2 subunit | |
| SWISS-PROT: O75909 | Cyclin K | |
| SWISS-PROT: P78396 | Cyclin A1 | |
| SWISS-PROT: P09874 | poly(ADP-ribosyl)transferase | |
| SWISS-PROT: O43823 | A-kinase anchor protein 8 | |
| ENSP00000262971 | PIAS1 | |
| ENSP00000296215 | Smad nuclear-interacting protein 1 | |
| ENSP00000234443 | Protein kinase, interferon-inducible double stranded RNA dependent activator; protein activator of the interferon-induced protein kinase | |
| ENSP00000300630 | Ubiquitin | |
| ENSP00000271238 | Phosphatase 2A inhibitor | |
| SWISS-PROT: P19338 | Nucleolin | |
| SWISS-PROT: P55081 | Microfibrillar-associated protein 1 | |
| SWISS-PROT: P11142 | Heat shock cognate 71 kD protein | |
| ENSP00000286912 | Dynein heavy chain | |
| SWISS-PROT: P08670 | Vimentin | |
| ENSP00000243115 | Tubulin, alpha | |
| ENSP00000259925 | Tubulin, beta 5 | | a SWISSPROT or ENSEMBL accession numbers are given. (http://srs.embl-heidelberg.de:8000/srs5/ and www.ensembl.org)

TABLE 3

Transcription Factors
TFFACTOR sorted by molecular weight (SZ field)
Database: TFFACTOR
TRANSFAC database, binding factor information
Release 3.3, January 1998
E. Wingender, R. Knueppel, P. Dietze, H. Karas (GBF-Braunschweig)
2,285 entries

| | | | |
|---|---|---|---|
| 1. | T01627 | 8.3 | kDa; lin-32 |
| 2. | T02213 | 9.0 | kDa; PC4 p9 |
| 3. | T01972 | 10.0 | kDa; DMLP1 |
| 4. | T01852 | 10.5 | kDa; HMG I(Y) |
| 5. | T01980 | 10.5 | kDa; HMG Y |
| 6. | T01714 | 11.5 | kDa; HOXA10 PL2 |
| 7. | T01851 | 11.5 | kDa; HMG I |
| 8. | T01859 | 11.8 | kDa; HMGI-C |
| 9. | T01860 | 11.8 | kDa; HMGI-C |
| 10. | T01322 | 12.1 | kDa; ICER-Igamma |
| 11. | T01324 | 12.1 | kDa; ICER-IIgamma |
| 12. | T01566 | 12.1 | kDa; deltaMax |
| 13. | T02230 | 12.1 | kDa; TFIIA-S |
| 14. | T02226 | 12.2 | kDa; TFIIA-S |
| 15. | T01630 | 12.3 | kDa; Tal-2 |
| 16. | T01631 | 12.3 | kDa; Tal-2 |
| 17. | T02180 | 12.5 | kDa; SIII-p15 |
| 18. | T02224 | 12.5 | kDa; TFIIA-gamma |
| 19. | T02232 | 12.5 | kDa; TFIIA-S |
| 20. | T02269 | 12.5 | kDa; SIII-p15 |
| 21. | T01263 | 12.9 | kDa; HAP3 |
| 22. | T01809 | 13.0 | kDa; Id3 |
| 23. | T00367 | 13.1 | kDa; Id3 |
| 24. | T01811 | 13.1 | kDa; Id3 |
| 25. | T02179 | 13.1 | kDa; SIII-p18 |
| 26. | T02268 | 13.1 | kDa; SIII-p18 |
| 27. | T01325 | 13.3 | kDa; ATF-3deltaZIP |
| 28. | T01319 | 13.4 | kDa; ICER |
| 29. | T01321 | 13.4 | kDa; ICER-I |
| 30. | T01323 | 13.4 | kDa; ICER-II |
| 31. | T02228 | 13.5 | kDa; TFIIA (13.5 kDa subunit) |
| 32. | T02150 | 13.9 | kDa; SRB6 |
| 33. | T02117 | 14.3 | kDa; TAF(II)18 |
| 34. | T02137 | 14.4 | kDa; PC4 |
| 35. | T02138 | 14.4 | kDa; PC4 |
| 36. | T01654 | 14.6 | kDa; HEN1 |
| 37. | T00488 | 14.8 | kDa; MATa1 |

TABLE 3-continued

Transcription Factors
TFFACTOR sorted by molecular weight (SZ field)
Database: TFFACTOR
TRANSFAC database, binding factor information
Release 3.3, January 1998
E. Wingender, R. Knueppel, P. Dietze, H. Karas (GBF-Braunschweig)
2,285 entries

| # | ID | MW; Name |
|---|----|----|
| 38. | T01655 | 14.8 kDa; HEN1 |
| 39. | T01212 | 14.9 kDa; Id2 |
| 40. | T00404 | 15.0 kDa; Id2 |
| 41. | T01656 | 15.0 kDa; HEN2 |
| 42. | T01657 | 15.0 kDa; HEN2 |
| 43. | T01808 | 15.0 kDa; Id2 |
| 44. | T00441 | 15.4 kDa; KBP-1 |
| 45. | T00403 | 15.6 kDa; Id1 |
| 46. | T01420 | 15.6 kDa; LIP |
| 47. | T01807 | 15.6 kDa; Id1 |
| 48. | T02274 | 15.6 kDa; Id1H' |
| 49. | T00350 | 16.0 kDa; HAP3 |
| 50. | T01810 | 16.1 kDa; Id3/Heir-1 |
| 51. | T02151 | 16.1 kDa; SRB7 |
| 52. | T01801 | 16.2 kDa; Id1 |
| 53. | T01384 | 16.5 kDa; pX |
| 54. | T01448 | 16.5 kDa; Tal-1beta |
| 55. | T01436 | 16.6 kDa; MafF |
| 56. | T01658 | 16.6 kDa; Id4 |
| 57. | T01600 | 16.8 kDa; CREMdeltaC-G |
| 58. | T01120 | 17.0 kDa; MCBF |
| 59. | T01650 | 17.0 kDa; HES-2 |
| 60. | T01060 | 17.1 kDa; MNB1b |
| 61. | T00489 | 17.2 kDa; Max1 |
| 62. | T01591 | 17.3 kDa; P (short form) |
| 63. | T01593 | 17.3 kDa; C1 (short form) |
| 64. | T01301 | 17.4 kDa; E4 |
| 65. | T01606 | 17.4 kDa; Id1.25 |
| 66. | T01639 | 17.4 kDa; INO4 |
| 67. | T02311 | 17.4 kDa; CSE2 |
| 68. | T01434 | 17.5 kDa; MafK |
| 69. | T01435 | 17.5 kDa; MafK |
| 70. | T01622 | 17.6 kDa; ASH-3a |
| 71. | T01745 | 17.6 kDa; HOXC6 (PRI) |
| 72. | T01743 | 17.8 kDa; HOXC6 (PRI) |
| 73. | T02249 | 17.8 kDa; Lmo1 |
| 74. | T01742 | 17.9 kDa; HOXC6 |
| 75. | T02116 | 17.9 kDa; TAF(II)20 |
| 76. | T01274 | 18.0 kDa; DBF-A |
| 77. | T02254 | 18.0 kDa; PEBP2beta3 |
| 78. | T01437 | 18.1 kDa; MafG |
| 79. | T00523 | 18.3 kDa; Myn |
| 80. | T01567 | 18.3 kDa; Max2 |
| 81. | T02251 | 18.3 kDa; Lmo2 |
| 82. | T02250 | 18.4 kDa; Lmo2 |
| 83. | T01652 | 18.5 kDa; HES-5 |
| 84. | T02089 | 18.7 kDa; mat-Pc |
| 85. | T01636 | 18.8 kDa; X-Twist |
| 86. | T00127 | 19.0 kDa; CHOP-10 |
| 87. | T00224 | 19.0 kDa; EF1 |
| 88. | T00299 | 19.0 kDa; GADD 153 |
| 89. | T01206 | 19.0 kDa; EF1 |
| 90. | T02139 | 19.0 kDa; PC4 |
| 91. | T01651 | 19.1 kDa; HES-3 |
| 92. | T00197 | 19.3 kDa; Dr1 |
| 93. | T01687 | 19.3 kDa; Pcr1 |
| 94. | T00043 | 19.5 kDa; ARG RI |
| 95. | T01644 | 19.9 kDa; E(spl)m5 |
| 96. | T01447 | 20.0 kDa; HEN1 |
| 97. | T02216 | 20.0 kDa; TFIIA-alpha/beta precursor (major) |
| 98. | T02217 | 20.0 kDa; TFIIA-alpha/beta precursor (minor) |
| 99. | T01646 | 20.3 kDa; E(spl)m8 |
| 100. | T00486 | 20.4 kDa; MATalpha1 |
| 101. | T01310 | 20.4 kDa; S-CREM |
| 102. | T01313 | 20.6 kDa; ATF-3 |
| 103. | T01095 | 20.7 kDa; LRF-1 |
| 104. | T01612 | 20.7 kDa; Meso1 |
| 105. | T01645 | 20.7 kDa; E(spl)m7 |
| 106. | T01971 | 20.8 kDa; MLP |
| 107. | T01623 | 20.9 kDa; ASH-3b |
| 108. | T01637 | 20.9 kDa; EC2 |
| 109. | T02221 | 20.9 kDa; Bro |
| 110. | T01275 | 21.0 kDa; mat-Mc |
| 111. | T01635 | 21.2 kDa; M-Twist |
| 112. | T01065 | 21.5 kDa; PEBP2beta2 |
| 113. | T02259 | 21.5 kDa; PEBP2beta |
| 114. | T02126 | 21.6 kDa; TAF(II)30alpha |
| 115. | T02309 | 21.6 kDa; MET28 |
| 116. | T01754 | 21.7 kDa; HOXD8 |
| 117. | T02118 | 21.7 kDa; TAF(II)30 |
| 118. | T01890 | 21.8 kDa; Brn-5(c7) |
| 119. | T02222 | 21.8 kDa; Bgb |
| 120. | T00274 | 22.0 kDa; Emc |
| 121. | T02255 | 22.0 kDa; PEBP2beta1 |
| 122. | T02131 | 22.1 kDa; TAF(II)30beta |
| 123. | T00799 | 22.4 kDa; TBP-1 |
| 124. | T00800 | 22.4 kDa; TBP-2 |
| 125. | T01621 | 22.4 kDa; ASH-1 |
| 126. | T00005 | 22.7 kDa; Ac |
| 127. | T01813 | 22.7 kDa; Pax-3B |
| 128. | T00616 | 22.8 kDa; NF-YB |
| 129. | T02147 | 22.9 kDa; SRB2 |
| 130. | T01601 | 23.0 kDa; CREMdeltaC-F |
| 131. | T02275 | 23.1 kDa; SUP |
| 132. | T00216 | 23.3 kDa; C/EBPgamma |
| 133. | T02114 | 23.3 kDa; TAF(II)28 |
| 134. | T01018 | 23.6 kDa; CAP |
| 135. | T01569 | 23.8 kDa; Th1 |
| 136. | T00997 | 23.9 kDa; SRY |
| 137. | T01735 | 23.9 kDa; HOXB7 |
| 138. | T00179 | 24.0 kDa; CUP2 |
| 139. | T01704 | 24.0 kDa; HOXA7 |
| 140. | T01734 | 24.0 kDa; HOXB7 |
| 141. | T01812 | 24.1 kDa; Pax-3A |
| 142. | T01316 | 24.2 kDa; CREMgamma |
| 143. | T00487 | 24.3 kDa; MATalpha2 |
| 144. | T01803 | 24.3 kDa; CREMalpha |
| 145. | T00516 | 24.4 kDa; mtTF1 |
| 146. | T02061 | 24.4 kDa; K-2b |
| 147. | T01987 | 24.5 kDa; SRY |
| 148. | T01887 | 24.6 kDa; Brn-4 |
| 149. | T02211 | 24.6 kDa; BTEB2 |
| 150. | T01779 | 24.7 kDa; GLO |
| 151. | T02025 | 24.7 kDa; C/EBPalpha(p30) |
| 152. | T01059 | 24.8 kDa; MNB1a |
| 153. | T01619 | 24.8 kDa; MASH-1 |
| 154. | T00087 | 25.0 kDa; CBF-A |
| 155. | T00484 | 25.0 kDa; MASH-1 |
| 156. | T00520 | 25.0 kDa; Myf-4 |
| 157. | T01741 | 25.0 kDa; HOXC5 |
| 158. | T01736 | 25.1 kDa; HOXB7 |
| 159. | T00528 | 25.2 kDa; myogenin |
| 160. | T01565 | 25.3 kDa; Mad |
| 161. | T01733 | 25.3 kDa; HOXB6 |
| 162. | T00795 | 25.4 kDa; TBP |
| 163. | T01315 | 25.4 kDa; CREMbeta |
| 164. | T01778 | 25.4 kDa; GLO |
| 165. | T02198 | 25.4 kDa; FosB/SF |
| 166. | T00849 | 25.5 kDa; TRF |
| 167. | T01314 | 25.5 kDa; CREMalpha |
| 168. | T01732 | 25.5 kDa; HOXB6 |
| 169. | T02027 | 25.5 kDa; C/EBPalpha(p30) |
| 170. | T02026 | 25.6 kDa; C/EBPalpha(p30) |
| 171. | T01278 | 25.7 kDa; HOXA7 |
| 172. | T01533 | 25.7 kDa; myogenin |
| 173. | T01620 | 25.7 kDa; MASH-1 |
| 174. | T01531 | 25.8 kDa; myogenin |
| 175. | T00180 | 25.9 kDa; CYS3 |
| 176. | T01082 | 25.9 kDa; NRL |
| 177. | T01438 | 26.1 kDa; NRL |
| 178. | T01564 | 26.1 kDa; Mxi1 |
| 179. | T01740 | 26.2 kDa; HOXB9 |
| 180. | T01008 | 26.3 kDa; DEF A |
| 181. | T01538 | 26.4 kDa; MRF4 |

TABLE 3-continued

Transcription Factors
TFFACTOR sorted by molecular weight (SZ field)
Database: TFFACTOR
TRANSFAC database, binding factor information
Release 3.3, January 1998
E. Wingender, R. Knueppel, P. Dietze, H. Karas (GBF-Braunschweig)
2,285 entries

| | | |
|---|---|---|
| 182. | T01588 | 26.4 kDa; GL1 |
| 183. | T00967 | 26.5 kDa; E1A 12S protein |
| 184. | T01729 | 26.5 kDa; HOXB4 |
| 185. | T00888 | 26.6 kDa; v-Fos |
| 186. | T02039 | 26.6 kDa; HAC1 |
| 187. | T01746 | 26.7 kDa; HOXC6 (PRII) |
| 188. | T01753 | 26.7 kDa; HOXD4 |
| 189. | T00633 | 26.8 kDa; N-Oct-Sb |
| 190. | T00798 | 26.9 kDa; TBP |
| 191. | T00923 | 26.9 kDa; Zta |
| 192. | T01057 | 26.9 kDa; lin-31 |
| 193. | T01744 | 26.9 kDa; HOXC6 (PRII) |
| 194. | T01747 | 26.9 kDa; HOXC6 (PRII) |
| 195. | T00512 | 27.0 kDa; MRF4 |
| 196. | T00522 | 27.0 kDa; Myf-6 |
| 197. | T01537 | 27.0 kDa; MRF4 |
| 198. | T01777 | 27.0 kDa; GP |
| 199. | T01255 | 27.1 kDa; DAT1 |
| 200. | T01539 | 27.1 kDa; MRF4 |
| 201. | T00171 | 27.2 kDa; C/EBPepsilon |
| 202. | T02045 | 27.2 kDa; Flh |
| 203. | T02210 | 27.2 kDa; BTEB |
| 204. | T02212 | 27.2 kDa; BTEB |
| 205. | T01752 | 27.3 kDa; HOXD4 |
| 206. | T01776 | 27.3 kDa; APETALA3 |
| 207. | T02046 | 27.3 kDa; Gsc |
| 208. | T02060 | 27.3 kDa; K-2a |
| 209. | T01484 | 27.4 kDa; Cdx-1 |
| 210. | T02044 | 27.4 kDa; Flh |
| 211. | T02049 | 27.4 kDa; Gsc B |
| 212. | T02132 | 27.4 kDa; TAF(II)30 |
| 213. | T02141 | 27.4 kDa; OCA-B |
| 214. | T02256 | 27.4 kDa; AML1a |
| 215. | T01515 | 27.5 kDa; Pur factor |
| 216. | T01728 | 27.5 kDa; HOXB4 |
| 217. | T02069 | 27.5 kDa; Msx-1 |
| 218. | T01727 | 27.6 kDa; HOXB4 |
| 219. | T01737 | 27.6 kDa; HOXB8 |
| 220. | T02142 | 27.6 kDa; OCA-B |
| 221. | T00485 | 27.7 kDa; MASH-2 |
| 222. | T01749 | 27.7 kDa; HOXC8 |
| 223. | T01726 | 27.8 kDa; HOXB4 |
| 224. | T00376 | 27.9 kDa; HOXD4 |
| 225. | T00347 | 28.0 kDa; HAP2 |
| 226. | T01370 | 28.0 kDa; p28 modulator |
| 227. | T02047 | 28.0 kDa; Gsc |
| 228. | T01534 | 28.2 kDa; Myf-5 |
| 229. | T01535 | 28.2 kDa; Myf-5 |
| 230. | T02074 | 28.2 kDa; Msx-2 |
| 231. | T02077 | 28.2 kDa; Msx-2 |
| 232. | T01090 | 28.3 kDa; TAF-1 |
| 233. | T01846 | 28.3 kDa; TCF-1D |
| 234. | T02170 | 28.3 kDa; TFIIF-beta |
| 235. | T00521 | 28.4 kDa; Myf-5 |
| 236. | T00583 | 28.4 kDa; C/EBPdelta |
| 237. | T01536 | 28.4 kDa; Myf-5 |
| 238. | T01706 | 28.4 kDa; HOXA7 |
| 239. | T01986 | 28.4 kDa; SRY |
| 240. | T01999 | 28.4 kDa; Cdx-1 |
| 241. | T02007 | 28.4 kDa; Dlx-1 |
| 242. | T02169 | 28.4 kDa; TFIIF-beta |
| 243. | T02195 | 28.4 kDa; TBP |
| 244. | T00109 | 28.6 kDa; C/EBPdelta |
| 245. | T00949 | 28.6 kDa; Myf-5 |
| 246. | T01114 | 28.6 kDa; C/EBPdelta |
| 247. | T01981 | 28.6 kDa; TCF-1F |
| 248. | T00632 | 28.7 kDa; N-Oct-5a |
| 249. | T00902 | 28.7 kDa; XBP-1 |
| 250. | T00926 | 28.7 kDa; SUM-1 |
| 251. | T01632 | 28.7 kDa; Lyl-1 |
| 252. | T01401 | 28.8 kDa; Spi-B |
| 253. | T01592 | 28.8 kDa; C1 (long form) |
| 254. | T01773 | 28.8 kDa; AG |
| 255. | T02075 | 28.8 kDa; Msx-2 |
| 256. | T01880 | 28.9 kDa; Brn-3b |
| 257. | T02076 | 28.9 kDa; Msx-2 |
| 258. | T00003 | 29.0 kDa; AS-C T3 |
| 259. | T01086 | 29.0 kDa; beta-1 |
| 260. | T01982 | 29.0 kDa; TCF-1G |
| 261. | T02113 | 29.0 kDa; TAF(II)31 |
| 262. | T00871 | 29.1 kDa; USF |
| 263. | T01116 | 29.1 kDa; SAP1 |
| 264. | T02099 | 29.1 kDa; Zen-2 |
| 265. | T00008 | 29.2 kDa; Adf-1 |
| 266. | T00160 | 29.2 kDa; CPC1 |
| 267. | T00377 | 29.2 kDa; HOXA5 |
| 268. | T00968 | 29.2 kDa; ATF-1 |
| 269. | T01072 | 29.2 kDa; TEF |
| 270. | T01304 | 29.2 kDa; ATF-1 |
| 271. | T02105 | 29.2 kDa; C/EBPbeta(p34) |
| 272. | T02125 | 29.3 kDa; TAF(II)40 |
| 273. | T00925 | 29.4 kDa; AMT1 |
| 274. | T01462 | 29.4 kDa; Fra-1 |
| 275. | T01702 | 29.4 kDa; HOXA5 |
| 276. | T01730 | 29.4 kDa; HOXB5 |
| 277. | T02050 | 29.4 kDa; Gtx |
| 278. | T02090 | 29.4 kDa; Phox-2 |
| 279. | T01731 | 29.5 kDa; HOXB5 |
| 280. | T01648 | 29.6 kDa; HES-1 |
| 281. | T01649 | 29.7 kDa; HES-1 |
| 282. | T00349 | 29.8 kDa; HAP2 |
| 283. | T00292 | 29.9 kDa; Fra-1 |
| 284. | T01249 | 29.9 kDa; BUF1 |
| 285. | T00597 | 30.0 kDa; NF-kappaE2 |
| 286. | T01221 | 30.0 kDa; NF-kappaE2 |
| 287. | T01277 | 30.0 kDa; spE2F |
| 288. | T01762 | 30.0 kDa; HOXD12 |
| 289. | T01775 | 30.0 kDa; APETALA1 |
| 290. | T02092 | 30.0 kDa; Prh |
| 291. | T02225 | 30.0 kDa; TFIIA-L |
| 292. | T01208 | 30.1 kDa; Fra-1 |
| 293. | T01290 | 30.1 kDa; MATalpha1 |
| 294. | T01872 | 30.1 kDa; Oct-4B |
| 295. | T02172 | 30.1 kDa; TFIIF-beta |
| 296. | T01000 | 30.2 kDa; TCF-1B |
| 297. | T01633 | 30.2 kDa; Lyl-1 |
| 298. | T02091 | 30.2 kDa; Prh |
| 299. | T00999 | 30.3 kDa; TCF-1A |
| 300. | T01001 | 30.3 kDa; TCF-1C |
| 301. | T01763 | 30.3 kDa; HOXD12 |
| 302. | T01317 | 30.4 kDa; CREMepsilon |
| 303. | T02068 | 30.4 kDa; PU.1 |
| 304. | T02108 | 30.4 kDa; CREMtau1 |
| 305. | T02018 | 30.5 kDa; En-2 |
| 306. | T02070 | 30.5 kDa; Msx-1 |
| 307. | T00702 | 30.7 kDa; PU.1 |
| 308. | T02058 | 30.8 kDa; IPF1 |
| 309. | T02072 | 30.8 kDa; Msx-1 |
| 310. | T00845 | 30.9 kDa; Tra-1 (short form) |
| 311. | T01474 | 30.9 kDa; Athb-1 |
| 312. | T01996 | 31.0 kDa; dJRA |
| 313. | T02057 | 31.0 kDa; IPF1 |
| 314. | T02071 | 31.0 kDa; Msx-1 |
| 315. | T02073 | 31.0 kDa; Msx-1 |
| 316. | T00321 | 31.3 kDa; GCN4 |
| 317. | T00267 | 31.4 kDa; GATA-1 |
| 318. | T01426 | 31.4 kDa; HOXD8 |
| 319. | T00017 | 31.5 kDa; C/EBPbeta |
| 320. | T00459 | 31.5 kDa; C/EBPbeta |
| 321. | T02082 | 31.6 kDa; Otx2 |
| 322. | T02083 | 31.6 kDa; Otx2 |
| 323. | T02109 | 31.6 kDa; CREMtau2 |
| 324. | T00653 | 31.7 kDa; Oct-5 |
| 325. | T01720 | 31.7 kDa; HOXB1 |

TABLE 3-continued

Transcription Factors
TFFACTOR sorted by molecular weight (SZ field)
Database: TFFACTOR
TRANSFAC database, binding factor information
Release 3.3, January 1998
E. Wingender, R. Knueppel, P. Dietze, H. Karas (GBF-Braunschweig)
2,285 entries

| # | ID | MW; Name |
|---|---|---|
| 326. | T00209 | 31.8 kDa; E1A 13S protein |
| 327. | T01761 | 31.8 kDa; HOXD11 |
| 328. | T01389 | 31.9 kDa; LEF-1S |
| 329. | T01475 | 31.9 kDa; Athb-2 |
| 330. | T01759 | 31.9 kDa; HOXD11 |
| 331. | T00961 | 32.0 kDa; ANF-2 |
| 332. | T01381 | 32.0 kDa; deltaCREB |
| 333. | T01719 | 32.1 kDa; HOXB1 |
| 334. | T01816 | 32.1 kDa; Mab-18 (284 AA) |
| 335. | T02174 | 32.1 kDa; TFIIF-beta |
| 336. | T00815 | 32.2 kDa; TFIIA |
| 337. | T02227 | 32.2 kDa; TFIIA (32 kDa subunit) |
| 338. | T00524 | 32.3 kDa; MyoD |
| 339. | T01093 | 32.4 kDa; CPRF-3 |
| 340. | T01764 | 32.4 kDa; HOXD13 |
| 341. | T00893 | 32.5 kDa; v-Jun |
| 342. | T01532 | 32.5 kDa; myogenin |
| 343. | T01893 | 32.6 kDa; TCFbeta1 |
| 344. | T02166 | 32.6 kDa; TFIIE-beta |
| 345. | T01605 | 32.7 kDa; SGC1 |
| 346. | T01891 | 32.7 kDa; Brn-5 |
| 347. | T02111 | 32.7 kDa; TBP |
| 348. | T00500 | 32.8 kDa; MCM1 |
| 349. | T00325 | 32.9 kDa; Pit-1 |
| 350. | T01172 | 32.9 kDa; Pit-1 |
| 351. | T01516 | 32.9 kDa; Pit-1b |
| 352. | T01888 | 32.9 kDa; Brn-5(c2) |
| 353. | T01128 | 33.0 kDa; MyoD |
| 354. | T01551 | 33.0 kDa; MyoD |
| 355. | T02163 | 33.0 kDa; TFIIE-beta |
| 356. | T02238 | 33.0 kDa; TFIIE-beta |
| 357. | T01889 | 33.1 kDa; Brn-5(c1) |
| 358. | T01071 | 33.2 kDa; Hlf |
| 359. | T01641 | 33.2 kDa; PHO80 |
| 360. | T01817 | 33.2 kDa; Mab-18 (296 AA) |
| 361. | T02031 | 33.2 kDa; HSF24 |
| 362. | T02196 | 33.2 kDa; JunD |
| 363. | T01716 | 33.3 kDa; HOXA11 |
| 364. | T01751 | 33.3 kDa; HOXD1 |
| 365. | T01876 | 33.3 kDa; Brn-3a |
| 366. | T02304 | 33.4 kDa; Pur-1 |
| 367. | T00128 | 33.5 kDa; HOXA4 |
| 368. | T00874 | 33.5 kDa; USF |
| 369. | T01760 | 33.5 kDa; HOXD11 |
| 370. | T02002 | 33.5 kDa; Cdx-2 |
| 371. | T01691 | 33.6 kDa; TTP |
| 372. | T01847 | 33.6 kDa; TCF-1 |
| 373. | T01878 | 33.6 kDa; Brn-3a(s) |
| 374. | T02003 | 33.6 kDa; Cdx-3 |
| 375. | T01063 | 33.7 kDa; PEBP2alphaA2 |
| 376. | T01718 | 33.8 kDa; HOXB1 |
| 377. | T01800 | 33.8 kDa; Tal-1 |
| 378. | T02020 | 33.8 kDa; En-2 |
| 379. | T00134 | 33.9 kDa; c-Jun |
| 380. | T01078 | 33.9 kDa; GBF1 |
| 381. | T02188 | 33.9 kDa; TFIIH-p34 |
| 382. | T00615 | 34.0 kDa; NF-YA |
| 383. | T01513 | 34.0 kDa; AEF-1 |
| 384. | T01836 | 34.0 kDa; Sox-2 |
| 385. | T00690 | 34.1 kDa; PHO4 |
| 386. | T01628 | 34.1 kDa; Ato |
| 387. | T01750 | 34.1 kDa; HOXD1 |
| 388. | T01837 | 34.1 kDa; Sox-2 |
| 389. | T00526 | 34.2 kDa; MyoD |
| 390. | T01241 | 34.2 kDa; INO2 |
| 391. | T01388 | 34.2 kDa; C/EBP |
| 392. | T01675 | 34.2 kDa; Nkx-2.5 |
| 393. | T02019 | 34.2 kDa; En-2 |
| 394. | T02234 | 34.2 kDa; TFIIB |
| 395. | T00790 | 34.3 kDa; Tal-1 |
| 396. | T00881 | 34.3 kDa; VBP |
| 397. | T01453 | 34.3 kDa; v-Fos |
| 398. | T01799 | 34.3 kDa; Tal-1 |
| 399. | T01976 | 34.3 kDa; c-Jun |
| 400. | T02149 | 34.3 kDa; SRB5 |
| 401. | T02233 | 34.3 kDa; TFIIB |
| 402. | T00183 | 34.4 kDa; DBP |
| 403. | T01242 | 34.4 kDa; SNP1 |
| 404. | T02054 | 34.4 kDa; Hox11 |
| 405. | T02158 | 34.4 kDa; TFIIB |
| 406. | T00519 | 34.5 kDa; Myf-3 |
| 407. | T00525 | 34.5 kDa; MyoD |
| 408. | T00548 | 34.5 kDa; NF-AB |
| 409. | T00707 | 34.5 kDa; PUF-I |
| 410. | T01703 | 34.5 kDa; HOXA4 |
| 411. | T02014 | 34.5 kDa; En-1 |
| 412. | T00293 | 34.6 kDa; FRG Y1 |
| 413. | T02055 | 34.6 kDa; Hox11 |
| 414. | T00796 | 34.7 kDa; TBP |
| 415. | T02009 | 34.7 kDa; Dlx-2 |
| 416. | T02160 | 34.7 kDa; TFIIB |
| 417. | T00818 | 34.8 kDa; TFIIB |
| 418. | T02159 | 34.8 kDa; TFIIB |
| 419. | T00348 | 34.9 kDa; HAP2 |
| 420. | T00437 | 34.9 kDa; JunD |
| 421. | T01826 | 34.9 kDa; Pax-8c |
| 422. | T02197 | 34.9 kDa; JunD |
| 423. | T00165 | 35.0 kDa; deltaCREB |
| 424. | T00166 | 35.0 kDa; deltaCREB |
| 425. | T00816 | 35.0 kDa; TFIIA |
| 426. | T00846 | 35.0 kDa; TREB-1 |
| 427. | T01755 | 35.0 kDa; HOXD9 |
| 428. | T01938 | 35.0 kDa; IkappaB-alpha |
| 429. | T02022 | 35.0 kDa; C/EBPbeta |
| 430. | T01311 | 35.1 kDa; deltaCREB |
| 431. | T01552 | 35.2 kDa; TFEC |
| 432. | T01701 | 35.2 kDa; HOXA4 |
| 433. | T01939 | 35.2 kDa; IkappaB-alpha |
| 434. | T01990 | 35.2 kDa; Fra-2 |
| 435. | T01991 | 35.2 kDa; Fra-2 |
| 436. | T02005 | 35.2 kDa; Dll |
| 437. | T02194 | 35.2 kDa; TFIIH-KIN28 |
| 438. | T01881 | 35.3 kDa; Brn-3b |
| 439. | T02199 | 35.3 kDa; Fra-2 |
| 440. | T00186 | 35.4 kDa; DbpB |
| 441. | T00910 | 35.4 kDa; YB-1 |
| 442. | T01937 | 35.4 kDa; IkappaB-alpha |
| 443. | T01978 | 35.4 kDa; JunD |
| 444. | T02200 | 35.4 kDa; Fra-2 |
| 445. | T00421 | 35.5 kDa; IREBF-1 |
| 446. | T01433 | 35.5 kDa; MafB |
| 447. | T02202 | 35.5 kDa; MafB |
| 448. | T00950 | 35.6 kDa; IkappaB-alpha |
| 449. | T01424 | 35.6 kDa; HOXD9 |
| 450. | T01681 | 35.6 kDa; PTFdelta |
| 451. | T00107 | 35.7 kDa; C/EBPalpha |
| 452. | T00133 | 35.7 kDa; c-Jun |
| 453. | T00235 | 35.7 kDa; EFIA |
| 454. | T01570 | 35.7 kDa; FlbD |
| 455. | T00236 | 35.8 kDa; EFIA |
| 456. | T00436 | 35.8 kDa; JunB |
| 457. | T00691 | 35.8 kDa; Pit-1a |
| 458. | T01439 | 35.8 kDa; kreisler |
| 459. | T02187 | 35.8 kDa; TFIIH-MAT1 |
| 460. | T00131 | 35.9 kDa; c-Jun |
| 461. | T01977 | 35.9 kDa; JunB |
| 462. | T00132 | 36.0 kDa; c-Jun |
| 463. | T00291 | 36.0 kDa; FosB |
| 464. | T00538 | 36.0 kDa; NF-1 |
| 465. | T01696 | 36.0 kDa; HOXA1 |
| 466. | T00581 | 36.1 kDa; C/EBPbeta |
| 467. | T01055 | 36.2 kDa; Slp1 |
| 468. | T01098 | 36.2 kDa; EmBP-1 |
| 469. | T01540 | 36.2 kDa; Nau |

TABLE 3-continued

Transcription Factors
TFFACTOR sorted by molecular weight (SZ field)
Database: TFFACTOR
TRANSFAC database, binding factor information
Release 3.3, January 1998
E. Wingender, R. Knueppel, P. Dietze, H. Karas (GBF-Braunschweig)
2,285 entries

| | | |
|---|---|---|
| 470. | T01992 | 36.2 kDa; abd-A |
| 471. | T00110 | 36.5 kDa; CeMyoD |
| 472. | T00423 | 36.5 kDa; IRF-1 |
| 473. | T01309 | 36.6 kDa; CREMtau |
| 474. | T01589 | 36.6 kDa; MybSt1 |
| 475. | T01695 | 36.6 kDa; HOXA1 |
| 476. | T01919 | 36.6 kDa; CREMtau |
| 477. | T02112 | 36.6 kDa; TBP |
| 478. | T00163 | 36.7 kDa; CREB |
| 479. | T00937 | 36.7 kDa; HBP-1a |
| 480. | T00989 | 36.7 kDa; CREB |
| 481. | T01602 | 36.7 kDa; CREMtaualpha |
| 482. | T00938 | 36.8 kDa; HBP-1b |
| 483. | T01970 | 36.8 kDa; Mec-3 |
| 484. | T00157 | 36.9 kDa; CP1B |
| 485. | T01386 | 36.9 kDa; C/EBP |
| 486. | T01392 | 36.9 kDa; GABP-beta2 |
| 487. | T01404 | 36.9 kDa; GABP-beta2 |
| 488. | T00164 | 37.0 kDa; CREB |
| 489. | T00185 | 37.0 kDa; DbpA |
| 490. | T00345 | 37.0 kDa; H |
| 491. | T00547 | 37.0 kDa; NF-AB |
| 492. | T01555 | 37.0 kDa; USF2 |
| 493. | T01892 | 37.0 kDa; Sprm-1 |
| 494. | T00424 | 37.1 kDa; IRF-1 |
| 495. | T00498 | 37.1 kDa; MBP-1 (2) |
| 496. | T01076 | 37.1 kDa; Mec-3 |
| 497. | T02240 | 37.1 kDa; TFIIE-beta |
| 498. | T00294 | 37.2 kDa; FRG Y2 |
| 499. | T01595 | 37.2 kDa; CBF-C |
| 500. | T00422 | 37.3 kDa; IRF-1 |
| 501. | T02079 | 37.3 kDa; Otx1 |
| 502. | T01785 | 37.4 kDa; xMEF-2 |
| 503. | T02080 | 37.5 kDa; Otx1 |
| 504. | T00105 | 37.6 kDa; C/EBPalpha |
| 505. | T01607 | 37.6 kDa; E2F-5 |
| 506. | T02081 | 37.6 kDa; Otx1 |
| 507. | T02184 | 37.6 kDa; TFIIH-cyclin H |
| 508. | T00104 | 37.7 kDa; C/EBPalpha |
| 509. | T00108 | 37.7 kDa; C/EBPalpha |
| 510. | T00794 | 37.7 kDa; TBP |
| 511. | T01050 | 37.7 kDa; HNF-3gamma |
| 512. | T01677 | 37.7 kDa; LKLF |
| 513. | T02201 | 37.7 kDa; c-Maf (short form) |
| 514. | T02220 | 37.7 kDa; AML1DeltaN |
| 515. | T01676 | 37.8 kDa; EKLF |
| 516. | T02093 | 37.8 kDa; Ro |
| 517. | T02155 | 37.8 kDa; SRB11 |
| 518. | T00677 | 37.9 kDa; Pax-1 |
| 519. | T01668 | 37.9 kDa; MATH-1 |
| 520. | T00651 | 38.0 kDa; Oct-4 |
| 521. | T00858 | 38.0 kDa; TTF-1 |
| 522. | T00859 | 38.0 kDa; TTF-1 |
| 523. | T00971 | 38.0 kDa; IkappaB-beta |
| 524. | T01604 | 38.0 kDa; dCREB2-a |
| 525. | T00004 | 38.1 kDa; Sc |
| 526. | T01407 | 38.1 kDa; NRF-2gamma1 |
| 527. | T01757 | 38.4 kDa; HOXD10 |
| 528. | T02087 | 38.4 kDa; Pbx-1b |
| 529. | T02088 | 38.4 kDa; Pbx-1b |
| 530. | T00797 | 38.5 kDa; TBP |
| 531. | T01303 | 38.5 kDa; CREB-2 |
| 532. | T01425 | 38.5 kDa; HOXD10 |
| 533. | T02098 | 38.5 kDa; TTF-1 |
| 534. | T00652 | 38.6 kDa; Oct-4A |
| 535. | T00746 | 38.6 kDa; SGF-3 |
| 536. | T00856 | 38.6 kDa; TTF-1 |
| 537. | T00857 | 38.6 kDa; TTF-1 |
| 538. | T01012 | 38.6 kDa; xMEF-2 |
| 539. | T01629 | 38.6 kDa; MATH-2 |
| 540. | T01432 | 38.7 kDa; c-Maf |
| 541. | T01957 | 38.7 kDa; Isl-1 |
| 542. | T00744 | 38.8 kDa; SGF-1 |
| 543. | T01079 | 38.8 kDa; GBF2 |
| 544. | T01430 | 38.9 kDa; v-Maf |
| 545. | T01431 | 38.9 kDa; c-Maf (long form) |
| 546. | T00125 | 39.0 kDa; c-Fos |
| 547. | T00268 | 39.0 kDa; GABP |
| 548. | T00304 | 39.0 kDa; GATA-1A |
| 549. | T01017 | 39.0 kDa; CRE-BP2 |
| 550. | T01035 | 39.0 kDa; Isl-1 |
| 551. | T01956 | 39.0 kDa; Isl-1 |
| 552. | T02186 | 39.0 kDa; TFIIH-MO15 |
| 553. | T00819 | 39.1 kDa; TFIIB |
| 554. | T02161 | 39.1 kDa; TFIIB |
| 555. | T01653 | 39.2 kDa; Delilah |
| 556. | T00917 | 39.3 kDa; Zen-1 |
| 557. | T01491 | 39.3 kDa; IRF-2 |
| 558. | T02301 | 39.3 kDa; CTF-7 |
| 559. | T02319 | 39.3 kDa; PEBP2alphaA/til-1(U) |
| 560. | T00080 | 39.4 kDa; CBF1 |
| 561. | T01884 | 39.4 kDa; Brn-4 |
| 562. | T01885 | 39.4 kDa; Brn-4 |
| 563. | T01886 | 39.4 kDa; Brn-4 |
| 564. | T00425 | 39.5 kDa; IRF-2 |
| 565. | T00732 | 39.5 kDa; Ro |
| 566. | T01625 | 39.7 kDa; NeuroD |
| 567. | T02295 | 39.7 kDa; TFIIIA |
| 568. | T02062 | 39.8 kDa; KN1 |
| 569. | T02312 | 39.8 kDa; GATA-1B |
| 570. | T01898 | 39.9 kDa; I-POU |
| 571. | T00154 | 40.0 kDa; CP1A |
| 572. | T00200 | 40.0 kDa; DTF |
| 573. | T00272 | 40.0 kDa; Eve |
| 574. | T00399 | 40.0 kDa; IBF |
| 575. | T00416 | 40.0 kDa; IkappaB-beta |
| 576. | T00466 | 40.0 kDa; LF-A1 |
| 577. | T00700 | 40.0 kDa; PTF |
| 578. | T00708 | 40.0 kDa; p40x |
| 579. | T00863 | 40.0 kDa; Ubx |
| 580. | T00868 | 40.0 kDa; URSF |
| 581. | T01106 | 40.0 kDa; EBP40 |
| 582. | T01626 | 40.0 kDa; NeuroD |
| 583. | T01674 | 40.0 kDa; BETA3 |
| 584. | T02015 | 40.0 kDa; En-1 |
| 585. | T01899 | 40.2 kDa; tI-POU |
| 586. | T02032 | 40.2 kDa; HSF30 |
| 587. | T02276 | 40.2 kDa; ATBP |
| 588. | T00782 | 40.3 kDa; TAF(II)55 |
| 589. | T01259 | 40.3 kDa; ARG RIII |
| 590. | T02063 | 40.3 kDa; Knox3 |
| 591. | T01288 | 40.6 kDa; PHD1 |
| 592. | T01979 | 40.6 kDa; TCF-1E |
| 593. | T00123 | 40.7 kDa; c-Fos |
| 594. | T01395 | 40.7 kDa; HBP-1a(c14) |
| 595. | T00122 | 40.8 kDa; c-Fos |
| 596. | T01400 | 40.8 kDa; Ets-1 deltaVII |
| 597. | T01698 | 40.8 kDa; HOXA2 |
| 598. | T01699 | 40.8 kDa; HOXA2 |
| 599. | T02205 | 40.8 kDa; c-Fos |
| 600. | T00124 | 40.9 kDa; c-Fos |
| 601. | T00083 | 41.0 kDa; CBF (2) |
| 602. | T00088 | 41.0 kDa; CBF-B |
| 603. | T00829 | 41.0 kDa; TGA1a |
| 604. | T00924 | 41.0 kDa; CIIIB1 |
| 605. | T01700 | 41.0 kDa; HOXA2 |
| 606. | T02016 | 41.0 kDa; En-1 |
| 607. | T01080 | 41.1 kDa; GBF3 |
| 608. | T00769 | 41.2 kDa; Sry-beta |
| 609. | T01391 | 41.3 kDa; GABP-beta1 |
| 610. | T01403 | 41.3 kDa; GABP-beta1 |
| 611. | T02241 | 41.3 kDa; PEBP2alphaB2 |
| 612. | T00265 | 41.4 kDa; Erg-1 |
| 613. | T01643 | 41.4 kDa; H |

TABLE 3-continued

Transcription Factors
TFFACTOR sorted by molecular weight (SZ field)
Database: TFFACTOR
TRANSFAC database, binding factor information
Release 3.3, January 1998
E. Wingender, R. Knueppel, P. Dietze, H. Karas (GBF-Braunschweig)
2,285 entries

| | | |
|---|---|---|
| 614. | T01715 | 41.4 kDa; HOXA10 |
| 615. | T02294 | 41.4 kDa; XFD-2 |
| 616. | T01440 | 41.6 kDa; NF-E2 p45 |
| 617. | T01441 | 41.6 kDa; NF-E2 p45 |
| 618. | T01452 | 41.6 kDa; v-Fos |
| 619. | T01843 | 41.6 kDa; Sox-18 |
| 620. | T02231 | 41.6 kDa; TFIIA-L |
| 621. | T01482 | 41.7 kDa; Exd |
| 622. | T01825 | 41.7 kDa; Pax-8b |
| 623. | T01286 | 41.8 kDa; Rox1 |
| 624. | T02052 | 41.8 kDa; CREB-2 |
| 625. | T02229 | 41.8 kDa; TFIIA-L |
| 626. | T01373 | 42.0 kDa; CBTF |
| 627. | T01822 | 42.0 kDa; Pax-2b |
| 628. | T01968 | 42.0 kDa; LH-2 |
| 629. | T02024 | 42.0 kDa; Evx-1 |
| 630. | T00070 | 42.1 kDa; Pax-5 |
| 631. | T01692 | 42.1 kDa; T3R-beta1 |
| 632. | T01201 | 42.2 kDa; Pax-5 |
| 633. | T01382 | 42.3 kDa; CRE-BP2 |
| 634. | T01823 | 42.3 kDa; Pax-2 |
| 635. | T02298 | 42.3 kDa; NF-1A3 |
| 636. | T02021 | 42.4 kDa; Evx-1 |
| 637. | T01406 | 42.5 kDa; NRF-2beta1 |
| 638. | T02103 | 42.5 kDa; p53as |
| 639. | T00243 | 42.6 kDa; EGR3 |
| 640. | T00305 | 42.6 kDa; GATA-1 |
| 641. | T01550 | 42.7 kDa; dDP |
| 642. | T00026 | 42.8 kDa; Antp |
| 643. | T00306 | 42.8 kDa; GATA-1 |
| 644. | T01877 | 42.8 kDa; Brn-3a(l) |
| 645. | T01958 | 42.8 kDa; Lmx-1 |
| 646. | T02252 | 42.8 kDa; Ldb1 |
| 647. | T02097 | 42.9 kDa; STM |
| 648. | T00135 | 43.0 kDa; c-Jun |
| 649. | T00242 | 43.0 kDa; EGR2 |
| 650. | T00414 | 43.0 kDa; IkappaB-beta |
| 651. | T00446 | 43.0 kDa; 43K protein |
| 652. | T01096 | 43.0 kDa; GHF3 |
| 653. | T01380 | 43.0 kDa; CREB |
| 654. | T01680 | 43.0 kDa; PTFgamma |
| 655. | T01827 | 43.0 kDa; Pax-8d |
| 656. | T01832 | 43.1 kDa; v-Qin |
| 657. | T01842 | 43.1 kDa; WT1 I-del2 |
| 658. | T01429 | 43.2 kDa; Sox-5 |
| 659. | T02023 | 43.2 kDa; Evx-1 |
| 660. | T01722 | 43.5 kDa; HOXB3 |
| 661. | T01806 | 43.5 kDa; p53 |
| 662. | T01896 | 43.5 kDa; t-Pou2 |
| 663. | T01866 | 43.6 kDa; Oct-2.4 |
| 664. | T00671 | 43.7 kDa; p53 |
| 665. | T01456 | 43.7 kDa; ISGF-3gamma |
| 666. | T01590 | 43.8 kDa; P (long form) |
| 667. | T01965 | 43.8 kDa; Lim-3 |
| 668. | T02253 | 43.8 kDa; Ch-runtB2 |
| 669. | T01874 | 43.9 kDa; Oct-11 |
| 670. | T00877 | 44.0 kDa; USF |
| 671. | T00878 | 44.0 kDa; USF2 |
| 672. | T01091 | 44.0 kDa; CPRF-1 |
| 673. | T01546 | 44.0 kDa; E2F-4 |
| 674. | T01942 | 44.0 kDa; IkappaB-gamma2 |
| 675. | T01963 | 44.0 kDa; Lim-3 |
| 676. | T01964 | 44.0 kDa; Lim-3 |
| 677. | T02115 | 44.0 kDa; USF2 |
| 678. | T00930 | 44.1 kDa; LEF-1 |
| 679. | T00802 | 44.2 kDa; TCF-1alpha |
| 680. | T01723 | 44.3 kDa; HOXB3 |
| 681. | T01414 | 44.4 kDa; Net |
| 682. | T01724 | 44.4 kDa; HOXB3 |
| 683. | T02185 | 44.4 kDa; TFIIH-p44 |
| 684. | T01051 | 44.5 kDa; XFD-1 |
| 685. | T01413 | 44.5 kDa; Net |
| 686. | T01830 | 44.5 kDa; XFD-1' |
| 687. | T01960 | 44.5 kDa; Lim-1 |
| 688. | T00278 | 44.6 kDa; delta factor |
| 689. | T00162 | 44.7 kDa; CreA |
| 690. | T00865 | 44.7 kDa; UCRBP |
| 691. | T01841 | 44.7 kDa; WT1-del2 |
| 692. | T02128 | 44.7 kDa; SAP-1b |
| 693. | T00678 | 44.8 kDa; Pax-2a |
| 694. | T00915 | 44.8 kDa; YY1 |
| 695. | T00955 | 44.8 kDa; DSXF |
| 696. | T01541 | 44.8 kDa; Esc1 |
| 697. | T01954 | 44.8 kDa; vHNF-1C |
| 698. | T01959 | 44.8 kDa; Lim-1 |
| 699. | T01961 | 44.8 kDa; Lim-1 |
| 700. | T00250 | 44.9 kDa; Elk-1 |
| 701. | T01962 | 44.9 kDa; Lim-1 |
| 702. | T00051 | 45.0 kDa; ATF |
| 703. | T00069 | 45.0 kDa; BrlA |
| 704. | T00215 | 45.0 kDa; muEBP-C2 |
| 705. | T00527 | 45.0 kDa; MyoD |
| 706. | T00563 | 45.0 kDa; NF-muE3 |
| 707. | T00834 | 45.0 kDa; TIN-1 |
| 708. | T00995 | 45.0 kDa; DBSF |
| 709. | T01052 | 45.0 kDa; XFD-1+ |
| 710. | T01107 | 45.0 kDa; EBP45 |
| 711. | T01215 | 45.0 kDa; NF-muE3 |
| 712. | T01353 | 45.0 kDa; PPARbeta |
| 713. | T01365 | 45.0 kDa; p45 |
| 714. | T02096 | 45.0 kDa; Scr |
| 715. | T01548 | 45.1 kDa; DP-1 |
| 716. | T01549 | 45.1 kDa; DP-1 |
| 717. | T01834 | 45.1 kDa; Axial |
| 718. | T01838 | 45.2 kDa; Sox-4 |
| 719. | T01850 | 45.2 kDa; DSP1 |
| 720. | T02193 | 45.2 kDa; TFIIH-CCL1 |
| 721. | T00656 | 45.3 kDa; Oct-6 |
| 722. | T00178 | 45.4 kDa; CTF-3 |
| 723. | T00969 | 45.5 kDa; Oct-6 |
| 724. | T01820 | 45.5 kDa; Gsb |
| 725. | T02288 | 45.5 kDa; HFH-1 |
| 726. | T00445 | 45.6 kDa; Kni |
| 727. | T01867 | 45.7 kDa; Oct-2.6 |
| 728. | T01075 | 45.8 kDa; lin-11 |
| 729. | T01239 | 45.8 kDa; CAD1 |
| 730. | T01921 | 45.9 kDa; Gfi-1 |
| 731. | T00141 | 46.0 kDa; c-Myc |
| 732. | T00786 | 46.0 kDa; TAF-II |
| 733. | T00836 | 46.0 kDa; T3R |
| 734. | T00837 | 46.0 kDa; T3R |
| 735. | T00838 | 46.0 kDa; T3R |
| 736. | T00839 | 46.0 kDa; T3R |
| 737. | T00840 | 46.0 kDa; T3R |
| 738. | T00854 | 46.0 kDa; T3R |
| 739. | T01385 | 46.0 kDa; CREB |
| 740. | T00763 | 46.1 kDa; SRF |
| 741. | T00149 | 46.2 kDa; COUP |
| 742. | T01543 | 46.3 kDa; E2F-1 |
| 743. | T01915 | 46.3 kDa; NF-1X1 |
| 744. | T01409 | 46.4 kDa; p38erg |
| 745. | T01265 | 46.5 kDa; MAC1 |
| 746. | T01647 | 46.5 kDa; Dpn |
| 747. | T02279 | 46.5 kDa; ZNF174 |
| 748. | T01122 | 46.6 kDa; Pax-6 |
| 749. | T01481 | 46.6 kDa; Pbx-1a |
| 750. | T02176 | 46.6 kDa; TFIIF-beta |
| 751. | T00681 | 46.7 kDa; Pax-6 |
| 752. | T01967 | 46.7 kDa; LH-2 |
| 753. | T00737 | 46.8 kDa; SAP-1a |
| 754. | T00841 | 46.8 kDa; T3R-alpha |
| 755. | T01152 | 46.8 kDa; T3R-alpha1 |
| 756. | T01173 | 46.8 kDa; T3R-alpha |
| 757. | T01342 | 46.8 kDa; T3R-alpha1 |

TABLE 3-continued

Transcription Factors
TFFACTOR sorted by molecular weight (SZ field)
Database: TFFACTOR
TRANSFAC database, binding factor information
Release 3.3, January 1998
E. Wingender, R. Knueppel, P. Dietze, H. Karas (GBF-Braunschweig)
2,285 entries

| # | ID | MW; Name |
|---|---|---|
| 758. | T01351 | 46.8 kDa; T3R-alpha |
| 759. | T01554 | 46.8 kDa; Mi |
| 760. | T01683 | 46.8 kDa; PTFbeta |
| 761. | T01928 | 46.8 kDa; Bcl-3 |
| 762. | T00295 | 46.9 kDa; Ftz |
| 763. | T00630 | 46.9 kDa; N-Oct-3 |
| 764. | T01542 | 46.9 kDa; E2F-1 |
| 765. | T01553 | 46.9 kDa; Mi |
| 766. | T01903 | 46.9 kDa; NF-1X |
| 767. | T00029 | 47.0 kDa; AP-1 |
| 768. | T00045 | 47.0 kDa; ARP-1 |
| 769. | T00388 | 47.0 kDa; H1TF2 |
| 770. | T00442 | 47.0 kDa; 47-kDa CRE bind. prot. |
| 771. | T00539 | 47.0 kDa; NF-1 |
| 772. | T01690 | 47.1 kDa; Elt-2 |
| 773. | T01873 | 47.1 kDa; N-Oct-3 |
| 774. | T00900 | 47.2 kDa; WT1 I-KTS |
| 775. | T01524 | 47.2 kDa; N-Oct-3 |
| 776. | T01276 | 47.3 kDa; Sox-4 |
| 777. | T02321 | 47.3 kDa; SRE-ZBP |
| 778. | T00552 | 47.4 kDa; NF-1B2 |
| 779. | T01526 | 47.4 kDa; Brachyury |
| 780. | T01966 | 47.4 kDa; LH-2 |
| 781. | T01544 | 47.5 kDa; E2F-2 |
| 782. | T01840 | 47.5 kDa; WT1 I |
| 783. | T02236 | 47.6 kDa; TFIIE |
| 784. | T02237 | 47.6 kDa; TFIIE-alpha |
| 785. | T02300 | 47.6 kDa; CTF-5 |
| 786. | T00882 | 47.8 kDa; VDR |
| 787. | T01774 | 47.8 kDa; APETALA2 |
| 788. | T00177 | 47.9 kDa; CTF-2 |
| 789. | T00806 | 47.9 kDa; TEF-1 |
| 790. | T01124 | 47.9 kDa; TEF-1 |
| 791. | T01768 | 47.9 kDa; MEF-2C/delta32 |
| 792. | T00310 | 48.0 kDa; GATA-3 |
| 793. | T00439 | 48.0 kDa; KBF1 |
| 794. | T00568 | 48.0 kDa; NF-E1c |
| 795. | T01213 | 48.0 kDa; KBF1 |
| 796. | T02156 | 48.0 kDa; Esc |
| 797. | T02157 | 48.0 kDa; TFIIA |
| 798. | T00035 | 48.1 kDa; AP-2 |
| 799. | T01824 | 48.1 kDa; Pax-8a |
| 800. | T00402 | 48.2 kDa; ICSBP |
| 801. | T01468 | 48.2 kDa; ZID |
| 802. | T01469 | 48.2 kDa; Ik-1 |
| 803. | T01814 | 48.2 kDa; Pax-6/Pd-5a |
| 804. | T01821 | 48.2 kDa; Gsbn |
| 805. | T00885 | 48.3 kDa; VDR |
| 806. | T01916 | 48.3 kDa; NF-1X2 |
| 807. | T02036 | 48.3 kDa; CRE-BP3 |
| 808. | T02038 | 48.3 kDa; ICSBP |
| 809. | T00682 | 48.4 kDa; Pax[zf-a] |
| 810. | T00716 | 48.5 kDa; RAR |
| 811. | T01049 | 48.5 kDa; HNF-3B |
| 812. | T00490 | 48.6 kDa; MAZ |
| 813. | T02235 | 48.6 kDa; PEBP2alphaB1 |
| 814. | T02245 | 48.7 kDa; AML1b |
| 815. | T00140 | 48.8 kDa; c-Myc |
| 816. | T00371 | 48.8 kDa; HNF-3 |
| 817. | T00610 | 48.8 kDa; NF-1X |
| 818. | T02303 | 48.8 kDa; Pur-1 |
| 819. | T00142 | 48.9 kDa; c-Myc |
| 820. | T01828 | 48.9 kDa; Pax-8 |
| 821. | T01833 | 48.9 kDa; c-Qin |
| 822. | T01839 | 48.9 kDa; WT1-KTS |
| 823. | T02056 | 48.9 kDa; CRE-BP1 |
| 824. | T00106 | 49.0 kDa; C/EBP |
| 825. | T00143 | 49.0 kDa; c-Myc |
| 826. | T01599 | 49.0 kDa; LCR-F1 |
| 827. | T02165 | 49.0 kDa; TFIIE-alpha |
| 828. | T01545 | 49.1 kDa; E2F-3 |
| 829. | T01869 | 49.1 kDa; Oct-2.8 |
| 830. | T01930 | 49.1 kDa; NF-kappaB2 (p49) |
| 831. | T02306 | 49.1 kDa; GCMa |
| 832. | T00554 | 49.2 kDa; NF-1C2 |
| 833. | T02037 | 49.3 kDa; ICSBP |
| 834. | T01819 | 49.4 kDa; Pax-6 |
| 835. | T01870 | 49.4 kDa; Oct-2.1 |
| 836. | T00646 | 49.5 kDa; Oct-2.1 |
| 837. | T00996 | 49.5 kDa; SRY |
| 838. | T01041 | 49.5 kDa; HSF |
| 839. | T01445 | 49.5 kDa; N-Myc |
| 840. | T01864 | 49.5 kDa; Oct-2.1 |
| 841. | T02162 | 49.5 kDa; TFIIE-alpha |
| 842. | T00053 | 49.6 kDa; ATF-adelta |
| 843. | T00767 | 49.7 kDa; Sry-delta |
| 844. | T00952 | 49.7 kDa; AP-2 |
| 845. | T02030 | 49.7 kDa; Sd |
| 846. | T02307 | 49.7 kDa; GCMa |
| 847. | T01341 | 49.8 kDa; RAR-gamma2 |
| 848. | T00718 | 49.9 kDa; RAR |
| 849. | T00033 | 50.0 kDa; AP-2 |
| 850. | T00034 | 50.0 kDa; AP-2 |
| 851. | T00037 | 50.0 kDa; AP-5 |
| 852. | T00201 | 50.0 kDa; DTF-1 |
| 853. | T00222 | 50.0 kDa; E4F |
| 854. | T00380 | 50.0 kDa; H2RIIBP |
| 855. | T00434 | 50.0 kDa; IUF-1 |
| 856. | T00435 | 50.0 kDa; JRF |
| 857. | T00479 | 50.0 kDa; LyF-1 |
| 858. | T00567 | 50.0 kDa; NF-E1b |
| 859. | T00719 | 50.0 kDa; RAR-alpha1 |
| 860. | T00733 | 50.0 kDa; RPF1 |
| 861. | T01465 | 50.0 kDa; TRF (2) |
| 862. | T01923 | 50.0 kDa; NF-kappaB1 |
| 863. | T00668 | 50.1 kDa; Opaque-2 |
| 864. | T02053 | 50.1 kDa; HB24 |
| 865. | T01260 | 50.2 kDa; STD1 |
| 866. | T00111 | 50.3 kDa; c-Ets-1 |
| 867. | T00721 | 50.3 kDa; RAR-beta |
| 868. | T01326 | 50.3 kDa; RAR-beta2 |
| 869. | T01330 | 50.3 kDa; RAR-gamma1 |
| 870. | T01338 | 50.3 kDa; RAR-beta2 |
| 871. | T01766 | 50.3 kDa; MEF-2C (465 AA form) |
| 872. | T02040 | 50.3 kDa; c-Ets-1A |
| 873. | T00112 | 50.4 kDa; c-Ets-1 |
| 874. | T00114 | 50.4 kDa; c-Ets-1 54 |
| 875. | T01769 | 50.4 kDa; MEF-2C |
| 876. | T01689 | 50.5 kDa; Staf-50 |
| 877. | T02292 | 50.5 kDa; BF-2 |
| 878. | T00372 | 50.6 kDa; HNF-4 |
| 879. | T01056 | 50.6 kDa; slp2 |
| 880. | T01337 | 50.6 kDa; RAR-beta1 |
| 881. | T02144 | 50.6 kDa; ADA2 |
| 882. | T01335 | 50.7 kDa; RAR-alpha1 |
| 883. | T01253 | 50.8 kDa; PUB1 |
| 884. | T01340 | 50.8 kDa; RAR-gamma1 |
| 885. | T01345 | 50.8 kDa; RXR-alpha |
| 886. | T02029 | 50.8 kDa; C/EBP |
| 887. | T02051 | 50.8 kDa; HB24 |
| 888. | T01333 | 50.9 kDa; RXR-gamma |
| 889. | T01336 | 50.9 kDa; RAR-alpha2 |
| 890. | T00396 | 51.0 kDa; Pax-7 |
| 891. | T00593 | 51.0 kDa; NF-kappaB1 |
| 892. | T01267 | 51.0 kDa; GAL80 |
| 893. | T01390 | 51.0 kDa; GABP-alpha |
| 894. | T01408 | 51.0 kDa; Fli-1 |
| 895. | T01906 | 51.0 kDa; NF-1A5 |
| 896. | T02066 | 51.0 kDa; Fli-1 |
| 897. | T02067 | 51.0 kDa; Fli-1 |
| 898. | T00647 | 51.1 kDa; Oct-2 |
| 899. | T01815 | 51.1 kDa; Vab-3 |
| 900. | T02305 | 51.1 kDa; MAZi |
| 901. | T00650 | 51.2 kDa; Oct-2 |

TABLE 3-continued

Transcription Factors
TFFACTOR sorted by molecular weight (SZ field)
Database: TFFACTOR
TRANSFAC database, binding factor information
Release 3.3, January 1998
E. Wingender, R. Knueppel, P. Dietze, H. Karas (GBF-Braunschweig)
2,285 entries

| # | ID | Value |
|---|---|---|
| 902. | T01331 | 51.2 kDa; RXR-alpha |
| 903. | T01663 | 51.2 kDa; TR2-9 |
| 904. | T02283 | 51.2 kDa; Kox1 |
| 905. | T00079 | 51.3 kDa; Cad |
| 906. | T00251 | 51.3 kDa; ELP |
| 907. | T00648 | 51.3 kDa; Oct-2 |
| 908. | T01402 | 51.4 kDa; GABP-alpha |
| 909. | T01428 | 51.4 kDa; E4BP4 |
| 910. | T01572 | 51.4 kDa; LSIRF-2 |
| 911. | T01831 | 51.5 kDa; BF-1 |
| 912. | T01895 | 51.5 kDa; Pou2 |
| 913. | T02145 | 51.5 kDa; GCN5 |
| 914. | T00764 | 51.6 kDa; SRF |
| 915. | T01412 | 51.6 kDa; NF-EM5 |
| 916. | T01865 | 51.8 kDa; Oct-2.3 |
| 917. | T02246 | 51.8 kDa; AML1c |
| 918. | T01046 | 51.9 kDa; HSF3 |
| 919. | T00266 | 52.0 kDa; Erg-2 |
| 920. | T00394 | 52.0 kDa; NF-kappaB2 |
| 921. | T00785 | 52.0 kDa; TAF-I |
| 922. | T00899 | 52.0 kDa; WT1 |
| 923. | T01074 | 52.1 kDa; Ap |
| 924. | T00851 | 52.2 kDa; T3R-beta |
| 925. | T01882 | 52.3 kDa; Unc-86 |
| 926. | T02191 | 52.3 kDa; TFIIH-p50 |
| 927. | T00694 | 52.4 kDa; PPAR |
| 928. | T00991 | 52.4 kDa; PPAR |
| 929. | T01618 | 52.5 kDa; EBNA-2 |
| 930. | T00077 | 52.6 kDa; CACCC-binding factor |
| 931. | T00853 | 52.7 kDa; T3R-beta1 |
| 932. | T01943 | 52.7 kDa; IkappaBR |
| 933. | T02085 | 52.7 kDa; Elg |
| 934. | T02135 | 52.7 kDa; TAF(I)48 |
| 935. | T01397 | 52.8 kDa; c-Ets-2 |
| 936. | T01951 | 52.8 kDa; HNF-1C |
| 937. | T02297 | 52.8 kDa; NF-1A2 |
| 938. | T01352 | 52.9 kDa; PPARalpha |
| 939. | T01868 | 52.9 kDa; Oct-2.7 |
| 940. | T02104 | 52.9 kDa; HSF1 (short) |
| 941. | T00113 | 53.0 kDa; c-Ets-2 |
| 942. | T00679 | 53.0 kDa; Pax-3 |
| 943. | T00680 | 53.0 kDa; Pax-3 |
| 944. | T01357 | 53.0 kDa; RAR-gamma1 |
| 945. | T01417 | 53.0 kDa; tel |
| 946. | T01662 | 53.0 kDa; TR2 |
| 947. | T00006 | 53.2 kDa; Ase |
| 948. | T01010 | 53.2 kDa; RSRFC9 |
| 949. | T01066 | 53.3 kDa; runt |
| 950. | T01339 | 53.3 kDa; RAR-beta3 |
| 951. | T00120 | 53.5 kDa; CF2-II |
| 952. | T01009 | 53.6 kDa; RSRFC4 |
| 953. | T01044 | 53.6 kDa; HSF1 |
| 954. | T00505 | 53.7 kDa; MEF-2 |
| 955. | T01933 | 53.8 kDa; Cactus |
| 956. | T02008 | 53.8 kDa; Ems |
| 957. | T02129 | 53.8 kDa; p55erg |
| 958. | T02130 | 53.8 kDa; p49erg |
| 959. | T01200 | 53.9 kDa; Egr-1 |
| 960. | T02041 | 53.9 kDa; c-Ets-2A |
| 961. | T02127 | 53.9 kDa; c-Ets-2B |
| 962. | T00220 | 54.0 kDa; E2F |
| 963. | T00221 | 54.0 kDa; E2F |
| 964. | T00373 | 54.0 kDa; HNF-4 |
| 965. | T01354 | 54.1 kDa; PPARgamma |
| 966. | T01771 | 54.1 kDa; MEF-2D |
| 967. | T00894 | 54.3 kDa; Vmw65 |
| 968. | T01054 | 54.3 kDa; Fkh |
| 969. | T01772 | 54.3 kDa; D-MEF2 |
| 970. | T00599 | 54.4 kDa; NF-1/L |
| 971. | T01517 | 54.4 kDa; Twi |
| 972. | T01571 | 54.4 kDa; IRF-3 |
| 973. | T00063 | 54.5 kDa; Bcd |
| 974. | T00116 | 54.5 kDa; c-Ets-2 58-64 |
| 975. | T00167 | 54.5 kDa; CRE-BP1 |
| 976. | T02291 | 54.5 kDa; Croc |
| 977. | T01905 | 54.6 kDa; NF-1A4 |
| 978. | T01713 | 54.7 kDa; HOXA10 |
| 979. | T01917 | 54.7 kDa; NF-1X3 |
| 980. | T02239 | 54.7 kDa; TFIIE-alpha |
| 981. | T00301 | 54.8 kDa; GAGA factor |
| 982. | T01005 | 54.8 kDa; MEF-2 |
| 983. | T01153 | 54.8 kDa; T3R-alpha2 |
| 984. | T00384 | 54.9 kDa; HSF |
| 985. | T01525 | 54.9 kDa; HSF1 |
| 986. | T00115 | 55.0 kDa; c-Ets-1 68 |
| 987. | T00117 | 55.0 kDa; CF1 |
| 988. | T00314 | 55.0 kDa; GATA-3 |
| 989. | T01198 | 55.0 kDa; NRF-2 |
| 990. | T01199 | 55.0 kDa; NRF-2 |
| 991. | T01240 | 55.0 kDa; ABF1 |
| 992. | T01349 | 55.0 kDa; RXR-beta |
| 993. | T01362 | 55.0 kDa; Hp55 |
| 994. | T01476 | 55.0 kDa; Abd-B |
| 995. | T01343 | 55.1 kDa; T3R-alpha2 |
| 996. | T01910 | 55.1 kDa; NF-1B3 |
| 997. | T01918 | 55.1 kDa; NF-1C1 |
| 998. | T02281 | 55.1 kDa; AML3 |
| 999. | T01084 | 55.2 kDa; TEC1 |
| 1000. | T01875 | 55.4 kDa; Oct-2 |
| 1001. | T00175 | 55.5 kDa; CTF-1 |
| 1002. | T01901 | 55.5 kDa; PDM-2 |
| 1003. | T00176 | 55.6 kDa; CTF-1 |
| 1004. | T01616 | 55.7 kDa; RBP-Jkappa |
| 1005. | T01062 | 55.8 kDa; PEBP2alphaA1 |
| 1006. | T00897 | 55.9 kDa; v-Rel |
| 1007. | T01770 | 55.9 kDa; MEF-2D |
| 1008. | T00307 | 56.0 kDa; GATA-2 |
| 1009. | T00509 | 56.0 kDa; MIG1 |
| 1010. | T00692 | 56.0 kDa; PO-B |
| 1011. | T00993 | 56.0 kDa; hsp56 |
| 1012. | T01226 | 56.0 kDa; PO-B |
| 1013. | T01904 | 56.0 kDa; NF-1A1.1 |
| 1014. | T02296 | 56.0 kDa; NF-1A1 |
| 1015. | T01853 | 56.1 kDa; SOX-9 |
| 1016. | T02308 | 56.1 kDa; GCMb |
| 1017. | T01597 | 56.2 kDa; NF2d9 |
| 1018. | T02302 | 56.2 kDa; GCM |
| 1019. | T01907 | 56.3 kDa; NF-1C1 |
| 1020. | T01784 | 56.4 kDa; MEF-2 |
| 1021. | T01603 | 56.5 kDa; dCREB-A |
| 1022. | T00244 | 56.6 kDa; Egr-1 |
| 1023. | T01941 | 56.6 kDa; IkappaB-gamma1 |
| 1024. | T01308 | 56.8 kDa; CRE-BPa |
| 1025. | T01334 | 56.9 kDa; RXR-beta |
| 1026. | T00152 | 57.0 kDa; CP2 |
| 1027. | T00807 | 57.0 kDa; TEF-2 |
| 1028. | T00151 | 57.2 kDa; CP2 |
| 1029. | T01998 | 57.2 kDa; Cnc |
| 1030. | T01042 | 57.3 kDa; HSF1 (long) |
| 1031. | T01568 | 57.3 kDa; MYB.Ph3 |
| 1032. | T00956 | 57.4 kDa; DSXM |
| 1033. | T02318 | 57.4 kDa; PEBP2alphaA/til-1 |
| 1034. | T00544 | 57.5 kDa; NF-1A1 |
| 1035. | T01088 | 57.7 kDa; ILF |
| 1036. | T01273 | 57.9 kDa; TAF(II)60 |
| 1037. | T01950 | 57.9 kDa; HNF-1B |
| 1038. | T00058 | 58.0 kDa; BAP |
| 1039. | T00389 | 58.0 kDa; H2TF1 |
| 1040. | T00440 | 58.0 kDa; KBF2 |
| 1041. | T01364 | 58.0 kDa; p58 |
| 1042. | T02164 | 58.0 kDa; TFIIE |
| 1043. | T01350 | 58.1 kDa; T3R-beta2 |
| 1044. | T00972 | 58.2 kDa; HSF2 |
| 1045. | T02168 | 58.3 kDa; TFIIF-alpha |

TABLE 3-continued

Transcription Factors
TFFACTOR sorted by molecular weight (SZ field)
Database: TFFACTOR
TRANSFAC database, binding factor information
Release 3.3, January 1998
E. Wingender, R. Knueppel, P. Dietze, H. Karas (GBF-Braunschweig)
2,285 entries

| | | |
|---|---|---|
| 1046. | T01953 | 58.4 kDa; vHNF-1B |
| 1047. | T01617 | 58.5 kDa; RBP-Jkappa |
| 1048. | T01909 | 58.6 kDa; NF-1B2 |
| 1049. | T02171 | 58.7 kDa; TFIIF-alpha |
| 1050. | T02320 | 58.7 kDa; PEBP2alphaA/til-1 (Y) |
| 1051. | T00358 | 59.0 kDa; HEF-1T |
| 1052. | T00990 | 59.0 kDa; FKBP59 |
| 1053. | T01527 | 59.0 kDa; RORalpha1 |
| 1054. | T01897 | 59.0 kDa; Cf1a |
| 1055. | T01523 | 59.1 kDa; p65delta |
| 1056. | T01934 | 59.1 kDa; c-Rel |
| 1057. | T00253 | 59.4 kDa; En |
| 1058. | T01883 | 59.5 kDa; CEH-18 |
| 1059. | T00252 | 60.0 kDa; embryo DNA binding protein |
| 1060. | T00448 | 60.0 kDa; 60K protein |
| 1061. | T00553 | 60.0 kDa; NF-BA1 |
| 1062. | T00608 | 60.0 kDa; NF-W1 |
| 1063. | T00622 | 60.0 kDa; NHP-2 |
| 1064. | T00649 | 60.0 kDa; Oct-2 |
| 1065. | T00734 | 60.0 kDa; RVF |
| 1066. | T00735 | 60.0 kDa; RVF |
| 1067. | T00736 | 60.0 kDa; RVF |
| 1068. | T00812 | 60.0 kDa; TFEB |
| 1069. | T00884 | 60.0 kDa; VDR |
| 1070. | T00906 | 60.0 kDa; XPF-1 |
| 1071. | T01133 | 60.0 kDa; TTF-2 |
| 1072. | T01195 | 60.0 kDa; NHP-2 |
| 1073. | T01196 | 60.0 kDa; NHP-2 |
| 1074. | T01489 | 60.0 kDa; RBP60 |
| 1075. | T01490 | 60.0 kDa; RBP60 |
| 1076. | T02167 | 60.0 kDa; TFIIE |
| 1077. | T00594 | 60.2 kDa; RelA |
| 1078. | T00595 | 60.2 kDa; RelA |
| 1079. | T00964 | 60.2 kDa; Oct-2B |
| 1080. | T01043 | 60.3 kDa; HSF2 |
| 1081. | T01932 | 60.3 kDa; RelB |
| 1082. | T00676 | 60.6 kDa; Pap1+ |
| 1083. | T01614 | 60.6 kDa; Skn-1 |
| 1084. | T00684 | 60.8 kDa; PEA3 |
| 1085. | T00263 | 61.0 kDa; ER |
| 1086. | T02154 | 61.2 kDa; SRB10 |
| 1087. | T00891 | 61.3 kDa; vHNF-1A |
| 1088. | T00889 | 61.4 kDa; vHNF-1 |
| 1089. | T01955 | 61.5 kDa; vHNF-1 |
| 1090. | T00890 | 61.7 kDa; vHNF-1 |
| 1091. | T00918 | 61.8 kDa; Zeste |
| 1092. | T02282 | 61.8 kDa; Glass |
| 1093. | T00289 | 62.0 kDa; f-EBP |
| 1094. | T00351 | 62.0 kDa; HAP4 |
| 1095. | T00449 | 62.0 kDa; 62K protein |
| 1096. | T00604 | 62.0 kDa; NF-1/Red1 |
| 1097. | T00936 | 62.0 kDa; ENKTF-1 |
| 1098. | T01070 | 62.0 kDa; TREF2 |
| 1099. | T01399 | 62.0 kDa; TCF |
| 1100. | T01931 | 62.0 kDa; RelB |
| 1101. | T02183 | 62.0 kDa; TFIIH-p62 |
| 1102. | T01040 | 62.1 kDa; Olf-1 |
| 1103. | T01529 | 62.3 kDa; RORalpha3 |
| 1104. | T00329 | 62.5 kDa; Glass |
| 1105. | T00551 | 62.6 kDa; NF-1B1 |
| 1106. | T01045 | 62.8 kDa; HSF2 |
| 1107. | T01997 | 62.8 kDa; dFRA |
| 1108. | T00474 | 63.0 kDa; LSF |
| 1109. | T00803 | 63.0 kDa; TCF-2alpha |
| 1110. | T00862 | 63.0 kDa; UBP-1 |
| 1111. | T01246 | 63.0 kDa; TBF1 |
| 1112. | T01528 | 63.0 kDa; RORalpha2 |
| 1113. | T02134 | 63.0 kDa; TAF(I)63 |
| 1114. | T01894 | 63.1 kDa; pou[c] |
| 1115. | T00689 | 63.4 kDa; PHO2 |
| 1116. | T01256 | 63.6 kDa; HCM1 |
| 1117. | T02248 | 63.6 kDa; StuAp |
| 1118. | T00193 | 63.8 kDa; Dfd |
| 1119. | T00095 | 64.0 kDa; CCAAT-binding factor |
| 1120. | T00701 | 64.0 kDa; PTF1-beta |
| 1121. | T01185 | 64.0 kDa; CCAAT-binding factor |
| 1122. | T01186 | 64.0 kDa; CCAAT-binding factor |
| 1123. | T01227 | 64.0 kDa; PTF1 |
| 1124. | T01254 | 64.3 kDa; PAB1 |
| 1125. | T02124 | 64.3 kDa; TAF(II)60 |
| 1126. | T01112 | 64.4 kDa; EBF |
| 1127. | T02173 | 64.5 kDa; TFIIF-alpha |
| 1128. | T01940 | 64.8 kDa; IkappaB-gamma |
| 1129. | T00169 | 65.0 kDa; c-Rel |
| 1130. | T00262 | 65.0 kDa; ER |
| 1131. | T00392 | 65.0 kDa; H4TF-2 |
| 1132. | T00560 | 65.0 kDa; NF-E4 |
| 1133. | T00587 | 65.0 kDa; NF-kappaB |
| 1134. | T00588 | 65.0 kDa; NF-kappaB |
| 1135. | T00590 | 65.0 kDa; NF-kappaB |
| 1136. | T01363 | 65.0 kDa; Hp65 |
| 1137. | T02247 | 65.0 kDa; Staf |
| 1138. | T01900 | 65.2 kDa; PDM-1 |
| 1139. | T02266 | 65.2 kDa; PEBP2alphaA/Osf2 |
| 1140. | T01598 | 65.3 kDa; ECH |
| 1141. | T01672 | 65.3 kDa; RFX5 |
| 1142. | T00049 | 65.5 kDa; Prd |
| 1143. | T00049 | 66.0 kDa; ATF |
| 1144. | T00062 | 66.0 kDa; BGP1 |
| 1145. | T00156 | 66.0 kDa; alpha-CP2a, alpha-CP2b |
| 1146. | T01443 | 66.1 kDa; Nrf2 |
| 1147. | T00261 | 66.2 kDa; ER |
| 1148. | T00463 | 66.3 kDa; Lc |
| 1149. | T00674 | 66.4 kDa; E47 |
| 1150. | T00710 | 66.6 kDa; R |
| 1151. | T00264 | 66.7 kDa; ER |
| 1152. | T01154 | 66.8 kDa; c-Rel |
| 1153. | T01415 | 66.8 kDa; pointedP1 |
| 1154. | T01615 | 66.9 kDa; Su(H) |
| 1155. | T02204 | 66.9 kDa; Nrf2 |
| 1156. | T00258 | 67.0 kDa; ER |
| 1157. | T00259 | 67.0 kDa; ER |
| 1158. | T00672 | 67.0 kDa; p67 |
| 1159. | T00761 | 67.0 kDa; SRF |
| 1160. | T00762 | 67.0 kDa; SRF |
| 1161. | T00765 | 67.0 kDa; SRF |
| 1162. | T01244 | 67.0 kDa; HSF |
| 1163. | T02272 | 67.0 kDa; HEB1-p67 |
| 1164. | T01211 | 67.2 kDa; HNF-1 |
| 1165. | T00207 | 67.3 kDa; E47 |
| 1166. | T00368 | 67.3 kDa; HNF-1A |
| 1167. | T01664 | 67.3 kDa; TR2-11 |
| 1168. | T00204 | 67.4 kDa; E12 |
| 1169. | T01113 | 67.5 kDa; Elf-1 |
| 1170. | T00675 | 67.7 kDa; E12 |
| 1171. | T01849 | 67.9 kDa; Ixr1 |
| 1172. | T02287 | 67.9 kDa; phiAP3 |
| 1173. | T00203 | 68.0 kDa; E1 |
| 1174. | T00791 | 68.0 kDa; TAR factor |
| 1175. | T01245 | 68.0 kDa; Reb1p |
| 1176. | T01374 | 68.0 kDa; URF |
| 1177. | T02100 | 68.1 kDa; Zeste |
| 1178. | T02064 | 68.2 kDa; Lab |
| 1179. | T00168 | 68.5 kDa; c-Rel |
| 1180. | T01292 | 68.6 kDa; RIM1 |
| 1181. | T00843 | 69.0 kDa; Ttk 69K |
| 1182. | T01835 | 69.2 kDa; Whn |
| 1183. | T01952 | 69.2 kDa; HNF-1 |
| 1184. | T01258 | 69.7 kDa; MSN4 |
| 1185. | T02078 | 69.7 kDa; Otd |
| 1186. | T00068 | 70.0 kDa; BRF1 |
| 1187. | T00621 | 70.0 kDa; NHP-1 |
| 1188. | T01165 | 70.0 kDa; H16 |
| 1189. | T01193 | 70.0 kDa; NHP-1 |

TABLE 3-continued

Transcription Factors
TFFACTOR sorted by molecular weight (SZ field)
Database: TFFACTOR
TRANSFAC database, binding factor information
Release 3.3, January 1998
E. Wingender, R. Knueppel, P. Dietze, H. Karas (GBF-Braunschweig)
2,285 entries

| # | ID | MW; Name |
|---|---|---|
| 1190. | T01194 | 70.0 kDa; NHP-1 |
| 1191. | T01787 | 70.0 kDa; E12 |
| 1192. | T01306 | 70.2 kDa; SKO1 |
| 1193. | T01250 | 70.3 kDa; BUF2 |
| 1194. | T02310 | 70.3 kDa; MET4 |
| 1195. | T01793 | 70.4 kDa; GE1 |
| 1196. | T00433 | 71.2 kDa; ITF-2 |
| 1197. | T00138 | 71.5 kDa; c-Myb |
| 1198. | T02208 | 71.5 kDa; TAF(II)70-gamma |
| 1199. | T01660 | 71.8 kDa; PR A |
| 1200. | T00976 | 72.0 kDa; NFdeltaE3A |
| 1201. | T00028 | 72.5 kDa; AP-1 |
| 1202. | T00137 | 72.5 kDa; c-Myb |
| 1203. | T00139 | 72.5 kDa; c-Myb |
| 1204. | T00783 | 72.7 kDa; TAF(II)70-alpha |
| 1205. | T01497 | 72.9 kDa; ALF1A |
| 1206. | T01503 | 72.9 kDa; HEB |
| 1207. | T01679 | 72.9 kDa; PacC |
| 1208. | T01789 | 72.9 kDa; SCBPgamma |
| 1209. | T02190 | 72.9 kDa; TFIIH-p73 |
| 1210. | T00064 | 73.0 kDa; BmFTZ-F1 |
| 1211. | T00887 | 73.0 kDa; VETF |
| 1212. | T01863 | 73.0 kDa; Oct-1C |
| 1213. | T01087 | 73.3 kDa; Vp1 |
| 1214. | T01783 | 73.5 kDa; RLM1 |
| 1215. | T00750 | 73.6 kDa; Sim |
| 1216. | T01251 | 73.7 kDa; PCT1 |
| 1217. | T01994 | 73.7 kDa; CAUP |
| 1218. | T01034 | 73.9 kDa; Da |
| 1219. | T00219 | 74.0 kDa; E2F |
| 1220. | T00495 | 74.0 kDa; MBF-I |
| 1221. | T01594 | 74.7 kDa; v-Myb/v-Ets |
| 1222. | T00054 | 75.0 kDa; ATF-like |
| 1223. | T00136 | 75.0 kDa; c-Myb |
| 1224. | T00443 | 75.0 kDa; 75 kDa protein |
| 1225. | T00662 | 75.0 kDa; Oct-2B |
| 1226. | T01421 | 75.0 kDa; PTF1-alpha |
| 1227. | T01264 | 75.4 kDa; HST |
| 1228. | T01993 | 75.4 kDa; ARA |
| 1229. | T00196 | 75.5 kDa; Dl |
| 1230. | T01791 | 75.7 kDa; SCBPbeta |
| 1231. | T01496 | 75.8 kDa; ALF1B |
| 1232. | T01790 | 75.8 kDa; SCBPalpha |
| 1233. | T01289 | 75.9 kDa; STE12 |
| 1234. | T00855 | 76.0 kDa; TSAP |
| 1235. | T01031 | 76.0 kDa; Oct-1 |
| 1236. | T00641 | 76.5 kDa; Oct-1 |
| 1237. | T01669 | 76.5 kDa; RFX2 |
| 1238. | T01862 | 76.8 kDa; Oct-1B |
| 1239. | T00386 | 76.9 kDa; HSTF |
| 1240. | T01416 | 77.6 kDa; pointedP2 |
| 1241. | T01586 | 77.7 kDa; B-Myb |
| 1242. | T01257 | 77.8 kDa; MSN2 |
| 1243. | T01945 | 77.8 kDa; NF-ATc |
| 1244. | T02209 | 77.9 kDa; TAF(II)70-beta |
| 1245. | T00772 | 78.0 kDa; STE12 |
| 1246. | T02148 | 78.5 kDa; SRB4 |
| 1247. | T01396 | 78.6 kDa; yan |
| 1248. | T00065 | 78.8 kDa; B-Myb |
| 1249. | T02322 | 78.8 kDa; BCL-6 |
| 1250. | T00922 | 79.1 kDa; Zmhox1a |
| 1251. | T01587 | 79.1 kDa; B-Myb |
| 1252. | T00315 | 79.3 kDa; GBF |
| 1253. | T02122 | 79.3 kDa; TAF(II)80 |
| 1254. | T02146 | 79.3 kDa; ADA3 |
| 1255. | T01670 | 79.4 kDa; RFX3 |
| 1256. | T00644 | 79.5 kDa; Oct-1A |
| 1257. | T01097 | 79.5 kDa; GT-2 |
| 1258. | T01975 | 79.9 kDa; RREB-1 |
| 1259. | T00211 | 80.0 kDa; EBNA-1 |
| 1260. | T01161 | 80.0 kDa; EBP-80 |
| 1261. | T01667 | 80.0 kDa; RFX2 |
| 1262. | T01856 | 80.7 kDa; SSRP1 |
| 1263. | T00754 | 81.0 kDa; Sp1 |
| 1264. | T01003 | 81.1 kDa; SSRP1 |
| 1265. | T01442 | 81.5 kDa; Nrf1 |
| 1266. | T01920 | 81.5 kDa; GR beta |
| 1267. | T02203 | 81.5 kDa; Nrf1 |
| 1268. | T01848 | 81.7 kDa; Dm-SSRP1 |
| 1269. | T02278 | 81.7 kDa; SEM-4 |
| 1270. | T00056 | 82.0 kDa; BAF1 |
| 1271. | T00451 | 82.0 kDa; 77 + 82K protein |
| 1272. | T01069 | 82.0 kDa; TREF1 |
| 1273. | T02175 | 82.2 kDa; TFIIF-alpha |
| 1274. | T01661 | 82.4 kDa; PR A |
| 1275. | T00172 | 82.8 kDa; CTCF |
| 1276. | T02284 | 82.8 kDa; CTCF |
| 1277. | T00383 | 83.0 kDa; HSF |
| 1278. | T01573 | 83.0 kDa; STAT1beta |
| 1279. | T02315 | 83.1 kDa; Rc |
| 1280. | T01454 | 83.2 kDa; Hsp90 |
| 1281. | T01585 | 83.6 kDa; A-Myb |
| 1282. | T02285 | 83.7 kDa; CTCF |
| 1283. | T01794 | 84.0 kDa; INSAF |
| 1284. | T00426 | 85.0 kDa; alpha-IRP |
| 1285. | T00867 | 85.0 kDa; UHF-1 |
| 1286. | T01295 | 85.0 kDa; FTS |
| 1287. | T01796 | 85.0 kDa; Arnt (774 AA form) |
| 1288. | T01583 | 85.1 kDa; A-Myb |
| 1289. | T01845 | 85.2 kDa; Sox-LZ |
| 1290. | T01252 | 85.5 kDa; CDC10 |
| 1291. | T01584 | 85.5 kDa; A-Myb |
| 1292. | T02084 | 85.6 kDa; Pb |
| 1293. | T02219 | 85.6 kDa; Lz |
| 1294. | T00337 | 85.7 kDa; GR alpha |
| 1295. | T00698 | 85.7 kDa; PR |
| 1296. | T00931 | 85.8 kDa; AmdR |
| 1297. | T01576 | 85.9 kDa; STAT4 |
| 1298. | T00914 | 86.0 kDa; YPF1 |
| 1299. | T01582 | 86.0 kDa; A-Myb |
| 1300. | T00335 | 86.1 kDa; GR |
| 1301. | T01988 | 86.4 kDa; STAT |
| 1302. | T00002 | 86.6 kDa; ACE2 |
| 1303. | T01346 | 86.6 kDa; Arnt |
| 1304. | T00784 | 86.7 kDa; TAF(II)100 |
| 1305. | T01684 | 86.9 kDa; TEA1 |
| 1306. | T02182 | 86.9 kDa; TFIIH-p80 |
| 1307. | T01797 | 87.0 kDa; Arnt |
| 1308. | T00208 | 87.1 kDa; E74A |
| 1309. | T01575 | 87.2 kDa; STAT1 |
| 1310. | T01844 | 87.2 kDa; Sox-LZ |
| 1311. | T02177 | 87.2 kDa; SIII-p110 |
| 1312. | T02178 | 87.2 kDa; SIII-p110 |
| 1313. | T01492 | 87.3 kDa; STAT1alpha |
| 1314. | T01642 | 87.3 kDa; NUC-1 |
| 1315. | T01547 | 87.5 kDa; dE2F |
| 1316. | T00455 | 88.0 kDa; Krox-24 |
| 1317. | T00929 | 88.0 kDa; PRDI-BF1 |
| 1318. | T01574 | 88.0 kDa; STAT3 |
| 1319. | T01493 | 88.1 kDa; STAT3 |
| 1320. | T00844 | 88.2 kDa; Ttk 88K |
| 1321. | T00709 | 89.0 kDa; qa-1F |
| 1322. | T01085 | 89.2 kDa; abaA |
| 1323. | T02181 | 89.3 kDa; TFIIH-p90 |
| 1324. | T02189 | 89.8 kDa; TFIIH-p85 |
| 1325. | T00055 | 90.0 kDa; B'' |
| 1326. | T00369 | 90.0 kDa; HNF-1 |
| 1327. | T00387 | 90.0 kDa; H1TF1 |
| 1328. | T00638 | 90.0 kDa; NTF |
| 1329. | T00944 | 90.0 kDa; STAT5B |
| 1330. | T00992 | 90.0 kDa; Hsp90 |
| 1331. | T01272 | 90.0 kDa; TAF-90 |
| 1332. | T02243 | 90.0 kDa; TFIIF |
| 1333. | T01013 | 90.6 kDa; SWI6 |

TABLE 3-continued

Transcription Factors
TFFACTOR sorted by molecular weight (SZ field)
Database: TFFACTOR
TRANSFAC database, binding factor information
Release 3.3, January 1998
E. Wingender, R. Knueppel, P. Dietze, H. Karas (GBF-Braunschweig)
2,285 entries

| # | ID | Value |
|---|---|---|
| 1334. | T01579 | 90.8 kDa; STAT5A |
| 1335. | T01578 | 90.9 kDa; STAT5 |
| 1336. | T00320 | 91.0 kDa; GCF |
| 1337. | T01247 | 91.0 kDa; UME6 |
| 1338. | T01795 | 91.7 kDa; AhR |
| 1339. | T00725 | 92.1 kDa; REB1 |
| 1340. | T00715 | 92.5 kDa; RAP1 |
| 1341. | T01610 | 92.7 kDa; HIF-1alpha |
| 1342. | T00385 | 93.3 kDa; HSTF |
| 1343. | T01818 | 93.3 kDa; Ey |
| 1344. | T01581 | 93.7 kDa; STAT6 |
| 1345. | T00333 | 94.0 kDa; GR |
| 1346. | T01611 | 94.0 kDa; HIF-1beta |
| 1347. | T02271 | 94.0 kDa; HEB1-p94 |
| 1348. | T00940 | 94.1 kDa; GRF-1 |
| 1349. | T01580 | 94.1 kDa; STAT6 |
| 1350. | T00322 | 94.3 kDa; GCR1 |
| 1351. | T00957 | 94.3 kDa; OBP |
| 1352. | T00210 | 94.8 kDa; E74B |
| 1353. | T00018 | 95.0 kDa; AhR |
| 1354. | T00739 | 95.0 kDa; SBF-1 |
| 1355. | T00759 | 95.0 kDa; Sp1 |
| 1356. | T01230 | 95.0 kDa; Vav |
| 1357. | T02133 | 95.3 kDa; TAF(I)110 |
| 1358. | T02192 | 95.3 kDa; TFIIH-SSL2/RAD25 |
| 1359. | T00768 | 95.4 kDa; Sry h-1 |
| 1360. | T02316 | 95.8 kDa; Blimp-1 |
| 1361. | T00453 | 96.0 kDa; 96K-protein |
| 1362. | T00019 | 96.2 kDa; AhR |
| 1363. | T00458 | 97.0 kDa; LAC9 |
| 1364. | T00779 | 97.0 kDa; TAF(II)125 |
| 1365. | T01494 | 97.9 kDa; STAT2 |
| 1366. | T00041 | 98.2 kDa; AR |
| 1367. | T00042 | 98.2 kDa; AR |
| 1368. | T00880 | 98.4 kDa; Vav |
| 1369. | T01562 | 98.5 kDa; ADD1 |
| 1370. | T00697 | 98.7 kDa; PR |
| 1371. | T00040 | 99.0 kDa; AR |
| 1372. | T00302 | 99.0 kDa; GAL4 |
| 1373. | T00696 | 99.0 kDa; PR |
| 1374. | T02121 | 99.3 kDa; TAF(II)110 |
| 1375. | T01929 | 99.7 kDa; NF-kappaB2 precursor |
| 1376. | T00194 | 100.0 kDa; dioxin receptor |
| 1377. | T00642 | 100.0 kDa; Oct-1 |
| 1378. | T00788 | 100.0 kDa; T-Ag |
| 1379. | T01305 | 100.0 kDa; CBP100 |
| 1380. | T01927 | 100.6 kDa; NF-kappaB2 precursor |
| 1381. | T01499 | 102.0 kDa; IL-6 RE-BP |
| 1382. | T01666 | 103.7 kDa; RFX1 |
| 1383. | T01673 | 104.7 kDa; RFX1 |
| 1384. | T01109 | 105.0 kDa; TCF-1 |
| 1385. | T01925 | 105.4 kDa; NF-kappaB1 precursor |
| 1386. | T01924 | 105.6 kDa; NF-kappaB1 precursor |
| 1387. | T01486 | 106.1 kDa; p107 |
| 1388. | T00805 | 106.2 kDa; Tsh |
| 1389. | T00774 | 106.3 kDa; su(Hw) |
| 1390. | T00511 | 106.6 kDa; MR |
| 1391. | T00513 | 106.9 kDa; MR |
| 1392. | T00970 | 108.0 kDa; MEP-1 |
| 1393. | T00161 | 110.0 kDa; CPE binding protein |
| 1394. | T00296 | 110.0 kDa; FTZ-F1 |
| 1395. | T00391 | 110.0 kDa; H4TF-1 |
| 1396. | T00420 | 110.0 kDa; IRBP |
| 1397. | T01271 | 110.0 kDa; TAF(II)110 |
| 1398. | T00669 | 110.6 kDa; Ovo |
| 1399. | T01558 | 111.1 kDa; SREBP-1c |
| 1400. | T01163 | 111.4 kDa; PUT3 |
| 1401. | T02143 | 112.8 kDa; TIF1 |
| 1402. | T00428 | 113.0 kDa; ISGF-3 |
| 1403. | T01243 | 113.0 kDa; TSF3 |
| 1404. | T01455 | 113.0 kDa; ISGF-3alpha |
| 1405. | T02034 | 113.4 kDa; SWI4 |
| 1406. | T01557 | 113.5 kDa; SREBP-1b |
| 1407. | T00086 | 114.1 kDa; CBF (5) |
| 1408. | T02314 | 114.2 kDa; BZP |
| 1409. | T00502 | 115.0 kDa; MEB-1 |
| 1410. | T00503 | 115.0 kDa; MEB-1 |
| 1411. | T01946 | 115.6 kDa; NF-ATx |
| 1412. | T01019 | 116.0 kDa; Elf-1 |
| 1413. | T02244 | 116.0 kDa; TFIIF |
| 1414. | T02215 | 116.7 kDa; TIF1 (1051 AA form) |
| 1415. | T00273 | 117.0 kDa; Evi-1 |
| 1416. | T00919 | 117.4 kDa; Zfh-1 |
| 1417. | T00330 | 118.0 kDa; GLI |
| 1418. | T00270 | 120.0 kDa; ETF |
| 1419. | T01379 | 120.0 kDa; 120-kDa CRE-binding protein |
| 1420. | T01944 | 120.0 kDa; NF-ATp |
| 1421. | T01948 | 120.0 kDa; NF-ATp |
| 1422. | T01559 | 120.5 kDa; SREBP-2 |
| 1423. | T01270 | 120.7 kDa; TAF(II)145 |
| 1424. | T01556 | 121.6 kDa; SREBP-1a |
| 1425. | T00842 | 122.8 kDa; Tra-1 (long form) |
| 1426. | T01467 | 123.1 kDa; deltaEF1 |
| 1427. | T01694 | 123.1 kDa; NF-X1 |
| 1428. | T00835 | 123.2 kDa; TMF |
| 1429. | T01688 | 123.3 kDa; STC |
| 1430. | T01560 | 123.7 kDa; SREBP-2 |
| 1431. | T01561 | 123.7 kDa; SREBP-2 |
| 1432. | T00775 | 123.8 kDa; SWI4 |
| 1433. | T00625 | 124.1 kDa; AREB6 |
| 1434. | T01608 | 128.4 kDa; p130 |
| 1435. | T00879 | 130.0 kDa; vaccinia virus DNA-binding protein |
| 1436. | T01367 | 133.0 kDa; E75A |
| 1437. | T02120 | 138.5 kDa; TAF(II)150 |
| 1438. | T01077 | 140.0 kDa; c-abl |
| 1439. | T02152 | 143.8 kDa; SRB8 |
| 1440. | T02042 | 144.3 kDa; Cux |
| 1441. | T00778 | 147.0 kDa; TAF |
| 1442. | T00382 | 150.0 kDa; HSE-binding protein |
| 1443. | T00011 | 151.0 kDa; ADR1 |
| 1444. | T01368 | 152.0 kDa; E75B |
| 1445. | T02153 | 160.0 kDa; SRB9 |
| 1446. | T01269 | 161.5 kDa; TAF(II)150 |
| 1447. | T02286 | 162.2 kDa; MTB-Zf |
| 1448. | T00346 | 164.0 kDa; HAP1 |
| 1449. | T00100 | 164.4 kDa; CDP |
| 1450. | T00401 | 170.0 kDa; ICP4 |
| 1451. | T01268 | 170.0 kDa; TAF(II)170 |
| 1452. | T00331 | 172.0 kDa; GLI3 |
| 1453. | T00366 | 180.0 kDa; HIP1 |
| 1454. | T01377 | 180.0 kDa; E2F-BF |
| 1455. | T01682 | 180.0 kDa; PTFalpha |
| 1456. | T01261 | 180.8 kDa; brahma |
| 1457. | T02207 | 189.4 kDa; TAF(II)250Delta |
| 1458. | T01949 | 190.0 kDa; NF-ATc3 |
| 1459. | T00473 | 200.0 kDa; LIT-1 |
| 1460. | T02206 | 212.7 kDa; CCG1 |
| 1461. | T00096 | 214.4 kDa; CCBF |
| 1462. | T00781 | 214.7 kDa; TAF(II)250 |
| 1463. | T01038 | 220.0 kDa; TFIIF |
| 1464. | T01378 | 220.0 kDa; E2F-I |
| 1465. | T00822 | 230.0 kDa; TFIIE |
| 1466. | T02262 | 230.0 kDa; TFIIH |
| 1467. | T02119 | 232.5 kDa; TAF(II)250 |
| 1468. | T02004 | 233.6 kDa; Cut |
| 1469. | T02317 | 243.7 kDa; Zn-15 |
| 1470. | T01427 | 264.1 kDa; p300 |
| 1471. | T02214 | 265.1 kDa; CBP |
| 1472. | T01318 | 265.5 kDa; CBP |
| 1473. | T02313 | 267.4 kDa; MIBP1 |
| 1474. | T00939 | 274.9 kDa; HIV-EP2 |
| 1475. | T00007 | 288.3 kDa; alphaA-CRYBP1 |
| 1476. | T00497 | 297.0 kDa; MBP-1 (1) |
| 1477. | T00071 | 300.0 kDa; B-TFIID |

TABLE 3-continued

Transcription Factors
TFFACTOR sorted by molecular weight (SZ field)
Database: TFFACTOR
TRANSFAC database, binding factor information
Release 3.3, January 1998
E. Wingender, R. Knueppel, P. Dietze, H. Karas (GBF-Braunschweig)
2,285 entries

| | | |
|---|---|---|
| 1478. | T02107 | 300.0 kDa; PC5 |
| 1479. | T00048 | 305.7 kDa; ATBF1-B |
| 1480. | T00920 | 332.1 kDa; Zfh-2 |
| 1481. | T00850 | 404.0 kDa; Ttx |
| 1482. | T01665 | 404.5 kDa; ATBF1-A |
| 1483. | T02140 | 500.0 kDa; PC2 |

TABLE 4

Selected examples of RS-related proteins identified from the database searches, sorted according to cluster assignment and functional association. [1]

| Functional association | Entry number | Cluster number | Species | Motifs (other than RS) | Name of protein/ homolog |
|---|---|---|---|---|---|
| Splicing (RS-related | 3 | 2 | Dm | | SRM300 |
| | 4 | 3 | Ce | | SWAP2 |
| | 5 | 3 | Dm | | SWAP2 |
| | 6 | 4 | Hs | | SWAP2 |
| | 9 | 6 | Hs | | SIP1 |
| | 23 | 7 | Hs | RRM | RNPS1 |
| | 35 | 7, 64 | Dm | RRM | U1-70K |
| | 38 | 7, 64, 110, 127, 131, 141 | Dm | RRM | U2AF-50 |
| | SWISS-PROT: P26368 | | | | U2AF-65 |
| | SWISS-PROT: Q16629 | | | | 9G8 |
| | 44 | 7, 64, 127, 141 | Ce | RRM | U1-70K |
| | 76 | 21 | Dm | SURP | SWAP1 |
| | 89 | 28 | Dm | KH-RBD/ZNF | SF1 |
| | 90 | 29 | Dm | PWI | SRM16O |
| | 101 | 38 | Dm | | TRA |
| | 111 | 46 | Ce | DEAD-BOX | U5-100K |
| | 114 | 46 | Dm | DEAD-BOX | U5-100K |
| | 115 | 47 | Ce | DEAD-BOX | HRH1 |
| | 116 | 47 | Dm | S1-RBD/DEAH-BOX | HRH1 |
| | 244 | 120 | Dm | RRM | TRA2 |
| | SWISS-PROT: P08621 | | | | U1 snRNP 70 kDa |
| | SWISS-PROT: Q01081 | | | | U2AF 35 kDa |
| | SWISS-PROT: P26368 | | | | U2AF 65 kDa |
| | ENSP00000261905, Q9BUQ8 | | | | U5 snRNP 100 kDa |
| | SWISS-PROT: Q01130 | | | | SC35 |
| | SWISS-PROT: P23152 | | | | SRp20 |
| | SWISS-PROT: Q13242 | | | | SRp30C |
| | SWISS-PROT: Q05519 | | | | SRp54 |
| | SWISS-PROT: Q13247 | | | | SRp55 |
| | SWISS-PROT: Q07955 | | | | SF2 |
| | SWISS-PROT: Q14562 | | | | DEAH-box protein 8 |
| | SWISS-PROT: P38159 | | hnRNPG | | |
| | SWISS-PROT: Q13523 | | | | Serine/threonine-protein kinase |

TABLE 4-continued

Selected examples of RS-related proteins identified from the database searches, sorted according to cluster assignment and functional association.[1]

| Functional association | Entry number | Cluster number | Species | Motifs (other than RS) | Name of protein/ homolog |
|---|---|---|---|---|---|
| | SWISS-PROT: Q9Y388 | | | | Hypothetical protein CGI-79.B |
| | SWISS-PROT: Q02040 | | | | B-lymphocyte antigen precursor |
| 3'-end processing | 97 | 36 | Ce | | FIP1 |
| | 98 | 36 | Dm | FF | FIP1 |
| | 119 | 50 | Ce | | CF-IM 68K |
| | 120 | 50 | Dm | | CF-IM 68K |
| Chromatin-associated | 108 | 44 | Dm | | CIR |
| | 190 | 87 | Hs | RRM | ACINUS |
| | 191 | 87 | Dm | (RRM) | ACINUS |
| | 212 | 103 | Dm | BROMO | GCN5 |
| Transcription (RNA pol II-associated) | 11 | 6 | Dm | PHD/ZNF/ RING | SCAF1 |
| | 17 | 7 | Hs | | SCAF4 |
| | 25 | 7, 17 | Hs | | SCAF10/SR-CYP |
| | 30 | 7,17,64,127, 131 | Dm | RRM | SCAF8 |
| | 63 | 16 | Hs | | SCAF9 |
| | 75 | 20 | Ce | | SRP129/SCAF11 |
| | 82 | 25 | Ce | ZNF/RING/ PHOS | FCP1a |
| | 99 | 36 | Dm | WW | CA150 |
| | 164 | 69 | Ce | CYCLIN | CYCLIN L |
| | 165 | 69 | Dm | CYCLIN | CYCLIN L |
| | 249 | 124 | Dm | | DSLF-P160/SPT5 |
| Transcription (other) | 24 | 7, 17, 64, 127 | Hs | | LISCH |
| | 85 | 27 | Hs | | CACTIN1 |
| | 87 | 27 | Dm | | CACTIN1 |
| | 133 | 60 | Dm | ZNF/RING | NF-X1/SHUTTLECRAFT |
| | 208 | 100 | Hs | | BTF |
| | 291 | 137 | Dm | PHD | ALHAMBRA |
| Kinases and phosphatases | 203 | 99 | Hs | KIN | PRP4-RELATED KINASE |
| | 204 | 99 | Hs | KIN | CLK-2 KINASE |
| | 206 | 99 | Dm | KIN | PITSLRE KINASE |
| | 207 | 99 | Dm | KIN | CRK7 KINASE |
| | 320 | 148 | Sc | RHOD | Ppz1p |
| | 324 | 152 | Sc | PHOS | Mip1p/Cdc25p |
| Cell structure | 168 | 72 | Hs | B41 | BAND 4 + 1-LIKE |
| | 169 | 72 | Dm | B41 | BAND 4 + 1-LIKE |
| | 235 | 114 | Sc | | Sla1p |

TABLE 5

Oligonucleotide sequences used for ChIP PCR and Real Time PCR analysis.

| Amplicon | Forward Primer | Reverse Primer |
|---|---|---|
| HIV LTR | ctgcatccggagtacttcaa gaac (SEQ ID NO 2) | aaccagagaagacccagtaca ggc (SEQ ID NO 3) |
| FFL | atgtatagatttgaagaaga gctgtttct (SEQ ID NO 4) | gataaatcgtatttgt-caatca gagtgct (SEQ ID NO 5) |
| gapdh | tactagcggttttacgggcg (SEQ ID NO 6) | tcgaacaggaggagca-gagagc ga (SEQ ID NO 7) |
| hsp70 | gaagagtctggagagttctg (SEQ ID NO 8) | cctttccttctgagccaa (SEQ ID NO 9) |
| p21/CIP | tatatcagggccgcgctg (SEQ ID NO 10) | ggctccacaaggaact-gacttc (SEQ ID NO 11) |
| cad | atcccgtggctccgcggac (SEQ ID NO 12) | gcaaactccactggaaccac (SEQ ID NO 13) |
| HLA-DRA | aaccctcccctagcaacag at (SEQ ID NO 14) | ctagcacagggactccactta tg (SEQ ID NO 15) |

TABLE 5-continued

Antibodies used in the IP and ChIP assays.

| Protein | Source (Company) | Catalog Number |
|---|---|---|
| GFP | Santa Cruz Biotechnologies | sc-8334 |
| RNA Polymerase II (N20) | Santa Cruz Biotechnologies | sc-899 |
| CTD (8WG16) | Covance | MMS-126R |
| S5P-CTD (H14) | Covance | MMS134R |
| S2P-CTD (H5) | Covance | MMS-129R |
| HA | Covance | MMS-101P |
| CyclinT1 | Santa Cruz Biotechnologies | sc-10750 |
| Normal Rabbit IgG | Upstate | 12-370 |
| HIV Tat | Covance | MMS-116P |
| Nucleolin | Santa Cruz | sc-13057 |

What is claimed is:

1. A method of inhibiting replication of an immunodeficiency virus, the method comprising the steps of expressing in a cell a nucleic acid construct in an amount sufficient for inhibition of viral transcription, the construct comprising a first nucleic acid sequence encoding HIV-Tat activation domain linked to a second nucleic acid sequence encoding U2AF65, Sfl, 9G8, CstFl, or hnRNP A1.

2. A method of treating a subject infected with an immunodeficiency virus, the method comprising the steps of administering a nucleic acid construct in an amount sufficient for inhibition of viral transcription, the construct comprising a first nucleic acid sequence encoding HIV-Tat activation domain linked to a second nucleic acid sequence encoding U2AF65, Sfl, 9G8, CstFl, or hnRNP A1.

3. The method of claim 1, wherein the inhibition of transcription is at least 25%.

4. The method of claim 1, wherein the inhibition of transcription is at least 50%.

5. The method of claim 1, wherein the inhibition of transcription is at least 75%.

6. The method of claim 1, wherein the inhibition of transcription is at least 95%.

7. The method of claim 1, wherein the cell is a T-cell infected with HIV.

8. The method of claim 2, wherein the inhibition of viral transcription is at least 25%.

9. The method of claim 2, wherein the inhibition of viral transcription is at least 50%.

10. The method of claim 2, wherein the inhibition of viral transcription is at least 75%.

11. The method of claim 2, wherein the inhibition of viral transcription is at least 95%.

12. The method of claim 1, wherein the second nucleic acid sequence encodes U2AF65.

13. The method of claim 1, wherein the second nucleic acid sequence encodes Sfl.

14. The method of claim 1, wherein the second nucleic acid sequence encodes 9G8.

15. The method of claim 1, wherein the second nucleic acid sequence encodes CstF1.

16. The method of claim 1, wherein the second nucleic acid sequence encodes hnRNP A 1.

17. The method of claim 2, wherein the second nucleic acid sequence encodes U2AF65.

18. The method of claim 2, wherein the second nucleic acid sequence encodes Sfl.

19. The method of claim 2, wherein the second nucleic acid sequence encodes 9G8.

20. The method of claim 2, wherein the second nucleic acid sequence encodes CstF1.

21. The method of claim 2, wherein the second nucleic acid sequence encodes hnRNP A1.

* * * * *